US012570661B2

(12) United States Patent
Chen et al.

(10) Patent No.: US 12,570,661 B2
(45) Date of Patent: Mar. 10, 2026

(54) ISOFORM-SPECIFIC ALDEHYDE DEHYDROGENASE INHIBITORS

(71) Applicant: The Board of Trustees of the Leland Stanford Junior University, Stanford, CA (US)

(72) Inventors: James Kenneth Chen, Stanford, CA (US); Zhiping Feng, Stanford, CA (US); Marisa E. Hom, Stanford, CA (US); Toni Kline, Stanford, CA (US); Cody R. Marshall, Stanford, CA (US); Alison E. Ondrus, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 553 days.

(21) Appl. No.: 17/923,819

(22) PCT Filed: Jun. 16, 2021

(86) PCT No.: PCT/US2021/037617
§ 371 (c)(1),
(2) Date: Nov. 7, 2022

(87) PCT Pub. No.: WO2021/257696
PCT Pub. Date: Dec. 23, 2021

(65) Prior Publication Data

US 2023/0174537 A1 Jun. 8, 2023

Related U.S. Application Data

(60) Provisional application No. 63/174,250, filed on Apr. 13, 2021, provisional application No. 63/040,873, filed on Jun. 18, 2020.

(51) Int. Cl.
*C07D 487/04* (2006.01)
*A61P 35/00* (2006.01)
*C07D 491/147* (2006.01)

(52) U.S. Cl.
CPC ............ *C07D 487/04* (2013.01); *A61P 35/00* (2018.01); *C07D 491/147* (2013.01)

(58) Field of Classification Search
None
See application file for complete search history.

(56) References Cited

U.S. PATENT DOCUMENTS

| | | | |
|---|---|---|---|
| 9,320,722 | B2 | 4/2016 | Hurley |
| 9,611,276 | B2 | 4/2017 | Chen et al. |
| 2015/0191489 | A1 | 7/2015 | Chen et al. |

FOREIGN PATENT DOCUMENTS

| | | | |
|---|---|---|---|
| CN | 112442035 A | * | 3/2021 |

OTHER PUBLICATIONS

Mazur et al., Khimiko-Farmatsevticheskii Zhurnal, 10(11), 60-63 (Year: 1976).*

Hom et al., Bicyclic Imidazolium Inhibitors of Gli Transcription Factor Activity, ChemMedChem. Jun. 17, 2020;15(12):1044-1049.

National Center for Biotechnology Information (2023). PubChem Substance Record for SID 376245235, 5H,6H,7H,8H,9H-Imidazo[1,2-a][1,3]diazepine, Source: Key Organics/BIONET. Retrieved Jan. 23, 2023 from https://pubchem.ncbi.nlm.nih.gov/substance/376245235.

Kunetskiy et al., A New Class of Organosuperbases, N-Alkyl- and N-Aryl-1,3-dialkyl-4,5-dimethylimidazol-2-ylidene Amines: Synthesis, Structure, pKBH+ Measurements, and Properties, Chem. Eur. J., 18(12):3621-3630, Mar. 19, 2012.

Lin et al., Synthesis and structure-activity relationships of imidazo[1,2-a]pyrimidin-5(1H)-ones as a novel series of beta isoform selective phosphatidylinositol 3-kinase inhibitors, Bioorg Med Chem Lett., Mar. 15, 2012; 22(6):2230-4.

Ostrowski et al., A Convenient Approach to N-3 Alkylation of 9-Substituted Guanines, Nucleosides and Nucleotides, 18(4-5):565-567, 1999.

Saksena et al., Synthesis of some new imidazo 2 3 b quinazolinones as potential cns active agents, Indian Drugs 24 (1): 16-20, 1986.

Takamizawa et al., Studies on pyrimidine derivatives and related compounds XLIX, Chemical and Pharmaceutical Bulletin, Jan. 1, 1967, 1294-1304.

Zeidler et al., A case of unusual sterically driven C-tritylation reaction of tricyclic analogues of acyclovir, Tetrahedron, 54(12):2941-2952, Mar. 19, 1998.

* cited by examiner

*Primary Examiner* — Adam C Milligan
*Assistant Examiner* — Jason M. Nolan
(74) *Attorney, Agent, or Firm* — Travis G. Young; Bret E. Field; Bozicevic, Field & Francis LLP

(57) ABSTRACT

Compounds and methods are provided for inhibiting an aldehyde dehydrogenase (ALDH). Methods of treating cancer are also provided. The ALDH-inhibitor can be a compound that is based on a cyclic guanidine, or an imidazolium core. In certain embodiments, the ALDH-inhibitor compound is a substituted cyclic guanidine, or a substituted imidazolium compound. Aspects of the methods include methods of selectively inhibiting a particular ALDH family member. In some cases, the subject compounds are ALDH1B1-selective inhibitors. In some cases, the subject compounds are ALDH1A3-selective inhibitors.

19 Claims, 30 Drawing Sheets

Specification includes a Sequence Listing.

FIG. 30

Nucleotides 1-450 of the *ALDH1B1* coding sequence (SEQ ID NO:12) are shown, revealing loss-of-function deletions in SW480 clone 2 (SEQ ID NO:13) and HCT116 clone 3 (SEQ ID NO:14). The *ALDH1B1* sequences in SW480 clone 3 and HCT116 clone 1 are identical to the parental line. Regions corresponding to the gRNA-1 and gRNA-2 targets are highlighted in gray.

```
Parental:          1   ATGCTGCGCTTCCTGGCACCCCGGCTGCTTAGCCTCCAGGGCAGGACCGC 50
SW480 Clone 2:     1   ATGCTGCGCTTCCTGGCACCCCGGCTGCTTAGCCTCCAGGGCAGGACCGC 50
HCT116 Clone 3:     1   ATGCTGCGCTTCCTGGCACCCCGGCTGCTTAGCCTCCAGGGCAGGACCGC 50

Parental:          51  CCGCTACTCCTCGGCAGCAGCCCTCCCAAGCCCCATTCTGAACCCAGACA 100
SW480 Clone 2:     51  CCGCTACTCCTCGGCAGCAGCCCTCCCAAGCCCCATTCTGAACCCAGACA 100
HCT116 Clone 3:     51  CCGCTACTCCTCGGCAGCAGCCCTCCCAAGCCCCATTCTGAACCCAGACA 100

Parental:          101 TCCCCTACAACCAGCTGTTCATCAACAATGAATGGCAAGATGCAGTCAGC 150
SW480 Clone 2:     101 TCCCCTACAACCAGCTGTTCATCAACAATGAATGGCAAGATGCAGTCAGC 136
HCT116 Clone 3:     101 TCCCCTACAACCAGCTGTTCATCAACAATGAATGGCAAGATGCAGTCAGC 150

Parental:          151 AAGAAGACCTTCCCGACGGTCAACCCTACCACCGGGGAGGTCATTGGGCA 200
SW480 Clone 2:     136 AAGAAGACCTTCCCGACG................................ 136
HCT116 Clone 3:     151 AAGAAGACCT.................ACCACCGGGGAGGTCATCGGGCA 183

Parental:          201 CGTGGCTGAAGGTGACCGGGCTGATGTGGATCGGGCCGTGAAAGCAGCCC 250
SW480 Clone 2:     136 .................................................. 136
HCT116 Clone 3:     184 CGTGGCTGAAGGTGACCGGGCTGATGTGGATCGGGCCGTGAAAGCAGCCC 233

Parental:          251 GGGAAGCCTTCCGCCTGGGGTCCCCATGGCGCCGGATGGATGCCTCTGAG 300
SW480 Clone 2:     136 .................................................. 136
HCT116 Clone 3:     234 GGGAAGCCTTCCGCCTGGGGTCCCCATGGCGCCGGATGGATGCCTCTGAG 283

Parental:          301 CGGGGCCGGCTGCTGAACCGCCTGGCAGACCTAGTGGAGCGGGATCGAGT 350
SW480 Clone 2:     136 .................................................. 166
HCT116 Clone 3:     284 CGGGGCCGGCTGCTGAACCGCCTGGCAGACCTAGTGGAGCGGGATCGAGT 333

Parental:          351 CTACTTGGCCTCACTCGAGACCTTGGACAATGGGAAGCCTTTCCAAGAGT 400
SW480 Clone 2:     167 ..ACTTGGCCTCACTCGAGACCTTGGACAATGGGAAGCCTTTCCAAGAGT 216
HCT116 Clone 3:     334 CTACTTGGCCTCACTCGAGACCTTGGACAATGGGAAGCCTTTCCAAGAGT 383

Parental:          401 CTTACGCCTTGGACTTGGATGAGGTCATCAAGGTGTATCGGTACTTTGCT 450
SW480 Clone 2:     217 CTTACGCCTTGGACTTGGATGAGGTCATCAAGGTGTATCGGTACTTTGCT 266
HCT116 Clone 3:     384 CTTACGCCTTGGACTTGGATGAGGTCATCAAGGTGTATCGGTACTTTGCT 433
```

(SEQ ID NOS: 12-14)

ISOFORM-SPECIFIC ALDEHYDE DEHYDROGENASE INHIBITORS

CROSS REFERENCE TO RELATED APPLICATION

This application is a U.S. National Stage Application of PCT Application No. PCT/US2021/037617 filed Jun. 16, 2021, which application, pursuant to 35 U.S.C. § 119 (e), claims priority to the filing date of U.S. Provisional Patent Application Ser. Nos. 63/040,873 filed Jun. 18, 2020 and 63/174,250 filed Apr. 13, 2021, the disclosures of which applications are incorporated herein by reference in its entirety.

GOVERNMENT RIGHTS

This invention was made with Government support under contract GM127030 awarded by the National Institutes of Health. The Government has certain rights in the invention.

REFERENCE TO AN ELECTRONIC SEQUENCE LISTING

The contents of the electronic sequence listing (STAN-1757_SEQLIST_ST25.txt; Size: 4,601 bytes; and Date of Creation: Mar. 6, 2023) is herein incorporated by reference in its entirety.

INTRODUCTION

Cancer therapies have traditionally targeted the molecular processes that drive rapid cell division, including critical steps in DNA replication or signaling pathways that promote cell growth. While these treatments can induce tumor regression, they often fail to eradicate slowly dividing stem cell-like populations that enable tumor relapse, drug resistance, and metastasis. Eliminating these cancer stem cells (CSCs) could lead to durable patient responses or even cures, and targeting the metabolic pathways that sustain these highly tumorigenic populations is emerging as a promising approach. In particular, certain aldehyde dehydrogenase family members (e.g., ALDH1A1, ALDH1A3, and ALDH1B1) are frequently upregulated in CSCs and promote their survival.

Accordingly, there is a need for new agents and methods that can selectively inhibit certain isoforms of aldehyde dehydrogenase (e.g., ALDH1A1, ALDH1A3, and ALDH1B1).

SUMMARY

Compounds and methods are provided for inhibiting an aldehyde dehydrogenase (ALDH). Methods of treating cancer are also provided. The ALDH-inhibitor can be a compound that is based on a bicyclic guanidine, or a bicyclic imidazolium core, e.g., as described herein. In certain embodiments, the ALDH-inhibitor compound is a substituted bicyclic guanidine, or a substituted bicyclic imidazolium compound.

Aspects of the methods include methods of selectively inhibiting a particular ALDH family member (e.g., ALDH1A1, ALDH1A3, and ALDH1B1). In some cases, the subject compounds are ALDH1B1-selective inhibitors. In some cases, the subject compounds are ALDH1A3-selective inhibitors.

Also provided are methods of treating a subject for cancer. Aspects of the methods include inhibiting an ALDH family member in a cancer cell to reduce cellular proliferation. The subject compounds may be formulated or provided to a subject in combination with one or more additional anti-cancer agents. Use of the ALDH-inhibitor compound in methods of reducing cancer stem cell proliferation and methods of treatment is provided in a variety of cancer cells and cancer subjects.

These and other advantages and features of the disclosure will become apparent to those persons skilled in the art upon reading the details of the compositions and methods of use, which are more fully described below.

Figure 25:
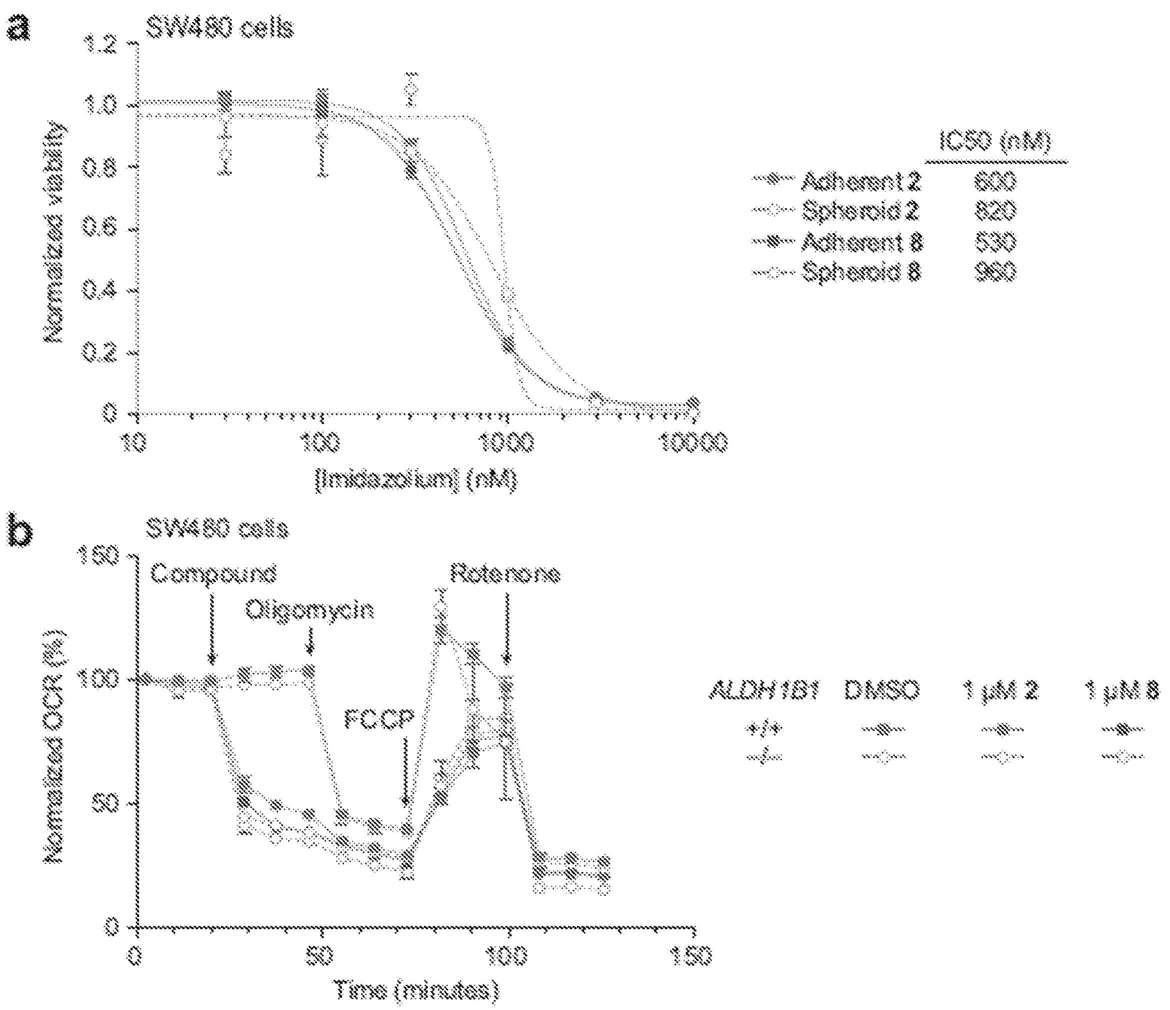

FIG. 25, Imidazoliums exhibit off-target mitochondrial toxicity. (a) Dose-response curves for imidazoliums 2 and 8 on SW480 cells cultured in either adherent or spheroid conditions. Data are the average of three biological replicates±s.e.m. (b) Seahorse assays evaluating the effects of imidazoliums on the oxygen consumption rates of $AWH1B1^{+/+}$ and $ALDH1B1^{-/-}$ SW480 cells. Data are the average of three biological replicates±s.e.m.

Figure 26:
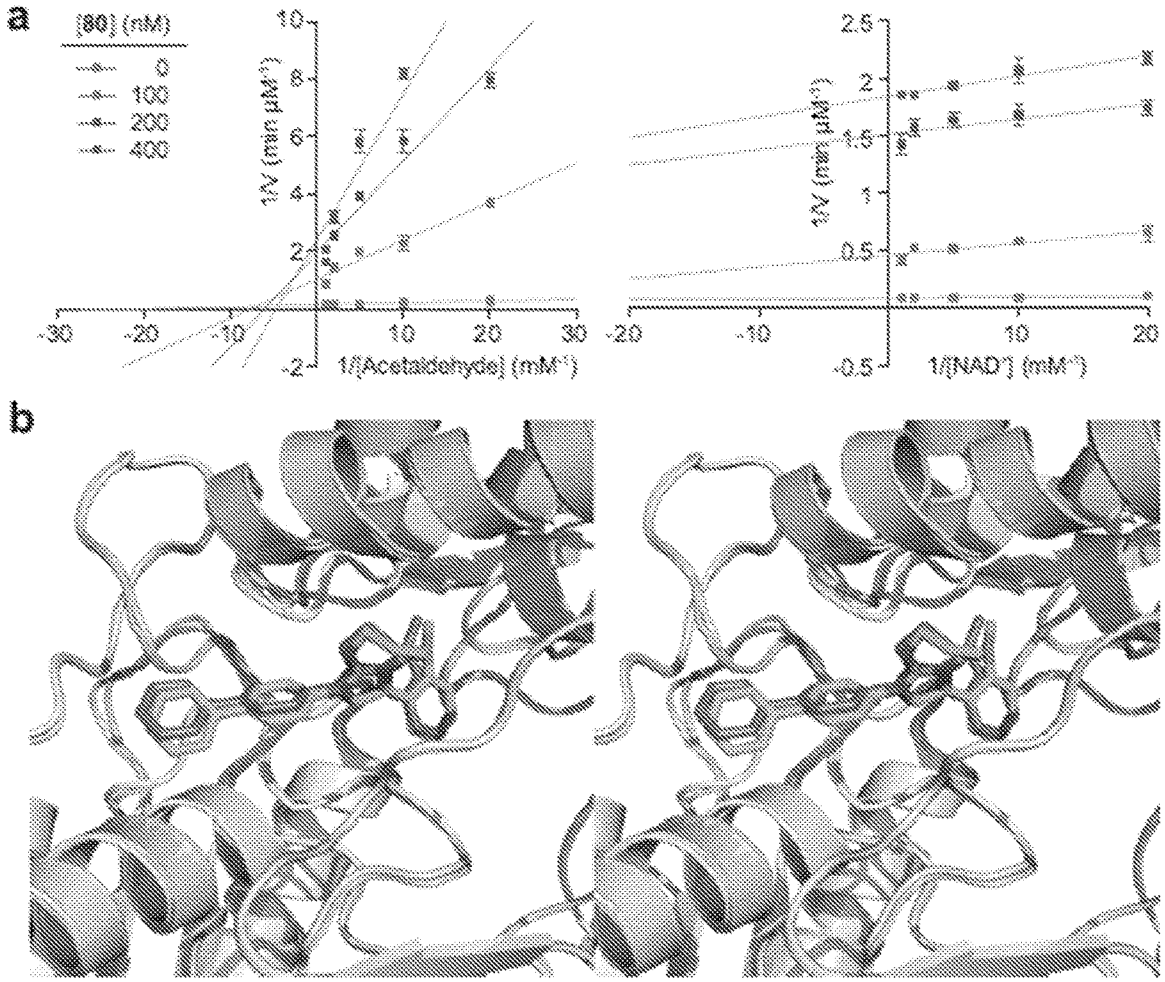

FIG. 26, Molecular basis of ALDH1B1-guanidine binding. (a) Lineweaver-Burk plots demonstrating that guanidine 80 exhibits non-competitive inhibition with respect to acetaldehyde and uncompetitive inhibition with respect to $NAD^+$. Data are the average of at least two biological replicates±s.e.m. (b) Stereoview of the ALDH1B1/imidazolium 2 (light blue cartoon and blue stick model) and ALDH1B1/guanidine 80 (light-green cartoon and green stick model) complexes shown as superimposed structures.

Figure 27:
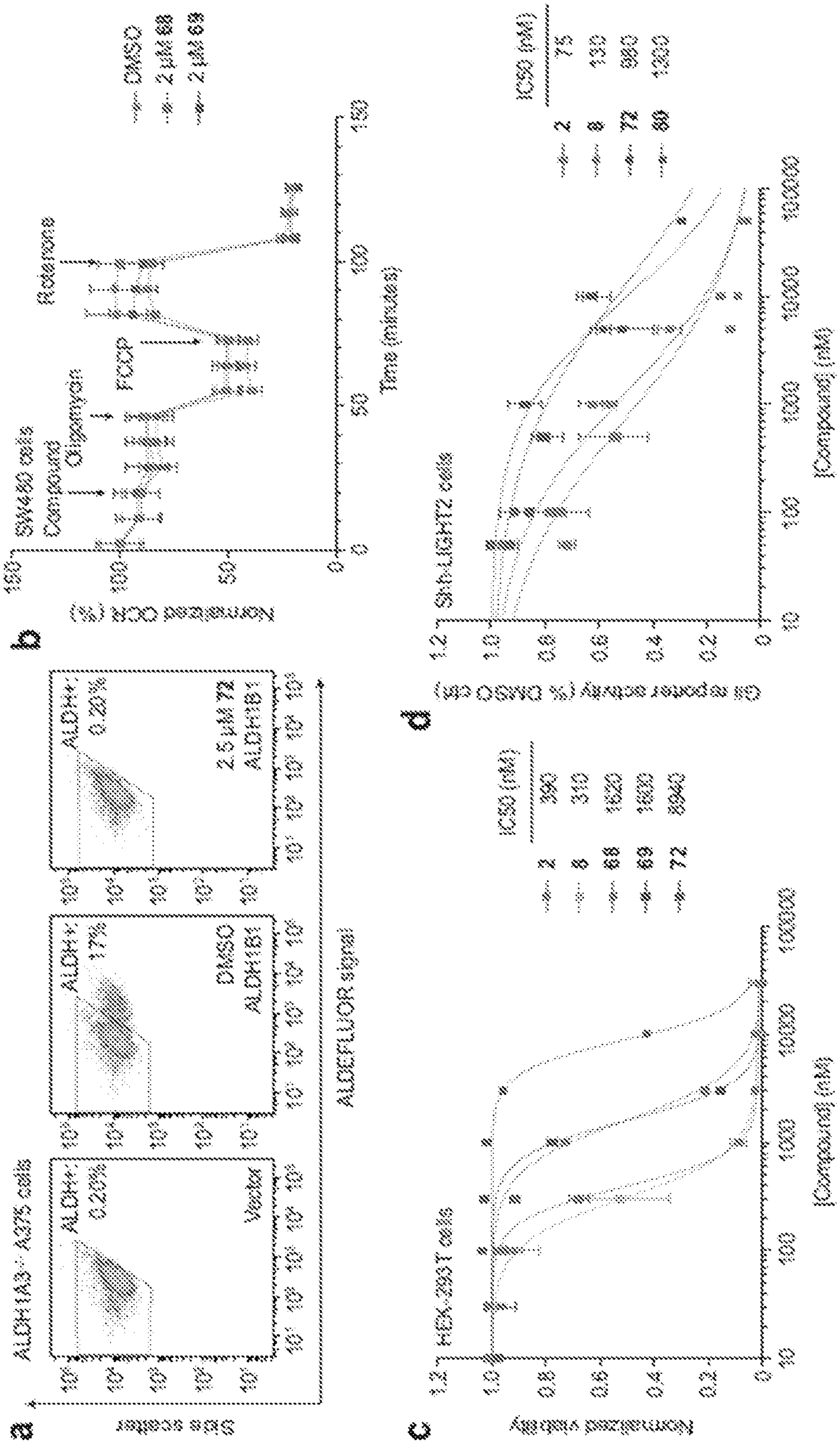

FIG. 27, Cellular activities of guanidine-based ALDH1B1 antagonists. (a) Flow cytometry-based ALDEFLUOR assays using $ALDH1A3^{-/-}$ A375 cells, demonstrating the ability of guanidine 72 to inhibit cellular ALDH1B1 activity. The percentage of cells outside of the negative control gate is shown for each condition. (b) Seahorse assays showing that guanidiums do not inhibit oxygen consumption rates of SW480 cells. (c) Dose-response curves for the indicated imidazoliums (2 and 8) and guanidines (68, 69, and 72) in the HEK-293T cell viability assay. Data are the average of three biological replicates±s.e.m. (d) Dose-response curves for the indicated compounds in NIH-3T3 cells stably transfected with Gli-dependent firefly luciferase reporter (Shh-LIGHT2 cells). Data are the average of three biological replicates±s.e.m.

Figure 28:
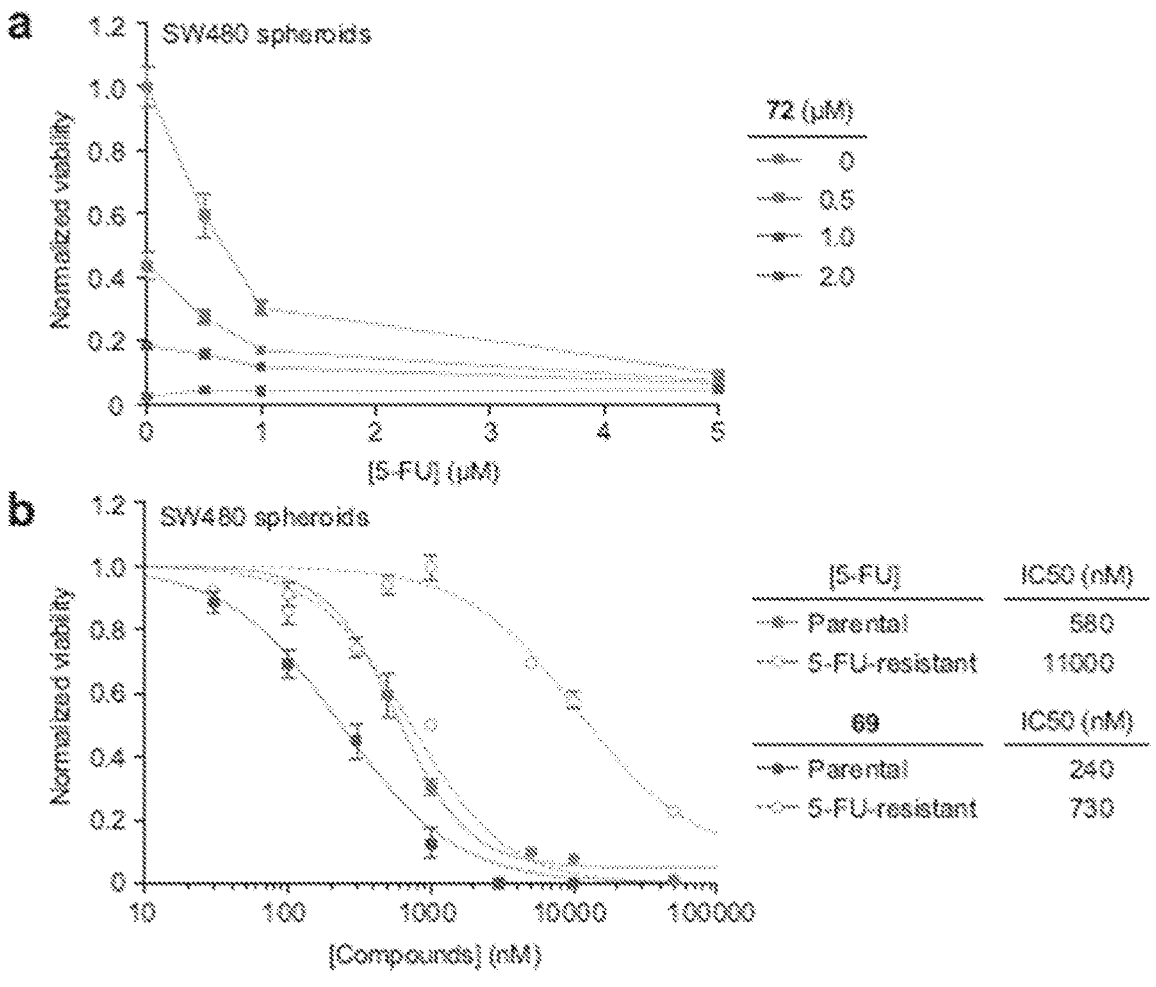

FIG. 28, Guanidine-based ALDH1B1 antagonists can block the growth 5-FU resistant colon cancer spheroids. (a) Combinatorial effects of 5-FU and guanidine 72 on SW480 spheroid growth, demonstrating the orthogonal, additive mechanisms of the two compounds. Data are the average of three biological replicates±s.e.m. (b) Activities of 5-FU and guanidine 69 against parental and 5-FU-resistant SW480 cell lines. The cells were cultured as spheroids, and data are the average of three biological replicates±s.e.m.

Figure 29:
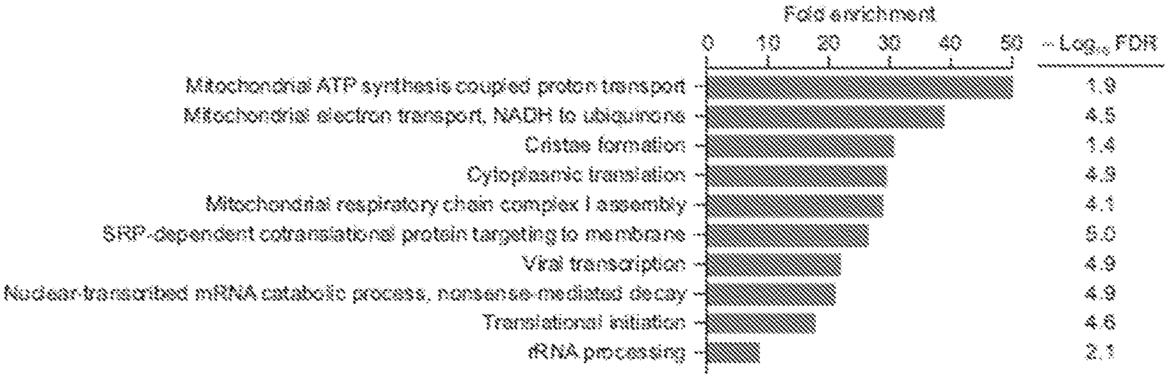

FIG. 29, Gene Ontology (GO) enrichment analysis of ALDH1B1-regulated genes. Transcriptional changes associated with both genetically and chemically induced loss of ALDH1B1 function (fold-change~1.3 and P~<0.05) were analyzed using the GO knowledgebase of biological processes. GO term subclasses are ranked according to their fold enrichment in the ALDH1B1 dataset, and their corresponding false discovery rates (FDRs) are shown.

FIG. 30, Nucleotides 1-450 of the ALDH1B1 coding sequence are shown, revealing loss-of-function deletions in SW480 clone 2 and HCT116 clone 3. The ALDH1B1 sequences in SW480 clone 3 (SEQ ID NO:13) and HCT116 clone 1 (SEQ ID NO:14) are identical to the parental line (SEQ ID NO:12). Regions corresponding to the gRNA-1 and gRNA-2 targets are highlighted in gray.

DEFINITIONS

Before embodiments of the present disclosure are further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112. In describing and claiming the present invention, certain terminology will be used in accordance with the definitions set out below. It will be appreciated that the definitions provided herein are not intended to be mutually exclusive. Accordingly, some chemical moieties may fall within the definition of more than one term.

As used herein, the phrases "for example," "for instance," "such as," or "including" are meant to introduce examples that further clarify more general subject matter. These examples are provided only as an aid for understanding the disclosure and are not meant to be limiting in any fashion.

The terms "active agent," "antagonist", "inhibitor", "drug" and "pharmacologically active agent" are used interchangeably herein to refer to a chemical material or compound which, when administered to an organism (human or animal) induces a desired pharmacologic and/or physiologic effect by local and/or systemic action.

As used herein, the terms "treatment," "treating," and the like, refer to obtaining a desired pharmacologic and/or physiologic effect, such as reduction of viral titer. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease (as in liver fibrosis that can result in the context of chronic HCV infection); (b) inhibiting the disease, i.e., arresting its development; and (c) relieving the disease, i.e., causing regression of the disease (e.g., reduction in viral titers).

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The terms "individual," "host," "subject," and "patient" are used interchangeably herein, and refer to an animal, including, but not limited to, human and non-human primates, including simians and humans; rodents, including rats and mice; bovines; equines; ovines; felines; canines; and the like. "Mammal" means a member or members of any mammalian species, and includes, by way of example, canines; felines; equines; bovines; ovines; rodentia, etc. and primates, e.g., non-human primates, and humans. Non-human animal models, e.g., mammals, e.g. non-human primates, murines, lagomorpha, etc. may be used for experimental investigations.

As used herein, the terms "determining," "measuring," "assessing," and "assaying" are used interchangeably and include both quantitative and qualitative determinations.

A "therapeutically effective amount" or "efficacious amount" means the amount of a compound that, when administered to a mammal or other subject for treating a disease, condition, or disorder, is sufficient to effect such treatment for the disease, condition, or disorder. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of a compound (e.g., an aminopyrimidine compound, as described herein) calculated in an amount sufficient to produce the desired effect in association with a pharmaceutically acceptable diluent, carrier or vehicle. The specifications for unit dosage forms depend on the particular compound employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general, a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

The term "aldehyde dehydrogenase" or "ALDH" refers to an enzyme that oxidizes an aldehyde to its corresponding acid in an NAD+-dependent or an NADP+-dependent reaction. The term encompasses ALDH found in the cytosol, in the mitochondria, microsome, or other cellular compartment. The term "ALDH" encompasses ALDH found primarily in one or a few tissues, or in stem cells and embryos.

The term "ALDH" encompasses any of the known ALDH isozymes, including ALDH1A1, ALDH1A2, ALDH1A3, ALDH1B1, ALDH1L1, ALDH1L2, ALDH2, ALDH3A1, ALDH3A2, ALDH3B1, ALDH3B2, ALDH4A1, ALDH5A1, ALDH6A1, ALDH7A1, ALDH8A1, ALDH9A1, ALDH16A1, ALDH18A1.

As used herein, "ALDH1" or "ALDH1A1" refers to a cytosolic aldehyde dehydrogenase that oxidizes an aldehyde to its corresponding acid in an NAD+-dependent reaction. The term "ALDH1" or "ALDH1A1" encompasses ALDH1 from various species. Amino acid sequences of ALDH1 from various species are publicly available. See, e.g., GenBank Accession Nos. AAC51652 (*Homo sapiens* ALDH1); NP_000680 (*Homo sapiens* ALDH1); AAH61526 (*Rattus norvegicus* ALDH1); AA105194 (*Bos taurus* ALDH1); and NP_036051 (*Mus musculus* ALDH1). The term "ALDH1" or "ALDH1A1" as used herein also encompasses fragments, fusion proteins, and variants (e.g., variants having one or more amino acid substitutions, addition, deletions, and/or insertions) that retain ALDH1 enzymatic activity. The term "ALDH1" or "ALDH1A1" encompasses an aldehyde dehydrogenase that oxidizes aromatic aldehydes, including those of the retinaldehyde, naphthaldehyde, phenanthrenealdehyde, and coumarinaldehyde series, as well as complex polyaromatic aldehydes. The term "ALDH1" or "ALDH1A1" encompasses a cytosolic aldehyde dehydrogenase.

The term "ALDH1B1" (also referred to as "ALDH5" and "aldehyde dehydrogenase family 1 member B1") encompasses an $NAD^+$-dependent enzyme that oxidizes succinic semialdehyde to succinate; retinaldehyde; and lipid peroxidation products. ALDH1B1 is involved in the catabolism of 4-aminobutyric acid (GABA). Naturally occurring ALDH1B1 can be found in the mitochondria of eukaryotic cells. The term "ALDH1B1" encompasses an enzymatically active polypeptide having at least about 75%, at least about 80%, at least about 85%, at least about 90%, at least about 95%, at least about 98%, at least about 99%, or 100%, amino acid sequence identity to the amino acid sequence set forth in GenBank Accession No. AAH34321.

The term "ALDH1A3" (also referred to as "ALDH6" and "aldehyde dehydrogenase family 1 member A3") encompasses ALDH1A3 from various species. Amino acid sequences of ALDH1A3 from various species are publicly available. See, e.g., GenBank Accession Nos. AAA79036.1 (*Homo sapiens* ALDH6), NP_000684.2 (*Homo sapiens* ALDH6) (FIG. 3A), P47895 (*Homo sapiens* ALDH6), AAG33935.1 (*Mus musculus* ALDH6), NP_444310.3 (*Mus musculus* ALDH6) (FIG. 3B), and NP_695212.1 (*Rattus norvegicus* ALDH6). The term "ALDH1A3" as used herein also encompasses fragments, fusion proteins, and variants (e.g., variants having one or more amino acid substitutions, addition, deletions, and/or insertions) that retain ALDH6 enzymatic activity. The term "ALDH6" encompasses an aldehyde dehydrogenase that exhibits specificity toward free retinal and cellular retinol-binding protein-bound retinal, and oxidizes retinal to form all-trans-retinoic acid (RA). The term "ALDH6" encompasses aldehyde dehydrogenase found naturally, e.g., in keratinocytes, in saliva, in salivary gland, in breast epithelium, in stomach, in kidney, etc.

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

As used herein, the terms "may," "optional," "optionally," or "may optionally" mean that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group $CH_3C(O)$—

The term "alkyl" as used herein refers to a branched or unbranched saturated hydrocarbon group (i.e., a mono-radical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(═O)— moiety). The terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "substituted alkyl" is meant to include an alkyl group as defined herein wherein one or more carbon atoms in the alkyl chain have been optionally replaced with a heteroatom such as —O—, —N—, —S—, —$S(O)_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —$SO_2$-alkyl, —$SO_2$-aryl, —$SO_2$-heteroaryl, and —$NR^aR^b$, wherein R' and R" may be the same or different and are chosen from hydrogen, optionally substituted alkyl, cycloalkyl, alkenyl, cycloalkenyl, alkynyl, aryl, heteroaryl and heterocyclic.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "C1-C6 alkoxy" or "lower alkoxy" herein may, for example, contain 1 to 3 carbon atoms, and as a further example, such substituents may contain 1 or 2 carbon atoms (i.e., methoxy and ethoxy).

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two or more fused or linked aromatic rings (i.e., biaryl, aryl-substituted aryl, etc.). Examples include phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. Aryl is intended to include stable cyclic, heterocyclic, polycyclic, and polyheterocyclic unsaturated $C_3$-$C_{14}$ moieties, exemplified but not limited to phenyl, biphenyl, naphthyl, pyridyl, furyl, thiophenyl, imidazoyl, pyrimidinyl, and oxazoyl; which may further be substituted with one to five members selected from the group consisting of hydroxy, $C_1$-$C_8$ alkoxy, $C_1$-$C_8$ branched or straight-chain alkyl, acyloxy, carbamoyl, amino, N-acylamino, nitro, halogen, trifluoromethyl, cyano, and carboxyl (see e.g. Katritzky, Handbook of Heterocyclic Chemistry). If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "alkylene" as used herein refers to a di-radical alkyl group. Unless otherwise indicated, such groups include saturated hydrocarbon chains containing from 1 to 24 carbon atoms, which may be substituted or unsubstituted, may contain one or more alicyclic groups, and may be heteroatom-containing. "Lower alkylene" refers to alkylene linkages containing from 1 to 6 carbon atoms. Examples include, methylene ($-CH_2-$), ethylene ($-CH_2CH_2-$), propylene ($-CH_2CH_2CH_2-$), 2-methylpropylene ($-CH_2-CH(CH_3)-CH_2-$), hexylene ($-(CH_2)_6-$) and the like.

Similarly, the terms "alkenylene," "alkynylene," "arylene," "aralkylene," and "alkarylene" as used herein refer to di-radical alkenyl, alkynyl, aryl, aralkyl, and alkaryl groups, respectively.

The term "amino" is used herein to refer to the group —NRR' wherein R and R' are independently hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

"Carboxyl," "carboxy" or "carboxylate" refers to $-CO_2H$ or salts thereof.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, [1.1.1.]bicyclopentyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO— substituted alkyl, —SO-aryl, —SO-heteroaryl, $-SO_2$-alkyl, $-SO_2$-substituted alkyl, $-SO_2$-aryl and $-SO_2$-heteroaryl.

The term "heteroatom-containing" as in a "heteroatom-containing alkyl group" (also termed a "heteroalkyl" group)

or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the terms "heterocyclic" or "heterocycle" refer to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl, and trihalomethyl.

As used herein, the terms "Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —$SO_2$— moieties.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO— alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl, and fused heterocycle.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. A hydrocarbyl may be substituted with one or more substituent groups. The term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups, and the hydrocarbyl moieties C1-C24 alkyl (including C1-C18 alkyl, further including C1-C12 alkyl, and further including C1-C6 alkyl), C2-C24 alkenyl (including C2-C18 alkenyl, further including C2-C12 alkenyl, and further including C2-C6 alkenyl), C2-C24 alkynyl (including C2-C18 alkynyl, further including C2-C12 alkynyl, and further including C2-C6 alkynyl), C5-C30 aryl (including C5-C20 aryl, and further including C5-C12 aryl), and C6-C30 aralkyl (including C6-C20 aralkyl, and further including C6-C12 aralkyl). The above-mentioned hydrocarbyl moieties may be further substituted with one or more functional groups or additional hydrocarbyl moieties such as those specifically enumerated. Unless otherwise indicated, any of the groups described herein are to be interpreted as including substituted and/or heteroatom-containing moieties, in addition to unsubstituted groups.

"Sulfonyl" refers to the group $SO_2$-alkyl, $SO_2$-substituted alkyl, $SO_2$-alkenyl, $SO_2$-substituted alkenyl, $SO_2$-cycloalkyl, $SO_2$-substituted cycloalkyl, $SO_2$-cycloalkenyl, $SO_2$-substituted cylcoalkenyl, $SO_2$-aryl, $SO_2$-substituted aryl, $SO_2$-heteroaryl, $SO_2$-substituted heteroaryl, $SO_2$-heterocyclic, and $SO_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-$SO_2$—, phenyl-$SO_2$—, and 4-methylphenyl-$SO_2$—.

By the term "functional groups" is meant chemical groups such as halo, hydroxyl, sulfhydryl, C1-C24 alkoxy, C2-C24 alkenyloxy, C2-C24 alkynyloxy, C5-C20 aryloxy, acyl (including C2-C24 alkylcarbonyl (—CO-alkyl) and C6-C20 arylcarbonyl (—CO-aryl)), acyloxy (—O-acyl), C2-C24 alkoxycarbonyl (—(CO)—O-alkyl), C6-C20 aryloxycarbonyl (—(CO)—O-aryl), halocarbonyl (—CO)—X where X is halo), C2-C24 alkylcarbonato (—O—(CO)—O-alkyl), C6-C20 arylcarbonato (—O—(CO)—O-aryl), carboxy (—COOH), carboxylato (—COO—), carbamoyl (—(CO)—NH2), mono-substituted C1-C24 alkylcarbamoyl (—(CO)—NH(C1-C24 alkyl)), di-substituted alkylcarbamoyl (—(CO)—N(C1-C24 alkyl)2), mono-substituted arylcarbamoyl (—(CO)—NH-aryl), thiocarbamoyl (—(CS)—NH2), carbamido (—NH—(CO)—NH2), cyano (—C≡N), isocyano (—N+≡C—), cyanato (—O—C≡N), isocyanato (—O—N+≡C—), isothiocyanato (—S—C≡N), azido (—N═N+=N—), formyl (—(CO)—H), thioformyl (—(CS)—H), amino (—NH2), mono- and di-(C1-C24 alkyl)-substituted amino, mono- and di-(C5-C20 aryl)-substituted amino, C2-C24 alkylamido (—NH—(CO)-alkyl), C5-C20 arylamido (—NH—(CO)-aryl), imino (—CR═NH where R=hydrogen, C1-C24 alkyl, C5-C20 aryl, C6-C20 alkaryl, C6-C20 aralkyl, etc.), alkylimino (—CR═N(alkyl), where R=hydrogen, alkyl, aryl, alkaryl, etc.), arylimino (—CR═N(aryl), where R=hydrogen, alkyl, aryl, alkaryl, etc.), nitro (—NO2), nitroso (—NO), sulfo (—$SO_2$—OH), sulfonato (—$SO_2$—O—), C1-C24 alkylsulfanyl (—S-alkyl; also termed "alkylthio"), arylsulfanyl (—S-aryl; also termed "arylthio"), C1-C24 alkylsulfinyl (—(SO)-alkyl), C5-C20 arylsulfinyl (—(SO)-aryl), C1-C24 alkylsulfonyl (—SO2-alkyl), C5-C20 arylsulfonyl (—$SO_2$-aryl), phosphono (—P(O)$(OH)_2$), phosphonato (—P(O)$(O—)_2$), phosphinato (—P(O)(O—)), phospho (—$PO_2$), and phosphino (—$PH_2$), mono- and di-(C1-C24 alkyl)-substituted phosphino, mono- and di-(C5-C20 aryl)-substituted phosphine. In addition, the aforementioned functional groups may, if a particular group permits, be further substituted with one or more additional functional groups or with one or more hydrocarbyl moieties such as those specifically enumerated above.

When the term "substituted" appears prior to a list of possible substituted groups, it is intended that the term apply to every member of that group. For example, the phrase "substituted alkyl and aryl" is to be interpreted as "substituted alkyl and substituted aryl."

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with ═O, ═$NR^{70}$, ═N—$OR^{70}$, ═$N_2$ or ═S) on saturated carbon atoms in the specified group or radical are, unless otherwise specified, —$R^{60}$, halo, ═O, —$OR^{70}$, —$SR^{70}$, —$NR^{80}R^{80}$, trihalomethyl, —CN, —OCN, —SCN, —NO, —NO2, ═$N_2$, —$N_3$, —$SO_2R^{70}$, —$SO_2O^-M^+$, —$SO_2OR^{70}$, —$OSO_2R^{70}$, —$OSO_2O^-M^+$, —$OSO_2OR^{70}$, —$P(O)(O^-)_2$, $(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$C(O)O^-M^+$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)O^-M^+$, —$OC(O)OR^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —$NR^{80}R^{80}$ is meant to include —$NH_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}$ $(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70}R^{70}$ and —$NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

In addition to the groups disclosed with respect to the individual terms herein, substituent groups for hydrogens on nitrogen atoms in "substituted" heteroalkyl and cycloheteroalkyl groups are, unless otherwise specified, —$R^{60}$, —$O^-M^+$, —$SR^{70}$, —$SR^{70}$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

In certain embodiments, a substituent may contribute to optical isomerism and/or stereo isomerism of a compound. Salts, solvates, hydrates, and prodrug forms of a compound are also of interest. All such forms are embraced by the present disclosure. Thus the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

Unless otherwise specified, reference to an atom is meant to include isotopes of that atom. For example, reference to H is meant to include $^{1}H$, $^{2}H$ (i.e., D) and $^{3}H$ (i.e., T), and reference to C is meant to include $^{12}C$ and all isotopes of carbon (such as $^{13}C$).

Definitions of other terms and concepts appear throughout the detailed description.

DETAILED DESCRIPTION

As summarized above, compounds and methods are provided for inhibiting an aldehyde dehydrogenase (ALDH). Methods of treating cancer are also provided. The ALDH-inhibitor can be a compound that is based on a bicyclic guanidine, or a bicyclic imidazolium core, e.g., as described herein. In certain embodiments, the ALDH-inhibitor compound is a substituted bicyclic guanidine, or a substituted bicyclic imidazolium compound.

In some embodiments, there are provided methods of selectively inhibiting a particular ALDH family member (e.g., ALDH1A1, ALDH1A3, and ALDH1B1). In some cases, the subject compounds are ALDH1B1-selective inhibitors, and the subject compound is brought into contact with the an ALDH1B1 in a dose for a period of time sufficient to inhibit activity of the enzyme. In some cases, the subject compounds are ALDH1A3-selective inhibitors, and the subject compound is brought into contact with the an ALDH1A3 in a dose for a period of time sufficient to inhibit activity of the enzyme.

Also provided are methods of treating a subject for cancer. In some embodiments, the ALDH-inhibitor compounds have broad spectrum activity against a variety of cancers. In some embodiments, the subject compound inhibits an ALDH family member in a cancer cell to reduce cellular proliferation. The subject compounds may be formulated or provided to a subject in combination with one or more additional anti-cancer agents. Use of the ALDH-inhibitor compound in methods of reducing cellular proliferation and methods of treatment is provided in a variety of cancer cells and cancer subjects.

Also provided are pharmaceutical compositions that include the subject compounds, wherein the compound of the present invention can be formulated with a pharmaceutically acceptable excipient. Formulations may be provided in a unit dose, where the dose provides an amount of the compound effective to achieve a desired result, including without limitation inhibition of one or more ALDH family members.

The compounds and methods find use in a variety of applications in which inhibition of ALDH is desired.

Compounds

Aspects of the disclosure include particular ALDH-inhibitor compounds. In general, the compounds include a bicyclic guanidine, or a bicyclic imidazolium core structure (as described herein). The bicyclic guanidine, or bicyclic imidazolium core may be fused ring structures that include at least one or more further substituents. In some cases, the cyclic guanidine or imidazolium core is substituted at the N-1 position and one or more carbon positions of the ring. In some cases, the substituents at the N-1 position and the one or more carbon positions of the bicyclic guanidine or bicyclic imidazolium core is selected from a cyclic group, such as an aryl group, a substituted aryl group, a biaryl group, a substituted biaryl group, a heteroaryl group, a substituted heteroaryl group, a heterocyclic group, a substituted heterocyclic group, a cycloalkyl, and a substituted cycloalkyl. In some cases, the cyclic groups may be further substituted with any convenient substituents including but not limited to alkyl, alkoxy, acyloxy, aminoalkoxy, cyano, halogen, hydroxyl, nitro, —$NR_2$, —NHCOR, —$SO_2NHR$, —CONHR or —$NHSO_2R$, where R is H, alkyl, heteroalkyl, heterocycle or aryl. Exemplary compounds are set forth in the following structures and formulae.

In some cases, the subject compound is described by the structure of formula (I):

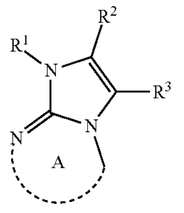

wherein:

$R^1$ and $R^3$ are each independently selected from alkyl, substituted alkyl, alkenyl, substituted alkenyl, alkynyl, substituted alkynyl, aryl, substituted aryl, heterocycle, substituted heterocycle, heteroaryl, substituted heteroaryl, cycloalkyl, and substituted cycloalkyl;

$R^2$ is selected from H, alkyl, substituted alkyl, alkenyl, substituted alkenyl, alkynyl, substituted alkynyl, alkoxy, substituted alkoxy, halogen, hydroxyl, acyl, substituted acyl, carboxy, substituted carboxy, amino, substituted amino, aryl, substituted aryl, heterocycle, substituted heterocycle, heteroaryl, substituted heteroaryl, cycloalkyl, and substituted cycloalkyl; and Ring A is an optionally substituted cyclic group;

or a pharmaceutically acceptable salt, solvate, isomer, or prodrug thereof.

In some embodiments of formula (I), the A ring is selected from a 6-10 membered cycle.

In some cases, the A ring includes one or more unsaturated bonds. In some cases, the A ring contains one or more carbon-carbon double bonds. In some cases, the A ring contains a carbon-carbon triple bond. In some other cases, the A ring contains only saturated carbon-carbon bonds.

In some embodiments, the A ring is described by the formula (A1):

(A1)

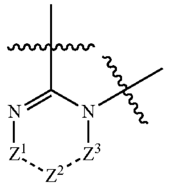

where each --- represent a saturated bond or an unsaturated bond, and $Z^1$-$Z^3$ are independently selected from $C(R^{33})_2$, $CR^{33}$, N, S, $NR^{33}$, O, and CO, provided that valency requirements are fulfilled, where each $R^{33}$ are independently selected from hydrogen, alkyl, substituted alkyl, hydroxy, alkoxy, substituted alkoxy, trifluoromethyl, halogen, acyl, substituted acyl, carboxy, carboxyamide, substituted carboxyamide, sulfonyl, substituted sulfonyl, sulfonamide, and substituted sulfonamide. In certain cases, each of $Z^1$-$Z^3$ are $C(R^{33})_2$, wherein each $R^{33}$ group is hydrogen. In some cases, one of $Z^1$ and $Z^2$, or $Z^2$ and $Z^3$ is connected by a double bond, and the remaining groups are connected by single bonds. In some cases, one of $Z^1$-$Z^3$ is CO and the remaining groups are $C(R^{33})_2$. In certain cases, $Z^2$ is CO.

In some embodiments, the A ring is described by formula (A1a)-(A1f):

(A1a)

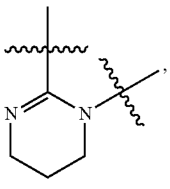

, (A1b)

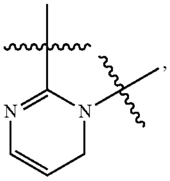

, (A1c)

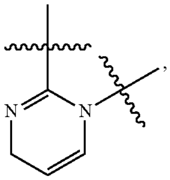

, (A1d)

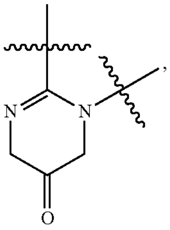

,

-continued (A1e)

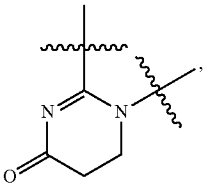

, and (A1f)

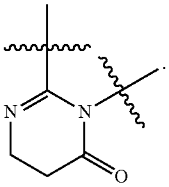

.

In some embodiments, the A ring is described by the formula (A2):

(A2)

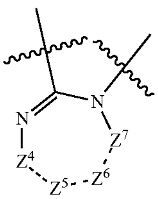

where each --- represent a saturated bond or an unsaturated bond, and $Z^4$-$Z^7$ are independently selected from $C(R^{33})_2$, $CR^{33}$, N, S, $NR^{33}$, O, and CO, provided that valency requirements are fulfilled, where each $R^{33}$ are independently selected from hydrogen, alkyl, substituted alkyl, hydroxy, alkoxy, substituted alkoxy, trifluoromethyl, halogen, acyl, substituted acyl, carboxy, carboxyamide, substituted carboxyamide, sulfonyl, substituted sulfonyl, sulfonamide, and substituted sulfonamide. In certain cases, each of $Z^4$-$Z^7$ are $C(R^{33})_2$, wherein each $R^{33}$ are hydrogen. In certain cases, each of $Z^4$-$Z^7$ are $C(R^{33})_2$, wherein a $R^{33}$ group on $Z^4$ and $Z^7$ form a covalent bond to each other to form a bridged structure. In some cases, one of $Z^4$ and $Z^5$, $Z^5$ and $Z^6$, or $Z^6$ and $Z^7$ are connected by a double bond, and the remaining groups are connected by single bonds. In some cases, $Z^4$ and $Z^5$, and $Z^6$ and $Z^7$ are both connected by double bonds. In some cases, one of $Z^4$-$Z^7$ is CO and the remaining groups are $C(R^{33})_2$.

In some embodiments, the A ring is described by formula (A2a)-(A2h):

(A2a)

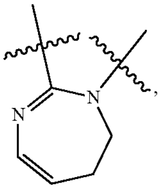

,

-continued (A2b)

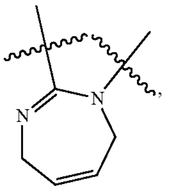

(A2c)

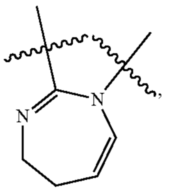

(A2d)

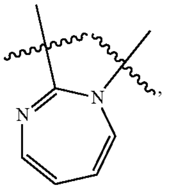

(A2e)

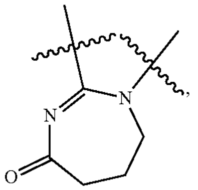

(A2f)

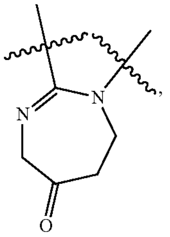

(A2g)

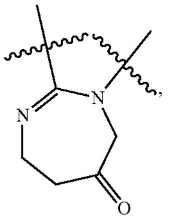

and (A2h)

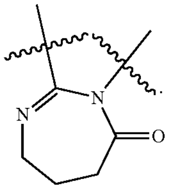

In some embodiments, the A ring is described by the formula (A3):

(A3)

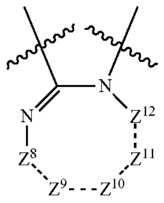

where each --- represent a saturated bond or an unsaturated bond, $Z^8$-$Z^{12}$ are independently selected from $C(R^{33})_2$, $CR^{33}$, N, S, $NR^{33}$, O, and CO, provided that valency requirements are fulfilled, where each $R^{33}$ are independently selected from hydrogen, alkyl, substituted alkyl, hydroxy, alkoxy, substituted alkoxy, trifluoromethyl, halogen, acyl, substituted acyl, carboxy, carboxyamide, substituted carboxyamide, sulfonyl, substituted sulfonyl, sulfonamide, and substituted sulfonamide. In certain cases, each of $Z^8$-$Z^{12}$ are $C(R^{33})_2$, wherein each $R^{33}$ are hydrogen. In certain cases, each of $Z^8$-$Z^{12}$ are $C(R^{33})_2$, wherein a $R^{33}$ group on $Z^8$ and $Z^{11}$ or $Z^9$ and $Z^{12}$ form a covalent bond to each other to form a bridged structure. In some cases, one of $Z^8$ and $Z^9$, $Z^9$ and $Z^{10}$, $Z^{10}$ and $Z^{11}$, or $Z^{11}$ and $Z^{12}$ are connected by a double bond, and the remaining groups are connected by single bonds. In some cases, $Z^8$ and $Z^9$, and $Z^{11}$ and $Z^{12}$ are both double bonds. In some cases, $Z^8$ and $Z^9$, and $Z^{10}$ and $Z^{11}$ are both double bonds. In some cases, $Z^9$ and $Z^{10}$, and $Z^{11}$ and $Z^{12}$ are both double bonds. In some cases, one of $Z^8$-$Z^{12}$ is CO and the remaining groups are $C(R^{33})_2$.

In some embodiments, the A ring is described by formula (A3a)-(A3o):

(A3a)

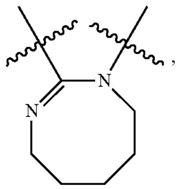

(A3b)

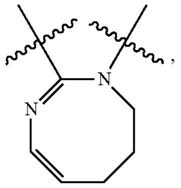

(A3c)

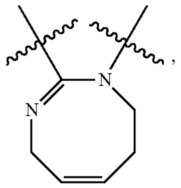

(A3d)

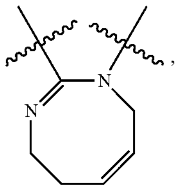

-continued (A3e)

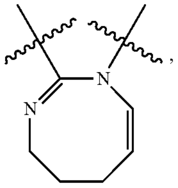

(A3f)

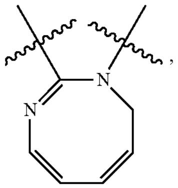

(A3g)

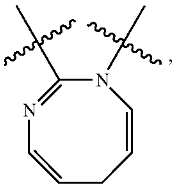

(A3h)

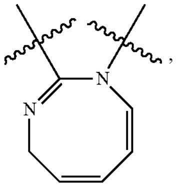

(A3i)

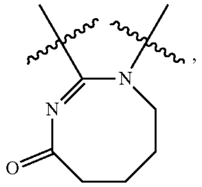

(A3j)

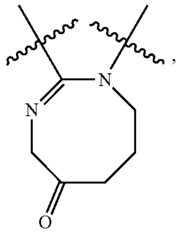

(A3k)

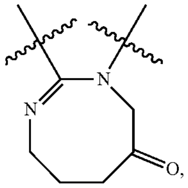

-continued (A3l)

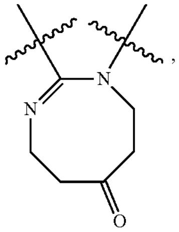

(A3m)

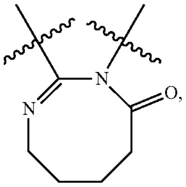

(A3n)

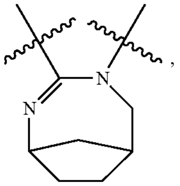

(A3o)

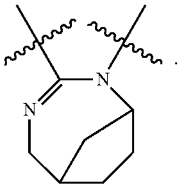

In some cases, the compound is described by the formula (II):

(II)

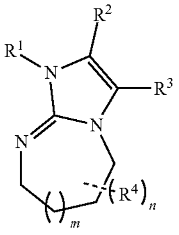

wherein:

each ------ represents a C—C bond, wherein one or more of the C—C bonds is optionally unsaturated;

$R^1$ and $R^3$ are each independently selected from alkyl, substituted alkyl, alkenyl, substituted alkenyl, alkynyl, substituted alkynyl, aryl, substituted aryl, heterocycle, substituted heterocycle, heteroaryl, substituted heteroaryl, cycloalkyl, and substituted cycloalkyl;

$R^2$ is selected from H, alkyl, substituted alkyl, alkenyl, substituted alkenyl, alkynyl, substituted alkynyl, alkoxy, substituted alkoxy, halogen, hydroxyl, acyl, substituted acyl, carboxy, substituted carboxy, amino, substituted amino, aryl, substituted aryl, heterocycle, substituted heterocycle, heteroaryl, substituted heteroaryl, cycloalkyl, and substituted cycloalkyl;

$R^4$ is an optional substituent selected from alkyl, substituted alkyl, hydroxy, carbonyl, amino, substituted amino, halogen, nitrile, nitro, acyl, substituted acyl, carboxy, and substituted carboxy; or two $R^4$ groups together with the atoms to which they are attached form an optionally substituted cyclic group;

n is an integer from 0 to 10; and m is an integer from 0 to 2, wherein if m is 0, then n is an integer from 0 to 6, and if m is 1, then n is an integer from 0 to 8.

In certain embodiments of formula (II), each --- represents a C—C single bond. In certain cases of formula (II), at least one of --- represents a C—C double bond. In some cases m is 0, and each --- represents a C—C single bond. In certain cases, m is 0 and one of --- represents a C—C double bond. In some cases, m is 1, and each --- represents a C—C single bond. In certain cases, m is 1 and one of --- represents a C—C double bond. In certain cases, m is 1 and two of --- represent C—C double bonds. In some cases, m is 2, and each --- represents a C—C single bond. In certain cases, m is 2 and one of --- represents a C—C double bond. In certain cases, m is 2 and two of --- represent C—C double bonds.

In certain embodiments of formula (II), the compound is of one of formulae (IIA)-(IIG):

(IIA)

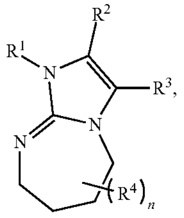

(IIB)

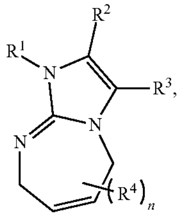

(IIC)

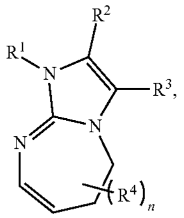

(IID)

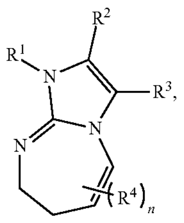

-continued (IIE)

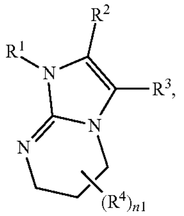

(IIF)

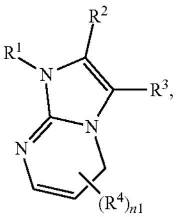

and (IIG)

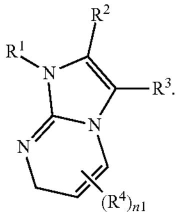

In certain embodiments of formula (I) or (II), $R^1$ is independently selected from alkyl, substituted alkyl, alkenyl, substituted alkenyl, alkynyl, substituted alkynyl, aryl, substituted aryl, heterocycle, substituted heterocycle, heteroaryl, substituted heteroaryl, cycloalkyl, and substituted cycloalkyl. In certain case, $R^1$ is selected from alkyl and substituted alkyl. In certain cases, $R^1$ is selected from alkenyl and substituted alkenyl. In some cases, $R^1$ is selected from alkynyl and substituted alkynyl.

In some embodiments of formula (I) or (II), $R^1$ is selected from aryl and substituted aryl. In some cases, the aryl group is substituted with any convenient substituents including but not limited to alkyl, alkoxy, acyloxy, aminoalkoxy, cyano, halogen, hydroxyl, nitro, —$NR_2$, —NHCOR, —$SO_2NHR$, —CONHR or —$NHSO_2R$, where R is H, alkyl, heteroalkyl, heterocycle or aryl. In some case, the substituted aryl is substituted with an aryl, substituted aryl heteroaryl, or substituted heteroaryl group, such that the $R^1$ group is a biaryl group.

In some embodiments of formula (I) or (II), $R^1$ is selected from heterocycle, and substituted heterocycle. In some cases, the heterocyclic group is substituted with any convenient substituents including but not limited to alkyl, alkoxy, acyloxy, aminoalkoxy, cyano, halogen, hydroxyl, nitro, nitrile, —$NR_2$, —NHCOR, —$SO_2NHR$, —CONHR or —$NHSO_2R$, where R is H, alkyl, heteroalkyl, heterocycle or aryl.

In some embodiments of formula (I) or (II), $R^1$ is selected from heteroaryl, and substituted heteroaryl. In some cases, the heteroaryl group is substituted with any convenient substituents including but not limited to alkyl, alkoxy, acyloxy, aminoalkoxy, cyano, halogen, hydroxyl, nitro, —$NR_2$, —NHCOR, —$SO_2NHR$, —CONHR or —$NHSO_2R$, where R is H, alkyl, heteroalkyl, heterocycle or aryl. In some case, the substituted heteroaryl is substituted with an aryl, substituted aryl, heteroaryl, or substituted heteroaryl group.

In some embodiments of formula (I) or (II), $R^1$ is selected from cycloalkyl, and substituted cycloalkyl. In some cases, the cycloalkyl group is substituted with any convenient substituents including but not limited to alkyl, alkoxy, acyloxy, aminoalkoxy, cyano, halogen, hydroxyl, nitro, —$NR_2$, —NHCOR, —$SO_2$NHR, —CONHR or —$NHSO_2R$, where R is H, alkyl, heteroalkyl, heterocycle or aryl.

In some embodiments of formula (I) or (II), $R^1$ is selected from biaryl, and substituted cycloalkyl. In some cases, the cycloalkyl group is substituted with any convenient substituents including but not limited to alkyl, alkoxy, acyloxy, aminoalkoxy, cyano, halogen, hydroxyl, nitro, —$NR_2$, —NHCOR, —$SO_2$NHR, —CONHR or —$NHSO_2R$, where R is H, alkyl, heteroalkyl, heterocycle or aryl.

In certain embodiments of formula (I) or (II), $R^3$ is independently selected from alkyl, substituted alkyl, alkenyl, substituted alkenyl, alkynyl, substituted alkynyl, aryl, substituted aryl, heterocycle, substituted heterocycle, heteroaryl, substituted heteroaryl, cycloalkyl, and substituted cycloalkyl. In certain case, $R^3$ is selected from alkyl and substituted alkyl. In certain cases, $R^3$ is selected from alkenyl and substituted alkenyl. In some cases, $R^3$ is selected from alkynyl and substituted alkynyl.

In some embodiments of formula (I) or (II), $R^3$ is selected from aryl, and substituted aryl. In some cases, the aryl group is substituted with any convenient substituents including but not limited to alkyl, alkoxy, acyloxy, aminoalkoxy, cyano, halogen, hydroxyl, nitro, —$NR_2$, —NHCOR, —$SO_2$NHR, —CONHR or —$NHSO_2R$, where R is H, alkyl, heteroalkyl, heterocycle or aryl. In some case, the substituted aryl is substituted with an aryl, substituted aryl heteroaryl, or substituted heteroaryl group, such that the $R^3$ group is a biaryl group.

In some embodiments of formula (I) or (II), $R^3$ is selected from heterocycle, and substituted heterocycle. In some cases, the heterocyclic group is substituted with any convenient substituents including but not limited to alkyl, alkoxy, acyloxy, aminoalkoxy, cyano, halogen, hydroxyl, nitro, —$NR_2$, —NHCOR, —$SO_2$NHR, —CONHR or —$NHSO_2R$, where R is H, alkyl, heteroalkyl, heterocycle or aryl.

In some embodiments of formula (I) or (II), $R^3$ is selected from heteroaryl, and substituted heteroaryl. In some cases, the heteroaryl group is substituted with any convenient substituents including but not limited to alkyl, alkoxy, acyloxy, aminoalkoxy, cyano, halogen, hydroxyl, nitro, —$NR_2$, —NHCOR, —$SO_2$NHR, —CONHR or —$NHSO_2R$, where R is H, alkyl, heteroalkyl, heterocycle or aryl. In some cases, the substituted heteroaryl is substituted with an aryl, substituted aryl, heteroaryl, or substituted heteroaryl group.

In some embodiments of formula (I) or (II), $R^3$ is selected from cycloalkyl, and substituted cycloalkyl. In some cases, the cycloalkyl group is substituted with any convenient substituents including but not limited to alkyl, alkoxy, acyloxy, aminoalkoxy, cyano, halogen, hydroxyl, nitro, —$NR_2$, —NHCOR, —$SO_2$NHR, —CONHR or —$NHSO_2R$, where R is H, alkyl, heteroalkyl, heterocycle or aryl.

In some embodiments of formula (I) or (II), $R^3$ is selected from biaryl, and substituted cycloalkyl. In some cases, the cycloalkyl group is substituted with any convenient substituents including but not limited to alkyl, alkoxy, acyloxy, aminoalkoxy, cyano, halogen, hydroxyl, nitro, —$NR_2$, —NHCOR, —$SO_2$NHR, —CONHR or —$NHSO_2R$, where R is H, alkyl, heteroalkyl, heterocycle or aryl.

In certain embodiments, the compound is of formula (III):

(III)

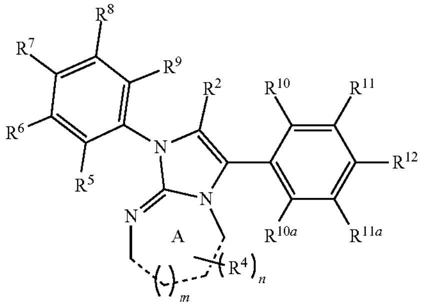

wherein:

each ------ represents a C—C bond, wherein one or more of the C—C bonds is optionally unsaturated;

$R^2$ is selected from H, alkyl, substituted alkyl, alkenyl, substituted alkenyl, alkynyl, substituted alkynyl, alkoxy, substituted alkoxy, halogen, hydroxyl, acyl, substituted acyl, carboxy, substituted carboxy, amino, substituted amino, aryl, substituted aryl, heterocycle, substituted heterocycle, heteroaryl, substituted heteroaryl, cycloalkyl, and substituted cycloalkyl;

$R^5$-$R^{12}$ are each independently selected from H, alkyl, substituted alkyl, alkenyl, substituted alkenyl, alkynyl, substituted alkynyl, alkoxy, substituted alkoxy, halogen, hydroxy, nitro, nitrile, amino, substituted amino, acyl, substituted acyl, carboxy, substituted carboxy, aryl, substituted aryl, heterocycle, substituted heterocycle, heteroaryl, substituted heteroaryl, cycloalkyl, and substituted cycloalkyl; or any two adjacent $R^5$-$R^{12}$ groups together with the atoms to which they are attached form an optionally substituted cyclic group;

$R^4$ is an optional substituent selected from alkyl, substituted alkyl, hydroxy, carbonyl, amino, substituted amino, halogen, nitrile, nitro, acyl, substituted acyl, carboxy, and substituted carboxy; or two $R^4$ groups together with the atoms to which they are attached form an optionally substituted cyclic group;

n is an integer from 0 to 10; and m is an integer from 0 to 2, wherein if m is 0, then n is an integer from 0 to 6, and if m is 1, then n is an integer from 0 to 8.

In some embodiments of formula (III), $R^5$-$R^{12}$ are each independently selected from H, alkyl, substituted alkyl, alkoxy, substituted alkoxy, halogen, hydroxy, nitro, amino, substituted amino, acyl, substituted acyl, carboxy, and substituted carboxy.

In certain embodiments, at least one of $R^5$-$R^{12}$ is a substituent other than H. In some cases, at least one of $R^5$-$R^9$, and at least one of $R^{10}$-$R^{12}$ are substituents other than H. In certain cases, $R^9$ is a substituent other than H. In certain cases, $R^8$ is a substituent other than H. In some cases, $R^7$ is a substituent other than H. In certain cases, $R^9$ and $R^5$ are substituents other than H. In certain cases, $R^9$ and $R^7$ are substituents other than H. In some cases, $R^9$ and $R^6$ are substituents other than H. In certain cases, $R^5$, $R^7$ and $R^9$ are each substituents other than H. In certain cases, $R^8$ and $R^6$ are substituents other than H. In certain cases, $R^{10}$ is a substituent other than H. In some cases, $R^{12}$ is a substituent other than H. In certain cases, $R^{10}$ and $R^{14}$ are substituents other than H. In certain cases, $R^{10}$ and $R^{12}$ are substituents other than H. In some cases, $R^{10}$ and $R^{14}$ are substituents other than H. In certain cases, $R^{10}$, $R^{12}$ and $R^{14}$ are each substituents other than H. In certain cases, $R^{11}$ and $R^{11a}$ are substituents other than H.

In certain cases, at least one of $R^5$-$R^9$ is selected from alkyl, substituted alkyl, alkoxy, substituted alkoxy, halogen, hydroxy, nitro, amino, substituted amino, acyl, substituted acyl, carboxy, substituted carboxy, aryl, substituted aryl, heterocycle, substituted heterocycle, heteroaryl, substituted heteroaryl, cycloalkyl, and substituted cycloalkyl. In certain cases, at least one of $R^5$-$R^9$ is selected from alkyl, and substituted alkyl. In certain cases, at least one of $R^5$-$R^9$ is selected from alkoxy, and substituted alkoxy. In certain cases, at least one of $R^5$-$R^9$ is halogen. In certain cases, at least one of $R^5$-$R^9$ is hydroxy. In certain cases, at least one of $R^5$-$R^9$ is nitro. In certain cases, at least one of $R^5$-$R^9$ is selected from amino and substituted amino. In certain cases, at least one of $R^5$-$R^9$ is selected from acyl and substituted acyl. In certain cases, at least one of $R^5$-$R^9$ is selected from carboxy, and substituted carboxy. In certain cases, at least one of $R^5$-$R^9$ is selected from aryl and substituted aryl. In certain cases, at least one of $R^5$-$R^9$ is selected from heterocycle, and substituted heterocycle. In certain cases, at least one of $R^5$-$R^9$ is selected from heteroaryl, and substituted heteroaryl. In certain cases, at least one of $R^5$-$R^9$ is selected from cycloalkyl, and substituted cycloalkyl.

In certain cases, at least one of $R^{10}$-$R^{12}$ is selected from alkyl, substituted alkyl, alkoxy, substituted alkoxy, halogen, hydroxy, nitro, amino, substituted amino, acyl, substituted acyl, carboxy, substituted carboxy, aryl, substituted aryl, heterocycle, substituted heterocycle, heteroaryl, substituted heteroaryl, cycloalkyl, and substituted cycloalkyl. In certain cases, at least one of $R^{10}$-$R^{12}$ is selected from alkyl, and substituted alkyl. In certain cases, at least one of $R^{10}$-$R^{12}$ is selected from alkoxy, and substituted alkoxy. In certain cases, at least one of $R^{10}$-$R^{12}$ is halogen. In certain cases, at least one of $R^{10}$-$R^{12}$ is hydroxy. In certain cases, at least one of $R^{10}$-$R^{12}$ is nitro. In certain cases, at least one of $R^{10}$-$R^{14}$ is selected from amino and substituted amino. In certain cases, at least one of $R^{10}$-$R^{12}$ is selected from acyl and substituted acyl. In certain cases, at least one of $R^{10}$-$R^{12}$ is selected from carboxy, and substituted carboxy. In certain cases, at least one of $R^{10}$-$R^{12}$ is selected from aryl and substituted aryl. In certain cases, at least one of $R^{10}$-$R^{12}$ is selected from heterocycle, and substituted heterocycle. In certain cases, at least one of $R^{10}$-$R^{12}$ is selected from heteroaryl, and substituted heteroaryl. In certain cases, at least one of $R^{10}$-$R^{12}$ is selected from cycloalkyl, and substituted cycloalkyl.

In certain embodiments of formula (III), $R^9$ is selected from alkyl, substituted alkyl, alkoxy, substituted alkoxy, halogen, hydroxy, nitro, amino, substituted amino, acyl, substituted acyl, carboxy, and substituted carboxy.

In certain embodiments of formula (III), $R^8$ is selected from alkyl, substituted alkyl, alkoxy, substituted alkoxy, halogen, hydroxy, nitro, amino, substituted amino, acyl, substituted acyl, carboxy, and substituted carboxy.

In certain embodiments of formula (III), $R^7$ is selected from alkyl, substituted alkyl, alkoxy, substituted alkoxy, halogen, hydroxy, nitro, amino, substituted amino, acyl, substituted acyl, carboxy, substituted carboxy, aryl, substituted aryl, heteroaryl, substituted heteroaryl, heterocycle, substituted heterocycle, cycloalkyl, and substituted cycloalkyl.

In certain embodiments of formula (III), $R^9$ and $R^5$ are selected from alkyl, substituted alkyl, alkoxy, substituted alkoxy, halogen, hydroxy, nitro, amino, substituted amino, acyl, substituted acyl, carboxy, and substituted carboxy.

In certain embodiments of formula (III), $R^9$ and $R^7$ are selected from alkyl, substituted alkyl, alkoxy, substituted alkoxy, halogen, hydroxy, nitro, amino, substituted amino, acyl, substituted acyl, carboxy, substituted carboxy, aryl, substituted aryl, heteroaryl, substituted heteroaryl, heterocycle, substituted heterocycle, cycloalkyl, and substituted cycloalkyl.

In certain embodiments of formula (III), $R^9$ and $R^6$ are selected from alkyl, substituted alkyl, alkoxy, substituted alkoxy, halogen, hydroxy, nitro, amino, substituted amino, acyl, substituted acyl, carboxy, and substituted carboxy.

In certain embodiments of formula (III), $R^5$, $R^7$ and $R^9$ are selected from alkyl, substituted alkyl, alkoxy, substituted alkoxy, halogen, hydroxy, nitro, amino, substituted amino, acyl, substituted acyl, carboxy, substituted carboxy, aryl, substituted aryl, heteroaryl, substituted heteroaryl, heterocycle, substituted heterocycle, cycloalkyl, and substituted cycloalkyl.

In certain embodiments of formula (III), $R^8$ and $R^6$ are selected from alkyl, substituted alkyl, alkoxy, substituted alkoxy, halogen, hydroxy, nitro, amino, substituted amino, acyl, substituted acyl, carboxy, and substituted carboxy.

In certain embodiments of formula (III), $R^{10}$ is selected from alkyl, substituted alkyl, alkoxy, substituted alkoxy, halogen, hydroxy, nitro, amino, substituted amino, acyl, substituted acyl, carboxy, and substituted carboxy.

In certain embodiments of formula (III), $R^{11}$ is selected from alkyl, substituted alkyl, alkoxy, substituted alkoxy, halogen, hydroxy, nitro, amino, substituted amino, acyl, substituted acyl, carboxy, and substituted carboxy.

In certain embodiments of formula (III), $R^{12}$ is selected from alkyl, substituted alkyl, alkoxy, substituted alkoxy, halogen, hydroxy, nitro, amino, substituted amino, acyl, substituted acyl, carboxy, substituted carboxy, aryl, substituted aryl, heteroaryl, substituted heteroaryl, heterocycle, substituted heterocycle, cycloalkyl, and substituted cycloalkyl.

In certain embodiments of formula (III), $R^{10}$ and $R^{10a}$ are selected from alkyl, substituted alkyl, alkoxy, substituted alkoxy, halogen, hydroxy, nitro, amino, substituted amino, acyl, substituted acyl, carboxy, and substituted carboxy.

In certain embodiments of formula (III), $R^{10}$ and $R^{12}$ are selected from alkyl, substituted alkyl, alkoxy, substituted alkoxy, halogen, hydroxy, nitro, amino, substituted amino, acyl, substituted acyl, carboxy, substituted carboxy, aryl, substituted aryl, heteroaryl, substituted heteroaryl, heterocycle, substituted heterocycle, cycloalkyl, and substituted cycloalkyl.

In certain embodiments of formula (III), $R^{10}$ and $R^{11a}$ are selected from alkyl, substituted alkyl, alkoxy, substituted alkoxy, halogen, hydroxy, nitro, amino, substituted amino, acyl, substituted acyl, carboxy, and substituted carboxy.

In certain embodiments of formula (III), $R^{10}$, $R^{12}$ and $R^{14}$ are selected from alkyl, substituted alkyl, alkoxy, substituted alkoxy, halogen, hydroxy, nitro, amino, substituted amino, acyl, substituted acyl, carboxy, substituted carboxy, aryl, substituted aryl, heteroaryl, substituted heteroaryl, heterocycle, substituted heterocycle, cycloalkyl, and substituted cycloalkyl.

In certain embodiments of formula (III), $R^{11}$ and $R^{11a}$ are selected from alkyl, substituted alkyl, alkoxy, substituted alkoxy, halogen, hydroxy, nitro, amino, substituted amino, acyl, substituted acyl, carboxy, and substituted carboxy.

In some embodiments, the compound is described by formula (IV):

(IV)

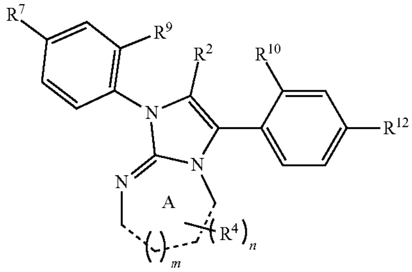

wherein:

each ------ represents a C—C bond, wherein one or more of the C—C bonds is optionally unsaturated;

$R^2$ is selected from H, alkyl, substituted alkyl, alkenyl, substituted alkenyl, alkynyl, substituted alkynyl, alkoxy, substituted alkoxy, halogen, hydroxyl, acyl, substituted acyl, carboxy, substituted carboxy, amino, substituted amino, aryl, substituted aryl, heterocycle, substituted heterocycle, heteroaryl, substituted heteroaryl, cycloalkyl, and substituted cycloalkyl;

$R^9$ and $R^{10}$ are independently selected from H, alkyl, substituted alkyl, alkoxy, substituted alkoxy, halogen, hydroxy, acyl, substituted acyl, carboxy, substituted carboxy, amino, and substituted amino;

$R^7$ and $R^{12}$ are each independently selected from H, aryl, substituted aryl, heteroaryl, substituted heteroaryl, heterocycle, substituted heterocycle, cycloalkyl, substituted cycloalkyl, alkyl, substituted alkyl, alkoxy, substituted alkoxy, halogen, hydroxy, acyl, substituted acyl, carboxy, substituted carboxy, amino, and substituted amino;

$R^4$ is an optional substituent selected from alkyl, substituted alkyl, hydroxy, amino, substituted amino, halogen, nitrile, nitro, acyl, substituted acyl, carboxy, and substituted carboxy; or two adjacent $R^4$ groups together with the atoms to which they are attached form an optionally substituted cyclic group;

n is an integer from 0 to 10; and m is an integer from 0 to 2, wherein if m is 0, then n is an integer from 0 to 6, and if m is 1, then n is an integer from 0 to 8.

In some embodiments of formula (IV), $R^9$ and $R^{10}$ are independently selected from H, alkoxy, substituted alkoxy, halogen, hydroxy, amino, and substituted amino; and $R^7$ and $R^{12}$ are each independently selected from H, aryl, substituted aryl, heteroaryl, substituted heteroaryl, alkoxy, substituted alkoxy, halogen, hydroxy, amino, and substituted amino.

In certain cases of formula (IV), $R^9$ is selected from alkoxy, substituted alkoxy, halogen, hydroxy, amino, and substituted amino;

$R^7$ and $R^{10}$ are each H; and $R^{12}$ is selected from aryl, substituted aryl, heteroaryl, substituted heteroaryl, alkoxy, substituted alkoxy, halogen, hydroxy, amino, and substituted amino.

In certain cases of formula (IV), $R^7$ is selected from alkoxy, substituted alkoxy, halogen, hydroxy, amino, and substituted amino;

$R^9$ and $R^{10}$ are each H; and $R^{12}$ is selected from aryl, substituted aryl, heteroaryl, substituted heteroaryl, alkoxy, substituted alkoxy, halogen, hydroxy, amino, and substituted amino.

In certain cases of formula (IV), $R^{10}$ is selected from alkoxy, substituted alkoxy, halogen, hydroxy, amino, and substituted amino;

$R^9$ and $R^{12}$ are each H; and $R^7$ is selected from aryl, substituted aryl, heteroaryl, substituted heteroaryl, alkoxy, substituted alkoxy, halogen, hydroxy, amino, and substituted amino.

In certain cases of formula (IV), $R^{12}$ is selected from alkoxy, substituted alkoxy, halogen, hydroxy, amino, and substituted amino;

$R^9$ and $R^{10}$ are each H; and $R^7$ is selected from aryl, substituted aryl, heteroaryl, substituted heteroaryl, alkoxy, substituted alkoxy, halogen, hydroxy, amino, and substituted amino.

In certain embodiments, the compound is of the formula (IVa)-(IVh):

(IVa)

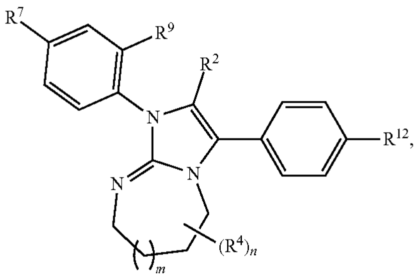

(IVb)

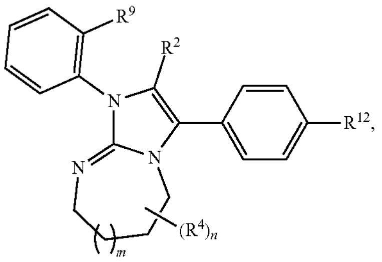

(IVc)

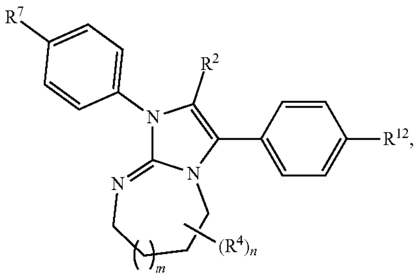

(IVd)

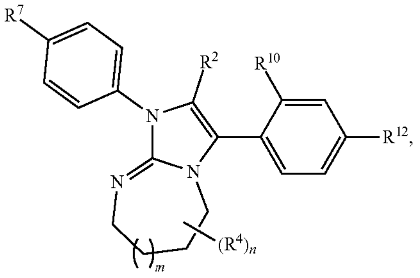

-continued (IVe)

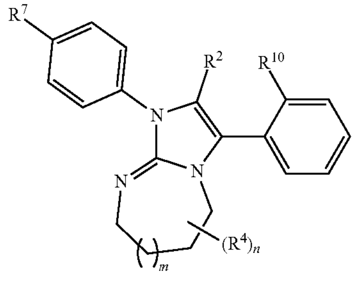

, (IVf)

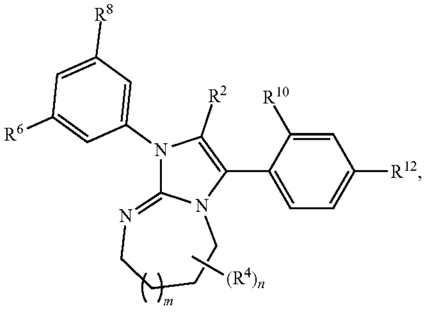

(IVg)

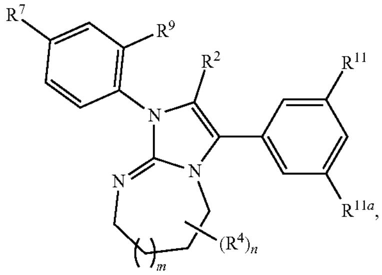

and (IVh)

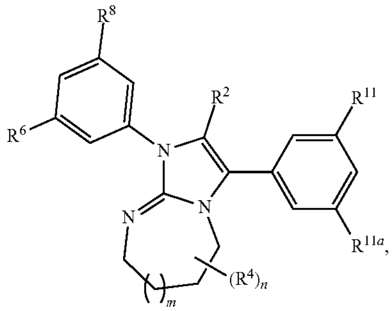

wherein each of $R^2$, $R^4$, $R^6$_$R^{11a}$, m and n are as defined herein above. In some embodiments, the compound is described by the formula (VA) or (VB):

(VA)

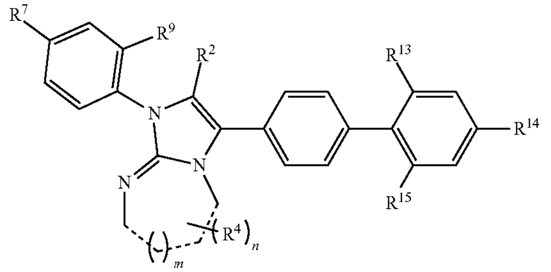

(VB)

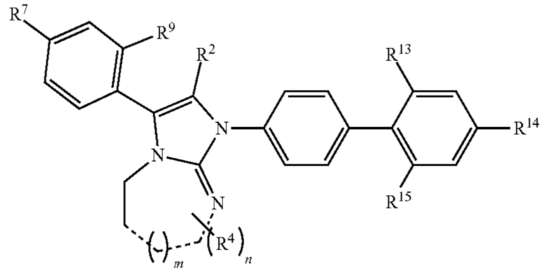

wherein:

each ------ represents a C—C bond, wherein one or more of the C—C bonds is optionally unsaturated;

$R^2$ is selected from H, alkyl, substituted alkyl, alkenyl, substituted alkenyl, alkynyl, substituted alkynyl, alkoxy, substituted alkoxy, halogen, hydroxyl, acyl, substituted acyl, carboxy, substituted carboxy, amino, substituted amino, aryl, substituted aryl, heterocycle, substituted heterocycle, heteroaryl, substituted heteroaryl, cycloalkyl, and substituted cycloalkyl;

$R^9$ is selected from H, alkyl, substituted alkyl, alkoxy, substituted alkoxy, halogen, hydroxy, acyl, substituted acyl, carboxy, substituted carboxy, amino, and substituted amino;

$R^7$, and $R^{13}$-$R^{15}$ are each independently selected from H, aryl, substituted aryl, alkyl, substituted alkyl, alkoxy, substituted alkoxy, halogen, hydroxy, acyl, substituted acyl, carboxy, substituted carboxy, amino, and substituted amino;

$R^4$ is an optional substituent selected from alkyl, substituted alkyl, hydroxy, amino, substituted amino, halogen, nitrile, nitro, acyl, substituted acyl, carboxy, and substituted carboxy; or two adjacent $R^4$ groups together with the atoms to which they are attached form an optionally substituted cyclic group;

n is an integer from 0 to 10; and m is an integer from 0 to 2, wherein if m is 0, then n is an integer from 0 to 6, and if m is 1, then n is an integer from 0 to 8.

In certain embodiments of formula (VA) or (VB), at least one of $R^7$, $R^9$ and $R^{13}$-$R^{15}$ is a substituent other than H. In some cases, at least one of $R^7$-$R^9$, and at least one of $R^{13}$-$R^{15}$ are substituents other than H. In certain cases, $R^9$ is a substituent other than H. In certain cases, $R^7$ is a substituent other than H. In some cases, $R^7$ and $R^9$ are both substituents other than H. In certain cases $R^{13}$ is a substituent other than H. In certain cases, $R^{14}$ is a substituent other than H. In some cases, $R^{15}$ is a substituent other than H. In certain cases, $R^{13}$ and $R^{14}$ are substituents other than H. In certain cases, $R^{13}$ and $R^{15}$ are substituents other than H. In certain cases $R^{13}$-$R^{15}$ are each substituents other than H.

In certain cases of formula (VA) or (VB), at least one of $R^7$-$R^9$ is selected from alkyl, substituted alkyl, alkoxy, substituted alkoxy, halogen, hydroxy, acyl, substituted acyl, carboxy, substituted carboxy, amino, and substituted amino. In certain cases, at least one of $R^7$-$R^9$ is selected from alkyl, and substituted alkyl. In certain cases, at least one of $R^7$-$R^9$ is selected from alkoxy, and substituted alkoxy. In certain cases, at least one of $R^7$-$R^9$ is halogen. In certain cases, at least one of $R^7$-$R^9$ is hydroxy. In certain cases, at least one of $R^7$-$R^9$ is selected from acyl and substitute acyl. In certain cases, at least one of $R^7$-$R^9$ is selected from carboxy, and substituted carboxy. In certain cases, at least one of $R^7$-$R^9$ is selected from amino and substituted amino.

In certain cases of formula (VA) or (VB), at least one of $R^{13}$-$R^{15}$ is selected from alkyl, substituted alkyl, alkoxy, substituted alkoxy, halogen, hydroxy, acyl, substituted acyl, carboxy, substituted carboxy, amino, and substituted amino. In certain cases, at least one of $R^{13}$-$R^{15}$ is selected from alkyl, and substituted alkyl. In certain cases, at least one of $R^{13}$-$R^{15}$ is selected from alkoxy, and substituted alkoxy. In certain cases, at least one of $R^{13}$-$R^{15}$ is halogen. In certain cases, at least one of $R^{13}$-$R^{15}$ is hydroxy. In certain cases, at least one of $R^{13}$-$R^{15}$ is selected from amino and substituted amino. In certain cases, at least one of $R^{13}$-$R^{15}$ is selected from acyl and substituted acyl. In certain cases, at least one of $R^{13}$-$R^{15}$ is selected from carboxy, and substituted carboxy In certain embodiments of formula (VA) or (VB), $R^9$ is selected from alkoxy, substituted alkoxy, acyl, substituted acyl, carboxy, substituted carboxy, amino, and substituted amino.

In certain embodiments of formula (VA) or (VB), $R^7$ is selected from alkoxy, substituted alkoxy, acyl, substituted acyl, carboxy, substituted carboxy, amino, and substituted amino.

In certain cases of formula (VA) or (VB), $R^{13}$ is selected from alkyl, substituted alkyl, alkoxy, substituted alkoxy, halogen, hydroxy, acyl, substituted acyl, carboxy, substituted carboxy, amino, and substituted amino.

In certain cases of formula (VA) or (VB), $R^{14}$ is selected from alkyl, substituted alkyl, alkoxy, substituted alkoxy, halogen, hydroxy, acyl, substituted acyl, carboxy, substituted carboxy, amino, and substituted amino.

In certain cases of formula (VA) or (VB), $R^{15}$ is selected from alkyl, substituted alkyl, alkoxy, substituted alkoxy, halogen, hydroxy, acyl, substituted acyl, carboxy, substituted carboxy, amino, and substituted amino.

In certain embodiments of formula (VA) or (VB), $R^9$, $R^{13}$, and $R^{15}$ are independently selected from H, alkoxy, substituted alkoxy, halogen, hydroxy, amino, and substituted amino; and $R^7$ and $R^{14}$ are each independently selected from H, alkoxy, substituted alkoxy, halogen, hydroxy, acyl, substituted acyl, carboxy, substituted carboxy, amino, and substituted amino.

In certain cases of formula (VA), $R^{13}$ is alkoxy; $R^{14}$ is H; and $R^{15}$ is H. In certain cases of formula (VB), $R^{13}$ is alkoxy; $R^{14}$ is H; and $R^{15}$ is H. In certain embodiments of formula (VA), $R^{13}$ is H; $R^{14}$ is alkoxy or carboxy; and $R^{15}$ is H. In certain embodiments of formula (VB), $R^{13}$ is H; $R^{14}$ is alkoxy or carboxy; and $R^{15}$ is H. In certain embodiments of formula (VA), each of $R^{13}$-$R^{15}$ are H. In certain embodiments of formula (VB), each of $R^{13}$-$R^{15}$ are H.

In certain cases of formula (VA), $R^7$ and $R^9$ are each independently selected from H and alkoxy. In certain cases, $R^7$ is H and $R^9$ is alkoxy. In certain cases, $R^7$ is alkoxy and $R^9$ is H. In certain other cases, $R^7$ and $R^9$ are alkoxy.

In certain cases of formula (VB), $R^7$ and $R^9$ are each independently selected from H and alkoxy. In certain cases, $R^7$ is H and $R^9$ is alkoxy. In certain cases, $R^7$ is alkoxy and $R^9$ is H. In certain other cases, $R^7$ and $R^9$ are alkoxy.

In certain embodiments, the compound is of the formula (VC)-(VO):

(VC)

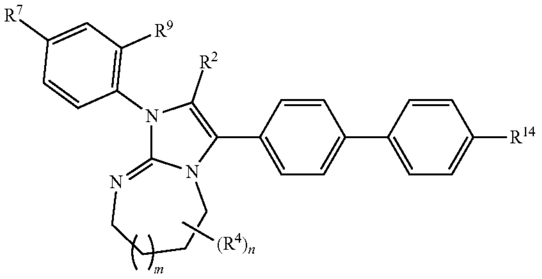

(VD)

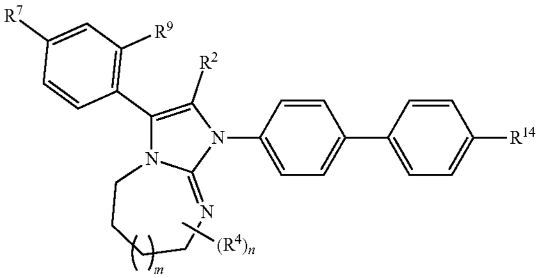

(VE)

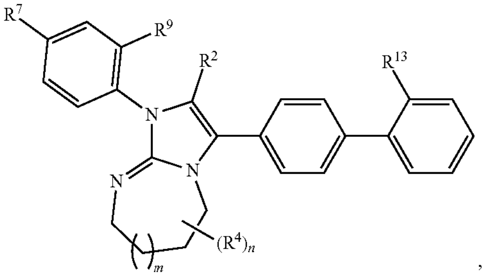

, (VF)

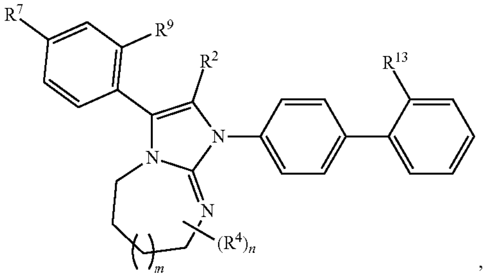

, (VG)

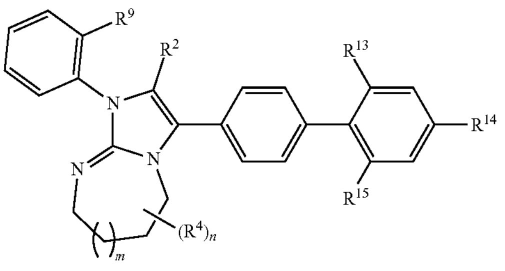

-continued (VH)

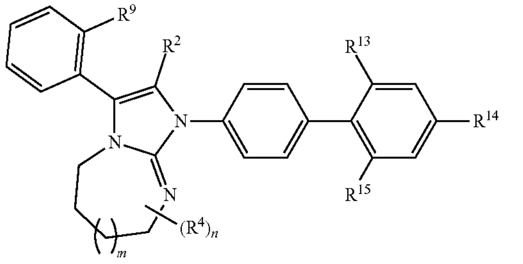

(VJ)

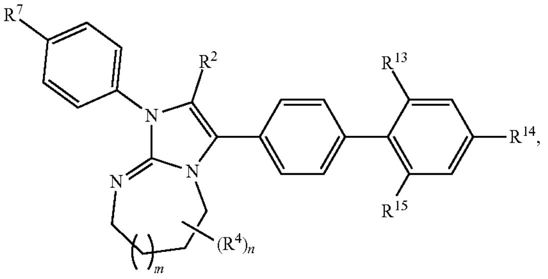

(VK)

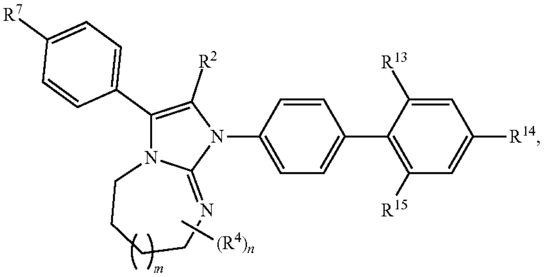

(VL)

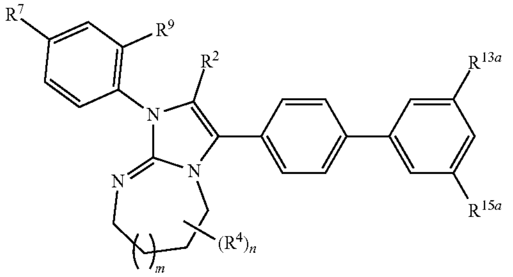

(VM)

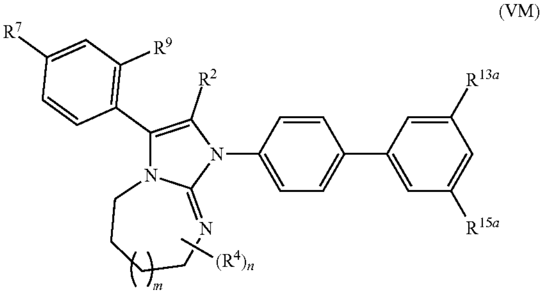

-continued (VN)

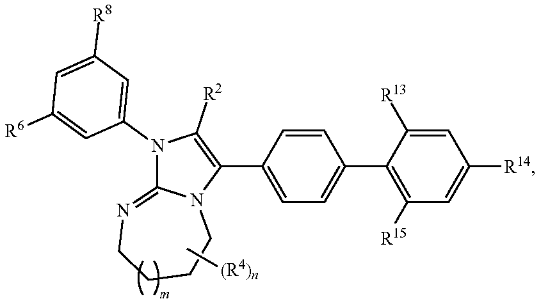

and (VO)

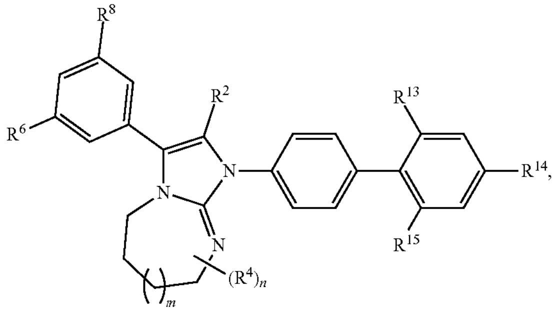

wherein:

$R^{13a}$, and $R^{15a}$ are each independently selected from H, aryl, substituted aryl, alkyl, substituted alkyl, alkoxy, substituted alkoxy, halogen, hydroxy, acyl, substituted acyl, carboxy, substituted carboxy, amino, and substituted amino; and each of $R^2$, $R^4$, $R^6$-$R^9$, $R^{13}$-$R^{15}$, m and n are as defined herein above.

In certain embodiments of any one of formulae (II)-(VO), each --- represents a C—C single bond. In certain cases of any one of formulae (II)-(VO), at least one of --- represents a C—C double bond. In some cases, m is 0, and each --- represents a C—C single bond. In certain cases, m is 0 and one of --- represents a C—C double bond and the remaining --- C—C bonds are single bonds. In some cases, m is 1, and each --- represents a C—C single bond. In certain cases, m is 1 and one of --- represents a C—C double bond and the remaining --- C—C bonds are single bonds. In certain cases, m is 1 and two of --- represent C—C double bonds, and the remaining --- C—C bonds are single bonds. In some cases, m is 2, and each --- represents a C—C single bond. In certain cases, m is 2 and one of --- represents a C—C double bond, and the remaining --- C—C bonds are single bonds. In certain cases, m is 2 and two of --- represent C—C double bonds, and the remaining --- C—C bonds are single bonds.

In certain cases of any one of formulae (II)-(VO), m is 1. In certain cases, m is 0. In certain other cases, m is 2.

In certain embodiments of any one of formulae (II)-(VO), n is 0, such that there are no $R^4$ substituents.

In certain embodiments of any one of formulae (II)-(VO), n is more than 0, such as 1 or more, 2 or more, 3 or more, 4 or more, 5 or more, 6 or more, or even more when m is 1 or 2.

In certain embodiments of any one of formulae (II)-(VO), n is 1, and $R^4$ is selected from alkyl, substituted alkyl, hydroxy, carbonyl, amino, substituted amino, halogen, nitrile, nitro, acyl, substituted acyl, carboxy, and substituted carboxy. In some cases, $R^4$ is carbonyl. In some cases, $R^4$ is a $C_{1-6}$ alkyl group, or substituted $C_{1-6}$ alkyl group. In some cases, $R^4$ is hydroxyl. In some cases, $R^4$ is amino or substituted amino. In some cases, $R^4$ is halogen. In some cases, $R^4$ is nitrile. In some cases, $R^4$ is nitro. In some cases, $R^4$ is acyl, or substituted acyl. In some cases, $R^4$ is carboxy, or substituted carboxy.

In certain embodiments of any one of formulae (II)-(VO), n is 2, and each $R^4$ is independently selected from alkyl, substituted alkyl, hydroxy, carbonyl, amino, substituted amino, halogen, nitrile, nitro, acyl, substituted acyl, carboxy, and substituted carboxy. In certain cases, n is 2, and each $R^4$ is $C_{1-6}$ alkyl. In certain cases, the $C_{1-6}$ alkyl group is selected from methyl, ethyl and propyl. In certain cases, the $C_{1-6}$ alkyl group is methyl.

In certain embodiments of any one of formulae (II)-(VO), n is 2, the two $R^4$ groups are adjacent to each other, and the two $R^4$ groups forms an optionally substituted cyclic group. In certain cases, the cyclic group is selected from cycloalkyl, substituted cycloalkyl, heterocycle, and substituted heterocycle. In certain cases, n is 2, and the two $R^4$ groups form a covalent bond to each other to form a bridged structure, wherein the bridged structure is optionally further substituted.

In certain embodiments of any one of formulae (II)-(VO), $R^2$ is selected from H, alkyl, substituted alkyl, alkoxy, substituted alkoxy, halogen, hydroxyl, acyl, substituted acyl, carboxy, substituted carboxy, amino, and substituted amino. In certain cases, $R^2$ is selected from aryl, substituted aryl, heterocycle, substituted heterocycle, heteroaryl, substituted heteroaryl, cycloalkyl, and substituted cycloalkyl. In certain cases, $R^2$ is H.

In certain embodiments, the compound is described by formula (XI):

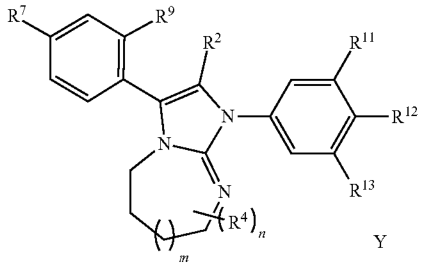

(XI)

wherein:

$R^2$ is selected from H, alkyl, substituted alkyl, alkenyl, substituted alkenyl, alkynyl, substituted alkynyl, alkoxy, substituted alkoxy, halogen, hydroxyl, acyl, substituted acyl, carboxy, substituted carboxy, amino, substituted amino, aryl, substituted aryl, heterocycle, substituted heterocycle, heteroaryl, substituted heteroaryl, cycloalkyl, and substituted cycloalkyl;

$R^7$ and $R^9$ are each independently selected from H, alkyl, substituted alkyl, heteroalkyl, alkoxy, substituted alkoxy, halogen, hydroxy, nitro, acyl, substituted acyl, carboxy, substituted carboxy, amino, and substituted amino;

$R^{11'}$ is independently selected from H, alkyl, substituted alkyl, alkoxy, substituted alkoxy, halogen, hydroxy, acyl, substituted acyl, carboxy, substituted carboxy, nitro, amino, and substituted amino;

$R^{12}$ and $R^{13}$ are each independently selected from H, aryl, substituted aryl, alkyl, substituted alkyl, heteroalkyl, alkoxy, substituted alkoxy, halogen, hydroxy, nitro, heterocyclic, substituted heterocyclic, acyl, substituted acyl, carboxy, substituted carboxy, amino, and substituted amino;

$R^4$ is an optional substituent selected from alkyl, substituted alkyl, hydroxy, amino, substituted amino, halogen, nitrile, nitro, acyl, substituted acyl, carboxy, and substituted carboxy; or two $R^4$ groups together with the atoms to which they are attached form an optionally substituted cyclic group;

$Y^-$ is a pharmaceutically acceptable salt selected from a hydrobromide, a hydrochloride or a formate salt;

n is an integer from 0 to 10; and m is an integer from 0 to 2, wherein if m is 0, then n is an integer from 0 to 6, and if m is 1, then n is an integer from 0 to 8.

In certain embodiments, the compound is described by formula (XII):

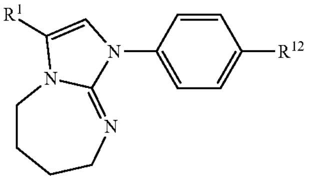

(XII)

wherein:

$R^1$ is selected from H, alkyl, substituted alkyl, alkoxy, substituted alkoxy, halogen, hydroxy, heterocyclic, substituted heterocyclic, acyl, substituted acyl, carboxy, substituted carboxy, amino, and substituted amino;

$R^{12}$ is selected from H, alkyl, substituted alkyl, alkoxy, substituted alkoxy, halogen, hydroxy, heterocyclic, substituted heterocyclic, acyl, substituted acyl, aryl, substituted aryl, carboxy, substituted carboxy, amino, and substituted amino.

In certain embodiments, the subject compound is selected from any one of compounds 64-73. In certain embodiments, the subject compound is selected from 74-81. In certain cases, the subject compound is any one of the structures of Table 1.

TABLE 1
| Bicyclic Guanidine Compounds | | | |
|---|---|---|---|
| No. | Structure | No. | Structure |
| 64 | 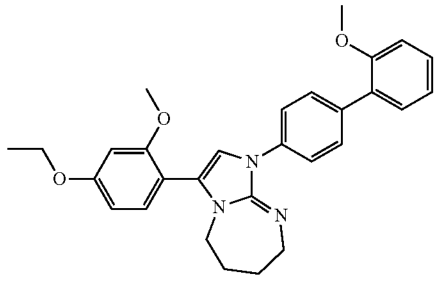 [SMILES: CCOc1ccc(C2=CN(c3ccc(-c4ccccc4OC)cc3)C3=NCCCCN23)c(OC)c1] | 65 | 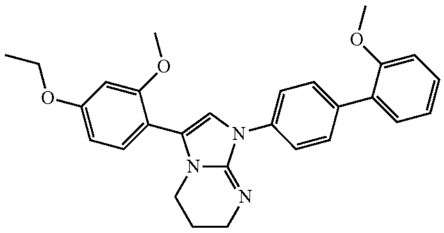 [SMILES: CCOc1ccc(C2=CN(c3ccc(-c4ccccc4OC)cc3)C3=NCCCN23)c(OC)c1] |
| 66 | 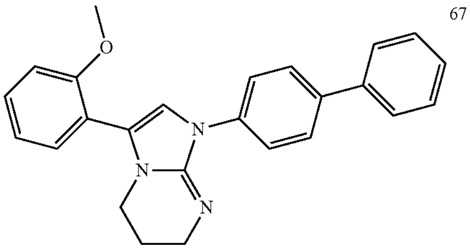 | 67 | 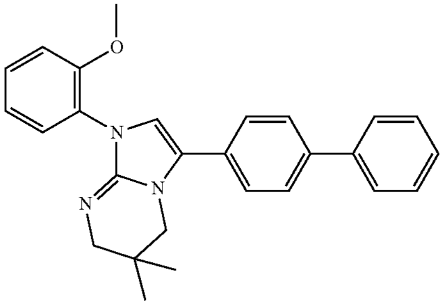 [SMILES: COc1ccccc1N1C=C(c2ccc(-c3ccccc3)cc2)N2CC(C)(C)CN=C21] |
| 68 | 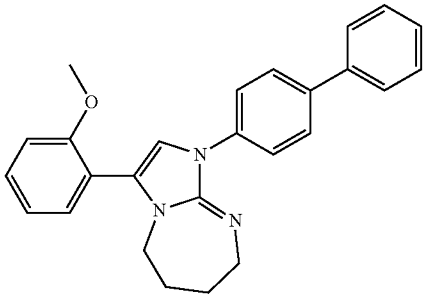 [SMILES: COc1ccccc1C1=CN(c2ccc(-c3ccccc3)cc2)C2=NCCCCN12] | 69 | 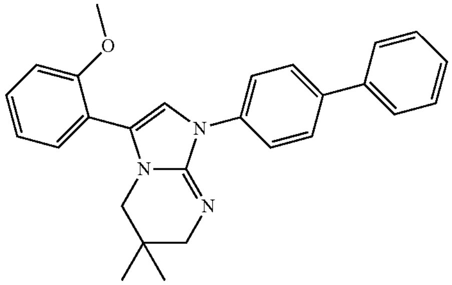 [SMILES: COc1ccccc1C1=CN(c2ccc(-c3ccccc3)cc2)C2=NCC(C)(C)CN12] |
| 70 | 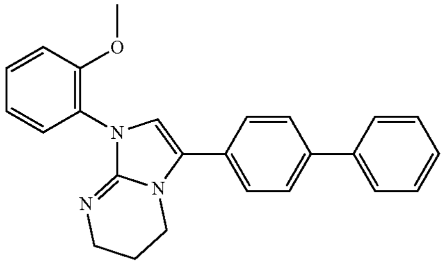 [SMILES: COc1ccccc1N1C=C(c2ccc(-c3ccccc3)cc2)N2CCCN=C21] | 71 | 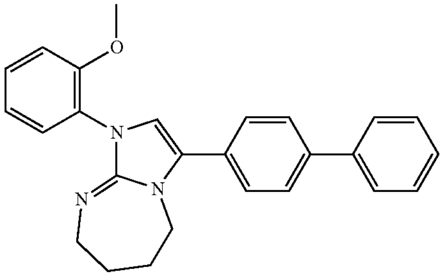 [SMILES: COc1ccccc1N1C=C(c2ccc(-c3ccccc3)cc2)N2CCCCN=C21] |
| 72 | 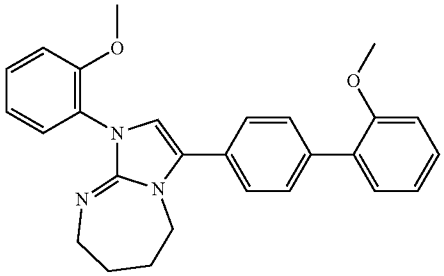 [SMILES: COc1ccccc1-c1ccc(C2=CN(c3ccccc3OC)C3=NCCCCN23)cc1] | 73 | 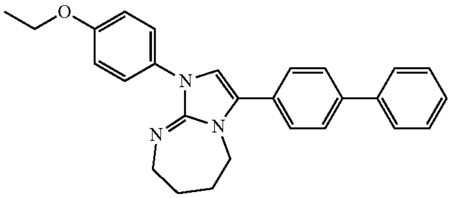 [SMILES: CCOc1ccc(N2C=C(c3ccc(-c4ccccc4)cc3)N3CCCCN=C32)cc1] |

TABLE 1-continued
| Bicyclic Guanidine Compounds | | | |
|---|---|---|---|
| No. | Structure | No. | Structure |
| 74 | 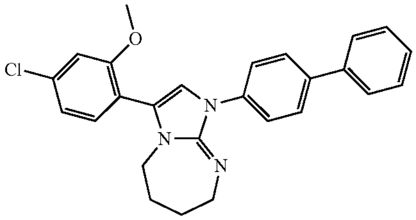 [SMILES: COc1cc(Cl)ccc1C1=CN(c2ccc(-c3ccccc3)cc2)C2=NCCCCN12] | 75 | 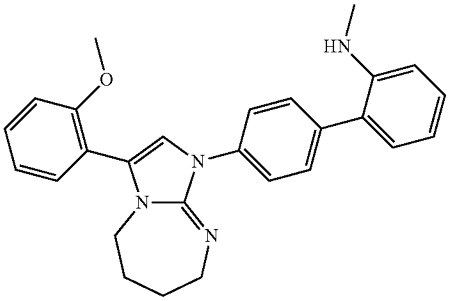 [SMILES: CNc1ccccc1-c1ccc(N2C=C(c3ccccc3OC)N3CCCCN=C32)cc1] |
| 76 | 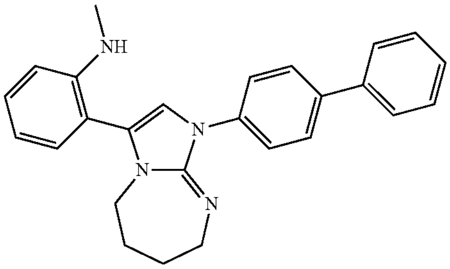 [SMILES: CNc1ccccc1C1=CN(c2ccc(-c3ccccc3)cc2)C2=NCCCCN12] | 77 | 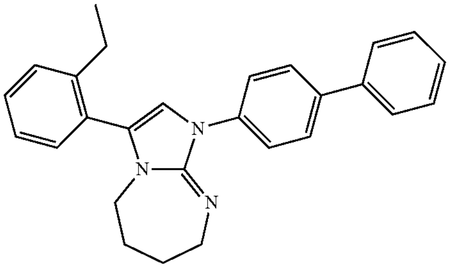 [SMILES: CCc1ccccc1C1=CN(c2ccc(-c3ccccc3)cc2)C2=NCCCCN12] |
| 78 | 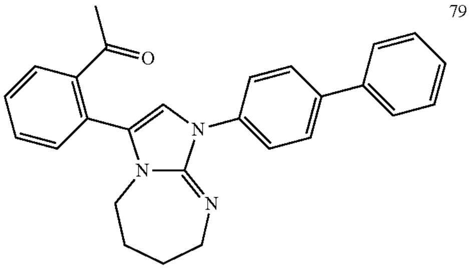 | 79 | 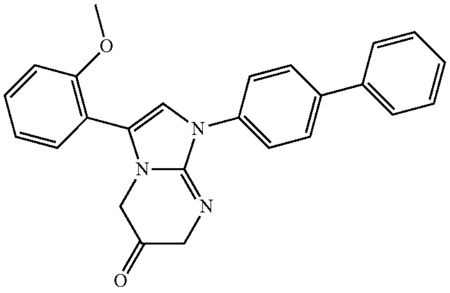 [SMILES: COc1ccccc1C1=CN(c2ccc(-c3ccccc3)cc2)C2=NCC(=O)CN12] |
| 80 | 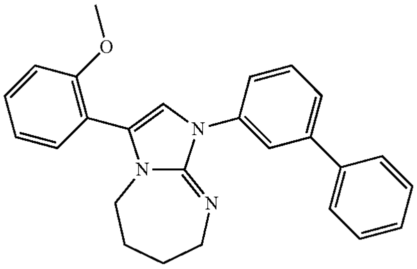 [SMILES: COc1ccccc1C1=CN(c2cccc(-c3ccccc3)c2)C2=NCCCCN12] | 81 | 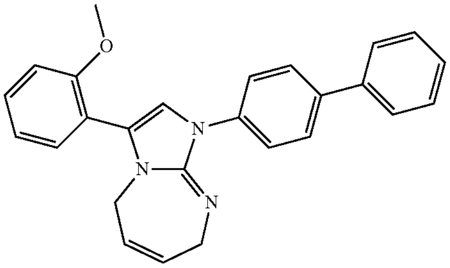 [SMILES: COc1ccccc1C1=CN(c2ccc(-c3ccccc3)cc2)C2=NCC=CCN12] |

In some cases, the subject compound is described by the structure of formula (VI):

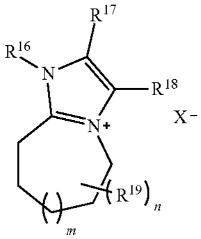

(VI)

wherein:

$R^{16}$ is selected from alkyl, substituted alkyl, alkenyl, substituted alkenyl, alkynyl, substituted alkynyl, substituted aryl, heterocycle, substituted heterocycle, heteroaryl, substituted heteroaryl, cycloalkyl, and substituted cycloalkyl;

$R^{17}$ is selected from H, alkyl, substituted alkyl, alkenyl, substituted alkenyl, alkynyl, substituted alkynyl, alkoxy, substituted alkoxy, halogen, hydroxyl, acyl, substituted acyl, carboxy, substituted carboxy, amino, substituted amino, aryl, substituted aryl, heterocycle, substituted heterocycle, heteroaryl, substituted heteroaryl, cycloalkyl, and substituted cycloalkyl;

$R^{18}$ is selected from alkyl, substituted alkyl, alkenyl, substituted alkenyl, alkynyl, substituted alkynyl, substituted aryl, heterocycle, substituted heterocycle, heteroaryl, substituted heteroaryl, cycloalkyl, and substituted cycloalkyl;

$R^{19}$ is an optional substituent selected from alkyl, substituted alkyl, hydroxy, carbonyl, amino, substituted amino, halogen, nitrile, nitro, acyl, substituted acyl, carboxy, substituted carboxy; or two $R^{19}$ groups together with the atoms to which they are attached form an optionally substituted cyclic group;

$X^-$ is a counterion;

n is an integer from 0 to 10; and m is an integer from 0 to 2, wherein if m is 0, then n is an integer from 0 to 6, and if m is 1, then n is an integer from 0 to 8;

or pharmaceutically acceptable salt, solvate, isomer, or prodrug thereof;

with the proviso that when $R^{16}$ and $R^{17}$ are both substituted aryl, at least one of the aryl groups is substituted with a group selected from $—N(R^{20})_2$, $—(CH_2)_pNR^{20}$, $—NO_2$, $—C(O)N(R^{20})_2$, wherein each $R^{20}$ is independently selected from H, alkyl, substituted alkyl, $—C(O)R^{21}$, $—SO_2R^{21}$, and $—C(O)CHCH_2$, or two $R^{20}$ substituents together with the nitrogen to which they are attached form an optionally substituted cyclic structure; and $R^{21}$ is selected from H, alkyl, substituted alkyl, aryl, substituted aryl, heterocycle, substituted heterocycle, heteroaryl, and substituted heteroaryl.

In some embodiments of formula (VI), the 6-8 membered fused ring optionally includes one or more unsaturated bonds, such that the 6-8 membered fused ring is described by any one of the following structures:

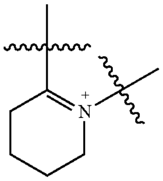
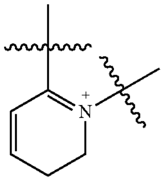
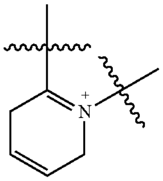
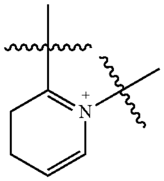
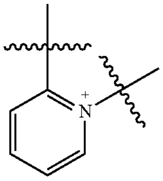
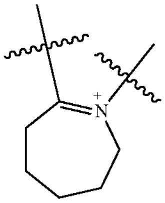
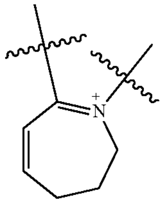
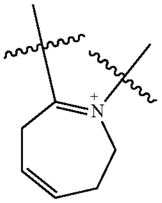
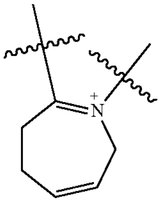
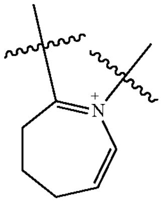
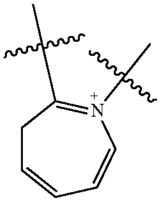
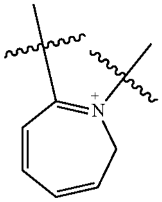
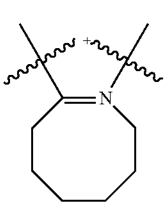
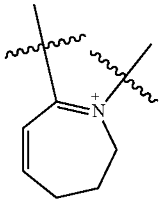
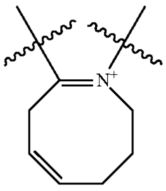
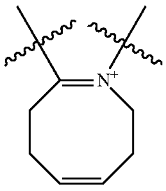

-continued

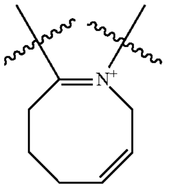 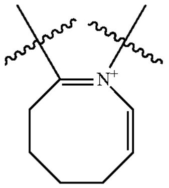

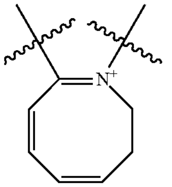 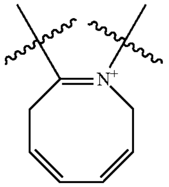

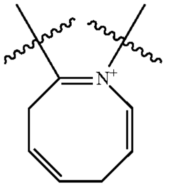 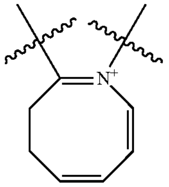

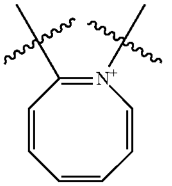 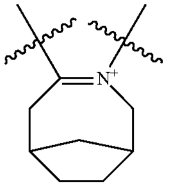

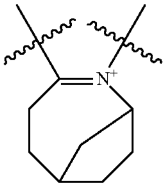.

In certain embodiments of formula (VI), $R^{16}$ is independently selected from alkyl, substituted alkyl, alkenyl, substituted alkenyl, alkynyl, substituted alkynyl, aryl, substituted aryl, heterocycle, substituted heterocycle, heteroaryl, substituted heteroaryl, cycloalkyl, and substituted cycloalkyl. In certain case, $R^{16}$ is selected from alkyl and substituted alkyl. In certain cases, $R^{16}$ is selected from alkenyl and substituted alkenyl. In some cases, $R^{16}$ is selected from alkynyl and substituted alkynyl.

In some embodiments of formula (VI), $R^{16}$ is selected from aryl and substituted aryl. In some cases, the aryl group is substituted with any convenient substituents including but not limited to alkyl, alkoxy, acyloxy, aminoalkoxy, cyano, halogen, hydroxyl, nitro, —$NR_2$, —NHCOR, —$SO_2$NHR, —CONHR or —$NHSO_2R$, where R is H, alkyl, heteroalkyl, heterocycle or aryl. In some case, the substituted aryl is substituted with an aryl, substituted aryl heteroaryl, or substituted heteroaryl group, such that the $R^{16}$ group is a biaryl group.

In some embodiments of formula (VI), $R^{16}$ is selected from heterocycle, and substituted heterocycle. In some cases, the heterocyclic group is substituted with any convenient substituents including but not limited to alkyl, alkoxy, acyloxy, aminoalkoxy, cyano, halogen, hydroxyl, nitro, —$NR_2$, —NHCOR, —$SO_2$NHR, —CONHR or —$NHSO_2R$, where R is H, alkyl, heteroalkyl, heterocycle or aryl.

In some embodiments of formula (VI), $R^{16}$ is selected from heteroaryl, and substituted heteroaryl. In some cases, the heteroaryl group is substituted with any convenient substituents including but not limited to alkyl, alkoxy, acyloxy, aminoalkoxy, cyano, halogen, hydroxyl, nitro, —$NR_2$, —NHCOR, —$SO_2$NHR, —CONHR or —$NHSO_2R$, where R is H, alkyl, heteroalkyl, heterocycle or aryl. In some cases, the substituted heteroaryl is substituted with an aryl, substituted aryl, heteroaryl, or substituted heteroaryl group.

In some embodiments of formula (VI), $R^{16}$ is selected from cycloalkyl, and substituted cycloalkyl. In some cases, the cycloalkyl group is substituted with any convenient substituents including but not limited to alkyl, alkoxy, acyloxy, aminoalkoxy, cyano, halogen, hydroxyl, nitro, —$NR_2$, —NHCOR, —$SO_2$NHR, —CONHR or —$NHSO_2R$, where R is H, alkyl, heteroalkyl, heterocycle or aryl.

In some embodiments of formula (VI), $R^{16}$ is selected from biaryl, and substituted cycloalkyl. In some cases, the cycloalkyl group is substituted with any convenient substituents including but not limited to alkyl, alkoxy, acyloxy, aminoalkoxy, cyano, halogen, hydroxyl, nitro, —$NR_2$, —NHCOR, —$SO_2$NHR, —CONHR or —$NHSO_2R$, where R is H, alkyl, heteroalkyl, heterocycle or aryl.

In certain embodiments of formula (VI), $R^{18}$ is independently selected from alkyl, substituted alkyl, alkenyl, substituted alkenyl, alkynyl, substituted alkynyl, aryl, substituted aryl, heterocycle, substituted heterocycle, heteroaryl, substituted heteroaryl, cycloalkyl, and substituted cycloalkyl. In certain case, $R^{18}$ is selected from alkyl and substituted alkyl. In certain cases, $R^{18}$ is selected from alkenyl and substituted alkenyl. In some cases, $R^{18}$ is selected from alkynyl and substituted alkynyl.

In some embodiments of formula (VI), $R^{18}$ is selected from aryl and substituted aryl. In some cases, the aryl group is substituted with any convenient substituents including but not limited to alkyl, alkoxy, acyloxy, aminoalkoxy, cyano, halogen, hydroxyl, nitro, —$NR_2$, —NHCOR, —$SO_2$NHR, —CONHR or —$NHSO_2R$, where R is H, alkyl, heteroalkyl, heterocycle or aryl. In some cases, the substituted aryl is substituted with an aryl, substituted aryl heteroaryl, or substituted heteroaryl group, such that the $R^{18}$ group is a biaryl group.

In some embodiments of formula (VI), $R^{18}$ is selected from heterocycle, and substituted heterocycle. In some cases, the heterocyclic group is substituted with any convenient substituents including but not limited to alkyl, alkoxy, acyloxy, aminoalkoxy, cyano, halogen, hydroxyl, nitro, —$NR_2$, —NHCOR, —$SO_2$NHR, —CONHR or —$NHSO_2R$, where R is H, alkyl, heteroalkyl, heterocycle or aryl.

In some embodiments of formula (VI), $R^{18}$ is selected from heteroaryl, and substituted heteroaryl. In some cases, the heteroaryl group is substituted with any convenient substituents including but not limited to alkyl, alkoxy, acyloxy, aminoalkoxy, cyano, halogen, hydroxyl, nitro, —$NR_2$, —NHCOR, —$SO_2$NHR, —CONHR or —$NHSO_2R$, where R is H, alkyl, heteroalkyl, heterocycle or aryl. In some cases, the substituted heteroaryl is substituted with an aryl, substituted aryl, heteroaryl, or substituted heteroaryl group.

In some embodiments of formula (VI), $R^{18}$ is selected from cycloalkyl, and substituted cycloalkyl. In some cases, the cycloalkyl group is substituted with any convenient substituents including but not limited to alkyl, alkoxy, acyloxy, aminoalkoxy, cyano, halogen, hydroxyl, nitro, —$NR_2$, —NHCOR, —$SO_2NHR$, —CONHR or —$NHSO_2R$, where R is H, alkyl, heteroalkyl, heterocycle or aryl.

In some embodiments of formula (VI), $R^{18}$ is selected from biaryl, and substituted cycloalkyl. In some cases, the cycloalkyl group is substituted with any convenient substituents including but not limited to alkyl, alkoxy, acyloxy, aminoalkoxy, cyano, halogen, hydroxyl, nitro, —$NR_2$, —NHCOR, —$SO_2NHR$, —CONHR or —$NHSO_2R$, where R is H, alkyl, heteroalkyl, heterocycle or aryl.

In certain embodiments, the compound is described by formula (VII):

(VII)

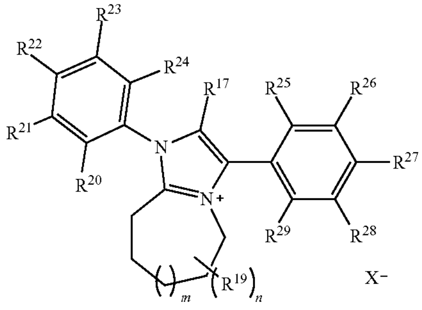

wherein:

$R^{17}$ is selected from H, alkyl, substituted alkyl, alkenyl, substituted alkenyl, alkynyl, substituted alkynyl, alkoxy, substituted alkoxy, halogen, hydroxyl, acyl, substituted acyl, carboxy, substituted carboxy, amino, substituted amino, aryl, substituted aryl, heterocycle, substituted heterocycle, heteroaryl, substituted heteroaryl, cycloalkyl, and substituted cycloalkyl;

$R^{20}$-$R^{29}$ are each independently selected from H, alkyl, substituted alkyl, alkenyl, substituted alkenyl, alkynyl, substituted alkynyl, alkoxy, substituted alkoxy, halogen, hydroxy, nitro, nitrile, amino, substituted amino, acyl, substituted acyl, carboxy, substituted carboxy, aryl, substituted aryl, heterocycle, substituted heterocycle, heteroaryl, substituted heteroaryl, cycloalkyl, and substituted cycloalkyl, wherein at least one of $R^{20}$-$R^{29}$ is selected from —$N(R^{20})_2$, —$(CH_2)_pNR^{20}$, —$NO_2$, —$C(O)N(R^{20})_2$, wherein each $R^{20}$ is independently selected from H, alkyl, substituted alkyl, C(O)$R^{21}$, —$SO_2R^{21}$, and —$C(O)CHCH_2$, or two $R^{20}$ substituents together with the nitrogen to which they are attached form an optionally substituted cyclic structure; and $R^{21}$ is selected from H, alkyl, substituted alkyl, aryl, substituted aryl, heterocycle, substituted heterocycle, heteroaryl, and substituted heteroaryl; or any two adjacent $R^{20}$-$R^{29}$ groups together with the atoms to which they are attached form an optionally substituted cyclic group;

$R^{19}$ is an optional substituent selected from alkyl, substituted alkyl, hydroxy, amino, substituted amino, halogen, nitrile, nitro, acyl, substituted acyl, carboxy, substituted carboxy; or two $R^{19}$ groups together with the atoms to which they are attached form an optionally substituted cyclic group;

$X^-$ is a counterion;

n is an integer from 0 to 10; and m is an integer from 0 to 2, wherein if m is 0, then n is an integer from 0 to 6, and if m is 1, then n is an integer from 0 to 8.

In certain embodiments of formula (VII), at least one of $R^{20}$-$R^{29}$ is a substituent other than H. In some cases, at least one of $R^{20}$-$R^{24}$, and at least one of $R^{25}$-$R^{29}$ are substituents other than H. In certain cases, $R^{22}$ is a substituent other than H. In certain cases, $R^{23}$ is a substituent other than H. In some cases, $R^{24}$ is a substituent other than H. In certain cases, $R^{22}$ and $R^{24}$ are substituents other than H. In certain cases, $R^{20}$ and $R^{24}$ are substituents other than H. In some cases, $R^{24}$ and $R^{21}$ are substituents other than H. In certain cases, $R^{20}$, $R^{22}$ and $R^{24}$ are each substituents other than H. In certain cases, $R^{21}$ and $R^{23}$ are substituents other than H. In certain cases, $R^{25}$ is a substituent other than H. In some cases, $R^{27}$ is a substituent other than H. In certain cases, $R^{25}$ and $R^{29}$ are substituents other than H. In certain cases, $R^{25}$ and $R^{27}$ are substituents other than H. In certain cases, $R^{25}$, $R^{27}$ and $R^{29}$ are each substituents other than H. In certain cases, $R^{26}$ and $R^{28}$ are substituents other than H.

In certain cases of formula (VII), at least one of $R^{20}$-$R^{24}$ is selected from alkyl, substituted alkyl, alkoxy, substituted alkoxy, halogen, hydroxy, nitro, amino, substituted amino, acyl, substituted acyl, carboxy, substituted carboxy, aryl, substituted aryl, heterocycle, substituted heterocycle, heteroaryl, substituted heteroaryl, cycloalkyl, and substituted cycloalkyl. In certain cases, at least one of $R^{20}$-$R^{24}$ is selected from alkyl, and substituted alkyl. In certain cases, at least one of $R^{20}$-$R^{24}$ is selected from alkoxy, and substituted alkoxy. In certain cases, at least one of $R^{20}$-$R^{24}$ is halogen. In certain cases, at least one of $R^{20}$-$R^{24}$ is hydroxy. In certain cases, at least one of $R^{20}$-$R^{24}$ is nitro. In certain cases, at least one of $R^{20}$-$R^{24}$ is selected from amino and substituted amino. In certain cases, at least one of $R^{20}$-$R^{24}$ is selected from acyl and substituted acyl. In certain cases, at least one of $R^{20}$-$R^{24}$ is selected from carboxy and substituted carboxy. In certain cases, at least one of $R^{20}$-$R^{24}$ is selected from aryl and substituted aryl. In certain cases, at least one of $R^{20}$-$R^{24}$ is selected from heterocycle, and substituted heterocycle. In certain cases, at least one of $R^{20}$-$R^{24}$ is selected from heteroaryl, and substituted heteroaryl. In certain cases, at least one of $R^{20}$-$R^{24}$ is selected from cycloalkyl, and substituted cycloalkyl.

In certain cases, at least one of $R^{25}$-$R^{29}$ is selected from alkyl, substituted alkyl, alkoxy, substituted alkoxy, halogen, hydroxy, nitro, amino, substituted amino, acyl, substituted acyl, carboxy, substituted carboxy, aryl, substituted aryl, heterocycle, substituted heterocycle, heteroaryl, substituted heteroaryl, cycloalkyl, and substituted cycloalkyl. In certain cases, at least one of $R^{25}$-$R^{29}$ is selected from alkyl, and substituted alkyl. In certain cases, at least one of $R^{25}$-$R^{29}$ is selected from alkoxy, and substituted alkoxy. In certain cases, at least one of $R^{25}$-$R^{29}$ is halogen. In certain cases, at least one of $R^{25}$-$R^{29}$ is hydroxy. In certain cases, at least one of $R^{25}$-$R^{29}$ is nitro. In certain cases, at least one of $R^{25}$-$R^{29}$ is selected from amino and substituted amino. In certain cases, at least one of $R^{25}$-$R^{29}$ is selected from acyl and substituted acyl. In certain cases, at least one of $R^{25}$-$R^{29}$ is selected from carboxy and substituted carboxy. In certain cases, at least one of $R^{25}$-$R^{29}$ is selected from aryl and substituted aryl. In certain cases, at least one of $R^{25}$-$R^{29}$ is selected from heterocycle, and substituted heterocycle. In certain cases, at least one of $R^{25}$-$R^{29}$ is selected from heteroaryl, and substituted heteroaryl. In certain cases, at least one of $R^{25}$-$R^{29}$ is selected from cycloalkyl, and substituted cycloalkyl.

In certain embodiments of formula (VII), $R^{24}$ is selected from alkyl, substituted alkyl, alkoxy, substituted alkoxy, halogen, hydroxy, nitro, amino, substituted amino, acyl, substituted acyl, carboxy, and substituted carboxy.

In certain embodiments of formula (VII), $R^{23}$ is selected from alkyl, substituted alkyl, alkoxy, substituted alkoxy, halogen, hydroxy, nitro, amino, substituted amino, acyl, substituted acyl, carboxy, and substituted carboxy.

In certain embodiments of formula (VII), $R^{22}$ is selected from alkyl, substituted alkyl, alkoxy, substituted alkoxy, halogen, hydroxy, nitro, amino, substituted amino, acyl, substituted acyl, carboxy, substituted carboxy, aryl, substituted aryl, heteroaryl, substituted heteroaryl, heterocycle, substituted heterocycle, cycloalkyl, and substituted cycloalkyl.

In certain embodiments of formula (VII), $R^{20}$ and $R^{24}$ are selected from alkyl, substituted alkyl, alkoxy, substituted alkoxy, halogen, hydroxy, nitro, amino, substituted amino, acyl, substituted acyl, carboxy, and substituted carboxy.

In certain embodiments of formula (VII), $R^{20}$ and $R^{24}$ are selected from alkyl, substituted alkyl, alkoxy, substituted alkoxy, halogen, hydroxy, nitro, amino, substituted amino, acyl, substituted acyl, carboxy, substituted carboxy, aryl, substituted aryl, heteroaryl, substituted heteroaryl, heterocycle, substituted heterocycle, cycloalkyl, and substituted cycloalkyl.

In certain embodiments of formula (VII), $R^{21}$ and $R^{24}$ are selected from alkyl, substituted alkyl, alkoxy, substituted alkoxy, halogen, hydroxy, nitro, amino, substituted amino, acyl, substituted acyl, carboxy, and substituted carboxy.

In certain embodiments of formula (VII), $R^{20}$, $R^{22}$ and $R^{24}$ are selected from alkyl, substituted alkyl, alkoxy, substituted alkoxy, halogen, hydroxy, nitro, amino, substituted amino, acyl, substituted acyl, carboxy, substituted carboxy, aryl, substituted aryl, heteroaryl, substituted heteroaryl, heterocycle, substituted heterocycle, cycloalkyl, and substituted cycloalkyl.

In certain embodiments of formula (VII), $R^{21}$ and $R^{23}$ are selected from alkyl, substituted alkyl, alkoxy, substituted alkoxy, halogen, hydroxy, nitro, amino, substituted amino, acyl, substituted acyl, carboxy, and substituted carboxy.

In certain embodiments of formula (VII), $R^{25}$ is selected from alkyl, substituted alkyl, alkoxy, substituted alkoxy, halogen, hydroxy, nitro, amino, substituted amino, acyl, substituted acyl, carboxy, and substituted carboxy.

In certain embodiments of formula (VII), $R^{26}$ is selected from alkyl, substituted alkyl, alkoxy, substituted alkoxy, halogen, hydroxy, nitro, amino, substituted amino, acyl, substituted acyl, carboxy, and substituted carboxy.

In certain embodiments of formula (VII), $R^{27}$ is selected from alkyl, substituted alkyl, alkoxy, substituted alkoxy, halogen, hydroxy, nitro, amino, substituted amino, acyl, substituted acyl, carboxy, substituted carboxy, aryl, substituted aryl, heteroaryl, substituted heteroaryl, heterocycle, substituted heterocycle, cycloalkyl, and substituted cycloalkyl.

In certain embodiments of formula (VII), $R^{25}$ and $R^{29}$ are selected from alkyl, substituted alkyl, alkoxy, substituted alkoxy, halogen, hydroxy, nitro, amino, substituted amino, acyl, substituted acyl, carboxy, and substituted carboxy.

In certain embodiments of formula (VII), $R^{25}$ and $R^{27}$ are selected from alkyl, substituted alkyl, alkoxy, substituted alkoxy, halogen, hydroxy, nitro, amino, substituted amino, acyl, substituted acyl, carboxy, substituted carboxy, aryl, substituted aryl, heteroaryl, substituted heteroaryl, heterocycle, substituted heterocycle, cycloalkyl, and substituted cycloalkyl.

In certain embodiments of formula (VII), $R^{25}$ and $R^{28}$ are selected from alkyl, substituted alkyl, alkoxy, substituted alkoxy, halogen, hydroxy, nitro, amino, substituted amino, acyl, substituted acyl, carboxy, and substituted carboxy.

In certain embodiments of formula (VII), $R^{25}$, $R^{27}$ and $R^{29}$ are selected from alkyl, substituted alkyl, alkoxy, substituted alkoxy, halogen, hydroxy, nitro, amino, substituted amino, acyl, substituted acyl, carboxy, substituted carboxy, aryl, substituted aryl, heteroaryl, substituted heteroaryl, heterocycle, substituted heterocycle, cycloalkyl, and substituted cycloalkyl.

In certain embodiments of formula (VII), $R^{26}$ and $R^{28}$ are selected from alkyl, substituted alkyl, alkoxy, substituted alkoxy, halogen, hydroxy, nitro, amino, substituted amino, acyl, substituted acyl, carboxy, and substituted carboxy.

As disclosed herein for a compound of formula (VII), at least one of $R^{20}$-$R^{29}$ is selected from —$N(R^{20})_2$, —$(CH_2)_p NR^{20}$, —$NO_2$, —$C(O)N(R^{20})_2$, wherein each $R^{20}$ is independently selected from H, alkyl, substituted alkyl, $C(O)R^{21}$, —$SO_2R^{21}$, and —$C(O)CHCH_2$, or two $R^{20}$ substituents together with the nitrogen to which they are attached form an optionally substituted cyclic structure; and $R^{21}$ is selected from H, alkyl, substituted alkyl, aryl, substituted aryl, heterocycle, substituted heterocycle, heteroaryl, and substituted heteroaryl. In some cases, one of $R^{20}$-$R^{24}$ is selected from —$N(R^{20})_2$, —$(CH_2)_p NR^{20}$, —$NO_2$, —$C(O)N(R^{20})_2$, wherein each $R^{20}$ is independently selected from H, alkyl, substituted alkyl, $C(O)R^{21}$, —$SO_2R^{21}$, and —$C(O)CHCH_2$, or two $R^{20}$ substituents together with the nitrogen to which they are attached form an optionally substituted cyclic structure; and $R^{21}$ is selected from H, alkyl, substituted alkyl, aryl, substituted aryl, heterocycle, substituted heterocycle, heteroaryl, and substituted heteroaryl. In some cases, one of $R^{20}$-$R^{24}$ is —$N(R^{20})_2$, where each $R^{20}$ is as described above. In some cases, one of $R^{20}$-$R^{24}$ is —$(CH_2)_p NR^{20}$, where $R^{20}$ is as described above. In some cases, one of $R^{20}$-$R^{24}$ is —$NO_2$. In some cases, one of $R^{20}$-$R^{24}$ is —$C(O)N(R^{20})_2$, wherein each $R^{20}$ is as described above. In some other cases, one of $R^{25}$-$R^{29}$ is selected from —$N(R^{20})_2$, —$(CH_2)_p NR^{20}$, —$NO_2$, —$C(O)N(R^{20})_2$, wherein each $R^{20}$ is independently selected from H, alkyl, substituted alkyl, $C(O)R^{21}$, $SO_2R^{21}$, and —$C(O)CHCH_2$, or two $R^{20}$ substituents together with the nitrogen to which they are attached form an optionally substituted cyclic structure; and $R^{21}$ is selected from H, alkyl, substituted alkyl, aryl, substituted aryl, heterocycle, substituted heterocycle, heteroaryl, and substituted heteroaryl. In some cases, one of $R^{25}$-$R^{29}$ is —$N(R^{20})_2$, where each $R^{20}$ is as described above. In some cases, one of $R^{25}$-$R^{29}$ is —$(CH_2)_p NR^{20}$, where $R^{20}$ is as described above. In some cases, one of $R^{25}$-$R^{29}$ is —$NO_2$. In some cases, one of $R^{25}$-$R^{29}$ is —$C(O)N(R^{20})_2$, wherein each $R^{20}$ is as described above.

In some embodiments, the compound is described by formula (VIII):

(VIII)

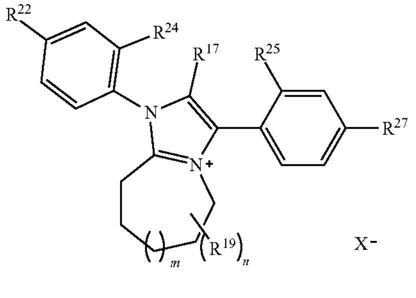

wherein:

$R^{17}$ is selected from H, alkyl, substituted alkyl, alkenyl, substituted alkenyl, alkynyl, substituted alkynyl, alkoxy, substituted alkoxy, halogen, hydroxyl, acyl, substituted acyl, carboxy, substituted carboxy, amino, substituted amino, aryl, substituted aryl, heterocycle, substituted heterocycle, heteroaryl, substituted heteroaryl, cycloalkyl, and substituted cycloalkyl;

$R^{24}$ and $R^{25}$ are independently selected from H, alkyl, substituted alkyl, alkoxy, substituted alkoxy, halogen, hydroxy, acyl, substituted acyl, carboxy, substituted carboxy, amino, and substituted amino;

$R^{22}$ and $R^{27}$ are each independently selected from H, alkyl, substituted alkyl, alkenyl, substituted alkenyl, alkynyl, substituted alkynyl, alkoxy, substituted alkoxy, halogen, hydroxy, amino, substituted amino, acyl, substituted acyl, carboxy, substituted carboxy, aryl, substituted aryl, heterocycle, substituted heterocycle, heteroaryl, substituted heteroaryl, cycloalkyl, and substituted cycloalkyl;

$R^{19}$ is an optional substituent selected from alkyl, substituted alkyl, hydroxy, amino, substituted amino, halogen, nitrile, nitro, acyl, substituted acyl, carboxy, and substituted carboxy, or two $R^{19}$ groups together with the atoms to which they are attached form an optionally substituted cyclic group;

$X^-$ is a counterion;

n is an integer from 0 to 10; and m is an integer from 0 to 2, wherein if m is 0, then n is an integer from 0 to 6, and if m is 1, then n is an integer from 0 to 8;

wherein at least one of $R^{22}$, $R^{24}$, $R^{25}$ or $R^{27}$ is selected from —$N(R^{20})_2$, —$(CH_2)_pNR^{20}$, —$NO_2$, —$C(O)N(R^{20})_2$, wherein each $R^{20}$ is independently selected from H, alkyl, substituted alkyl, $C(O)R^{21}$, —$SO_2R^{21}$, and —$C(O)CHCH_2$, or two $R^{20}$ substituents together with the nitrogen to which they are attached form an optionally substituted cyclic structure; and $R^{21}$ is selected from H, alkyl, substituted alkyl, aryl, substituted aryl, heterocycle, substituted heterocycle, heteroaryl, and substituted heteroaryl.

In some embodiments of formula (VIII), $R^{24}$ and $R^{25}$ are independently selected from H, alkoxy, substituted alkoxy, halogen, hydroxy, amino, and substituted amino; and $R^{22}$ and $R^{27}$ are each independently selected from H, aryl, substituted aryl, heteroaryl, substituted heteroaryl, alkoxy, substituted alkoxy, halogen, hydroxy, amino, and substituted amino.

In certain cases of formula (VIII), $R^{24}$ is selected from alkoxy, substituted alkoxy, halogen, hydroxy, amino, and substituted amino;

$R^{22}$ and $R^{25}$ are each H; and $R^{27}$ is selected from aryl, substituted aryl, heteroaryl, substituted heteroaryl, alkoxy, substituted alkoxy, halogen, hydroxy, amino, and substituted amino.

In certain cases of formula (VIII), $R^{22}$ is selected from alkoxy, substituted alkoxy, halogen, hydroxy, amino, and substituted amino;

$R^{24}$ and $R^{25}$ are each H; and $R^{27}$ is selected from aryl, substituted aryl, heteroaryl, substituted heteroaryl, alkoxy, substituted alkoxy, halogen, hydroxy, amino, and substituted amino.

In certain cases of formula (VIII), $R^{25}$ is selected from alkoxy, substituted alkoxy, halogen, hydroxy, amino, and substituted amino;

$R^{24}$ and $R^{27}$ are each H; and $R^{22}$ is selected from aryl, substituted aryl, heteroaryl, substituted heteroaryl, alkoxy, substituted alkoxy, halogen, hydroxy, amino, and substituted amino.

In certain cases of formula (VIII), $R^{27}$ is selected from alkoxy, substituted alkoxy, halogen, hydroxy, amino, and substituted amino;

$R^{24}$ and $R^{25}$ are each H; and $R^{22}$ is selected from aryl, substituted aryl, heteroaryl, substituted heteroaryl, alkoxy, substituted alkoxy, halogen, hydroxy, amino, and substituted amino.

As disclosed herein for a compound of formula (VIII), at least one of $R^{22}$, $R^{24}$, $R^{25}$ or $R^{27}$ is selected from —$N(R^{20})_2$, —$(CH_2)_pNR^{20}$, —$NO_2$, —$C(O)N(R^{20})_2$, wherein each $R^{20}$ is independently selected from H, alkyl, substituted alkyl, $C(O)R^{21}$, —$SO_2R^{21}$, and —$C(O)CHCH_2$, or two $R^{20}$ substituents together with the nitrogen to which they are attached form an optionally substituted cyclic structure; and $R^{21}$ is selected from H, alkyl, substituted alkyl, aryl, substituted aryl, heterocycle, substituted heterocycle, heteroaryl, and substituted heteroaryl. In some cases, one of $R^{22}$, $R^{24}$, $R^{25}$ or $R^{27}$ is —$N(R^{20})_2$, where each $R^{20}$ is as described above. In some cases, one of $R^{22}$, $R^{24}$, $R^{25}$ or $R^{27}$ is $(CH_2)_pNR^{20}$, where $R^{20}$ is as described above. In some cases, one of $R^{22}$, $R^{24}$, $R^{25}$ or $R^{27}$ is —$NO_2$. In some cases, one of $R^{22}$, $R^{24}$, $R^{25}$ or $R^{27}$ is —$C(O)N(R^{20})_2$, wherein each $R^{20}$ is as described above.

In some embodiments of any one of formulae (VI)-(VIII), the compound includes the substituent —$N(R^{20})_2$, where each $R^{20}$ is independently selected from H, alkyl, substituted alkyl, $C(O)R^{21}$, —$SO_2R^{21}$, and —$C(O)CHCH_2$, or two $R^{20}$ substituents together with the nitrogen to which they are attached form an optionally substituted cyclic structure; and $R^{21}$ is selected from H, alkyl, substituted alkyl, aryl, substituted aryl, heterocycle, substituted heterocycle, heteroaryl, and substituted heteroaryl. In some cases, each $R^{20}$ is H. In some cases, each $R^{20}$ is alkyl or substituted alkyl. In some cases, one $R^{20}$ is H and the other $R^{20}$ is alkyl or substituted alkyl. In some cases, one $R^{20}$ group is $C(O)R^{21}$, where $R^{21}$ is selected from H, alkyl, substituted alkyl, aryl, substituted aryl, heterocycle, substituted heterocycle, heteroaryl, and substituted heteroaryl. In some cases, one $R^{20}$ group is —$SO_2R^{21}$, where $R^{21}$ is selected from H, alkyl, substituted alkyl, aryl, substituted aryl, heterocycle, substituted heterocycle, heteroaryl, and substituted heteroaryl. In some cases, one $R^{20}$ is —$C(O)CHCH_2$. In certain cases, two $R^{20}$ substituents together with the nitrogen to which they are attached forms an optionally substituted cyclic structure, e.g., a 5 or 6 membered saturated or unsaturated ring.

In some embodiments of any one of formulae (VI)-(VIII), the compound includes the substituent —$(CH_2)_pNR^{20}$, where $R^{20}$ is selected from H, alkyl, substituted alkyl, $C(O)R^{21}$, —$SO_2R^{21}$, and —$C(O)CHCH_2$; and $R^{21}$ is selected from H, alkyl, substituted alkyl, aryl, substituted aryl, heterocycle, substituted heterocycle, heteroaryl, and substituted heteroaryl. In some cases, $R^{20}$ is H. In some cases, $R^{20}$ is alkyl or substituted alkyl. In some cases, $R^{20}$ is $C(O)R^{21}$, where $R^{21}$ is selected from H, alkyl, substituted alkyl, aryl, substituted aryl, heterocycle, substituted heterocycle, heteroaryl, and substituted heteroaryl. In some cases, $R^{20}$ is —$SO_2R^{21}$, where $R^{21}$ is selected from H, alkyl, substituted alkyl, aryl, substituted aryl, heterocycle, substituted heterocycle, heteroaryl, and substituted heteroaryl. In some cases, $R^{20}$ is —$C(O)CHCH_2$.

In some embodiments of any one of formulae (VI)-(VIII), the compound includes the substituent —$NO_2$.

In some embodiments of any one of formulae (VI)-(VIII), the compound includes the substituent —$C(O)N(R^{20})_2$, where each $R^{20}$ is independently selected from H, alkyl, substituted alkyl, $C(O)R^{21}$, —$SO_2R^{21}$, and —$C(O)CHCH_2$, or two $R^{20}$ substituents together with the nitrogen to which they are attached form an optionally substituted cyclic structure; and $R^{21}$ is selected from H, alkyl, substituted alkyl, aryl, substituted aryl, heterocycle, substituted heterocycle, heteroaryl, and substituted heteroaryl. In some cases, each $R^{20}$ is H. In some cases, each $R^{20}$ is alkyl or substituted alkyl. In some cases, one $R^{20}$ is H and the other $R^{20}$ is alkyl or substituted alkyl. In some cases, one $R^{20}$ group is $C(O)R^{21}$, where $R^{21}$ is selected from H, alkyl, substituted alkyl, aryl, substituted aryl, heterocycle, substituted heterocycle, heteroaryl, and substituted heteroaryl. In some cases, one $R^{20}$ group is —$SO_2R^{21}$, where $R^{21}$ is selected from H, alkyl, substituted alkyl, aryl, substituted aryl, heterocycle, substituted heterocycle, heteroaryl, and substituted heteroaryl. In some cases, one $R^{20}$ is —$C(O)CHCH_2$. In certain cases, two $R^{20}$ substituents together with the nitrogen to which they are attached forms an optionally substituted cyclic structure, e.g., a 5 or 6 membered saturated or unsaturated ring.

In some embodiments, the compound is described by the formula (IX)

(IX)

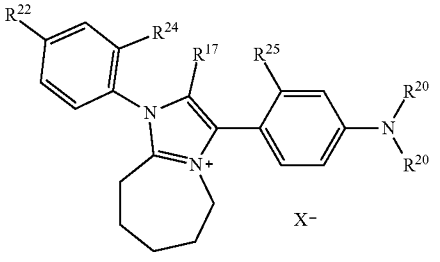

wherein:

$R^{17}$ is selected from H, alkyl, substituted alkyl, alkenyl, substituted alkenyl, alkynyl, substituted alkynyl, alkoxy, substituted alkoxy, halogen, hydroxyl, acyl, substituted acyl, carboxy, substituted carboxy, amino, substituted amino, aryl, substituted aryl, heterocycle, substituted heterocycle, heteroaryl, substituted heteroaryl, cycloalkyl, and substituted cycloalkyl;

$R^{24}$ and $R^{25}$ are independently selected from H, alkyl, substituted alkyl, alkoxy, substituted alkoxy, halogen, hydroxy, acyl, substituted acyl, carboxy, substituted carboxy, amino, and substituted amino;

$R^{22}$ is selected from H, alkyl, substituted alkyl, alkenyl, substituted alkenyl, alkynyl, substituted alkynyl, alkoxy, substituted alkoxy, halogen, hydroxy, amino, substituted amino, acyl, substituted acyl, carboxy, substituted carboxy, aryl, substituted aryl, heterocycle, substituted heterocycle, heteroaryl, substituted heteroaryl, cycloalkyl, and substituted cycloalkyl;

each $R^{20}$ is independently selected from H, alkyl, substituted alkyl, $C(O)R^{21}$, —$SO_2R^{21}$, and —$C(O)CHCH_2$, where $R^{21}$ is selected from H, alkyl, substituted alkyl, aryl, substituted aryl, heterocycle, substituted heterocycle, heteroaryl, substituted heteroaryl, or two $R^{20}$ substituents together with the nitrogen to which they are attached form an optionally substituted cyclic structure; and $X^-$ is a counterion.

In some embodiments of formula (IX), $R^{24}$ and $R^{25}$ are independently selected from H, alkoxy, substituted alkoxy, halogen, hydroxy, amino, and substituted amino; and $R^{22}$ is selected from H, aryl, substituted aryl, heteroaryl, substituted heteroaryl, alkoxy, substituted alkoxy, halogen, hydroxy, amino, and substituted amino.

In certain cases of formula (IX), $R^{24}$ is selected from alkoxy, substituted alkoxy, halogen, hydroxy, amino, and substituted amino; and $R^{22}$ and $R^{25}$ are each H.

In certain cases of formula (IX), $R^{22}$ is selected from alkoxy, substituted alkoxy, halogen, hydroxy, amino, and substituted amino; and $R^{24}$ and $R^{25}$ are each H.

In certain cases of formula (IX), $R^{25}$ is selected from alkoxy, substituted alkoxy, halogen, hydroxy, amino, and substituted amino;

$R^{24}$ is H; and $R^{22}$ is selected from aryl, substituted aryl, heteroaryl, substituted heteroaryl, alkoxy, substituted alkoxy, halogen, hydroxy, amino, and substituted amino.

In certain cases of formula (IX), $R^{24}$ and $R^{25}$ are each H; and $R^{22}$ is selected from aryl, substituted aryl, heteroaryl, substituted heteroaryl, alkoxy, substituted alkoxy, halogen, hydroxy, amino, and substituted amino.

In certain embodiments, the compound is selected from any one of the following structures:

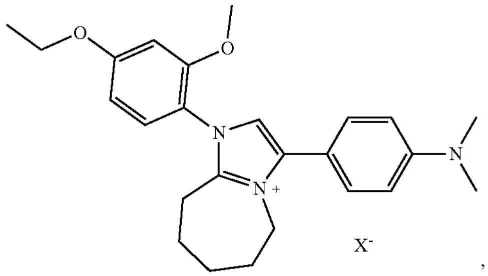

,

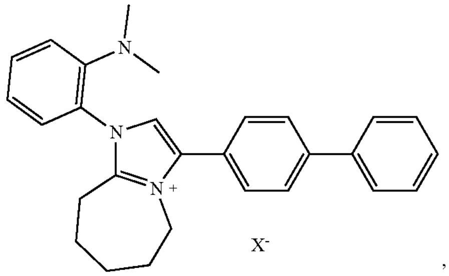

,

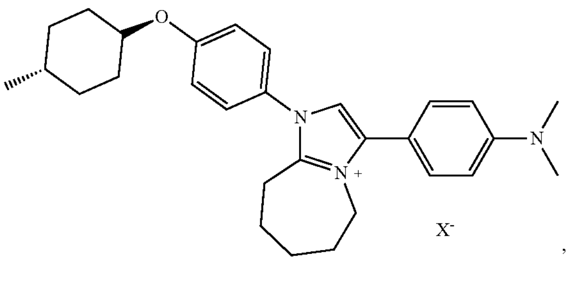

,

-continued
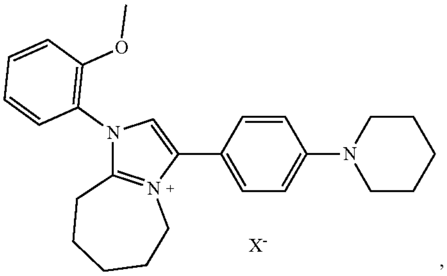
,
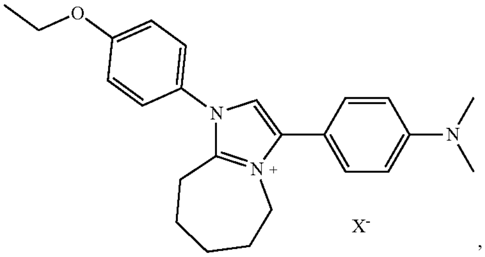
,
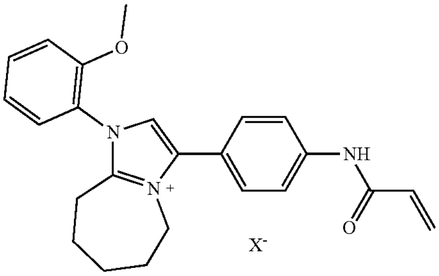
,
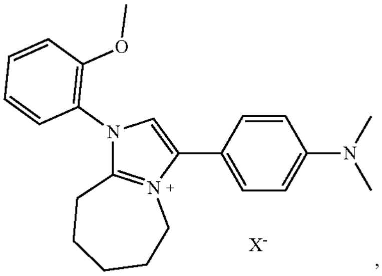
,
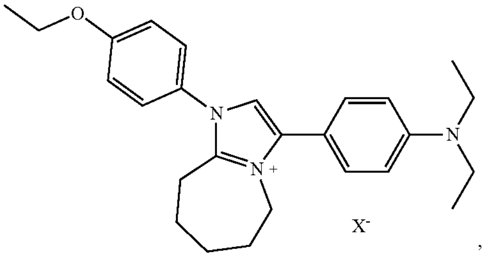
,
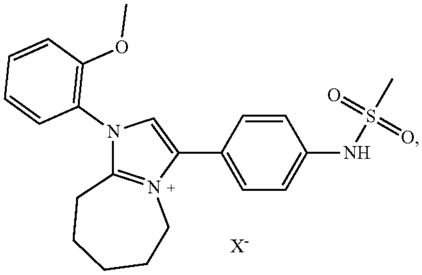
-continued
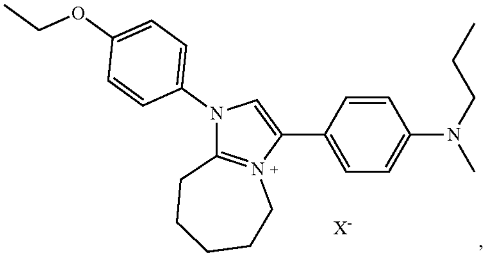
,
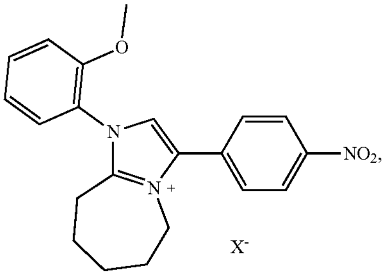
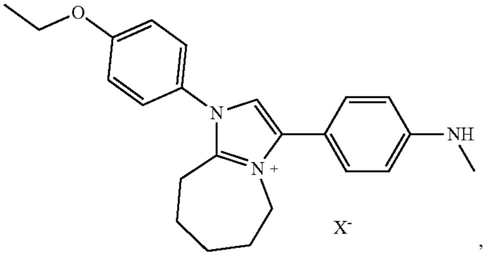
,
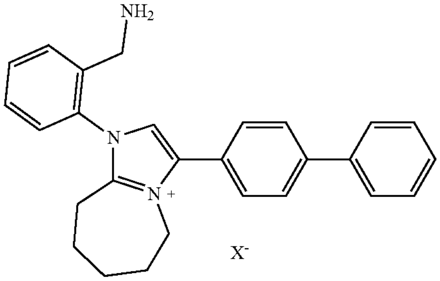
,
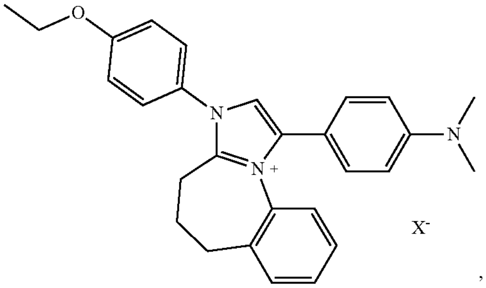
,
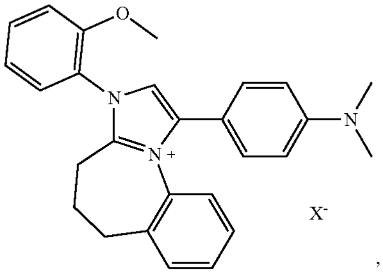
, -continued

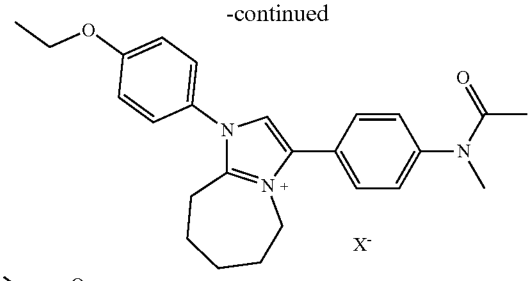

,

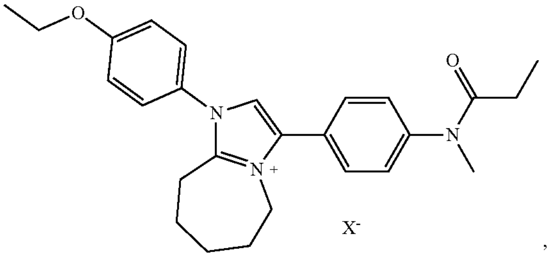

,

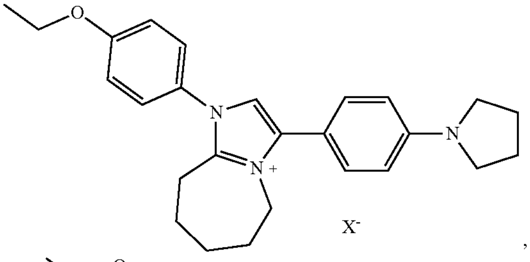

, and

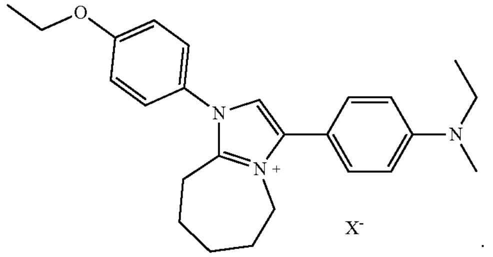

.

In some embodiments, the compound is of formula (VI) (e.g., as described herein), wherein $R^{16}$ or $R^{18}$ is a fused heterocyclic group. In some embodiments, $R^{18}$ is a fused heterocyclic group. In some cases, $R^{16}$ is a fused heterocycle. In some cases, the fused heterocycle is selected from Indoline, indole, indazole, benzofuran, benzothiophene, benzoisothiazole, benzoxazole, benzodioxan, quinoline, quinazoline, chromene, chromen-2-one, carbazole, and dibenzofuran, wherein any of the fused heterocyclic groups are optionally further substituted.

In some embodiments of formula (VI), the compound is selected from one of the following structures:

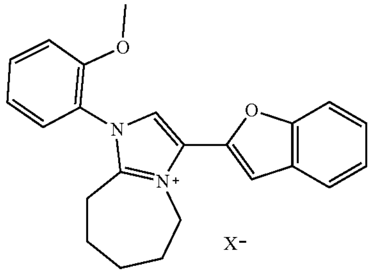

,

-continued

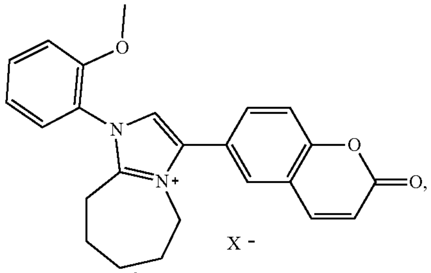

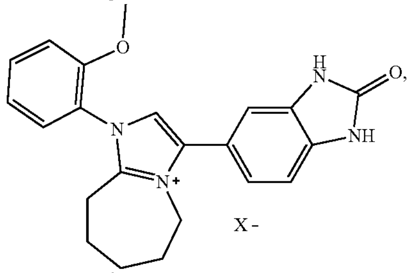

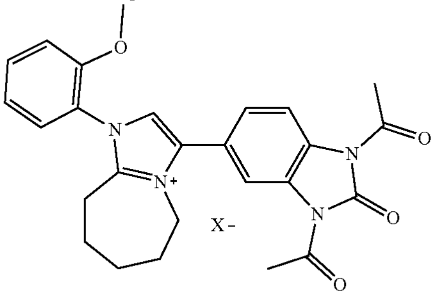

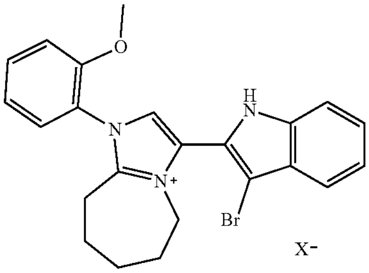

, and

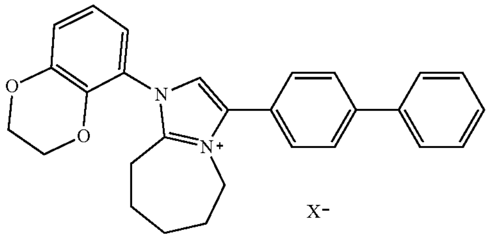

.

In some embodiments, the compound is of formula (VI) (e.g., as described herein), wherein the $R^{16}$ or $R^{18}$ is heteroaryl, substituted heteroaryl, heterocycle, substituted heterocycle, or an aryl group substituted with a heteroaryl group or a heterocyclic group. In some cases, $R^{16}$ is selected from heteroaryl, or heterocycle. In some cases, $R^{18}$ is selected from heteroaryl, or heterocycle. In some cases, $R^{16}$ or $R^{18}$ is selected from pyridyl, pyrimidinyl, pyrrolyl, pyrrolidinyl, quinolinyl, indolyl, furyl, imidazolyl, oxazolyl, thiazolyl, 1,2,4-triazolyl, tetrazolyl, pyrrolidino, morpholino, piperazino, piperidino, tetrahydrofuranyl. In some cases, $R^{16}$ is selected from morpholino, piperazino, piperidino, tetrahydrofuranyl. In some cases, $R^{16}$ or $R^{18}$ is selected from a pyridyl group, a substituted pyridyl group, or an aryl group substituted with a pyridyl group. In some cases, $R^{18}$ is a pyridyl group, a substituted pyridyl group, or an aryl group substituted with a pyridyl group.

In some embodiments of formula (VI), the compound is selected from one of the following structures:

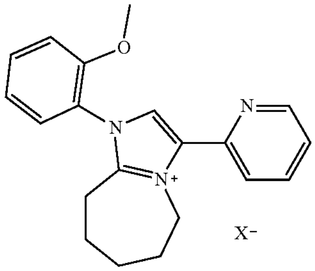

,

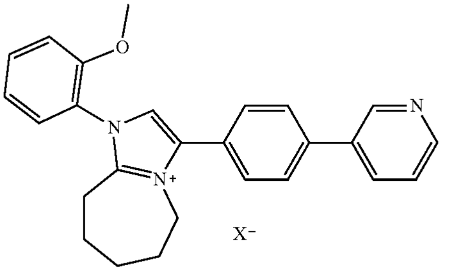

,

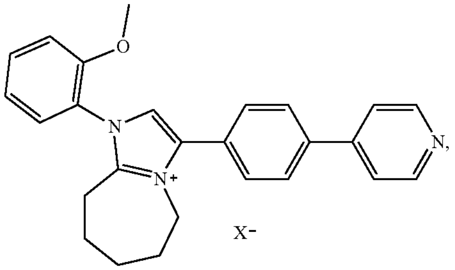

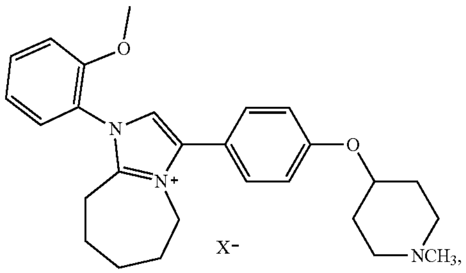

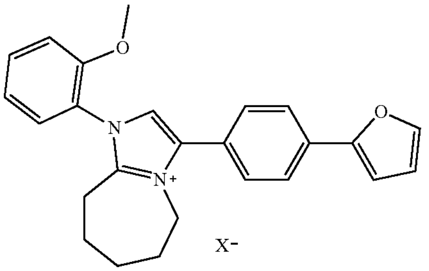

, and

-continued

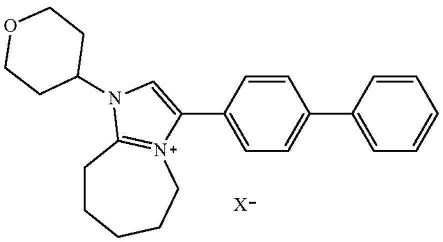

.

In some embodiments, the compound is of formula (VI) (e.g., as described herein), wherein the $R^{16}$ or $R^{18}$ is an alkene or a substituted alkene. In certain cases, $R^{16}$ is a substituted alkene. In certain cases, $R^{16}$ is an alkene group substituted with an aryl or substituted aryl group. In certain cases, $R^{18}$ is a substituted alkene. In certain cases, $R^{18}$ is an alkene group substituted with an aryl or substituted aryl group. In certain cases, the alkene has E geometry. In some cases, the alkene has Z geometry.

In some embodiments of formula (VI), the compound is selected from one of the following structures:

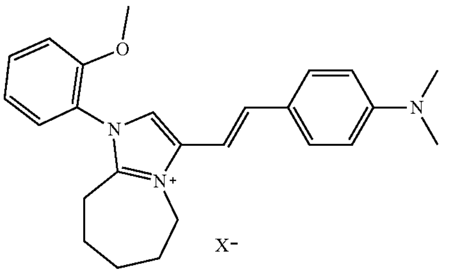

,

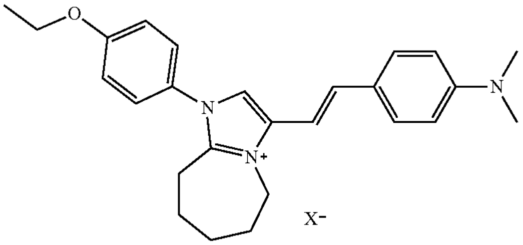

and

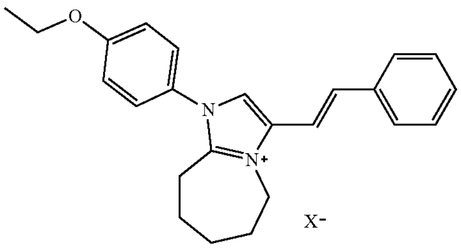

.

In some embodiments, the compound is of formula (VI) (e.g., as described herein), wherein $R^{16}$ or $R^{18}$ is selected from a cycloalkyl group, a substituted cycloalkyl group, a heterocyclic group, or a substituted heterocyclic group. In some embodiments, $R^{16}$ or $R^{18}$ is selected from a $C_{5-6}$ cycloalkyl group, or $O_{5-6}$ substituted cycloalkyl group. In some other embodiments, $R^{16}$ or $R^{18}$ is selected from a $C_{5-6}$ heterocyclic group, or $O_{5-6}$ substituted heterocyclic group.

In some embodiments of formula (VI), the compound is selected from one of the following structures:

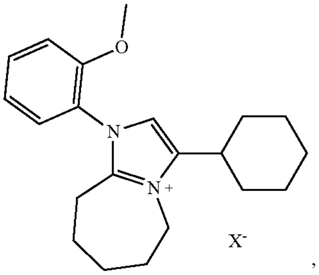

,

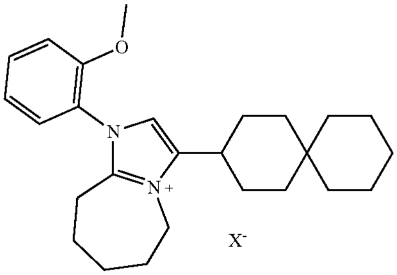

,

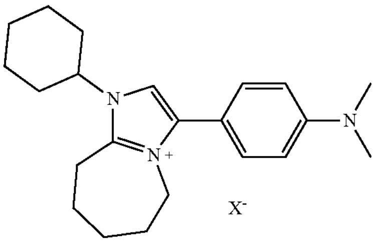

,

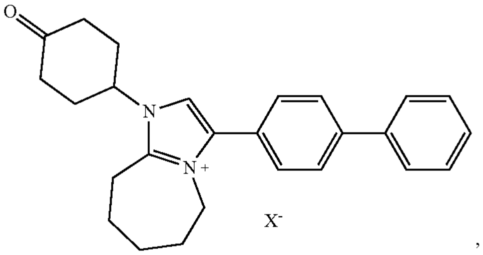

,

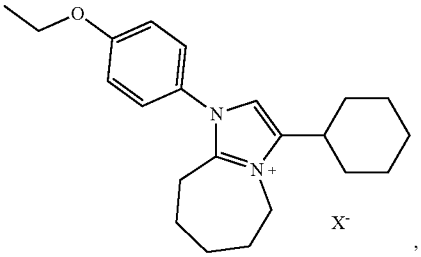

,

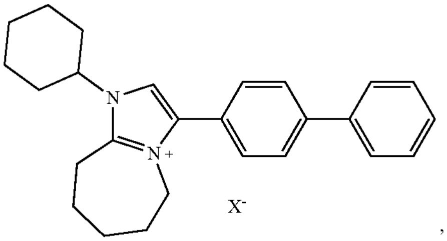

, and

-continued

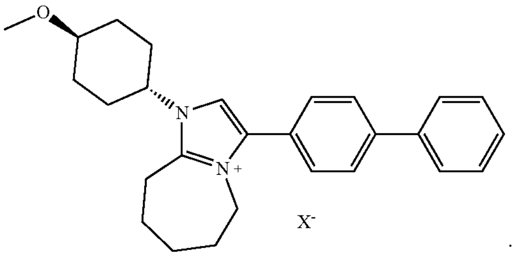

.

In certain embodiments of formula (VI), n is 0, such that there are no $R^{19}$ substituents. In certain embodiments of formula (VI), n is more than 0, such as 1 or more, 2 or more, 3 or more, 4 or more, 5 or more, 6 or more, or even more when m is 1 or 2. In certain embodiments of formula (VI), n is 1, and $R^{19}$ is selected from alkyl, substituted alkyl, hydroxy, carbonyl, amino, substituted amino, halogen, nitrile, nitro, acyl, substituted acyl, carboxy, and substituted carboxy. In some cases, $R^{19}$ is carbonyl. In some cases, $R^{19}$ is a $C_{1-6}$ alkyl group, or substituted $C_{1-6}$ alkyl group. In some cases, $R^{19}$ is hydroxyl. In some cases, $R^{19}$ is amino or substituted amino. In some cases, $R^{19}$ is halogen. In some cases, $R^{19}$ is nitrile. In some cases, $R^{19}$ is nitro. In some cases, $R^{19}$ is acyl, or substituted acyl. In some cases, $R^{19}$ is carboxy, or substituted carboxy.

In certain embodiments of formula (VI), n is 2, and each $R^{19}$ is independently selected from alkyl, substituted alkyl, hydroxy, carbonyl, amino, substituted amino, halogen, nitrile, nitro, acyl, substituted acyl, carboxy, and substituted carboxy. In certain cases, n is 2, and each $R^{19}$ is $C_{1-6}$ alkyl. In certain cases, the $C_{1-6}$ alkyl group is selected from methyl, ethyl and propyl. In certain cases, the $C_{1-6}$ alkyl group is methyl.

In certain embodiments of formula (VI), n is 2, and the two $R^{19}$ groups together with the atoms to which they are attached form a cyclic group selected from aryl, substituted aryl, cycloalkyl, substituted cycloalkyl, heterocycle, substituted heterocycle, heteroaryl, substituted heteroaryl. In some cases, the two $R^{19}$ groups are adjacent to each other, and the two $R^{19}$ groups forms an optionally substituted cyclic group. In certain cases, the cyclic group is selected from cycloalkyl, substituted cycloalkyl, heterocycle, and substituted heterocycle. In certain cases, n is 2, and the two $R^{19}$ groups form a covalent bond to each other to form a bridged structure, wherein the bridged structure is optionally further substituted.

In some embodiments, the compound is selected from one of the following structures:

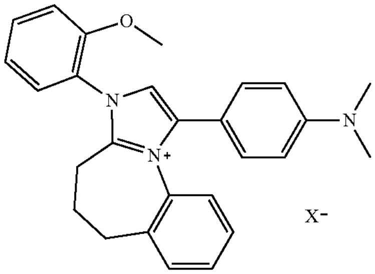

,

-continued

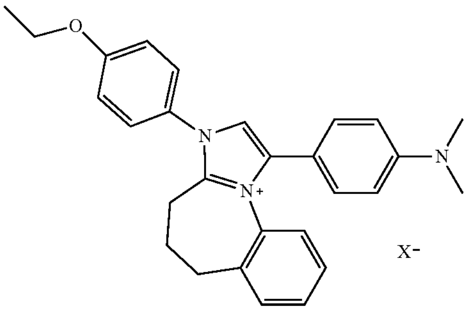

,

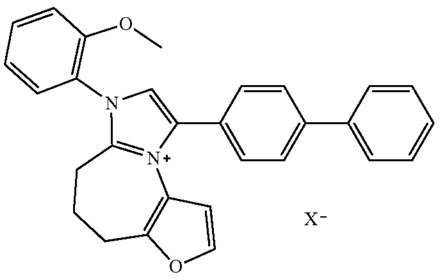

,

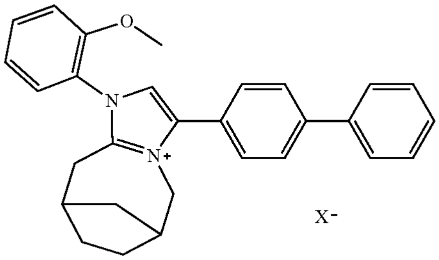

, and

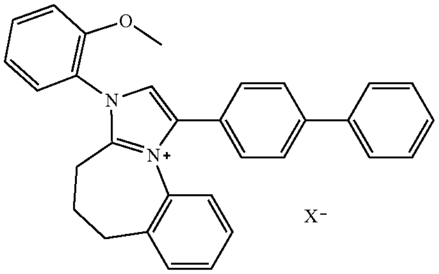

.

In some embodiments, the compound is described by the formula (XA) or (XB):

(XA)

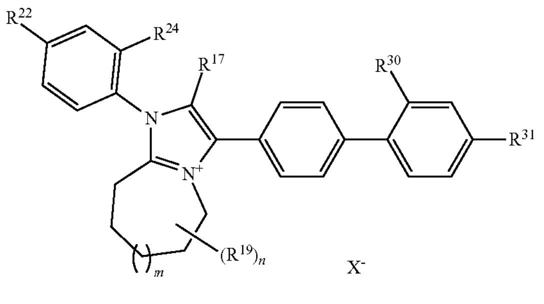

-continued (XB)

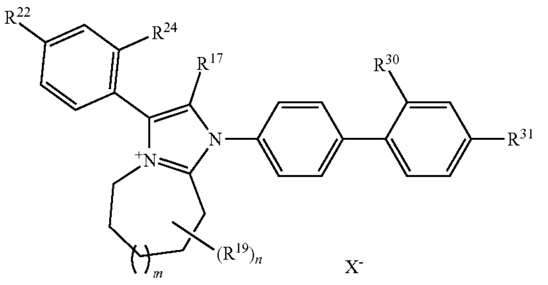

wherein:

$R^{17}$ is selected from H, alkyl, substituted alkyl, alkenyl, substituted alkenyl, alkynyl, substituted alkynyl, alkoxy, substituted alkoxy, halogen, hydroxyl, acyl, substituted acyl, carboxy, substituted carboxy, amino, substituted amino, aryl, substituted aryl, heterocycle, substituted heterocycle, heteroaryl, substituted heteroaryl, cycloalkyl, and substituted cycloalkyl;

$R^{22}$ and $R^{24}$ are each independently selected from H, alkyl, substituted alkyl, alkoxy, substituted alkoxy, halogen, hydroxy, nitro, acyl, substituted acyl, carboxy, substituted carboxy, amino, and substituted amino;

$R^{30}$, and $R^{31}$ are each independently selected from H, alkyl, substituted alkyl, alkoxy, substituted alkoxy, halogen, hydroxy, acyl, substituted acyl, carboxy, substituted carboxy, nitro, amino, and substituted amino;

$R^{19}$ is an optional substituent selected from alkyl, substituted alkyl, hydroxy, amino, substituted amino, halogen, nitrile, nitro, acyl, substituted acyl, carboxy, and substituted carboxy; or two $R^{19}$ groups together with the atoms to which they are attached form an optionally substituted cyclic group;

$X^-$ is a counterion;

n is an integer from 0 to 10; and m is an integer from 0 to 2, wherein if m is 0, then n is an integer from 0 to 6, and if m is 1, then n is an integer from 0 to 8;

or pharmaceutically acceptable salt, solvate, or prodrug thereof, provided that when $R^{22}$, $R^{30}$ and $R^{31}$ are each H, $R^{24}$ is not methoxy; and when $R^{24}$, $R^{30}$ and $R^{31}$ are each H, $R^{22}$ is not ethoxy.

As disclosed herein, formula (XA) or (XB) does not include the following compound:

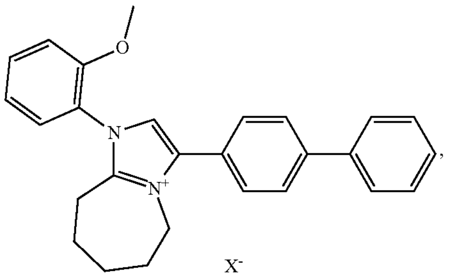

-continued

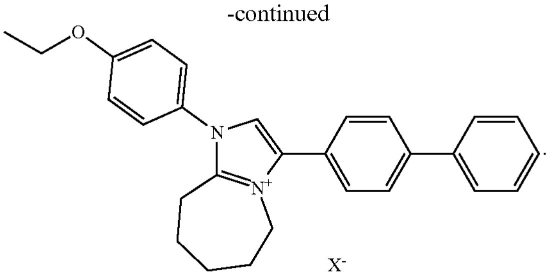

In certain embodiments of formula (XA) or (XB), at least one of $R^{22}$, $R^{24}$ and $R^{30}$-$R^{31}$ is a substituent other than H. In some cases, at least one of $R^{22}$ or $R^{24}$, and at least one of $R^{30}$-$R^{31}$ are substituents other than H. In certain cases, $R^{22}$ is a substituent other than H. In certain cases, $R^{24}$ is a substituent other than H. In some cases, $R^{22}$ and $R^{24}$ are both substituents other than H. In certain cases, $R^{30}$ is a substituent other than H. In certain cases, $R^{31}$ is a substituent other than H. In certain cases, $R^{30}$ and $R^{31}$ are substituents other than H.

In certain cases of formula (XA) or (XB), at least one of $R^{22}$ or $R^{24}$ is selected from alkyl, substituted alkyl, alkoxy, substituted alkoxy, halogen, hydroxy, acyl, substituted acyl, carboxy, substituted carboxy, amino, and substituted amino. In certain cases, at least one of $R^{22}$ or $R^{24}$ is selected from alkyl, and substituted alkyl. In certain cases, at least one of $R^{22}$ or $R^{24}$ is selected from alkoxy, and substituted alkoxy. In certain cases, at least one of $R^{22}$ or $R^{24}$ is halogen. In certain cases, at least one of $R^{22}$ or $R^{24}$ is hydroxy. In certain cases, at least one of $R^{22}$ or $R^{24}$ is selected from acyl and substitute acyl. In certain cases, at least one of $R^{22}$ or $R^{24}$ is selected from carboxy and substituted carboxy. In certain cases, at least one of $R^{22}$ or $R^{24}$ is selected from amino and substituted amino.

In certain cases of formula (XA) or (XB), at least one of $R^{30}$ or $R^{31}$ is selected from alkyl, substituted alkyl, alkoxy, substituted alkoxy, halogen, hydroxy, acyl, substituted acyl, carboxy, substituted carboxy, amino, and substituted amino. In certain cases, at least one of $R^{30}$ or $R^{31}$ is selected from alkyl, and substituted alkyl. In certain cases, at least one of $R^{30}$ or $R^{31}$ is selected from alkoxy, and substituted alkoxy. In certain cases, at least one of $R^{30}$ or $R^{31}$ is halogen. In certain cases, at least one of $R^{30}$ or $R^{31}$ is hydroxy. In certain cases, at least one of $R^{30}$ or $R^{31}$ is selected from amino and substituted amino. In certain cases, at least one of $R^{30}$ or $R^{31}$ is selected from acyl and substituted acyl. In certain cases, at least one of $R^{30}$ or $R^{31}$ is selected from carboxy and substituted carboxy.

In certain embodiments of formula (XA) or (XB), $R^{24}$ is selected from alkoxy, substituted alkoxy, acyl, substituted acyl, carboxy, substituted carboxy, amino, and substituted amino.

In certain embodiments of formula (XA) or (XB), $R^{22}$ is selected from alkoxy, substituted alkoxy, acyl, substituted acyl, carboxy, substituted carboxy, amino, and substituted amino.

In certain cases of formula (XA) or (XB), $R^{30}$ is selected from alkyl, substituted alkyl, alkoxy, substituted alkoxy, halogen, hydroxy, acyl, substituted acyl, carboxy, substituted carboxy, amino, and substituted amino.

In certain cases of formula (XA) or (XB), $R^{31}$ is selected from alkyl, substituted alkyl, alkoxy, substituted alkoxy, halogen, hydroxy, acyl, substituted acyl, carboxy, substituted carboxy, amino, and substituted amino.

In certain embodiments of formula (XA) or (XB), $R^{24}$, $R^{30}$, and $R^{31}$ are independently selected from H, alkoxy, substituted alkoxy, halogen, hydroxy, amino, and substituted amino.

In certain cases of formula (XA), $R^{30}$ is alkoxy; and $R^{31}$ is H. In certain cases of formula (XB), $R^{30}$ is alkoxy; and $R^{31}$ is H. In certain embodiments of formula (XA), $R^{30}$ is H; and $R^{31}$ is alkoxy or carboxy. In certain embodiments of formula (XB), $R^{30}$ is H; and $R^{31}$ is alkoxy or carboxy. In certain embodiments of formula (XA), each of $R^{30}$-$R^{31}$ are H. In certain embodiments of formula (XB), each of $R^{30}$-$R^{31}$ are H.

In certain cases of formula (XA), $R^{22}$ and $R^{24}$ are each independently selected from H and alkoxy. In certain cases, $R^{22}$ is H and $R^{24}$ is alkoxy. In certain cases, $R^{22}$ is alkoxy and $R^{24}$ is H. In certain other cases, $R^{22}$ and $R^{24}$ are alkoxy.

In certain cases of formula (XB), $R^{22}$ and $R^{24}$ are each independently selected from H and alkoxy. In certain cases, $R^{22}$ is H and $R^{24}$ is alkoxy. In certain cases, $R^{22}$ is alkoxy and $R^{24}$ is H. In certain other cases, $R^{22}$ and $R^{24}$ are alkoxy.

In certain embodiments of formula (XA) or (XB), $R^{22}$ and $R^{24}$ are each independently selected from H, $C_{1-6}$ alkoxy, substituted $C_{1-6}$ alkoxy, amino, and substituted amino. In certain cases, both $R^{22}$ and $R^{24}$ are both $C_{1-6}$ alkoxy. In certain cases, $R^{30}$ is selected from $C_{1-6}$ alkoxy, substituted $C_{1-6}$ alkoxy, halogen, hydroxy, acyl, substituted acyl, carboxy, substituted carboxy, amino, and substituted amino. In certain cases, $R^{30}$ is $C_{1-6}$ alkoxy. In certain cases, $R^{31}$ is selected from $C_{1-6}$ alkoxy, substituted $C_{1-6}$ alkoxy, halogen, hydroxy, acyl, substituted acyl, carboxy, substituted carboxy, amino, and substituted amino. In certain cases, $R^{31}$ is $-CO_2R^{32}$, wherein $R^{32}$ is selected from H, a counter ion, alkyl, and substituted alkyl.

In certain embodiments, the compound is selected from one of the following structures:

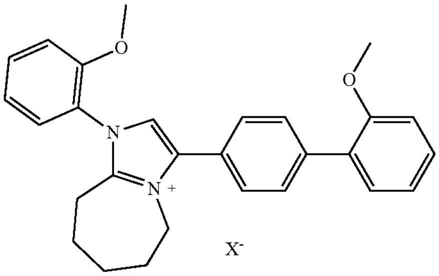

,

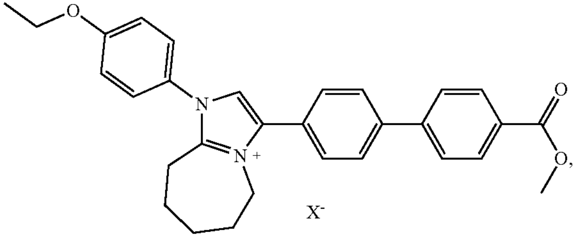

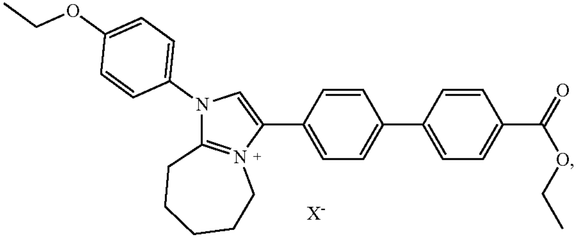

-continued
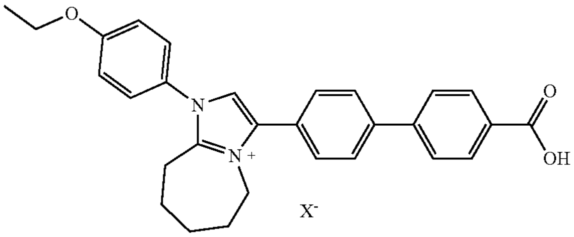
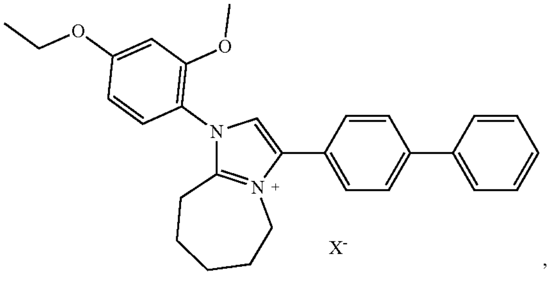
,
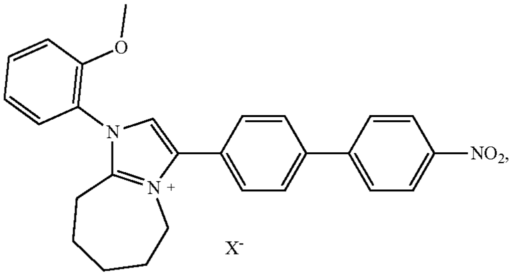
,
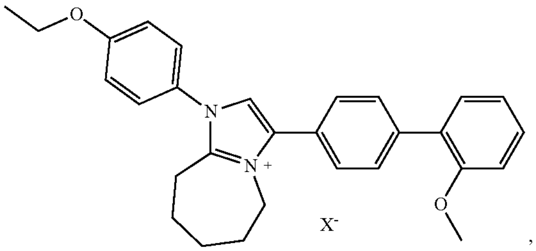
, and
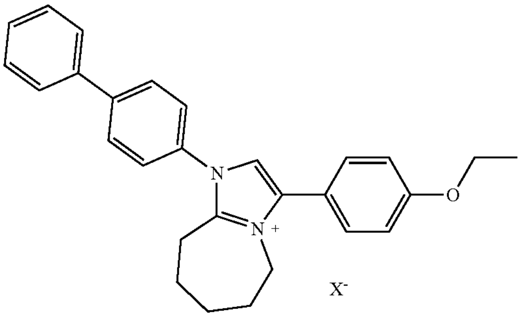
.
In certain cases, the compound is selected from one of the following structures:
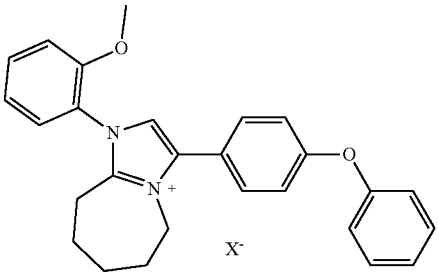
,
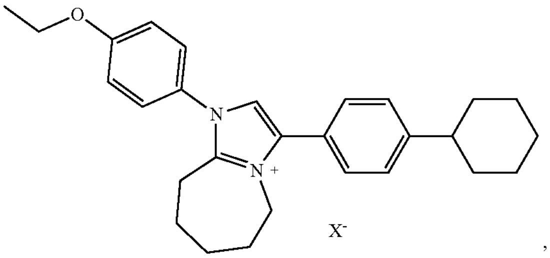
,
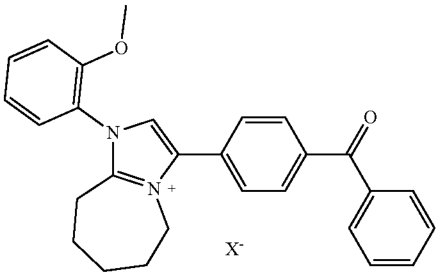
,
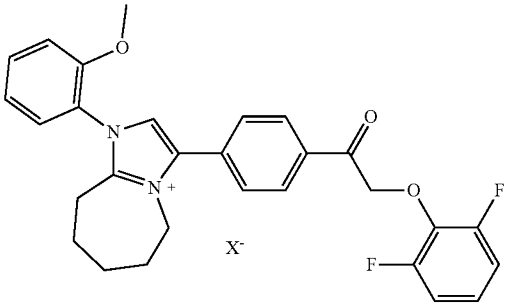
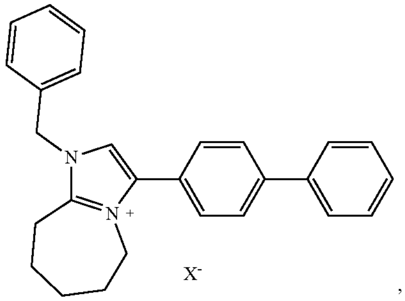
,
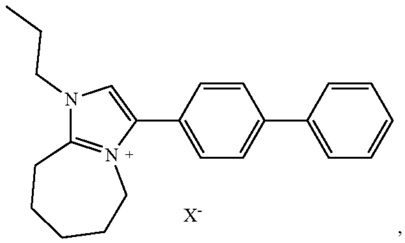
, -continued

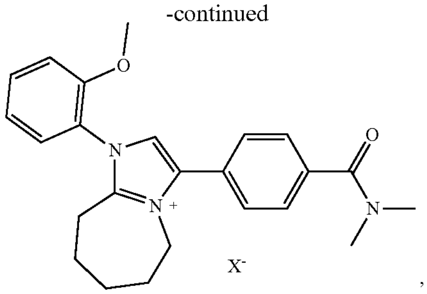

,

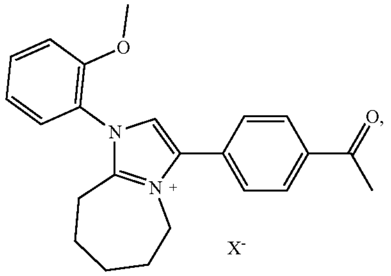

, and

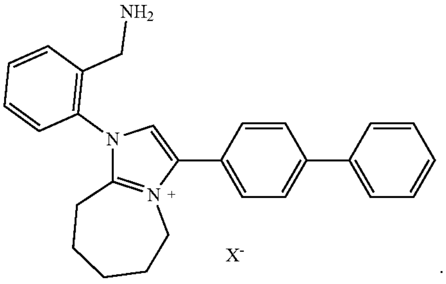

.

In certain cases of any one of formulae (VI)-(XB), m is 1. In certain cases, m is 0. In certain other cases, m is 2.

In certain embodiments of any one of formulae (VI)-(XB), n is 0, such that there are no $R^{19}$ substituents.

In certain embodiments of any one of formulae (VI)-(XB), n is more than 0, such as 1 or more, 2 or more, 3 or more, 4 or more, 5 or more, 6 or more, or even more when m is 1 or 2.

In certain embodiments of any one of formulae (VI)-(XB), n is 1, and $R^{19}$ is selected from alkyl, substituted alkyl, hydroxy, carbonyl, amino, substituted amino, halogen, nitrile, nitro, acyl, substituted acyl, carboxy, and substituted carboxy. In some cases, $R^{19}$ is carbonyl. In some cases, $R^{19}$ is a $C_{1-6}$ alkyl group, or substituted $C_{1-6}$ alkyl group. In some cases, $R^{19}$ is hydroxyl. In some cases, $R^{19}$ is amino or substituted amino. In some cases, $R^{19}$ is halogen. In some cases, $R^{19}$ is nitrile. In some cases, $R^{19}$ is nitro. In some cases, $R^{19}$ is acyl, or substituted acyl. In some cases, $R^{19}$ is carboxy, or substituted carboxy.

In certain embodiments of any one of formulae (VI)-(XB), n is 2, and each $R^{19}$ is independently selected from alkyl, substituted alkyl, hydroxy, carbonyl, amino, substituted amino, halogen, nitrile, nitro, acyl, substituted acyl, carboxy, and substituted carboxy. In certain cases, n is 2, and each $R^{19}$ is $C_{1-6}$ alkyl. In certain cases, the $C_{1-6}$ alkyl group is selected from methyl, ethyl and propyl. In certain cases, the $C_{1-6}$ alkyl group is methyl.

In certain embodiments of any one of formulae (VI)-(XB), n is 2, the two $R^{19}$ groups are adjacent to each other, and the two $R^{19}$ groups forms an optionally substituted cyclic group. In certain cases, the cyclic group is selected from cycloalkyl, substituted cycloalkyl, heterocycle, and substituted heterocycle. In certain cases, n is 2, and the two $R^{19}$ groups form a covalent bond to each other to form a bridged structure, wherein the bridged structure is optionally further substituted.

In certain embodiments of any one of formulae (VI)-(XB), $R^{17}$ is selected from H, alkyl, substituted alkyl, alkoxy, substituted alkoxy, halogen, hydroxyl, acyl, substituted acyl, carboxy, substituted carboxy, amino, substituted amino. In certain cases, $R^{17}$ is selected from aryl, substituted aryl, heterocycle, substituted heterocycle, heteroaryl, substituted heteroaryl, cycloalkyl, and substituted cycloalkyl. In certain cases, $R^{17}$ is H.

In certain embodiments, the subject compound is selected from any one of compounds 4-63. In certain cases, the subject compound is any one of the structures of Table 2.

TABLE 2

| Imidazolium compounds | | | |
|---|---|---|---|
| No. | Structure | No. | Structure |
| 5 | 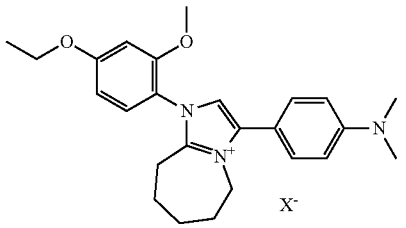 | 6 | 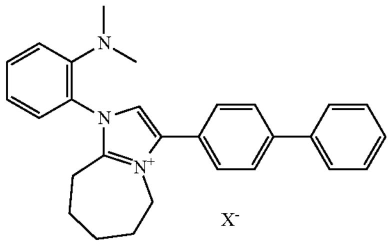 |
| 12 | 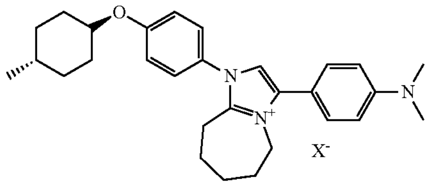 | 14 | 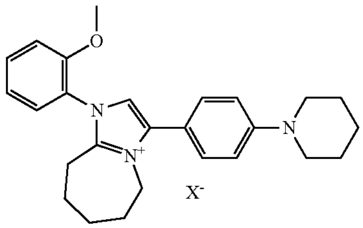 |

TABLE 2-continued
| Imidazolium compounds | | | |
|---|---|---|---|
| No. | Structure | No. | Structure |
| 15 | 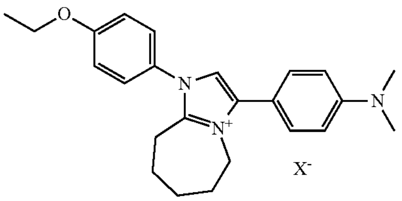 | 82 | 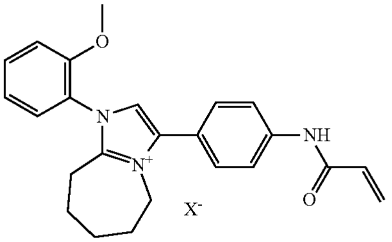 |
| 83 | 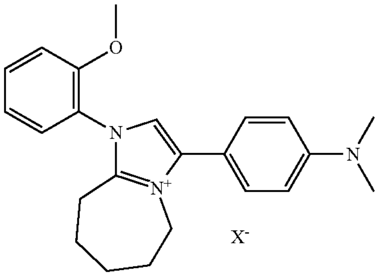 | 84 | 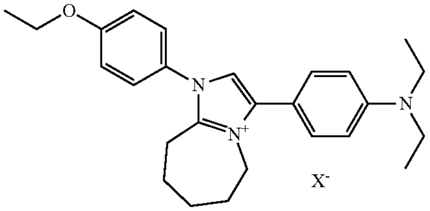 |
| 31 | 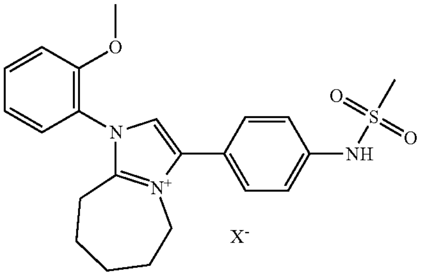 | 33 | 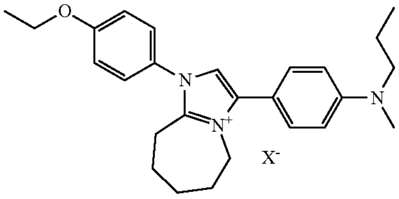 |
| 39 | 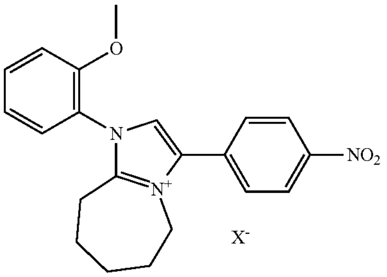 | 49 | 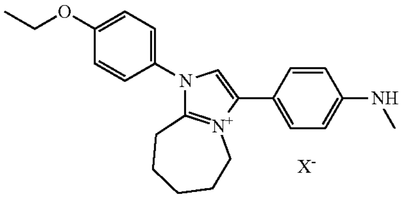 |
| 85 | 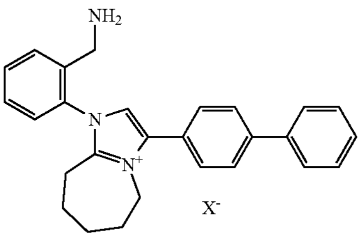 | 86 | 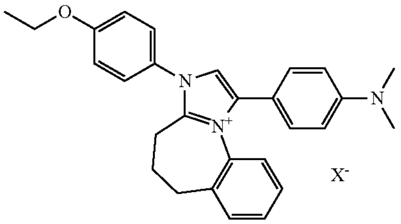 |

TABLE 2-continued
| Imidazolium compounds | | | |
|---|---|---|---|
| No. | Structure | No. | Structure |
| 87 | 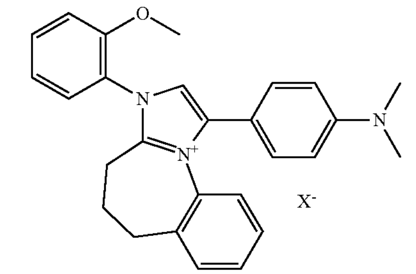 | 60 | 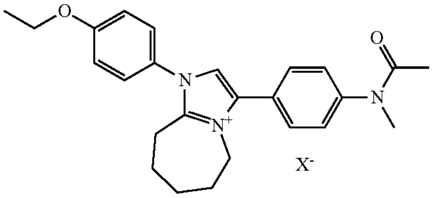 |
| 62 | 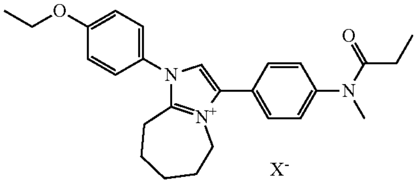 [SMILES: CCOc1ccc(-n2cc(-c3ccc(N(C)C(=O)CC)cc3)[n+]3c2CCCCC3)cc1 ; "X-"] | 41 | 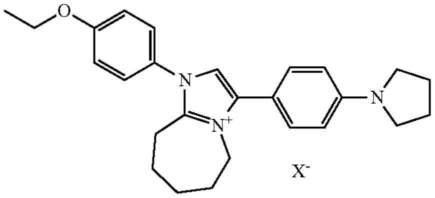 |
| 30 | 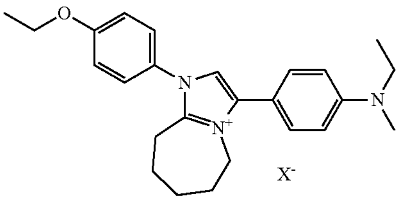 | 42 | 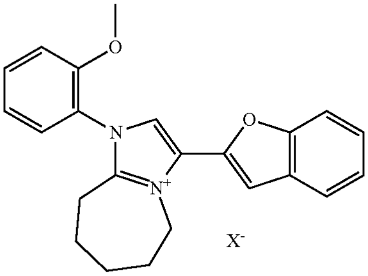 |
| 38 | 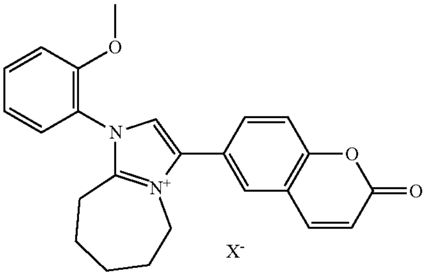 [SMILES: COc1ccccc1-n1cc(-c2ccc3oc(=O)ccc3c2)[n+]2c1CCCCC2 ; "X-"] | 37 | 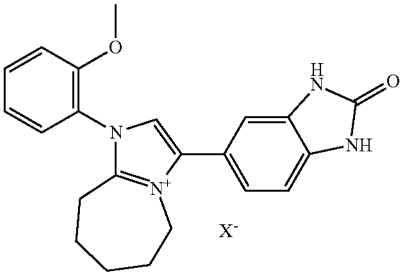 |
| 22 | 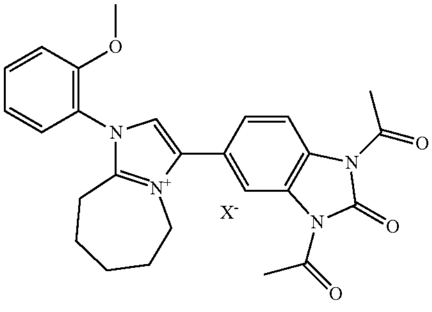 | 20 | 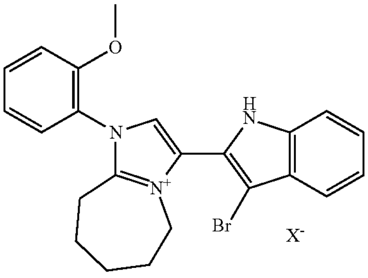 |

TABLE 2-continued
| Imidazolium compounds | | | |
|---|---|---|---|
| No. | Structure | No. | Structure |
| 11 | 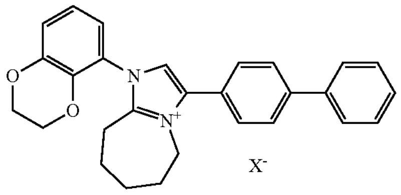 | 63 | 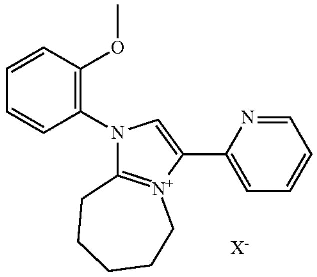 |
| 13 | 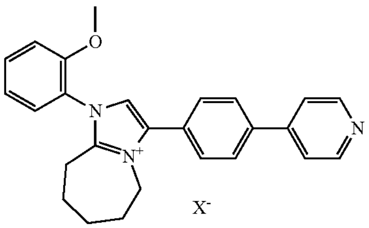 [SMILES: COc1ccccc1-n1cc(-c2ccc(-c3ccncc3)cc2)[n+]2c1CCCCC2 ; "X-"] | 19 | 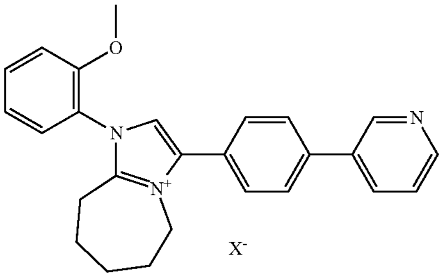 |
| 17 | 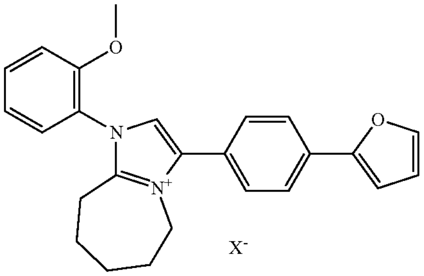 | 16 | 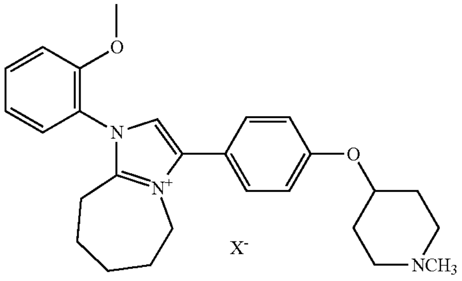 |
| 51 | 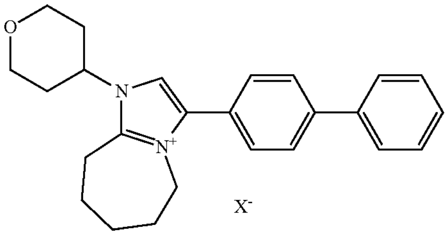 | 40 | 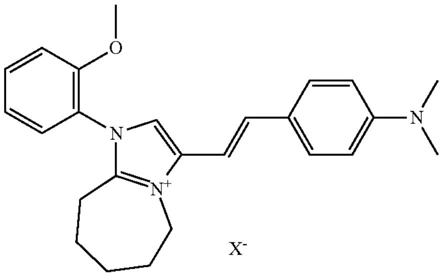 [SMILES: COc1ccccc1-n1cc(/C=C/c2ccc(N(C)C)cc2)[n+]2c1CCCCC2 ; "X-"] |
| 55 | 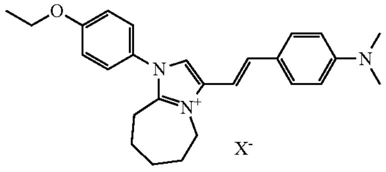 [SMILES: CCOc1ccc(-n2cc(/C=C/c3ccc(N(C)C)cc3)[n+]3c2CCCCC3)cc1 ; "X-"] | 29 | 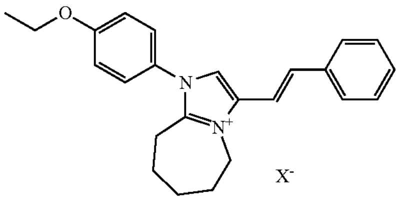 [SMILES: CCOc1ccc(-n2cc(/C=C/c3ccccc3)[n+]3c2CCCCC3)cc1 ; "X-"] |

TABLE 2-continued
| Imidazolium compounds | | | |
|---|---|---|---|
| No. | Structure | No. | Structure |
| 88 | 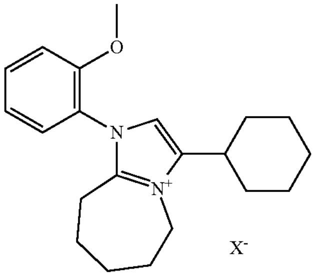 | 26 | 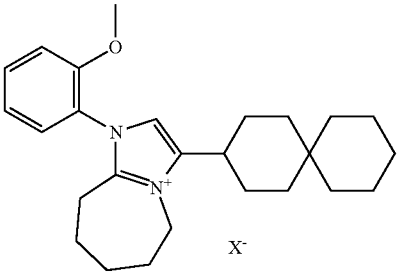 |
| 59 | 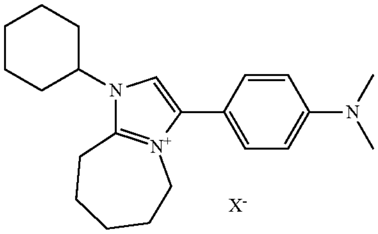 | 56 | 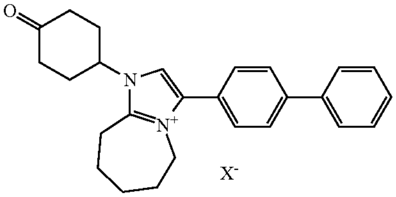 |
| 44 | 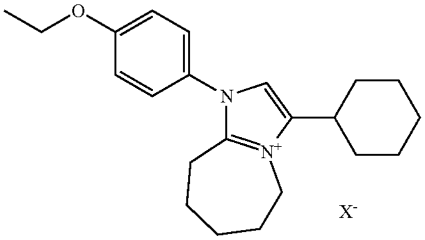 | 53 | 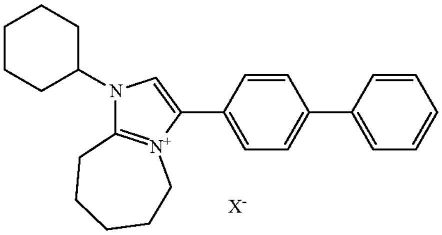 |
| 58 | 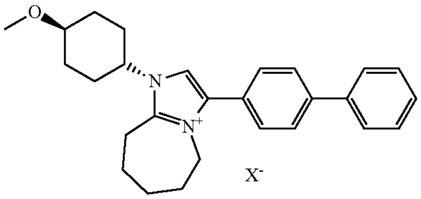 | 47 | 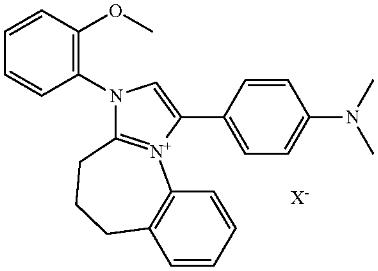 |
| 57 | 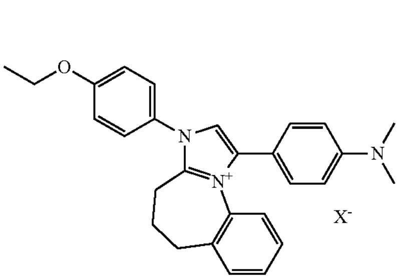 | 35 | 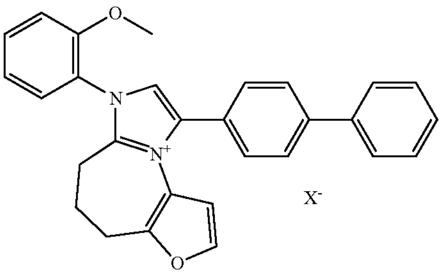 |

TABLE 2-continued
| Imidazolium compounds | | | |
|---|---|---|---|
| No. | Structure | No. | Structure |
| 9 | 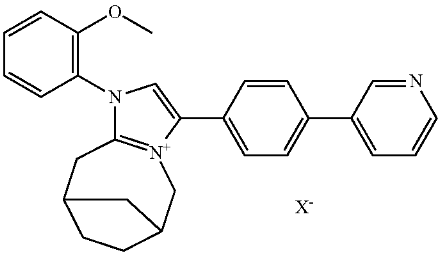 | 7 | 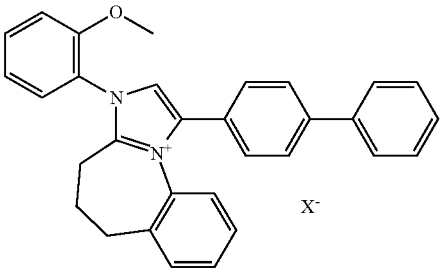 |
| 8 | 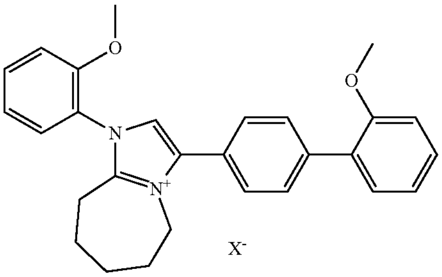 | 46 | 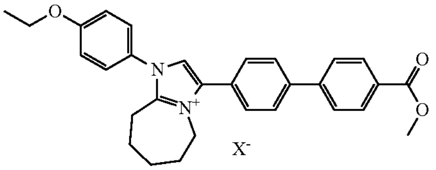 |
| 54 | 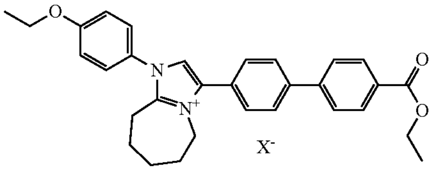 | 61 | 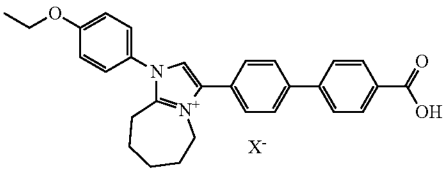 |
| 4 | 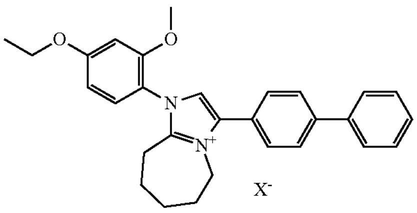 | 10 | 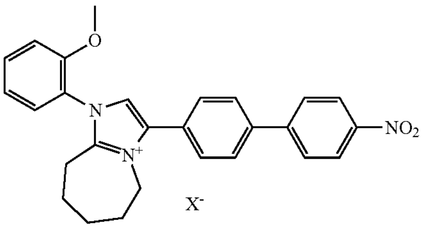 |
| 32 | 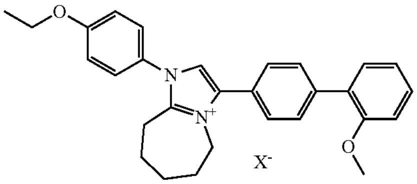 | 25 | 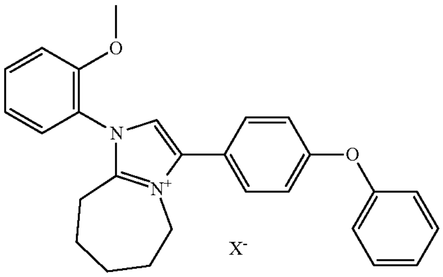 |
| 27 | 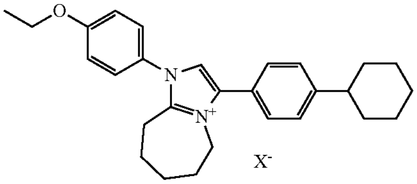 | 34 | 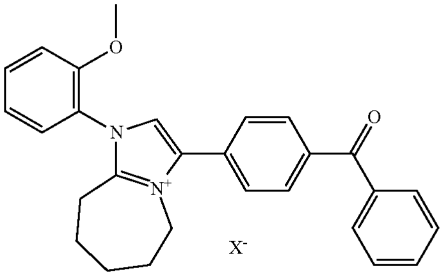 |

TABLE 2-continued

| Imidazolium compounds | | | |
|---|---|---|---|
| No. | Structure | No. | Structure |
| 36 | 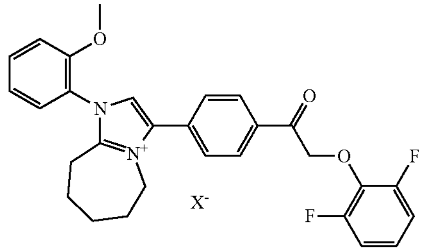 | 43 | 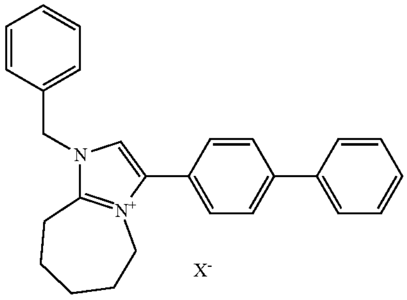 |
| 45 | 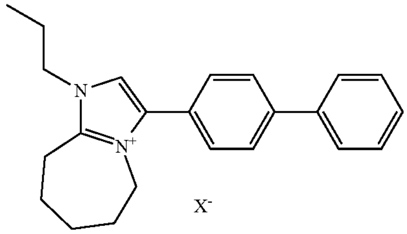 | 48 | 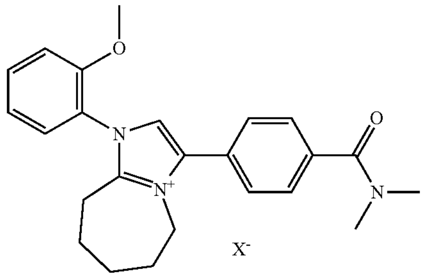 |
| 50 | 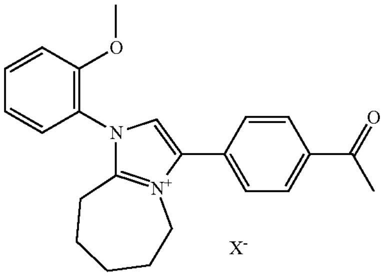 | 52 | 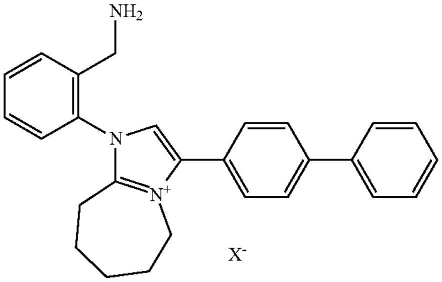 |
| 24 | 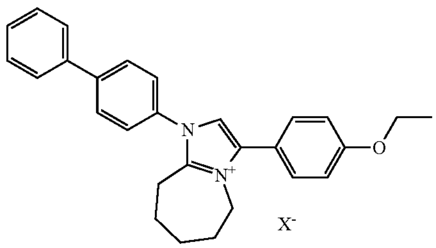 | 23 | 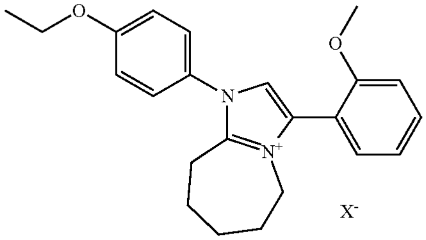 |

In certain embodiments of any one of formulae (VI)-(XB), or a compound of Table 2, the counter ion "X−" may be any convenient counterion. In certain cases, the counterion is selected from bromide, chloride, and trifluoroacetate.

In certain embodiments, the compound is described by the structure of one of the compounds of Table 1. In certain embodiments, the compound is described by the structure of one of the compounds of Table 2. It is understood that any of the compounds shown in Table 1, or 2 may be present in a salt form, such as a bromide salt, chloride salt, hydrobromide salt, hydrochloride salt, and trifluoroacetate salt (e.g., $CF_3COOH$ salt). In some cases, the salt form of the compound is a pharmaceutically acceptable salt.

In certain embodiments, the subject bicyclic imidazolium compound is not one of the following structures:

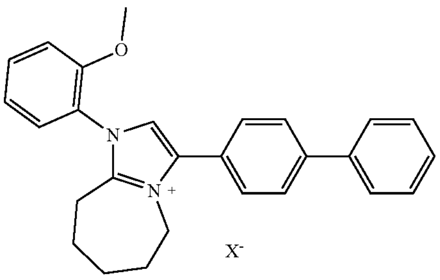

,

-continued

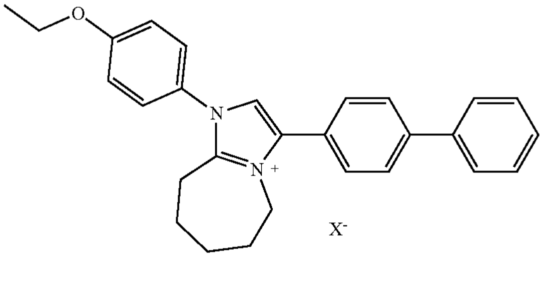

,

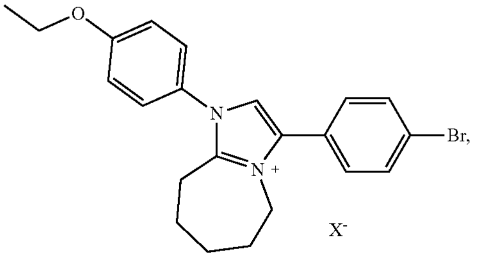

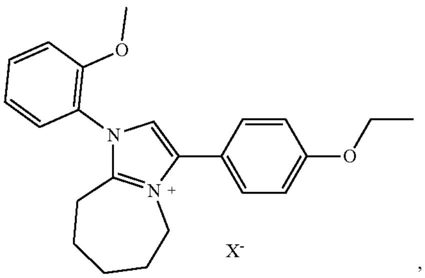

,

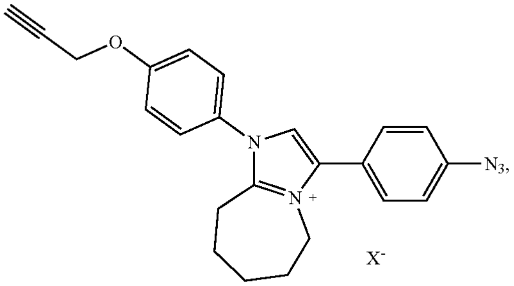

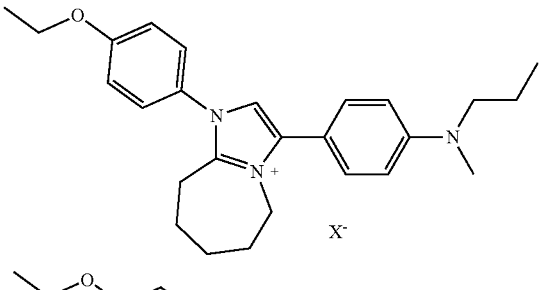

,

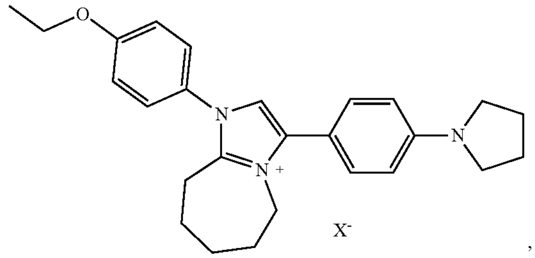

,

-continued

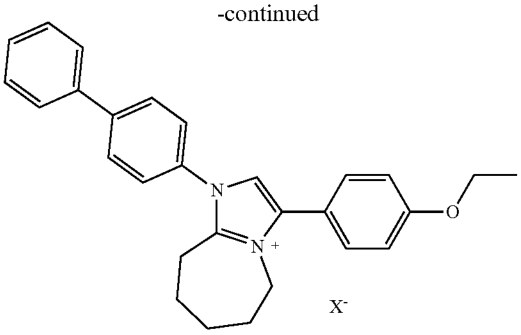

,

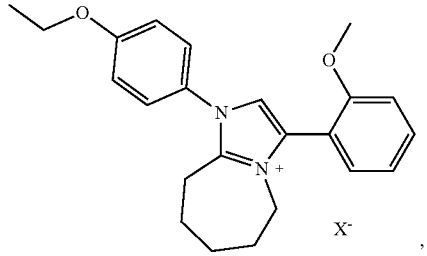

,

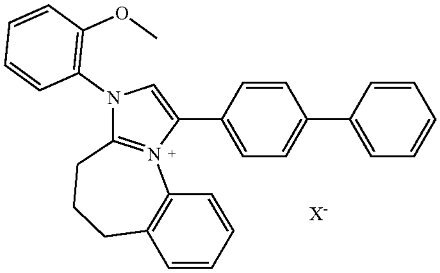

,

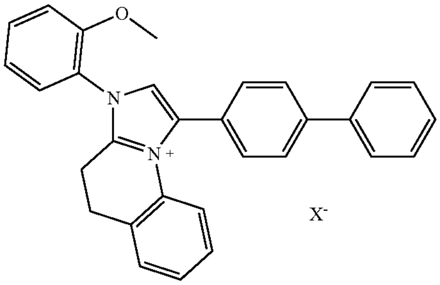

.

Aspects of the present disclosure include ALDH-inhibiting compounds, salts thereof (e.g., pharmaceutically acceptable salts), and/or solvate, hydrate and/or prodrug forms thereof. In addition, it is understood that, in any compound described herein having one or more chiral centers, if an absolute stereochemistry is not expressly indicated, then each center may independently be of R-configuration or S-configuration or a mixture thereof. It will be appreciated that all permutations of salts, solvates, hydrates, prodrugs and stereoisomers are meant to be encompassed by the present disclosure.

In some embodiments, the subject compounds, or a prodrug form thereof, are provided in the form of pharmaceutically acceptable salts. Compounds containing an amine or nitrogen containing heteroaryl group may be basic in nature and accordingly may react with any number of inorganic and organic acids to form pharmaceutically acceptable acid addition salts. Acids commonly employed to form such salts include inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-l,4-dioate, hexyne-l,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, 6-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts. In certain specific embodiments, pharmaceutically acceptable acid addition salts include those formed with mineral acids such as hydrochloric acid and hydrobromic acid, and those formed with organic acids such as fumaric acid and maleic acid.

In some embodiments, the subject compounds are provided in a prodrug form. "Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent. "Pro-moiety" refers to a form of protecting group that, when used to mask a functional group within an active agent, converts the active agent into a prodrug. In some cases, the pro-moiety will be attached to the drug via bond(s) that are cleaved by enzymatic or non-enzymatic means in vivo. Any convenient prodrug forms of the subject compounds can be prepared, e.g., according to the strategies and methods described by Rautio et al. ("Prodrugs: design and clinical applications", Nature Reviews Drug Discovery 7, 255-270 (February 2008)). In some cases, the pro-moiety is attached to a hydroxy or carboxylic acid group of the subject compounds. In certain cases, the pro-moiety is an acyl or substituted acyl group. In certain cases, the pro-moiety is an alkyl or substituted alkyl group, e.g., that forms an ester functional group when attached to a carboxylic acid group of the subject compounds.

In some embodiments, the subject compounds, prodrugs, stereoisomers or salts thereof are provided in the form of a solvate (e.g., a hydrate). The term "solvate" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

In some embodiments, the subject compounds are provided by oral dosing and absorbed into the bloodstream. In some embodiments, the oral bioavailability of the subject compounds is 30% or more. Modifications may be made to the subject compounds or their formulations using any convenient methods to increase absorption across the gut lumen or their bioavailability.

In some embodiments, the subject compounds are metabolically stable (e.g., remain substantially intact in vivo during the half-life of the compound). In certain embodiments, the compounds have a half-life (e.g., an in vivo half-life) of 5 minutes or more, such as 10 minutes or more, 12 minutes or more, 15 minutes or more, 20 minutes or more, 30 minutes or more, 60 minutes or more, 2 hours or more, 6 hours or more, 12 hours or more, 24 hours or more, or even more.

Methods

As summarized above, methods are provided for inhibiting an aldehyde dehydrogenase (ALDH). Aspects of the methods include methods of selectively inhibiting a particular ALDH-family member (e.g., ALDH1A1, ALDH1A3, and ALDH1B1). In some cases, the subject compounds are ALDH1B1-selective inhibitors. In some cases, the subject compounds are ALDH1A3-selective inhibitors. Methods of treating cancer are also provided. Aspects of the methods include inhibiting an ALDH family member in a cancer cell to reduce cancer stem cell proliferation.

ALDH Inhibition

The present disclosure provides compounds that function as inhibitors of aldehyde dehydrogenase (ALDH) activity; and pharmaceutical compositions comprising the compounds. The present disclosure provides compounds that function as inhibitors of cancer stem cell (CSC)-associated ALDHs. The present disclosure provides compounds that function as inhibitors of various ALDH isoforms, including but not limited to ALDH1A1, ALDH1A3, ALDH1B1, and ALDH3A1. In some cases, the ALDH isoform is an ALDH1 isoform. The present disclosure provides compounds that function as inhibitors of aldehyde dehydrogenase 1 family member B1 (ALDH1B1) activity. The present disclosure provides compounds that function as inhibitors of aldehyde dehydrogenase 1 family member A3 (ALDH1A3) activity. The present disclosure provides compounds that function as inhibitors of aldehyde dehydrogenase 1 family member A1 (ALDH1A1) activity. By inhibiting an ALDH it is meant that the activity of the enzyme is decreased by a factor of 2 or more, such as 3 or more, 5 or more, 10 or more, 100 or more, or 1000 or more, relative to its normal activity (e.g., relative to a positive control). In some instances, the types of cells in which the compounds exhibit activity are cancer cells, as described herein.

In one embodiment, there is provided a method of inhibiting an aldehyde dehydrogenase (ALDH), the method comprising: contacting a sample comprising an ALDH with a subject compound (e.g., as described herein) to inhibit the ALDH. In certain embodiments, the compound selectively inhibits an isoform of ALDH. In certain cases, the ALDH isoform is ALDH1B1.

Accordingly, provided herein is a method of selectively inhibiting ALDH1B1, the method comprising: contacting a sample comprising ALDH1B1 with a subject compound (e.g., as described herein) to inhibit ALDH1B1.

In some embodiments of the methods of selectively inhibiting ALDH1B1, the ALDH inhibitor compound is a compound of any one of the formulae (I)-(XB). In some cases, the ALDH inhibitor compound is any compound described in Table 1 or 2. In some embodiments of the methods of selectively inhibiting ALDH1B1, the compound is:

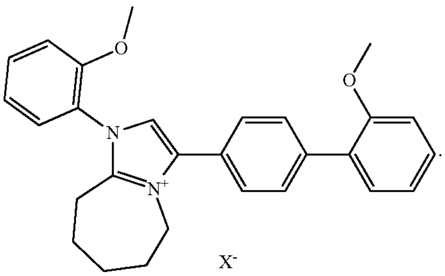 [SMILES: COc1ccccc1-c1ccc(-c2cn(-c3ccccc3OC)c3[n+]2CCCCC3)cc1 ; "X-"]

In certain other embodiments of the methods of selectively inhibiting ALDH1B1, the compound is selected from:

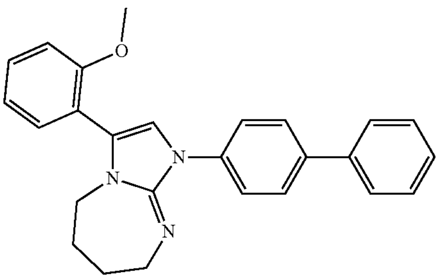

,

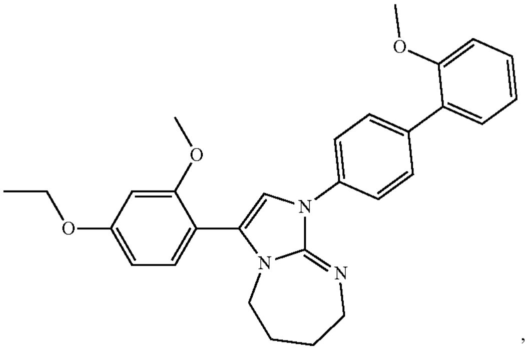

,

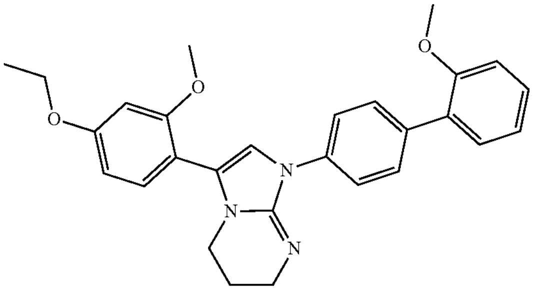

, and

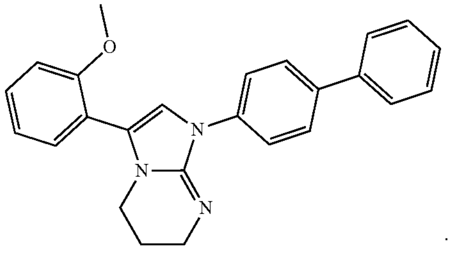

.

In certain embodiments, the compound selectively inhibits the ALDH isoform ALDH1A3. Accordingly, also provided herein is a method of selectively inhibiting ALDH1A3, the method comprising: contacting a sample comprising ALDH1A3 with a subject compound (e.g., as described herein) to inhibit ALDH1A3.

In some embodiments of the methods of selectively inhibiting ALDH1A3, the ALDH inhibitor compound is a compound of any one of the formulae (I)-(XB). In some cases, the ALDH inhibitor compound is any compound described in Table 1 or 2. In some embodiments of the methods of selectively inhibiting ALDH1A3, the compound is selected from:

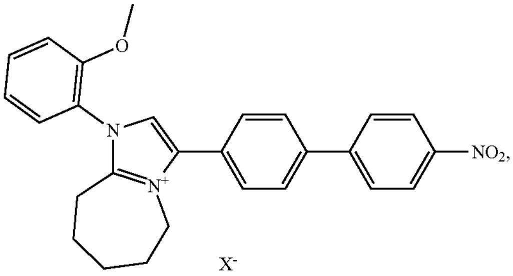

and

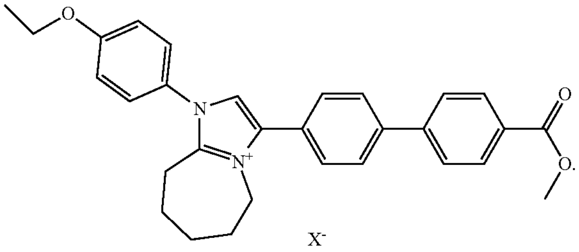

The methods of the present disclosure can target cancer cells, e.g., cancer stem cells (CSCs). Cancer cells of interest which can be targeted according to the subject methods include a wide variety of cancer cells. In some instances, the cancer cell is selected from colorectal cancer, bladder, breast, colon, endometrial, cervix, testicle, liver, lung, non-small cell lung cancer (NSCLC), ovarian, prostate, pancreatic, brain, thyroid, stomach, kidney, melanoma and sarcoma cancer cells.

Aspects of this disclosure include assessing or measuring the level of expression of a ALDH enzyme in a target cell. In some cases, the assessing or measuring step includes determining whether the target cells have an elevated level of expression of an ALDH enzyme. As used herein, the terms "elevated level of expression", "overexpression" and "overexpressed" are used interchangeably and refer to a level of expression in a target cell that is 20% or more than the native or basal level of expression in a control cell, such as 30% or more, 40% or more, 2-fold greater or more, 5-fold greater or more, 10-fold greater or more, 30-fold greater or more, 100-fold greater or more or 1000-fold greater or more, as compared to the native or basal level of expression in a control cell. In some cases, the control cell is one or more control cells from a plurality of subjects. In certain cases, the control cell is one or more control cells from a plurality of cells of the same type as the target cell from a plurality of subjects. In some cases, the control cells are normal cells.

The methods that may be employed in measuring or determining levels of expression in a cell are numerous and include but are not limited to cellular assays in which a cellular phenotype is measured, e.g., gene expression assays. The methods can be qualitative or quantitative. Expression levels can be determined directly or indirectly. In some cases, the gene copy number for the gene of interest in the target cells is measured. In certain cases, the gene copy number of ALDH is determined, e.g., ALDH1A1, ALDH1A2, ALDH1A3, ALDH1B1, ALDH1L1, ALDH1L2, ALDH2, ALDH3A1, ALDH3A2, ALDH3B1, ALDH3B2, ALDH4A1, ALDH5A1, ALDH6A1, ALDH7A1, ALDH8A1, ALDH9A1, ALDH16A1, ALDH18A1.

Aspects of this disclosure include assessing or measuring the level of activity of an ALDH enzyme in a target cell. In some cases, the assessing or measuring step includes determining whether the target cells have an elevated level of activity of an ALDH. The term "elevated level of activity" refers to a level of activity in a target cell that is 20% or more than the native or basal level of activity in a control cell, such as 30% or more, 40% or more, 2-fold greater or more, 5-fold greater or more, 10-fold greater or more, 30-fold greater or more, 100-fold greater or more or 1000-fold greater or more, as compared to the native or basal level of activity in a control cell. In some cases, the control cell is one or more control cells from a plurality of subjects. In certain cases, the control cell is one or more control cells from a plurality of cells of the same type as the target cell from a plurality of subjects. In some cases, the control cells are normal cells.

The methods that may be employed in determining ALDH activity are numerous, and include but are not limited to cell-free assays, e.g., binding assays; assays using purified enzymes, measurements of ALDH levels, cellular assays in which a cellular phenotype is measured, e.g., gene expression assays; and in vivo assays that involve a particular animal (which, in certain embodiments may be an animal model for a condition dependent on ALDH activity). In some cases, the target cancer cells have an elevated level of ALDH1B1 activity. In some embodiments of the subject methods, the target cancer cells are cells that are sensitive to ALDH1B1 inhibition. In certain cases, these ALDH1B1 inhibition-sensitive cells do not exhibit an elevated level of expression or activity of any other ALDH isoform. In some embodiments, the ALDH inhibitors are inhibitors of ALDH1A3. In some embodiments, the ALDH inhibitors have a ALDH inhibition profile that reflects activity against two or more ALDH isoforms. In some embodiments, the ALDH inhibitors specifically inhibit both ALDH1B1 and ALDH1A3. In some embodiments, the ALDH inhibitors specifically inhibit an ALDH enzyme without undesired inhibition of other protein enzymes. In some embodiments, the ALDH inhibitors specifically inhibit an ALDH1B1 without undesired inhibition of any other ALDH isoform. In some embodiments, the ALDH inhibitors specifically inhibit ALDH1A3 without undesired inhibition of any other ALDH isoform.

ALDH inhibition can be as determined by an inhibition assay, e.g., by an assay that determines the level of activity of the enzyme either in a cell-free system or in a cell after treatment with a subject compound, relative to a control, by measuring the $IC_{50}$ or $EC_{50}$ value, respectively. In certain embodiments, the subject compounds have an $IC_{50}$ value (or $EC_{50}$ value) of 10 μM or less, such as 3 μM or less, 1 μM or less, 500 nM or less, 300 nM or less, 200 nM or less, 100 nM or less, 50 nM or less, 30 nM or less, 10 nM or less, 5 nM or less, 3 nM or less, 1 nM or less, or even lower.

In some embodiments, the enzymatic and anti-cancer activities of the subject compounds diverge. In some embodiments, the anti-cancer activity of the subject compounds depends on a combination of inhibition of both ALDH1B1 and ALDH1A3, or a combination of inhibition of ALDH isoforms. The subject compound may have increased specificity for one isoform of these ALDH family members. In some cases, the compound may have increased specificity for ALDH1B1. In some other cases, the compound may have increased specificity for ALDH1A3. In some cases, the compound may have increased specificity for ALDH1A1.

In some embodiments, a subject ALDH inhibitor selectively inhibits an enzymatic activity of a particular ALDH isozyme. For example, in some embodiments, a subject ALDH inhibitor selectively inhibits an enzymatic activity of ALDH1B1. For example, in some embodiments, a subject compound inhibits an enzymatic activity of ALDH1B1, but does not substantially inhibit the same enzymatic activity of an ALDH isozyme other than ALDH1B1, e.g., the ALDH inhibitor inhibits an enzymatic activity of an ALDH isozyme other than ALDH1B1, if at all, by no more than about 15%, e.g., by less than 15%, less than 10%, less than 5%, or less than 1%. In some embodiments, a subject ALDH inhibitor selectively inhibits an enzymatic activity of ALDH1A3. For example, in some embodiments, a subject compound inhibits an enzymatic activity of ALDH1A3, but does not substantially inhibit the same enzymatic activity of an ALDH isozyme other than ALDH1A3, e.g., the ALDH inhibitor inhibits an enzymatic activity of an ALDH isozyme other than ALDH1B1, if at all, by no more than about 15%, e.g., by less than 15%, less than 10%, less than 5%, or less than 1%.

In certain embodiments, the ALDH inhibitors have no significant effect on the viability of a normal mammalian cell, as determined by a cell cytotoxicity assay, e.g., as determined by administering a compound to primary human liver cells and determining the number of viable cells present. The compound may exhibit a % cell viability, as compared to a control (e.g., a DMSO control), of 15% or more, such as 20% or more, 30% or more, 40% or more, 50% or more, 60% or more, 70% or more, 80% or more, 90% or more, 100% or more, 120% or more, or even higher. The subject compounds may exhibit a $CC_{50}$ value (the concentration at which 50% of the cells remain viable) of 1 nM or higher, such as 100 nM or higher, 300 nM or higher, 1 μM or higher, 3 μM or higher, 5 μM or higher, 10 μM or higher, 20 μM or higher, 30 μM or higher, 50 μM or higher, or even higher.

In certain embodiments, the ALDH inhibitors have a therapeutic index (e.g., the ratio of a compound's cytotoxicity (e.g., normal cell cytotoxicity, CC50) to bioactivity (e.g., anticancer activity, EC50—the concentration at which 50% of the cancer cells are inhibited)) that is 2 or more, such as 5 or more, such as 10 or more, such as 20 or more, 50 or more, 100 or more, 200 or more, 300 or more, 400 or more, 500 or more, or even more.

As summarized above, aspects of the disclosure include methods of inhibiting ALDH in a cell of interest. The compound (e.g., as described herein) may inhibit at least one activity of the ALDH in the range of 10% to 100%, e.g., by 10% or more, 20% or more, 30% or more, 40% or more, 50% or more, 60% or more, 70% or more, 80% or more, or 90% or more. In certain assays, a ALDH inhibitor may inhibit its target with an $IC_{50}$ (the concentration needed to inhibit 50% of the enzyme activity) of $1\times10^{-6}$ M or less (e.g., $1\times10^{-6}$ M or less, $1\times10^{-7}$ M or less, $1\times10^{-8}$ M or less, $1\times10^{-9}$ M or less, $1\times10^{-10}$ M or less, or $1\times10^{-11}$ M or less).

The protocols that may be employed in determining ALDH activity are numerous, and include but are not limited to cell-free assays, e.g., binding assays; assays using purified enzymes, cellular assays in which ALDH levels are measured or a cellular phenotype is measured, e.g., gene expression assays; and in vivo assays that involve a particular animal (which, in certain embodiments may be an animal model for a condition dependent on ALDH activity).

In some embodiments, the subject method is an in vitro method that includes contacting a sample with a compound that specifically inhibits a target ALDH. In certain embodiments, the sample is suspected of containing the ALDH and the subject method further comprises evaluating whether the compound inhibits the ALDH, or an ALDH dependent function such as cancer cell growth. In certain embodiments, the ALDH is ALDH1B1. In certain embodiments, the ALDH is ALDH1A3. In certain embodiments, the ALDH is ALDH1A1. In another embodiment of the subject method, the sample is known to contain the target ALDH.

Methods of Treating Cancer

In some embodiments, the subject method is an in vivo method that includes administering to a subject an effective amount of a compound that specifically inhibits an ALDH. An "effective amount" is an amount of a compound that, when administered to an individual in one or more doses, in monotherapy or in combination therapy, is effective to inhibit an ALDH by at least about 20% (20% inhibition), such as at least about 30% (30% inhibition), at least about 40% (40% inhibition), at least about 50% (50% inhibition), at least about 60% (60% inhibition), at least about 70% (70% inhibition), at least about 80% (80% inhibition), or at least about 90% (90% inhibition), compared to the ALDH activity in the individual in the absence of treatment with the compound, or alternatively, compared to the ALDH activity in the individual before or after treatment with the compound.

Accordingly, as disclosed herein there is provided method of treating cancer, the method comprising: administering to a subject with cancer a therapeutically effective amount of a pharmaceutical composition including one or more subject compounds (e.g., as described herein). In some cases, the cancer is a solid tumor cancer, and the administering inhibits the tumor growth. In some cases, the administering inhibits tumor growth by at least about 20%, such as at least about 30%, at least about 40%, at least about 50%, at least about 60%, at least about 70%, at least about 80%, or at least about 90%, compared to the solid tumor in the absence of treatment.

The subject may be one who has a cancer as described herein. Cancers of interest which can be treated according to the subject methods include, but are not limited to, colorectal, bladder, breast, endometrial, liver, cervical, testicular, lung, non-small cell lung cancer (NSCLC), ovarian, prostate, pancreatic, brain, melanoma, sarcoma, thyroid, stomach and kidney cancer. In some instances, the cancer is colorectal cancer. In some instances, the cancer is pancreatic cancer. In some instances, the cancer is breast cancer. In certain cases, the breast cancer is a breast adenocarcinoma. In some instances, the cancer is a melanoma. In some instances, the cancer is glioblastoma (GBM).

In some embodiments of the methods, the cancer is colorectal cancer. In some cases, the method includes administering a subject compound (e.g., as described herein) to inhibit colorectal cancer spheroid growth. In some cases, the administering inhibits colorectal cancer spheroid growth by at least about 20%, such as at least about 30%, at least about 40%, at least about 50%, at least about 60%, at least about 70%, at least about 80%, or at least about 90%, compared to the solid tumor in the absence of treatment.

By colorectal cancer is meant cancer of the colon or rectum. In some instances, colorectal cancer develops in the ascending colon, i.e., where the small intestine attaches to the colon and extends upward on the right side of the abdomen. In some instances, colorectal cancer develops in the transverse colon, i.e., the portion of the colon that crosses the body from the right to the left side. In some instances, colorectal cancer develops in the descending colon, i.e., the portion of the colon that continues downward on the left side. In some instances, colorectal cancer develops in the sigmoid colon, i.e., the "S" shaped portion of the colon that joins the rectum. In some instances, colorectal cancer develops in the rectum, i.e., the final straight portion of the large intestine that joins the anus.

In some instances, the cancer is a chemotherapeutic resistant cancer, e.g., a cancer which exhibits reduced or no response to chemotherapeutic agents, such as those listed below. In some instances, the cancer is a 5-fluorouracil (5-FU) resistant cancer. In such instances, e.g., where a patient has not responded to chemotherapeutic treatment, e.g., 5-FU treatment, the methods may include administering an effective amount of a compound of the invention to treat the patient for the chemotherapeutic resistant cancer.

In some embodiments, a "therapeutically effective amount" is an amount of a compound that, when administered to an individual in one or more doses, in monotherapy or in combination therapy, is effective to decrease tumor burden in the subject by at least about 20%, such as at least about 30%, at least about 40%, at least about 50%, at least about 60%, at least about 70%, at least about 80%, or at least about 90%, compared to tumor burden in the individual in the absence of treatment with the compound, or alternatively, compared to the tumor burden in the subject before treatment with the compound. As used herein the term "tumor burden" refers to the total mass of tumor tissue carried by a subject with cancer.

In some embodiments, a "therapeutically effective amount" is an amount of a subject compound that, when administered to an individual in one or more doses, in monotherapy or in combination therapy, is effective to reduce the dose of radiotherapy required to observe tumor shrinkage in the subject by at least about 20%, at least about 30%, at least about 40%, at least about 50%, at least about 60%, at least about 70%, at least about 80%, or at least about 90%, compared to the dose of radiotherapy required to observe tumor shrinkage in the individual in the absence of treatment with the compound.

In some embodiments, a "therapeutically effective amount" is an amount of a compound that, when administered to an individual in one or more doses, in monotherapy or in combination therapy, is effective to decrease metastases burden in the subject by at least about 20%, such as at least about 30%, at least about 40%, at least about 50%, at least about 60%, at least about 70%, at least about 80%, or at least about 90%, compared to metastases burden in the individual in the absence of treatment with the compound, or alternatively, compared to the metastases burden in the subject before treatment with the compound. As used herein the term "metastases burden" refers to the total mass or number of metastases tissue carried by a subject with cancer.

In some embodiments, an effective amount of a compound is an amount that ranges from about 50 ng/mL to about 50 μg/mL (e.g., from about 50 ng/mL to about 40 μg/mL, from about 30 ng/mL to about 20 μg/mL, from about 50 ng/mL to about 10 μg/mL, from about 50 ng/mL to about 1 μg/mL, from about 50 ng/mL to about 800 ng/mL, from about 50 ng/mL to about 700 ng/mL, from about 50 ng/mL to about 600 ng/mL, from about 50 ng/mL to about 500 ng/mL, from about 50 ng/mL to about 400 ng/mL, from about 60 ng/mL to about 400 ng/mL, from about 70 ng/mL to about 300 ng/mL, from about 60 ng/mL to about 100 ng/mL, from about 65 ng/mL to about 85 ng/mL, from about 70 ng/mL to about 90 ng/mL, from about 200 ng/mL to about 900 ng/mL, from about 200 ng/mL to about 800 ng/mL, from about 200 ng/mL to about 700 ng/mL, from about 200 ng/mL to about 600 ng/mL, from about 200 ng/mL to about 500 ng/mL, from about 200 ng/mL to about 400 ng/mL, or from about 200 ng/mL to about 300 ng/mL).

In some embodiments, an effective amount of a compound is an amount that ranges from about 10 pg to about 100 mg, e.g., from about 10 pg to about 50 pg, from about 50 pg to about 150 pg, from about 150 pg to about 250 pg, from about 250 pg to about 500 pg, from about 500 pg to about 750 pg, from about 750 pg to about 1 ng, from about 1 ng to about 10 ng, from about 10 ng to about 50 ng, from about 50 ng to about 150 ng, from about 150 ng to about 250 ng, from about 250 ng to about 500 ng, from about 500 ng to about 750 ng, from about 750 ng to about 1 μg, from about 1 μg to about 10 μg, from about 10 μg to about 50 μg, from about 50 μg to about 150 μg, from about 150 μg to about 250 μg, from about 250 μg to about 500 μg, from about 500 μg to about 750 μg, from about 750 μg to about 1 mg, from about 1 mg to about 50 mg, from about 1 mg to about 100 mg, or from about 50 mg to about 100 mg. The amount can be a single dose amount or can be a total daily amount. The total daily amount can range from 10 pg to 100 mg, or can range from 100 mg to about 500 mg, or can range from 500 mg to about 1000 mg or 3000 mg.

In some embodiments, a single dose of a compound is administered. In other embodiments, multiple doses are administered. Where multiple doses are administered over a period of time, the compound can be administered twice daily (bid), daily (qd), every other day (qod), every third day, once per week(qw), three times per week (tiw), or twice per week (biw) over a period of time. For example, a compound is administered bid, qd, qod, tiw, or biw over a period of from one day to about 2 years or more. For example, a compound is administered at any of the aforementioned frequencies for one week, two weeks, one month, two months, six months, one year, or two years, or more, depending on various factors. In some embodiments, the compound may be administered orally, intravenously, subcutaneously, intramuscularly, via inhalation, topically, or sublingually, among other routes of administration, including depot administration. In some embodiments, the compound is administered in combination with an inhibitor of its metabolism, such as an inhibitor of cytochrome P450 3A/4 (e.g. ritonavir or cobicistat). In some embodiments, the compound may be administered in courses wherein "drug holidays" are allowed that may last from 1-7 days.

Administration of a therapeutically effective amount of a subject compound to an individual with cancer can result in one or more of: 1) a reduction in tumor burden; 2) a reduction in the dose of radiotherapy required to effect tumor shrinkage; 3) a reduction in the spread of a cancer from one location to another in an individual; 4) a reduction of morbidity or mortality in clinical outcomes; 5) shortening the total length of treatment when combined with other anti-cancer agents; 6) a decrease in the size or number of metastases; and 7) an improvement in an indicator of disease response (e.g., a reduction in one or more symptoms of cancer). Any of a variety of methods can be used to determine whether a treatment method is effective. For example, a biological sample obtained from an individual who has been treated with a subject method can be assayed, or an imaging study may be performed.

Any of the ALDH inhibitor compounds described herein can be utilized in the subject methods of treatment. In certain instances, the ALDH inhibitor is of any one of formulae (I) to (XB). In certain cases, the compound is one of the compounds of Table 1, or 2.

In some embodiments, the compound specifically inhibits an ALDH1 family member. In some embodiments, the compound specifically inhibits ALDH1B1. In some embodiments, the compound specifically inhibits ALDH1A3. In some embodiments, the compound modulates the activity of a cancer cell that includes an elevated expression of an ALDH isoform. In some instances, the cancer cells include chromosome amplification of an ALDH gene (such as ALDH1B1 or ALDH1A3).

In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys). The subject may be in need of treatment for cancer. In some instances, the subject methods include diagnosing cancer, including any one of the cancers described herein. In some embodiments, the compound is administered as a pharmaceutical preparation.

In certain embodiments, the ALDH inhibitor is a modified compound that includes a label, and the method further includes detecting the label in the subject. The selection of the label depends on the means of detection. Any convenient labeling and detection systems may be used in the subject methods, see e.g., Baker, "The whole picture," Nature, 463, 2010, p 977-980. In certain embodiments, the compound includes a fluorescent label suitable for optical detection. In certain embodiments, the compound includes a radiolabel for detection using positron emission tomography (PET) or single photon emission computed tomography (SPECT). In some cases, the compound includes a paramagnetic label suitable for tomographic detection. The subject compound may be labeled, as described above, although in some methods, the compound is un-labeled and a secondary labeling agent is used for imaging.

Combination Therapies

The ALDH inhibitors disclosed herein can be administered to a subject alone or in combination with an additional, i.e., second, active agent. Combination therapeutic methods where the ALDH inhibitors may be used in combination with a second active agent or an additional therapy, e.g., radiation therapy. The terms "agent," "compound," and "drug" are used interchangeably herein. For example, ALDH inhibitors can be administered alone or in conjunction with one or more other drugs, such as drugs employed in the treatment of diseases of interest, including but not limited to, immunomodulatory diseases and conditions and cancer. In some embodiments, the subject method further includes co-administering concomitantly or in sequence a second agent, e.g., a small molecule, a chemotherapeutic, an antibody, an antibody fragment, an antibody-drug conjugate, an aptamer, a protein, or a checkpoint inhibitor. In some embodiments, the method further includes performing radiation therapy on the subject.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

"Concomitant administration" of a known therapeutic drug or additional therapy with a pharmaceutical composition of the present disclosure means administration of the compound and second agent or additional therapy at such time that both the known drug and the composition of the present invention will have a therapeutic effect. Such concomitant administration may involve concurrent (i.e. at the same time), prior, or subsequent administration of the drug with respect to the administration of a subject compound. Routes of administration of the two agents may vary, where representative routes of administration are described in greater detail below. A person of ordinary skill in the art would have no difficulty determining the appropriate timing, sequence and dosages of administration for particular drugs or therapies and compounds of the present disclosure.

In some embodiments, the compounds (e.g., an ALDH inhibitor and the at least one additional compound or therapy) are administered to the subject within twenty-four hours of each other, such as within 12 hours of each other, within 6 hours of each other, within 3 hours of each other, or within 1 hour of each other. In certain embodiments, the compounds are administered within 1 hour of each other. In certain embodiments, the compounds are administered substantially simultaneously. By administered substantially simultaneously is meant that the compounds are administered to the subject within about 10 minutes or less of each other, such as 5 minutes or less, or 1 minute or less of each other.

Also provided are pharmaceutical preparations of the ALDH inhibitor and the second active agent. In pharmaceutical dosage forms, the compounds may be administered in the form of their pharmaceutically acceptable salts, or they may also be used alone or in appropriate association, as well as in combination, with other pharmaceutically active compounds.

In conjunction with any of the subject methods, the ALDH inhibitors (e.g., as described herein) (or pharmaceutical compositions comprising such compounds) can be administered in combination with another drug designed to reduce or prevent inflammation, treat or prevent chronic inflammation or fibrosis, or treat cancer. In each case, the ALDH inhibitor can be administered prior to, at the same time as, or after the administration of the other drug. In certain cases, the cancer is selected from colorectal, adrenal, liver, kidney, bladder, breast, colon, gastric, ovarian, cervical, uterine, esophageal, prostate, pancreatic, lung (both small cell and non-small cell), thyroid, carcinomas, sarcomas, glioma, glioblastomas, melanoma and various head and neck tumors.

For the treatment of cancer, the ALDH inhibitors can be administered in combination with a chemotherapeutic agent selected from the group consisting of alkylating agents, nitrosoureas, antimetabolites, antitumor antibiotics, plant (vinca) alkaloids, steroid hormones, taxanes, nucleoside analogs, steroids, anthracyclines, thyroid hormone replacement drugs, thymidylate-targeted drugs, Chimeric Antigen Receptor/T cell therapies, Chimeric Antigen Receptor/NK cell therapies, apoptosis regulator inhibitors (e.g., B cell CLL/lymphoma 2 (BCL-2) BCL-2-like 1 (BCL-XL) inhibitors), CARP-1/CCAR1 (Cell division cycle and apoptosis regulator 1) inhibitors, colony-stimulating factor-1 receptor (CSF1R) inhibitors, CD47 inhibitors, cancer vaccine (e.g., a Th17-inducing dendritic cell vaccine, or a genetically modified tyrosinase such as Oncept®) and other cell therapies.

Specific chemotherapeutic agents of interest include, but are not limited to, Gemcitabine, Docetaxel, Bleomycin, Erlotinib, Gefitinib, Lapatinib, Imatinib, Dasatinib, Nilotinib, Bosutinib, Crizotinib, Ceritinib, Trametinib, Bevacizumab, Sunitinib, Sorafenib, Trastuzumab, Ado-trastuzumab emtansine, Rituximab, Ipilimumab, Rapamycin, Temsirolimus, Everolimus, Methotrexate, Doxorubicin, Abraxane, Folfirinox, Cisplatin, Carboplatin, 5-fluorouracil, Teysumo, Paclitaxel, Prednisone, Levothyroxine, Pemetrexed, navitoclax, and ABT-199. Peptidic compounds can also be used. Cancer chemotherapeutic agents of interest include, but are not limited to, dolastatin and active analogs and derivatives thereof; and auristatin and active analogs and derivatives thereof (e.g., Monomethyl auristatin D (MMAD), monomethyl auristatin E (MMAE), monomethyl auristatin F (MMAF), and the like). See, e.g., WO 96/33212, WO 96/14856, and U.S. Pat. No. 6,323,315. Suitable cancer chemotherapeutic agents also include maytansinoids and active analogs and derivatives thereof (see, e.g., EP 1391213; and Liu et al (1996) Proc. Natl. Acad. Sci. USA 93:8618-8623); duocarmycins and active analogs and derivatives thereof (e.g., including the synthetic analogues, KW-2189 and CB 1-TM1); and benzodiazepines and active analogs and derivatives thereof (e.g., pyrrolobenzodiazepine (PBD).

In some embodiments, the ALDH inhibitors can be administered in combination with a chemotherapeutic agent to treat cancer. In certain cases, the chemotherapeutic agent is Gemcitabine. In some cases, the chemotherapeutic agent is Docetaxel. In some cases, the chemotherapeutic agent is Abraxane.

For the treatment of cancer (e.g., solid tumor cancer), the ALDH inhibitors can be administered in combination an immunotherapeutic agent. An immunotherapeutic agent is any convenient agent that finds use in the treatment of disease by inducing, enhancing, or suppressing an immune response. In some cases, the immunotherapeutic agent is an immune checkpoint inhibitor. Any convenient checkpoint inhibitors can be utilized, including but not limited to, cytotoxic T-lymphocyte-associated antigen 4 (CTLA-4) inhibitors, programmed death 1 (PD-1) inhibitors and PD-L1 inhibitors. In certain instances, the checkpoint inhibitor is selected from a cytotoxic T-lymphocyte-associated antigen 4 (CTLA-4) inhibitor, a programmed death 1 (PD-1) inhibitor and a PD-L1 inhibitor. Exemplary checkpoint inhibitors of interest include, but are not limited to, ipilimumab, pembrolizumab and nivolumab. In certain embodiments, for treatment of cancer and/or inflammatory disease, the immunomodulatory polypeptide(s) can be administered in combination with a colony-stimulating factor-1 receptor (CSF1R) inhibitor. CSF1R inhibitors of interest include, but are not limited to, emactuzumab.

Any convenient cancer vaccine therapies and agents can be used in combination with the ALDH inhibitors, compositions and methods. For treatment of cancer, e.g., ovarian cancer, the ALDH inhibitors can be administered in combination with a vaccination therapy, e.g., a dendritic cell (DC)

vaccination agent that promotes Th1/Th17 immunity. Th17 cell infiltration correlates with markedly prolonged overall survival among ovarian cancer patients. In some cases, the ALDH inhibitor compound finds use as adjuvant treatment in combination with Th17-inducing vaccination.

Also of interest are agents that are CARP-1/CCAR1 (Cell division cycle and apoptosis regulator 1) inhibitors, including but not limited to those described by Rishi et al., Journal of Biomedical Nanotechnology, Volume 11, Number 9, September 2015, pp. 1608-1627(20), ENPP1 inhibitors, including but not limited to those described by Carozza et al, and CD47 inhibitors, including, but not limited to, anti-CD47 antibody agents such as Hu5F9-G4.

In certain instances, the combination provides an enhanced effect relative to either component alone; in some cases, the combination provides a supra-additive or synergistic effect relative to the combined or additive effects of the components. A variety of combinations of the subject compounds and the chemotherapeutic agent may be employed, used either sequentially or simultaneously. For multiple dosages, the two agents may directly alternate, or two or more doses of one agent may be alternated with a single dose of the other agent, for example. Simultaneous administration of both agents may also be alternated or otherwise interspersed with dosages of the individual agents. In some cases, the time between dosages may be for a period from about 1-6 hours, to about 6-12 hours, to about 12-24 hours, to about 1-2 days, to about 1-2 week or longer following the initiation of treatment.

Compositions

Aspects of the invention also include compositions, e.g., pharmaceutical compositions comprising a subject compound (e.g., as described herein), and a pharmaceutically acceptable excipient.

The herein-discussed compounds can be formulated using any convenient excipients, reagents and methods. Compositions are provided in formulation with a pharmaceutically acceptable excipient(s). A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, the subject compound is formulated in an aqueous buffer. Suitable aqueous buffers include, but are not limited to, acetate, succinate, citrate, and phosphate buffers varying in strengths from 5 mM to 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures. In some embodiments, the subject compound is formulated for sustained release. In some embodiments, the subject compound is formulated for depot release.

Combination Pharmaceutical Compositions for Treating Cancer

In some embodiments, the ALDH inhibitor and a second active agent (e.g., as described herein), e.g. a small molecule, a chemotherapeutic, an antibody, an antibody fragment, an antibody-drug conjugate, an aptamer, or a protein, etc. are administered to individuals in a formulation (e.g., in the same or in separate formulations) with a pharmaceutically acceptable excipient(s). In some embodiments, the second active agent is a checkpoint inhibitor, e.g., a cytotoxic T-lymphocyte-associated antigen 4 (CTLA-4) inhibitor, a programmed death 1 (PD-1) inhibitor, or a PD-L1 inhibitor.

In another aspect, a pharmaceutical composition is provided, comprising, or consisting essentially of, a subject ALDH inhibitor, or a pharmaceutically acceptable salt, isomer, tautomer or prodrug thereof, and further comprising one or more additional anti-cancer agents of interest. Any convenient anti-cancer agents can be utilized in the subject methods in conjunction with the subject compounds. The subject compounds may be administered in a unit dosage form and may be prepared by any methods well known in the art. Such methods include combining the subject compound with a pharmaceutically acceptable carrier or diluent which constitutes one or more accessory ingredients. A pharmaceutically acceptable carrier is selected on the basis of the chosen route of administration and standard pharmaceutical practice. Each carrier must be "pharmaceutically acceptable" in the sense of being compatible with the other ingredients of the formulation and not injurious to the subject. This carrier can be a solid or liquid and the type is generally chosen based on the type of administration being used.

Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also good carriers.

Any drug delivery device or system that provides for the dosing regimen of the instant disclosure can be used. A wide variety of delivery devices and systems are known to those skilled in the art.

Although such may not be necessary, compounds and agents described herein can optionally be targeted to the site of cancer, using any known targeting means. The compounds of the disclosure may be formulated with a wide variety of compounds that have been demonstrated to target compounds to the site of cancer. The terms "targeting to the site of cancer" and "cancer targeted" refer to targeting of a compound to a site of cancer, such that at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, or more, of the compound administered to the subject enters the site of cancer.

Subjects Amenable to Treatment Using the Compounds of the Disclosure

Individuals who have been clinically diagnosed as having cancer are suitable for treatment with the methods of the present disclosure. In particular embodiments of interest, individuals of interest for treatment according to the disclosure have detectable cancer. Any convenient methods may be used to determine whether subjects who have cancer are suitable for treatment using the subject methods. The effectiveness of the anti-cancer treatment may be determined using any convenient method. For example, whether a subject method is effective in treating cancer can be determined by measuring amelioration of one or more symptoms, decrease in tumor or metastasis size on imaging, or by measuring cancer cells in a biological sample of the subject being treated.

In certain embodiments, the individual has been diagnosed with colorectal cancer. In some instances, the individual has a clinically significant rate of colorectal polyp formation, i.e. an above-average rate of polyp formation over a healthy individual, e.g. due to any syndrome or cause that increases colorectal polyp formation. For example, methods of the present disclosure find use in colorectal cancer treatment of individuals with increased rates of polyp formation, e.g., treatments may be used for colorectal cancer treatment in individuals with one or more polyposis syndromes.

In some instances, the individual has an increased risk of developing colorectal polyps, or colorectal cancer. Such individuals may have an increased risk of colorectal polyp formation due to the presence of any known risk factor, e.g., family medical history or prior presence of colorectal polyps or prior removal of colorectal polyps.

Utility

The compounds and methods of the invention, e.g., as described herein, find use in a variety of applications. Applications of interest include, but are not limited to: research applications and therapeutic applications. Methods of the invention find use in a variety of different applications including any convenient application where inhibition of an ALDH is desired.

The subject compounds and methods find use in a variety of research applications. The subject compounds and methods may be used in the optimization of the bioavailability and metabolic stability of compounds.

The subject compounds and methods find use in a variety of therapeutic applications. Therapeutic applications of interest include those applications in which a cancer is the cause or a compounding factor in disease progression. As such, the subject compounds find use in the treatment of a variety of different conditions in which the inhibition and/or treatment of a cancer in the host is desired. For example, the subject compounds and methods may find use in treating a solid tumor cancer (e.g., as described herein).

The following example(s) is/are offered by way of illustration and not by way of limitation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, cells, and kits for methods referred to in, or related to, this disclosure are available from commercial vendors such as BioRad, Agilent Technologies, Thermo Fisher Scientific, Sigma-Aldrich, New England Biolabs (NEB), Takara Bio USA, Inc., and the like, as well as repositories such as e.g., Addgene, Inc., American Type Culture Collection (ATCC), and the like.

Example 1: Synthesis of Exemplary Compounds

General Procedure a for the Synthesis of Imidazolium Compounds

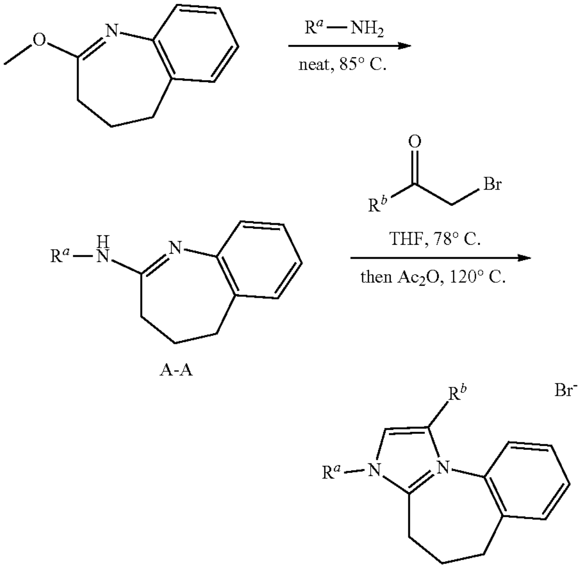

A-A

A mixture of aniline (1.0 equiv) and azepine (1.0 equiv) were heated to 85° C. and stirred under an $N_2$ atmosphere for 6 days. The resulting precipitate was collected by vacuum filtration and washed with $Et_2O$ (3×3 mL) to yield a 7-amino-azepine intermediate A-A. 2-Bromoketone (1.0 equiv) was added to a pressure vessel charged with a suspension of the corresponding 7-amino-azepine intermediate A-A (1.0 equiv) in THF (2.0 M) and the vessel was sealed and placed in an oil bath at 78° C. The reaction mixture was stirred at 78° C. for 16 h, then allowed to cool to room temperature and the reaction mixture was concentrated under reduced pressure. The crude hydrate was dissolved in acetic anhydride (to 1.5 M) in a pressure vessel, and the vessel was sealed and heated in an oil bath at 120° C. for 5 h. The vessel was then allowed to cool to room temperature and the reaction mixture was concentrated under reduced pressure. The residue was typically purified by flash column chromatography on silica gel to yield the desired imidazolium derivative.

General Procedure B for the Synthesis of Guanidinium Compounds

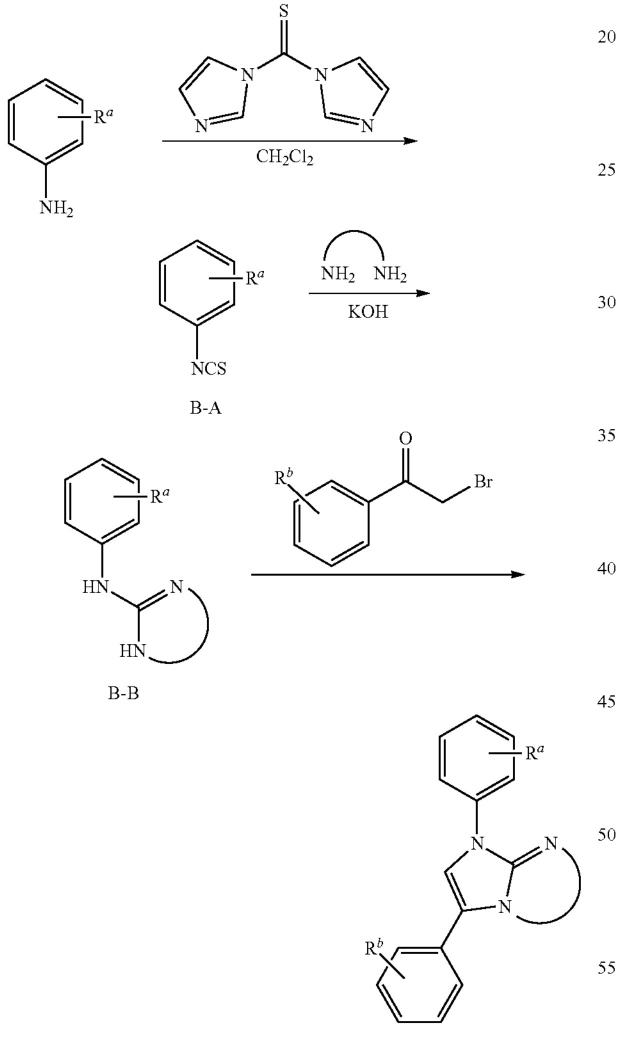

Aniline (1.0 equiv) was added to a flask charged with anhydrous $CH_2Cl_2$ (0.5 M) and stirred at 0° C. or room temperature. 1,1'-Thiocarbonyldiimidazole (1.2-3.0 equiv) was added dropwise and the mixture was stirred for 30 min to 5 h. After completion of reaction as indicated by TLC, the resulting reaction mixture was concentrated. The crude isothiocyanate B-A was purified by column chromatography.

A mixture of isothiocyanate B-A (1.0 equiv), diamine (1.2 equiv) and KOH (1.35 equiv), in 1,2-dichloroethane or ethanol (0.6 M) was heated at 80° C. for 16 h. 1,3-diaminopropane, 1,4-diaminobutane, or 2,2-dimethyl-1,3-diaminopropane were used depending on the target structure. After completion of the reaction as indicated by TLC, the reaction mixture was poured into a separatory funnel containing water and EtOAc or $CH_2Cl_2$. The aqueous phase was extracted with EtOAc or $CH_2Cl_2$ (3×). The combined organic layers were dried over $Na_2SO_4$ and concentrated under vacuum. The crude was purified by column chromatography to afford the cyclic guanidine B-B.

To a stirred solution of cyclic guanidine B-B (1.0 equiv) in 1,2-dichloroethane or acetonitrile (0.14-0.36 M) was added 2-bromoketone (1.0 equiv) and triethylamine (2.0-2.5 equiv). The reaction mixture was heated in a sealed tube to 100-130° C. for 16 h. After completion of the reaction as monitored by TLC, the reaction mixture was concentrated and purified by column chromatography or preparative HPLC.

Characterization Data (2)

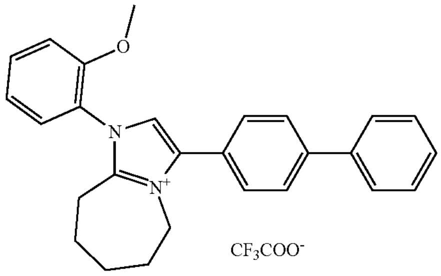

Imidazolium 2. General procedure A. $^1H$ NMR (500 MHz, $CDCl_3$) δ 7.75 (d, J=8.0 Hz, 2H), 7.45-7.63 (m, 8H), 7.39 (tt, J=7.4, 1.2 Hz, 1H), 7.11-7.16 (m, 2H), 7.11 (s, 1H), 4.22-4.40 (m, 2H), 3.88 (s, 3H), 2.90-3.04 (m, 2H), 1.64-2.10 (m, 6H). HRMS (m/z): calc. for $C_{27}H_{27}N_2O_2$ (M+) 395.2118, obs. 395.2119.

(3)

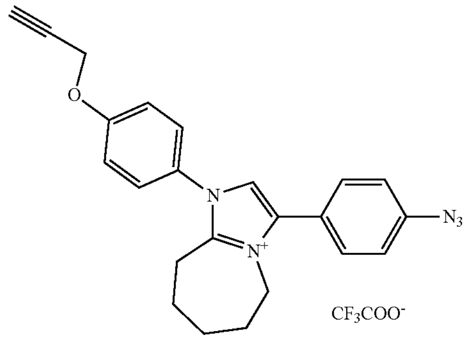

Imidazolium 3. General procedure A. $^1H$ NMR (500 MHz, $CD_3OD$) δ 7.74 (s, 1H), 7.57 (dd, J=19.0, 8.8 Hz, 3H), 7.31 (dd, J=17.2, 8.8 Hz, 3H), 4.90 (d, J=2.4 Hz, 2H), 4.34-4.22 (m, 2H), 3.13-3.09 (m, 2H), 3.07 (t, J=2.4 Hz, 1H), 2.09-2.01 (m, 1H), 2.01-1.93 (m, 1H), 1.87 (p, J=5.7, 4.9 Hz, 3H).

(4)

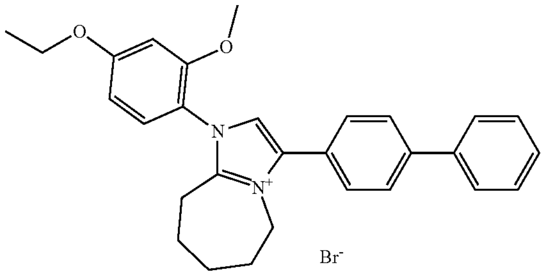

Imidazolium 4. General procedure A. $^1$H NMR (300 MHz, $CDCl_3$) δ 7.72 (d, J=8.2 Hz, 2H), 7.65-7.57 (m, 5H), 7.47 (t, J=7.3 Hz, 2H), 7.42-7.37 (m, 1H), 7.03 (s, 1H), 6.61 (d, J=8.1 Hz, 2H), 4.80-4.65 (m, 1H), 4.46 (dd, J=12.5, 4.4 Hz, 1H), 4.09 (q, J=7.0 Hz, 2H), 3.84 (s, 3H), 3.52 (d, J=11.1 Hz, 1H), 3.04 (dd, J=15.3, 7.6 Hz, 1H), 2.14-2.04 (m, 3H), 1.92 (s, 1H), 1.78 (d, J=13.5 Hz, 1H), 1.61 (s, 1H), 1.44 (t, J=7.0 Hz, 4H). HRMS (m/z): calc. for $C_{29}H_{31}N_2O_2$ (M+) 439.2380, obs. 439.2376.

(5)

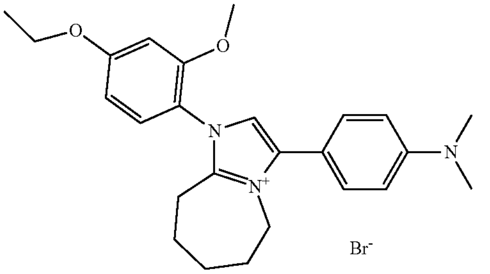

Imidazolium 5. General procedure A. $^1$H NMR (400 MHz, $CDCl_3$) δ 7.57 (d, J=8.4 Hz, 1H), 7.32 (d, J=8.4 Hz, 2H), 6.87 (s, 1H), 6.78 (d, J=8.8 Hz, 2H), 6.63 (d, J=8.8 Hz, 2H), 4.65-4.71 (m, 1H), 4.42-4.47 (m, 1H), 4.13 (q, J=6.8 Hz, 2H), 3.85 (s, 3H), 3.48-3.55 (m, 1H), 3.03-3.12 (m, 1H), 3.03 (s, 6H), 1.61-2.14 (m, 6H), 1.47 (t, J=6.8 Hz, 2H). HRMS (m/z): calc. for $C_{25}H_{32}N_3O_2$(M+) 406.2489, obs. 406.2489.

(6)

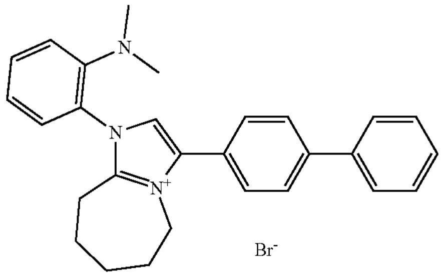

Imidazolium 6. General procedure A. $^1$H NMR (400 MHz, $CDCl_3$) δ 7.75 (d, J=8.1 Hz, 2H), 7.62 (m, 5H), 7.50 (m, 3H), 7.42 (d, J=7.3 Hz, 1H), 7.20 (d, J=7.3 Hz, 2H), 4.79 (dd, J=14.8, 10.0 Hz, 1H), 4.59 (dd, J=14.7, 6.9 Hz, 1H), 3.58 (dd, J=15.9, 10.7 Hz, 1H), 3.20 (dd, J=16.0, 7.9 Hz, 1H), 2.62 (s, 6H), 2.10 (m, 3H), 1.76 (bs, 3H). LRMS (m/z): calc. for $C_{28}H_{30}N_3$(M+) 408.2, obs. 408.6.

(7)

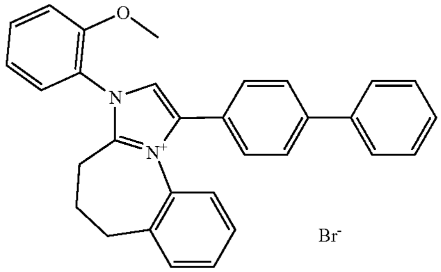

Imidazolium 7. General procedure A. $^1$H NMR (500 MHz, $CD_3CN$) δ 7.90 (m, 2H), 7.76 (m, 4H), 7.66 (m, 2H), 7.58 (m, 4H), 7.50 (m, 1H), 7.37-7.44 (m, 2H), 7.29 (m, 1H), 7.22 (m, 1H), 7.03 (d, J=8.5 Hz, 1H), 3.10-3.24 (m, 4H). HRMS (m/z): calc. for $C_{30}H_{25}N_2O$ (M+) 429.1961, obs. 429.1958.

(8)

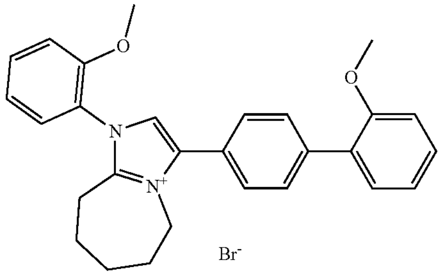

Imidazolium 8. General procedure A. $^1$H NMR (300 MHz, $CDCl_3$) δ 7.82 (dd, J=1.5, 7.8 Hz, 1H), 7.69 (d, J=8.4 Hz, 2H), 7.54-7.60 (m, 3H), 7.34-7.38 (m, 2H), 7.01-7.20 (m, 5H), 4.45-4.78 (m, 2H), 3.92 (s, 3H), 3.86 (s, 3H), 3.03-3.58 (m, 2H), 1.65-2.08 (m, 6H). HRMS (m/z): calc. for $C_{28}H_{29}N_2O_2$ (M+) 425.2224, obs. 425.2225.

(9)

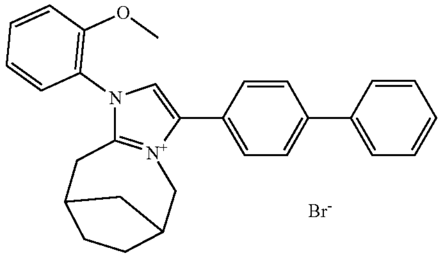

Imidazolium 9. General procedure A. $^1$H NMR (300 MHz, MeOD) δ 7.98 (d, J=8.0 Hz, 1H), 7.39-7.82 (m, 11H), 7.09-7.20 (m, 3H), 4.78-4.83 (m, 1H), 4.27 (br, 1H), 3.95 (s, 3H), 3.67-3.73 (m, 1H), 2.83-2.91 (m, 1H), 2.67-2.69 (m, 1H), 2.54-2.59 (m, 1H), 2.41-2.45 (m, 1H), 1.85-2.07 (m, 4H), 1.27-1.34 (m, 2H). HRMS (m/z): calc. for $C_{29}H_{29}N_2O$ (M+) 421.2274, obs. 421.2273.

(10)

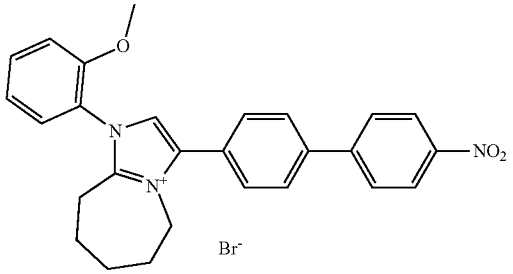

Imidazolium 10. General procedure A. $^1$H NMR (300 MHz, $CDCl_3$) δ 8.35 (d, J=7.2 Hz, 2H), 7.74-7.86 (m, 7H), 7.54-7.60 (m, 1H), 7.12-7.20 (m, 3H), 4.41-4.74 (m, 2H), 3.92 (s, 3H), 3.00-3.44 (m, 2H), 1.67-2.08 (m, 6H). HRMS (m/z): calc. for $C_{27}H_{26}N_3O_3$ (M+) 440.1969, obs. 440.1966.

(11)

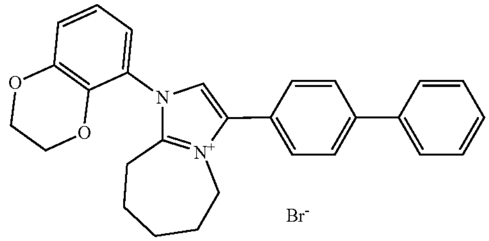

Imidazolium 11. General procedure A. $^1$H NMR (500 MHz, $CDCl_3$) δ 7.73 (d, J=6.5 Hz, 2H), 7.61 (t, J=6.5 Hz, 4H), 7.45-7.48 (m, 2H), 7.38-7.41 (m, 1H), 7.33-7.35 (m, 1H), 7.08-7.10 (m, 2H), 7.00 (d, J=8.0 Hz, 1H), 4.53-4.67 (m, 2H), 4.35-4.36 (m, 4H), 3.24-3.50 (m, 2H), 1.73-2.12 (m, 6H). HRMS (m/z): calc. for $C_{28}H_{27}N_2O_2$ (M+) 423.2067, obs. 423.2070.

(12)

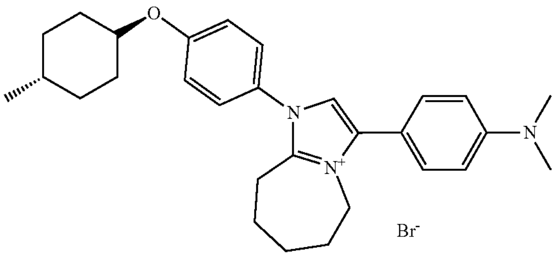

Imidazolium 12. General procedure A. $^1$H NMR (500 MHz, $CDCl_3$) δ 7.53 (d, J=9.0 Hz, 2H), 7.32 (d, J=8.5 Hz, 2H), 7.03 (d, J=9.0 Hz, 2H), 6.97 (s, 1H), 6.78 (d, J=8.5 Hz, 2H), 4.56 (d, J=9.0 Hz, 2H), 4.19-4.24 (m, 1H), 3.50 (d, J=6.5 Hz, 2H), 3.03 (s, 6H), 2.10-2.15 (m, 5H), 1.81-1.86 (m, 5H), 1.81-1.86 (m, 5H), 1.40-1.51 (m, 5H), 1.05-1.10 (m, 2H), 0.95 (d, J=6.5 Hz, 3H). HRMS (m/z): calc. for $C_{29}H_{38}N_3O$ (M+) 444.3009, obs. 444.3008.

(13)

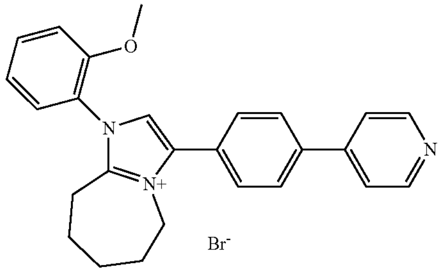

Imidazolium 13. General procedure A. $^1$H NMR (300 MHz, $CDCl_3$) δ 8.73 (d, J=5.4 Hz, 2H), 7.56-7.85 (m, 8H), 7.12-7.19 (m, 3H), 4.46-4.85 (m, 2H), 3.93 (s, 3H), 3.04-3.61 (m, 2H), 1.66-2.11 (m, 6H). HRMS (m/z): calc. for $C_{26}H_{26}N_3O$ (M+) 396.2070, obs. 396.2070.

(14)

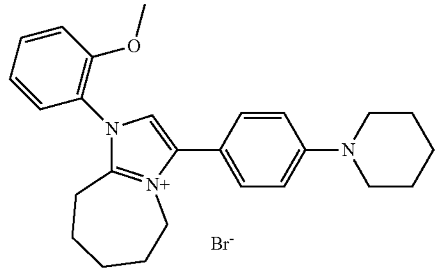

Imidazolium 14. General procedure A. $^1$H NMR (300 MHz, $CDCl_3$) δ 7.69 (d, J=7.2 Hz, 1H), 7.59 (t, J=7.2 Hz, 1H), 7.34 (d, J=8.7 Hz, 2H), 6.94-7.19 (m, 5H), 4.68-4.76 (m, 1H), 4.45-4.52 (m, 1H), 3.91 (s, 3H), 3.49-3.59 (m, 1H), 3.28-3.31 (m, 3H), 3.05-3.12 (m, 2H), 2.11-2.15 (m, 2H), 1.64-1.91 (m, 10H). HRMS (m/z): calc. for $C_{26}H_{32}N_3O$ (M+) 402.2540, obs. 402.2535.

(15)

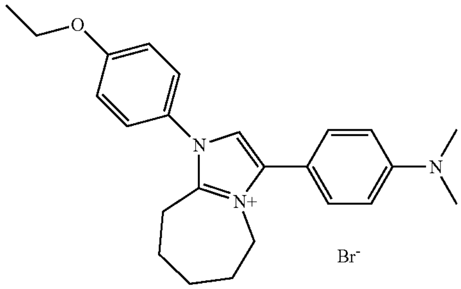

Imidazolium 15. General procedure A. $^1$H NMR (500 MHz, $CDCl_3$) δ 7.54 (d, J=9.0 Hz, 2H), 7.30 (t, J=8.5 Hz, 2H), 7.01 (d, J=9.0 Hz, 2H), 6.74 (d, J=9.0 Hz, 2H), 4.47 (t, J=5.0 Hz, 2H), 4.06 (q, J=7.0 Hz, 2H), 3.40 (t, J=6.5 Hz, 2H), 3.01 (s, 6H), 2.04-2.09 (m, 3H), 1.85 (q, J=5.0 Hz, 2H), 1.76 (s, 2H), 1.44 (t, J=6.5 Hz, 3H). HRMS (m/z): calc. for $C_{24}H_{30}N_3O$ (M+) 376.2383, obs. 376.2381.

(16)

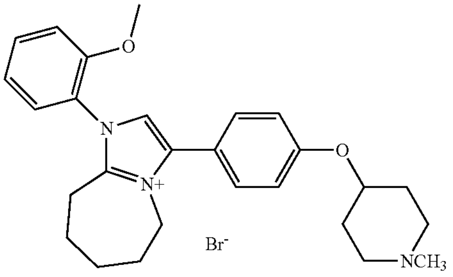

Imidazolium 16. General procedure A. $^1$H NMR (300 MHz, $CDCl_3$) δ 7.71 (d, J=7.5 Hz, 1H), 7.59-7.62 (m, 1H), 7.57 (d, J=1.5 Hz, 2H), 7.12-7.21 (m, 4H), 7.04 (s, 1H), 4.84 (br, 1H), 4.56-4.64 (m, 1H), 4.36-4.41 (m, 1H), 3.92 (s, 3H), 3.25-3.35 (m, 5H), 2.97-3.05 (m, 1H), 2.81 (s, 3H), 2.45 (br, 2H), 2.15-2.21 (m, 2H), 1.27-2.10 (m, 6H). HRMS (m/z): calc. for $C_{27}H_{34}N_3O_2$ (M+) 432.2646, obs. 432.2654.

(17)

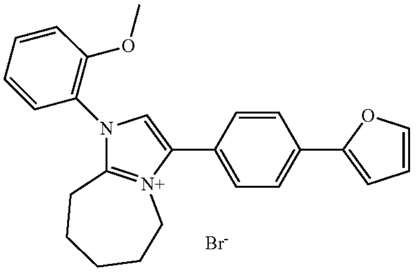

Imidazolium 17. General procedure A. $^1$H NMR (300 MHz, $CDCl_3$) δ 7.75-7.82 (m, 3H), 7.52-7.58 (m, 4H), 7.08-7.19 (m, 3H), 6.78 (d, J=3.6 Hz, 1H), 6.51 (dd, J=1.8, 3.3 Hz, 1H), 4.39-4.68 (m, 2H), 3.91 (s, 3H), 2.99-3.39 (m, 2H), 1.62-2.08 (m, 6H). HRMS (m/z): calc. for $C_{25}H_{25}N_2O_2$ (M+) 385.1911, obs. 385.1912.

(18)

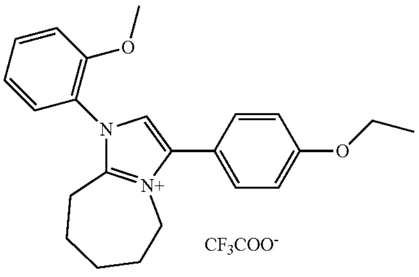

Imidazolium 18. General procedure A. $^1$H NMR (500 mHz, $CDCl_3$) δ 7.55 (td, J=7.9, 1.5 Hz), 7.45 (dd, J=8.2, 1.5 Hz, 1H), 7.34 (d, J=8.6 Hz, 2H), 7.13 (d, J=8.2 Hz, 1H), 7.10-7.14 (m, 1H), 7.00 (d, J=8.6 Hz, 2H), 7.01 (s, 1H), 4.24-4.29 (m, 2H), 4.06 (q, J=7.0 Hz, 2H), 3.86 (s, 3H), 2.87-3.02 (m, 2H), 1.62-2.09 (m, 6H), 1.41 (t, J=7.0 Hz, 3H). HRMS (m/z): calc. for $C_{23}H_{27}N_2O_2$ (M+) 363.2067, obs. 363.2067.

(19)

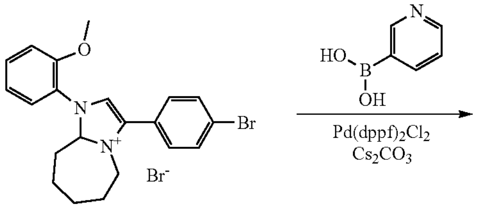

a

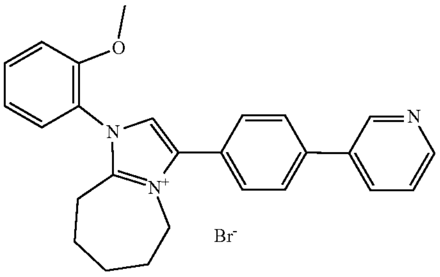

Imidazolium 19. The general procedure A was applied for the synthesis of a. Intermediate a (130 mg, 0.27 mmol), pyridin-3-ylboronic acid (70 mg, 0.57 mmol), $Pd(dppf)_2Cl_2$ (20 mg, 0.027 mmol), and $Cs_2CO_3$ (176 mg, 0.54 mmol) were mixed with anhydrous DMF (2 mL) under a $N_2$ atmosphere. The reaction mixture was then stirred at 80° C. for 8 h. EtOAc (5 mL) and water (5 mL) were then added, and the aqueous layer was extracted with EtOAc (3x20 mL), dried over $Na_2SO_4$, filtered, and concentrated. The residue was purified by silica gel column chromatography (MeOH: $CH_2CH_2Cl_2$=10:0.5) to afford crude product, which was then further purified by preparative TLC (MeOH: $CH_2Cl_2$=10:1) to yield 19. $^1$H NMR (500 MHz, $CDCl_3$) δ 8.85 (s, 1H), 8.63 (d, J=3.0 Hz, 1H), 7.92 (d, J=7.4 Hz, 1H), 7.74-7.63 (m, 5H), 7.51-7.56 (m, 1H), 7.40-7.42 (m, 1H), 7.11 (m, 3H), 4.71-4.59 (m, 1H), 4.42 (m, 1H), 3.88 (s, 3H), 3.36 (s, 1H), 3.00 (m, 1H), 1.91-2.07 (m, 2H), 1.82-1.73 (m, 1H), 1.70-1.56 (m, 2H). HRMS (m/z): calc. for $C_{26}H_{26}N_3O$ (M+), 396.2070, obs. 396.2068.

(20)

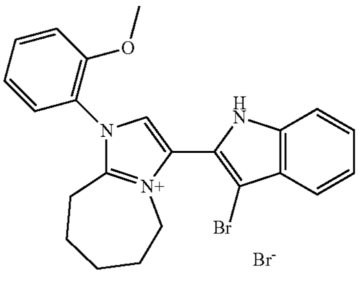

Imidazolium 20. General procedure A. $^1$H NMR (300 MHz, $CDCl_3$) δ 12.65 (s, 1H), 7.57-7.77 (m, 4H), 7.40 (s, 1H), 7.14-7.36 (m, 4H), 7.13 (t, J=8.4 Hz, 2H), 4.45 (br, 2H), 3.95 (s, 3H), 2.98-3.02 (m, 2H), 1.65-2.09 (m, 6H). HRMS (m/z): calc. for $C_{23}H_{23}BrN_3O$ (M+) 436.1019, obs. 436.0935.

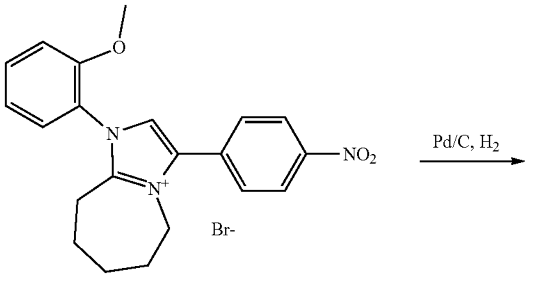

39

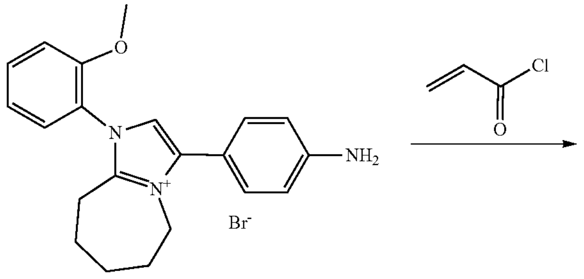

b

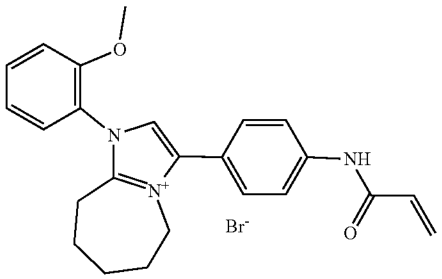

21

Imidazolium 21. A mixture of 39 (100 mg, 0.24 mmol) and Pd/C (10%, 50 mg) in MeOH (6 mL) was stirred under $H_2$ at atmospheric pressure for 3 h. The reaction mixture was filtered, and then concentrated under reduced pressure to afford intermediate b. To a solution of b (70 mg, 0.17 mmol) and triethylamine (0.1 mL) in $CH_2Cl_2$ (6 mL) was added acryloyl chloride (16 mg, 0.20 mmol) at 0° C. The reaction mixture was then stirred for 30 min. The solution was concentrated under vacuum, and the residue was purified by silica gel column chromatography (MeOH:$CH_2Cl_2$=1:20) to afford 21. $^1$H NMR (300 MHz, $CDCl_3$) δ 11.16 (s, 1H), 8.17 (d, J=8.4 Hz, 2H), 7.55-7.72 (m, 2H), 6.98-7.28 (m, 6H), 6.35-6.40 (m, 1H), 5.61-5.65 (m, 1H), 4.30-4.44 (m, 2H), 3.90 (s, 3H), 3.65-3.74 (m, 1H), 3.25-3.29 (m, 1H), 2.92-3.00 (m, 1H), 1.51-2.06 (m, 6H). HRMS (m/z): calc. for $C_{24}H_{26}N_3O_2$ (M+), 388.2020, obs. 388.2019.

(22)

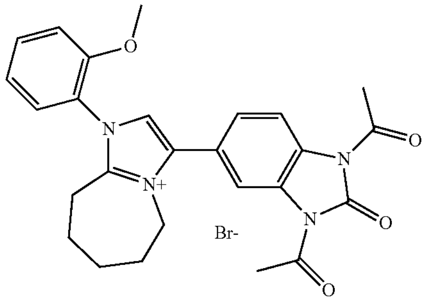

Imidazolium 22. General procedure A. $^1$H NMR (300 MHz, $CDCl_3$) δ 8.36-8.40 (m, 2H), 7.84 (d, J=7.8 Hz, 1H), 7.55-7.65 (m, 2H), 7.11-7.20 (m, 4H), 4.71-4.75 (m, 1H), 4.40-4.43 (m, 1H), 3.93 (s, 3H), 3.56-3.65 (m, 1H), 3.03-3.11 (m, 1H), 2.81 (s, 6H), 2.03 (br, 2H), 1.80 (br, 2H), 1.65 (br, 2H). HRMS (m/z): calc. for $C_{26}H_{27}N_4O_4$ (M+) 459.2027, obs. 459.2028.

(23)

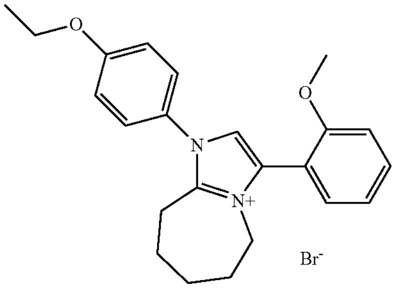

Imidazolium 23. General procedure A. $^1$H NMR (500 MHz, $CDCl_3$) δ 7.61 (d, J=9.0 Hz, 2H), 7.49-7.53 (m, 2H), 7.08 (t, J=6.5 Hz, 1H), 7.00-7.06 (m, 4H), 4.23 (t, J=5.0 Hz, 2H), 4.07 (q, J=7.0 Hz, 2H), 3.88 (s, 3H), 3.40 (t, J=5.0 Hz, 2H), 2.06-2.09 (m, 2H), 1.88-1.90 (m, 2H), 1.79-1.82 (m, 2H), 1.42 (t, J=7.0 Hz, 3H). HRMS (m/z): calc. for $C_{23}H_{27}N_2O_2$ (M+) 363.2067, obs. 363.2068.

(24)

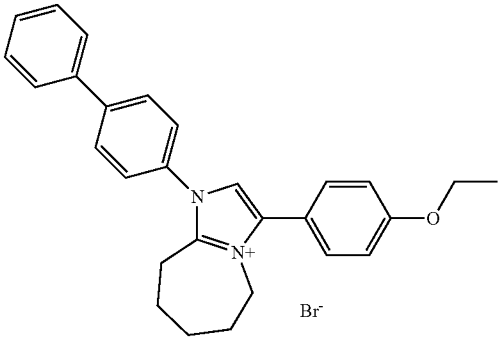

Imidazolium 24. General procedure A. $^1$H NMR (500 MHz, $CDCl_3$) δ 7.75-7.80 (m, 4H), 7.59-7.61 (m, 2H), 7.46-7.49 (m, 4H), 7.40-7.43 (m, 1H), 7.10 (s, 1H), 6.99 (d, J=9.0 Hz, 2H), 4.46 (t, J=5.0 Hz, 2H), 4.07 (q, J=7.0 Hz, 2H), 3.46 (t, J=5.5 Hz, 2H), 2.05-2.08 (m, 2H), 1.89-1.91 (m, 2H), 1.81-1.82 (m, 2H), 1.43 (t, J=7.0 Hz, 3H). HRMS (m/z): calc. for $C_{28}H_{29}N_2O$ (M+) 409.2274, obs. 409.2278.

(25)

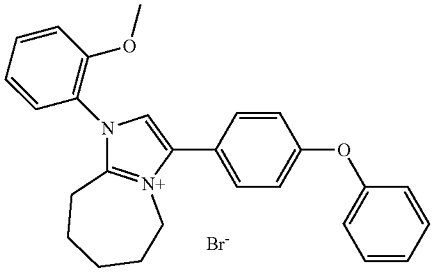

Imidazolium 25. General procedure A. $^{1}$H NMR (300 MHz, $CDCl_3$) δ 7.83 (dd, J=1.5, 7.8 Hz, 1H), 7.51-7.59 (m, 3H), 7.39-7.44 (m, 2H), 7.08-7.23 (m, 7H), 7.02 (s, 1H), 4.39-4.69 (m, 2H), 3.91 (s, 3H), 3.03-3.49 (m, 2H), 1.79-2.07 (m, 6H). HRMS (m/z): calc. for $C_{27}H_{27}N_2O_2$ (M+) 411.2067, obs. 411.2066.

(26)

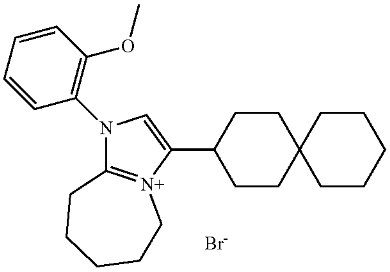

Imidazolium 26. General procedure A. $^{1}$H NMR (300 MHz, $CDCl_3$) δ 7.57 (t, J=7.8 Hz, 2H), 7.01-7.16 (m, 2H), 6.72 (s, 1H), 4.70-4.78 (m, 1H), 4.45-4.80 (m, 1H), 3.87 (s, 3H), 3.35-3.47 (m, 1H), 2.93-3.01 (m, 1H), 2.61-2.69 (m, 1H), 2.14 (br, 2H), 1.78-1.82 (m, 6H), 1.19-1.61 (m, 16H). HRMS (m/z): calc. for $C_{26}H_{37}N_2O$ (M+) 393.2900, obs. 393.2900.

(27)

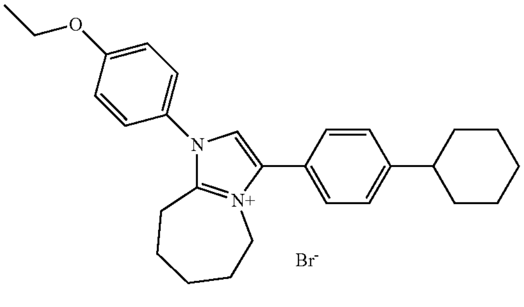

Imidazolium 27. General procedure A. $^{1}$H NMR (500 MHz, $CDCl_3$) δ 7.61 (d, J=8.5 Hz, 2H), 7.43 (d, J=8.5 Hz, 2H), 7.33 (d, J=8.5 Hz, 2H), 7.02-7.04 (m, 3H), 4.49 (t, J=5.0 Hz, 2H), 4.07 (q, J=7.0 Hz, 2H), 3.42 (t, J=5.0 Hz, 2H), 2.56-2.57 (m, 1H), 1.25-2.09 (m, 19H). HRMS (m/z): calc. for $C_{28}H_{35}N_2O$ (M+) 415.2744, obs. 415.2614.

(28)

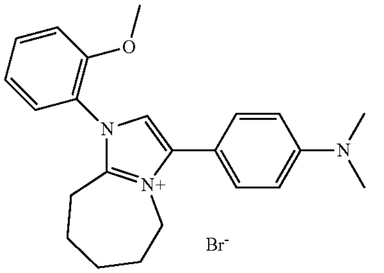

Imidazolium 28. General procedure A. $^{1}$H NMR (300 MHz, $CDCl_3$) δ 7.73 (dd, J=1.5, 7.8 Hz, 1H), 7.59 (t, J=8.1, Hz, 1H), 7.4 (dd, J=1.5, 9.7 Hz, 2H), 7.11-7.20 (m, 2H), 6.93 (s, 1H), 6.8 (d, J=8.7 Hz, 2H), 4.64-4.73 (m, 1H), 4.44-4.51 (m, 1H), 3.92 (s, 3H), 3.48-3.58 (m, 1H), 3.05-3.12 (m, 1H), 3.05 (s, 6H), 1.67-2.16 (m, 6H). HRMS (m/z): calc. for $C_{23}H_{28}N_3O$ (M+) 362.2227, obs. 362.2225.

(29)

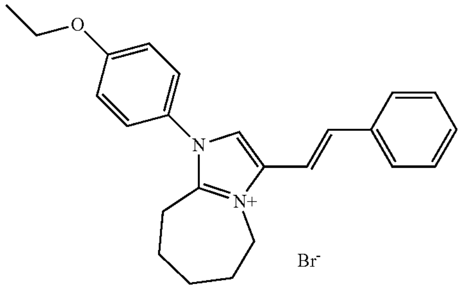

Imidazolium 29. General procedure A. $^{1}$H NMR (500 MHz, $CDCl_3$) δ 7.56 (dd, $J_1$=6.5 Hz, $J_2$=2.0 Hz, 2H), 7.51 (d, J=7.0 Hz, 2H), 7.34-7.40 (m, 3H), 7.29 (s, 1H), 7.12 (d, J=16.5 Hz, 1H), 7.02 (d, J=9.0 Hz, 2H), 6.89 (d, J=16.0 Hz, 1H), 4.59 (t, J=5.0 Hz, 2H), 4.07 (q, J=7.0 Hz, 2H), 3.35 (t, J=5.5 Hz, 2H), 2.03 (t, J=6.0 Hz, 2H), 1.95 (q, J=4.5 Hz, 2H), 1.73 (t, J=6.0 Hz, 2H), 1.45 (t, J=7.0 Hz, 3H). HRMS (m/z): calc. for $C_{24}H_{27}N_2O$ (M+) 359.2118, obs. 359.2112.

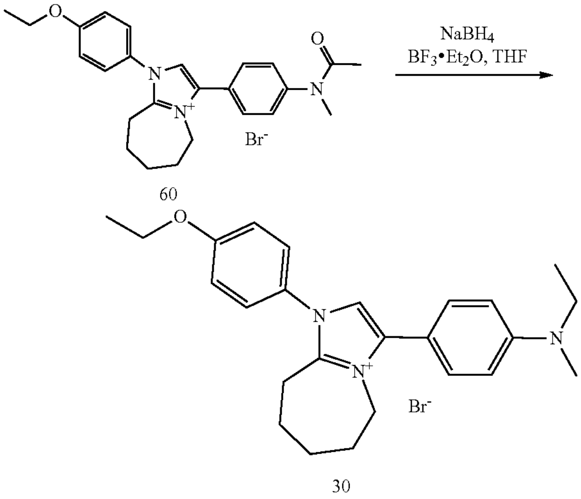

Imidazolium 30. To the solution of compound 60 (30 mg, 0.060 mmol) in anhydrous THF (5 mL) was added $NaBH_4$ (40 mg, 1.1 mmol) and $BF_3 \cdot OEt_2$ (0.2 mL, 0.16 mmol) at 0° C. The reaction mixture was stirred at 0° C. for 1 h and then at room temperature overnight. The reaction was then quenched with saturated aqueous $NaHCO_3$ (5 mL) and extracted with $CH_2Cl_2$ (3×10 mL). The combined organic phase was concentrated under reduced pressure, and the residue was purified by flash column chromatography on silica gel ($MeOH:CH_2Cl_2$, 1:20) to yield product 30. $^1H$ NMR (300 MHz, $CDCl_3$) δ 7.53 (d, J=8.4 Hz, 2H), 7.36 (d, J=6.9, Hz, 2H), 7.00-7.06 (m, 3H), 6.84 (br, 2H), 4.41 (s, 2H), 4.13 (q, J=6.6 Hz, 2H), 3.49 (d, J=6.6 Hz, 2H), 3.28 (s, 2H), 3.05 (s, 3H), 2.09 (br, 3H), 2.04 (br, 3H), 1.49 (t, J=6.6 Hz, 3H), 1.21 (t, J=6.9 Hz, 3H). HRMS (m/z): calc. for $C_{25}H_{32}N_3O$ (M+) 390.2540, obs. 390.2535.

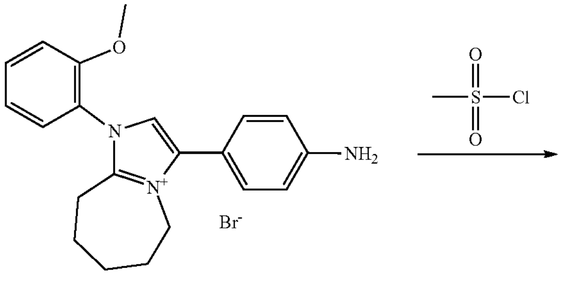

c

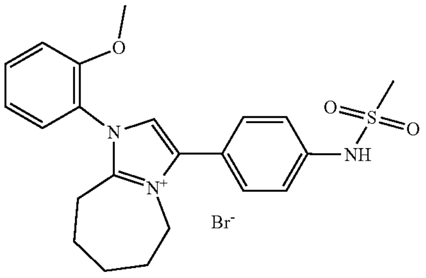

31

Imidazolium 31. The general procedure A was applied for the synthesis of c. To a solution of c (70 mg, 0.17 mmol) and triethylamine (0.1 mL) in anhydrous $CH_2Cl_2$ (6 mL) at 0° C. was added methanesulfonyl chloride (28 mg, 0.2 mmol). The mixture was then stirred at the room temperature for 3 h. The solution was concentrated under vacuum, and the resulting residue was purified by silica gel column chromatography ($MeOH:CH_2Cl_2$=1:20) to afford 31. $^1H$ NMR (300 MHz, $CDCl_3$) δ 10.58 (s, 1H), 7.90 (d, J=6.9 Hz, 1H), 7.55-7.65 (m, 3H), 7.31 (s, 3H), 7.19-7.24 (m, 1H), 7.13 (d, J=6.9 Hz, 2H), 4.58-4.65 (m, 1H), 4.25-4.32 (m, 1H), 3.91 (s, 3H), 3.31-3.40 (m, 1H), 3.11 (s, 3H), 2.91-2.98 (m, 1H), 2.11 (br, 3H), 1.97-2.04 (m, 2H), 1.68 (s, 1H). HRMS (m/z): calc. for $C_{22}H_{26}N_3O_3S$ (M+), 412.1689, obs. 412.1688.

(32)

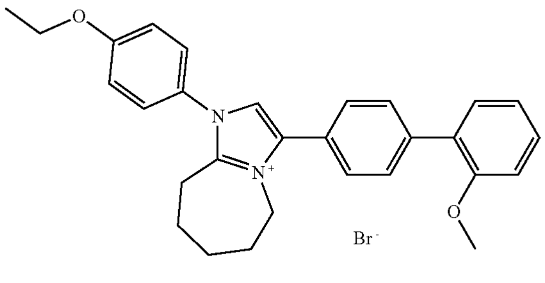

Imidazolium 32. General procedure A. $^1H$ NMR (500 MHz, $CDCl_3$) δ 7.67 (d, J=8.0 Hz, 2H), 7.62 (d, J=9.0 Hz, 2H), 7.60 (d, J=8.5 Hz, 2H), 7.33-7.37 (m, 2H), 5.30-7.10 (m, 5H), 4.57 (t, J=5.0 Hz, 2H), 4.07 (q, J=7.0 Hz, 2H), 3.85 (s, 3H), 3.43 (q, J=5.0 Hz, 2H), 2.08 (t, J=6.0 Hz, 2H), 1.92 (d, J=4.5 Hz, 2H), 1.79 (s, 2H), 1.46 (t, J=7.0 Hz, 3H). HRMS (m/z): calc. for $C_{29}H_{31}N_2O_2$ (M+) 439.2380, obs. 439.2381.

(33)

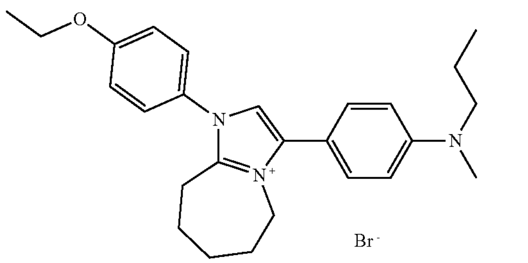

Imidazolium 33. General procedure A. $^1H$ NMR (400 MHz, $CDCl_3$) δ 7.49 (d, J=8.8 Hz, 2H), 7.3 (d, J=8.8 Hz, 2H), 7.04 (d, J=8.8 Hz, 2H), 6.95 (s, 1H), 6.74 (d, J=8.8 Hz, 2H), 4.4 (t, 1H), 4.4 Hz, 2H), 4.12 (q, J=6.8 Hz, 2H), 3.35 (t, J=7.2 Hz, 2H), 3.26 (t, J=5.2H, 2H), 3.0 (s, 3H), 2.03 (d, J=4.0 Hz, 2H), 1.84 (br, 2H), 1.74 (br, 2H), 1.59-1.68 (m, 2H), 1.47 (q, J=6.8 Hz, 3H), 0.97 (t, J=7.2 Hz, 3H). HRMS (m/z): calc. for $C_{26}H_{34}N_3O$ (M+) 404.2696, obs. 404.2694.

(34)

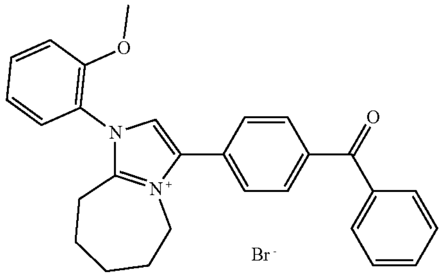

Imidazolium 34. General procedure A. $^1H$ NMR (300 MHz, $CDCl_3$) δ 7.74-7.93 (m, 7H), 7.49-7.66 (m, 4H), 7.11-7.17 (m, 3H), 4.72-4.80 (m, 1H), 4.43-4.47 (m, 1H), 3.91 (s, 3H), 3.50-3.55 (m, 1H), 2.99-3.07 (m, 1H), 1.61-2.11 (m, 6H). HRMS (m/z): calc. for $C_{28}H_{27}N_2O_2$ (M+), 423.2067, obs. 423.2067.

(35)

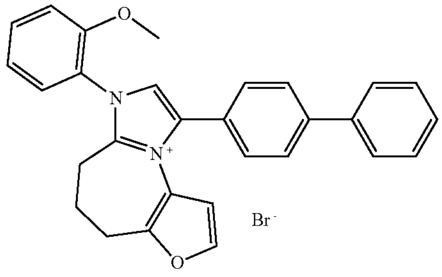

Imidazolium 35. General procedure A. $^{1}H$ NMR (300 MHz, $CDCl_3$) δ 7.88 (dd, J=1.5, 7.8 Hz, 1H), 7.59-7.78 (m, 4H), 7.47-7.70 (m, 3H), 7.39-7.44 (m, 3H), 7.15-7.26 (m, 4H), 5.52 (d, J=2.1 Hz, 1H), 4.62-4.69 (m, 1H), 4.45-4.53 (m, 1H), 3.84 (s, 3H), 3.35-3.44 (m, 2H), 2.71-2.76 (m, 1H), 2.36-2.40 (m, 1H). HRMS (m/z): calc. for $C_{29}H_{25}N_2O_2$ (M+) 433.1911, obs. 433.1908.

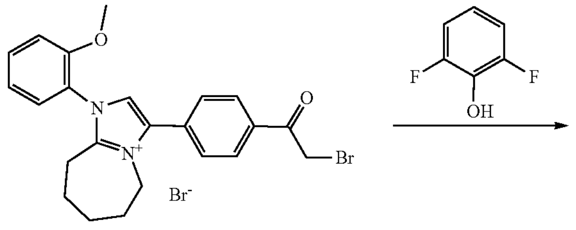

d

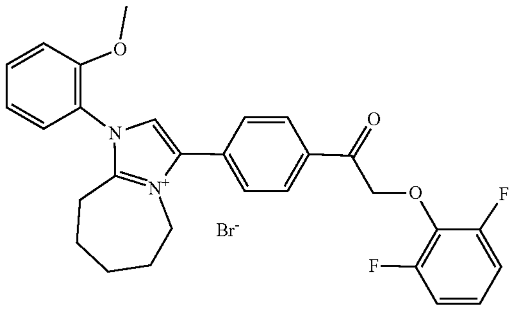

36

Imidazolium 36. The general procedure A was applied for the synthesis of d. To a solution of d (105 mg, 0.22 mmol) in acetonitrile (6 mL) was added 2,6-difluorophenol (34 mg, 0.27 mmol) and $K_2CO_3$ (45 mg, 0.33 mmol). The reaction mixture was heated to refluxed for 3 h. The reaction mixture was filtered, and the filtrate was concentrated under vacuum. The resulting residue was purified by silica gel column chromatography ($MeOH:CH_2Cl_2$=1:20) to give 36. $^{1}H$ NMR (300 MHz, $CDCl_3$) δ 8.14 (d, J=8.1 Hz, 2H), 7.79-7.89 (m, 3H), 7.60 (t, J=7.5 Hz, 1H), 7.11-7.21 (m, 3H), 6.91-7.02 (m, 3H), 4.74-4.82 (m, 1H), 4.40-4.44 (m, 1H), 3.92 (s, 3H), 3.56-3.59 (m, 1H), 3.01-3.09 (m, 1H), 2.10 (br, 4H), 1.79 (br, 2H). HRMS (m/z): calc. for $C_{29}H_{27}F_2N_2O_3$ (M+), 489.1984, obs. 489.1985.

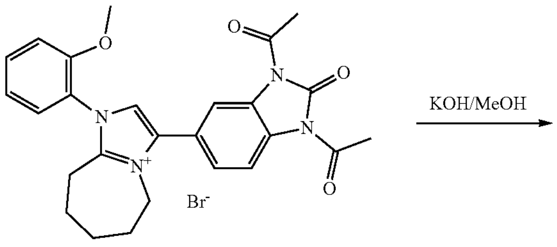

e

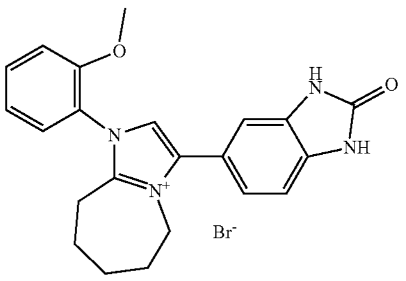

37

Imidazolium 37. The general procedure A was applied for the synthesis of e. Compound e (70 mg, 0.16 mmol) was added to a solution of methanol (6 mL) and potassium hydroxide (756 mg) and stirred at the room temperature for 30 min. Water (20 mL) was added and the solution was extracted with $CHCl_3$ (4×30 ml). The combined organic phase was dried over anhydrous $NaSO_4$, and then concentrated under reduced pressure. The residue was purified by silica gel column chromatography ($MeOH:CH_2Cl_2$=1:20) to give the desired product 37. $^{1}H$ NMR (300 MHz, MeOD) δ 7.60-7.71 (m, 1H), 7.57 (dd, J=1.8, 7.8 Hz, 2H), 7.39 (d, J=7.8 Hz, 1H), 7.20-7.27 (m, 4H), 4.28-4.36 (m, 2H), 3.95 (s, 3H), 3.00 (t, J=4.5 Hz, 2H), 1.87-2.04 (m, 6H). HRMS (m/z): calc. for $C_{22}H_{23}N_4O_2$ (M+), 375.1816, obs. 375.1815.

(38)

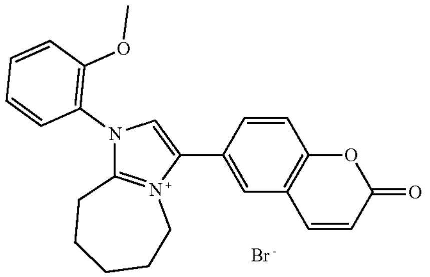

Imidazolium 38. General procedure A. $^{1}H$ NMR (300 MHz, $CDCl_3$) δ 8.20 (d, J=1.8 Hz, 1H), 8.00 (d, J=9.6 Hz, 1H), 7.87 (dd, J=1.5, 7.5 Hz, 1H), 7.69 (dd, J=1.8, 8.4 Hz, 1H), 7.55-7.60 (m, 1H), 7.44 (d, J=8.4 Hz, 1H), 7.11-7.20 (m, 3H), 6.50 (d, J=9.6 Hz, 1H), 4.32-4.70 (m, 2H), 3.92 (s, 3H), 2.95-3.41 (m, 2H), 1.62-2.10 (m, 6H). HRMS (m/z): calc. for $C_{24}H_{23}N_2O_3$ (M+) 387.1703, obs. 387.1704.

(39)

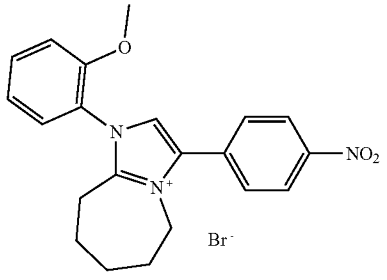

Imidazolium 39. General procedure A. $^{1}$H NMR (300 MHz, $CDCl_3$) δ 8.40 (d, J=8.7 Hz, 2H), 7.92-7.98 (m, 3H), 7.55-7.61 (m, 1H), 7.11-7.21 (m, 3H), 4.66-4.74 (m, 1H), 4.30-4.37 (m, 1H), 3.92 (s, 3H), 3.40-3.48 (m, 1H), 2.98-3.06 (m, 1H), 1.58-2.21 (m, 6H). HRMS (m/z): calc. for $C_{21}H_{22}N_3O_3$ (M+), 364.1656, obs. 364.1655.

(40)

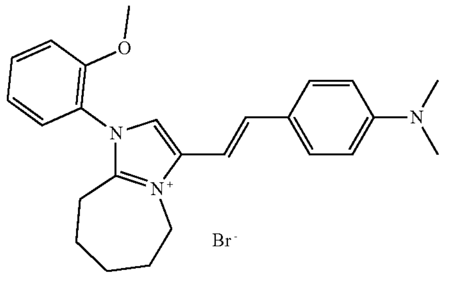

Imidazolium 40. General procedure A. $^{1}$H NMR (300 MHz, $CDCl_3$) δ 7.55-7.63 (m, 2H), 7.44 (d, J=8.7 Hz, 2H), 7.11-7.19 (m, 3H), 7.01-7.08 (m, 1H), 6.67-6.96 (m, 2H), 4.77-4.88 (m, 1H), 4.59-4.64 (m, 1H), 3.90 (s, 3H), 3.43-3.51 (m, 1H), 3.03 (s, 6H), 2.93-2.97 (m, 1H), 2.14 (br, 2H), 1.86 (br, 2H), 1.63 (br, 2H). HRMS (m/z): calc. for $C_{25}H_{30}N_3O$ (M+) 388.2383, obs. 388.2382.

(41)

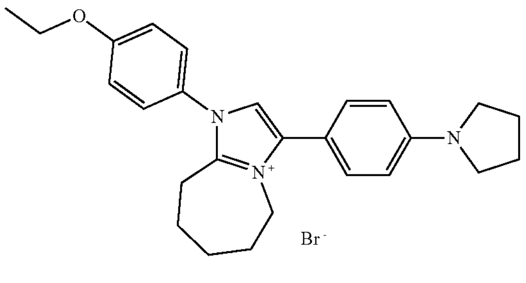

Imidazolium 41. General procedure A. $^{1}$H NMR (300 MHz, $CDCl_3$) δ 7.50-7.55 (m, 2H), 7.26-7.30 (m, 2H), 7.00-7.06 (m, 3H), 6.63 (d, J=8.7 Hz, 1H), 6.44 (s, 2H), 4.43-4.46 (m, 2H), 4.13 (q, J=6.9 Hz, 2H), 3.31-3.35 (m, 4H), 1.76-2.08 (m, 12H), 1.47 (t, J=6.9 Hz, 2H). HRMS (m/z): calc. for $C_{26}H_{32}N_3O$ (M+) 402.2540, obs. 402.2535.

(42)

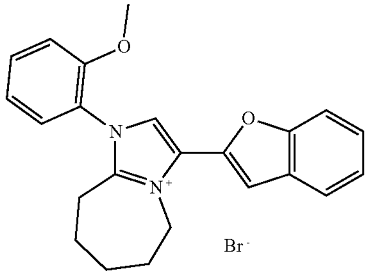

Imidazolium 42. General procedure A. $^{1}$H NMR (300 MHz, $CDCl_3$) δ 7.76 (d, J=7.8 Hz, 1H), 7.64 (d, J=7.8 Hz, 1H), 7.26-7.58 (m, 8H), 7.13 (t, J=8.4 Hz, 2H), 4.74-4.83 (m, 2H), 3.87 (s, 3H), 2.96-3.47 (m, 2H), 1.60-2.08 (m, 6H). HRMS (m/z): calc. for $C_{23}H_{23}N_2O_2$ (M+) 359.1754, obs. 359.1754.

(43)

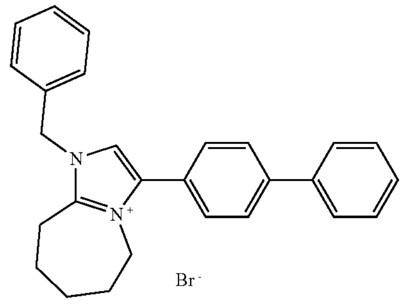

Imidazolium 43. General procedure A. $^{1}$H NMR (500 MHz, $CDCl_3$) δ 7.59 (d, J=7.5 Hz, 2H), 7.46 (q, J=13.5 Hz, 2H), 7.40-7.41 (m, 4H), 7.37-7.39 (m, 7H), 5.71 (s, 2H), 4.35 (t, J=5.0 Hz, 2H), 3.53 (t, J=5.5 Hz, 2H), 2.00 (t, J=5.0 Hz, 2H), 1.83 (d, J=4.5 Hz, 2H), 1.73 (q, J=5.5 Hz, 2H). HRMS (m/z): calc. for $C_{27}H_{27}N_2$ (M+) 379.2169, obs. 379.2170.

(44)

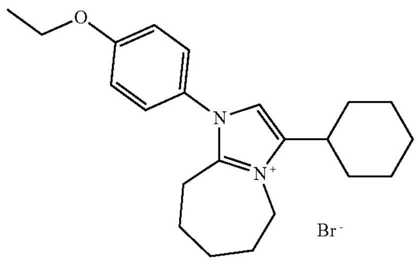

Imidazolium 44. General procedure A. $^{1}$H NMR (500 MHz, $CDCl_3$) δ 7.46 (d, J=9.0 Hz, 2H), 6.76 (d, J=9.0 Hz, 2H), 6.76 (s, 1H), 4.51 (t, J=5.0 Hz, 2H), 4.06 (q, J=7.0 Hz, 2H), 3.32 (t, J=5.0 Hz, 2H), 2.62-2.68 (m, 1H), 1.23-2.06 (m, 19H). HRMS (m/z): calc. for $C_{22}H_{31}N_2O$ (M+) 339.2431, obs. 339.2431.

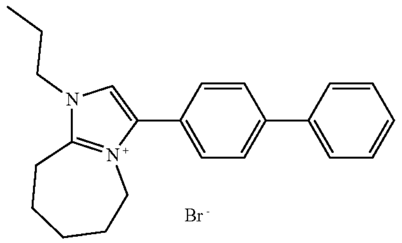

Imidazolium 45. General procedure A. $^1$H NMR (500 MHz, $CDCl_3$) δ 7.69 (dd, $J_1$=8.5 Hz, $J_2$=2.5 Hz, 4H), 7.40-7.62 (m, 16H), 4.59 (d, J=10.0 Hz, 2H), 4.15-4.34 (m, 5H), 3.43-3.45 (m, 4H), 2.05-2.09 (m, 4H), 1.89-1.95 (m, 10H), 1.67-1.69 (m, 9H), 1.05 (t, J=7.0 Hz, 2H), 0.85 (t, J=7.0 Hz, 3H). HRMS (m/z): calc. for $C_{23}H_{27}N_2$ (M+) 331.2169, obs. 331.2168.

(46)

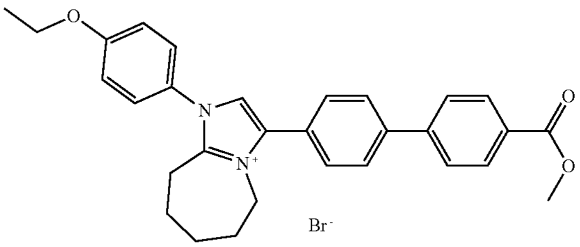

Imidazolium 46. General procedure A. $^1$H NMR (500 MHz, $CDCl_3$) δ 8.13 (d, J=8.5 Hz, 2H), 7.72-7.77 (m, 4H), 7.68-7.70 (m, 4H), 7.14 (s, 1H), 7.03 (d, J=8.5 Hz, 2H), 4.45 (t, J=4.5 Hz, 2H), 4.08 (q, J=7.0 Hz, 2H), 3.96 (s, 3H), 3.36 (t, J=5.5 Hz, 2H), 1.97-2.05 (m, 5H), 1.84 (s, 2H), 1.46 (t, J=7.0 Hz, 3H). HRMS (m/z): calc. for $C_{30}H_{31}N_2O_3$ (M+) 467.2329, obs. 467.2267.

(47)

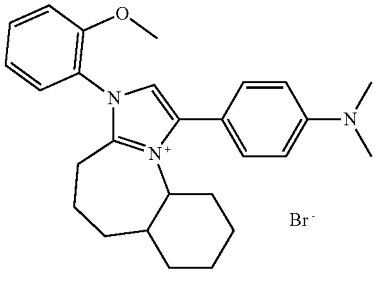

Imidazolium 47. General procedure A. $^1$H NMR (300 MHz, $CDCl_3$) δ 8.02 (s, 1H), 7.61 (t, J=7.8 Hz, 1H), 7.39-7.52 (m, 3H), 7.10-7.27 (m, 6H), 6.64 (d, J=8.7 Hz, 2H), 3.97 (s, 3H), 2.99 (s, 6H), 2.37-2.89 (m, 6H). HRMS (m/z): calc. for $C_{27}H_{28}N_3O$ (M+) 410.2227, obs. 410.2223.

(48)

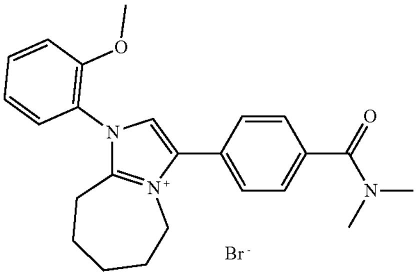

Imidazolium 48. General procedure A. $^1$H NMR (300 MHz, $CDCl_3$) δ 7.88 (dd, J=1.2, 7.8 Hz, 1H), 7.54-7.68 (m, 5H), 7.10-7.20 (m, 3H), 4.68-4.76 (m, 1H), 4.38-4.45 (m, 1H), 3.91 (s, 3H), 3.45-3.53 (m, 1H), 3.15 (s, 3H), 3.03-3.07 (m, 4H), 1.64-2.02 (m, 6H). HRMS (m/z): calc. for $C_{24}H_{28}N_3O_2$ (M+), 390.2176, obs. 390.2178.

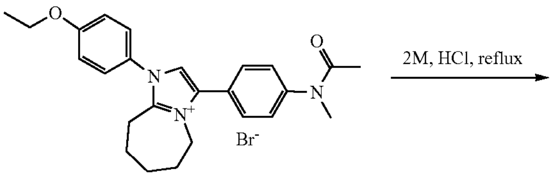

60

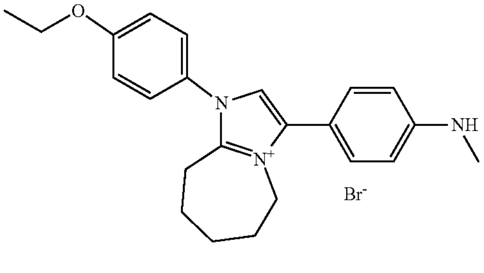

49

Imidazolium 49. Compound 60 (25 mg, 0.052 mmol) was suspended in the aqueous solution of 2 M HCl (2 mL), and the reaction mixture was stirred at reflux overnight. After cooling to the room temperature, an aqueous solution of $NaHCO_3$ was added to achieve a neutral pH. Then, the mixture was extracted with $CHCl_3$ (3×5 mL), and the combined organic phase was concentrated under reduced pressure, and the residue was purified by flash column chromatography on silica gel ($MeOH:CH_2Cl_2$, 1:20) to yield desired product 49. $^1$H NMR (300 MHz, $CDCl_3$) δ 7.57 (d, J=8.7 Hz, 2H), 7.27 (d, J=8.1 Hz, 2H), 7.06 (d, J=8.4 Hz, 2H), 6.97 (s, 1H), 6.71 (d, J=8.4 Hz, 2H), 4.52-4.55 (m, 2H), 4.14 (q, J=6.9 Hz, 2H), 3.46-3.47 (m, 2H), 2.89 (s, 3H), 1.77-2.11 (m, 6H), 1.49 (t, J=6.9 Hz, 3H). HRMS (m/z): calc. for $C_{23}H_{28}N_3O$ (M+) 362.2227, obs. 362.2183.

(50)

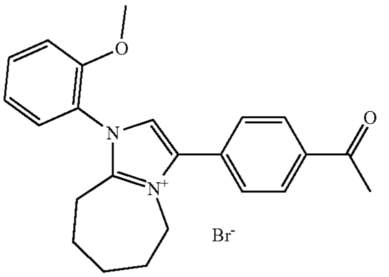

Imidazolium 50. General procedure A. $^1$H NMR (300 MHz, $CDCl_3$) δ 8.09-8.13 (m, 2H), 7.94 (dd, J=1.5, 7.5 Hz, 1H), 7.72-7.80 (m, 2H), 7.55-7.61 (m, 1H), 7.11-7.23 (m, 3H), 4.66-4.74 (m, 1H), 4.37-4.42 (m, 1H), 3.92 (s, 3H), 3.46-3.55 (m, 1H), 3.01-3.08 (m, 1H), 2.68 (s, 3H), 2.02-2.26 (m, 4H), 1.77-1.81 (m, 2H). HRMS (m/z): calc. for $C_{23}H_{25}N_2O_2$ (M+) 361.1911, obs. 361.1911.

(51)

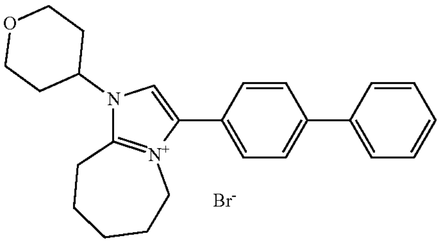

Imidazolium 51. General procedure A. $^1$H NMR (300 MHz, $CDCl_3$) δ 7.76 (d, J=8.1 Hz, 2H), 7.64-7.66 (m, 3H), 7.41-7.52 (m, 5H), 4.68-4.71 (m, 2H), 4.49-4.57 (m, 1H), 4.05-4.11 (m, 2H), 3.60-3.64 (m, 2H), 3.42 (t, J=8.4 Hz, 2H), 2.27-2.32 (m, 4H), 1.90-2.24 (m, 6H). HRMS (m/z): calc. for $C_{25}H_{29}N_2O$ (M+) 373.2274, obs. 373.2277.

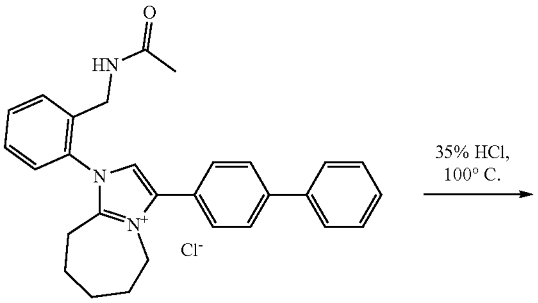

f

-continued

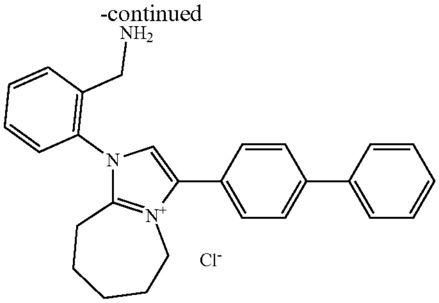

52

Imidazolium 52. The general procedure A was applied for the synthesis of intermediate f. A mixture of fin 35% HCl (2 mL) was stirred at the 100° C. overnight. The mixture was concentrated under reduced pressure. The residue was purified by silica gel column chromatography (MeOH: $CH_2Cl_2$=1:20) to give the desired product 52. $^1$H NMR (500 MHz, $CDCl_3$) δ 7.99 (s, 1H), 7.74 (s, 1H), 7.73-7.62 (m, 5H), 7.59-7.49 (m, 4H), 7.44 (s, 4H), 7.39-7.33 (m, 1H), 4.58-4.47 (m, 1H), 4.37 (s, 1H), 4.30 (s, 2H), 4.06 (s, 2H), 3.26-3.13 (m, 1H), 2.99-2.91 (m, 1H), 1.79-1.61 (m, 4H), 1.45-1.37 (m, 2H). HRMS (m/z): calc. for $C_{27}H_{28}N_3$ (M+) 394.2278, obs. 394.2276.

(53)

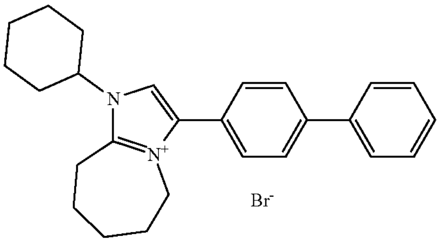

Imidazolium 53. General procedure A. $^1$H NMR (500 MHz, $CDCl_3$) δ 7.72 (d, J=8.5 Hz, 2H), 7.63-7.65 (m, 2H), 7.58 (s, 1H), 7.45-7.51 (m, 4H), 7.42 (t, J=7.0 Hz, 1H), 4.69 (t, J=5.0 Hz, 2H), 4.20 (s, 1H), 3.59 (q, J=4.0 Hz, 2H), 2.10 (t, J=2.5 Hz, 2H), 1.99 (t, J=5.5 Hz, 2H), 1.89 (t, J=11.0 Hz, 6H), 1.69 (d, J=10.0 Hz, 2H), 1.18-1.31 (m, 6H). HRMS (m/z): calc. for $C_{26}H_{31}N_2$ (M+) 371.2482, obs. 371.2478.

(54)

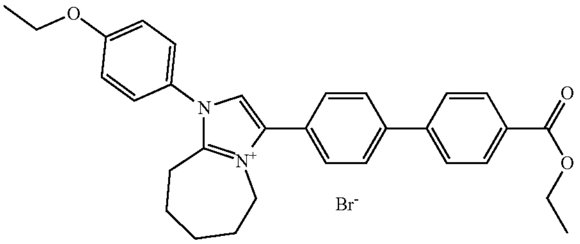

Imidazolium 54. General procedure A. $^1$H NMR (500 MHz, $CDCl_3$) δ 8.13 (s, 2H), 7.75 (d, J=8.5 Hz, 2H), 7.66-7.69 (m, 4H), 7.63 (d, J=9.0 Hz, 2H), 7.14 (s, 1H), 7.03 (d, J=9.0 Hz, 2H), 4.51 (t, J=4.5 Hz, 2H), 4.39 (q, J=7.5 Hz, 2H), 4.07 (q, J=6.5 Hz, 2H), 3.39 (dd, $J_1$=7.0 Hz, $J_2$=4.5 Hz, 2H), 2.06 (d, J=4.5 Hz, 2H), 1.93 (s, 2H), 1.80 (s, 2H), 1.45 (t, J=7.0 Hz, 3H), 1.42 (t, J=7.0 Hz, 3H). HRMS (m/z): calc. for $C_{31}H_{33}N_2O_3$ (M+) 481.2486, obs. 481.2400.

(55)

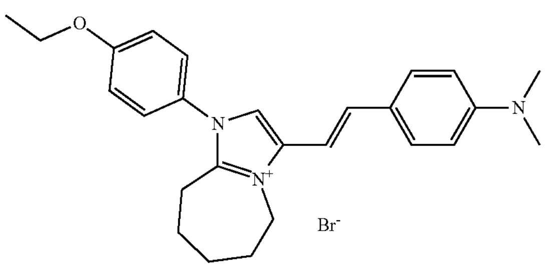

Imidazolium 55. General procedure A. $^1$H NMR (500 MHz, $CDCl_3$) δ 7.54 (d, J=9.0 Hz, 2H), 7.38 (d, J=9.0 Hz, 2H), 7.13 (s, 1H), 7.02 (d, J=9.0 Hz, 1H), 6.96 (d, J=16.0 Hz, 1H), 6.68 (d, J=8.5 Hz, 2H), 6.59 (d, J=16.0 Hz, 1H), 4.64 (t, J=4.5 Hz, 2H), 4.08 (q, J=6.5 Hz, 2H), 3.42 (t, J=5.5 Hz, 2H), 3.02 (s, 6H), 2.09 (t, J=5.0 Hz, 2H), 1.95 (s, 2H), 1.72 (s, 2H), 1.46 (t, J=7.0 Hz, 3H). HRMS (m/z): calc. for $C_{26}H_{32}N_3O$ (M+) 402.2540, obs. 402.2546.

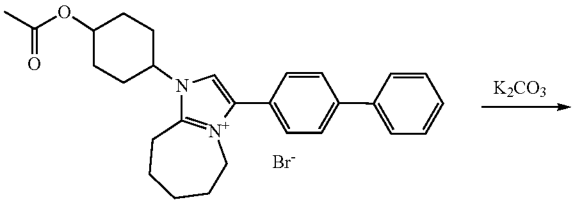

g

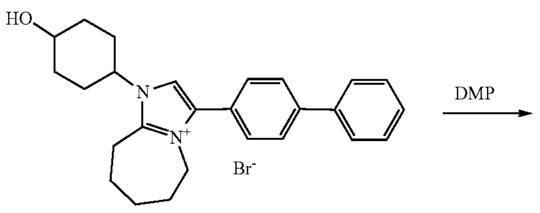

h

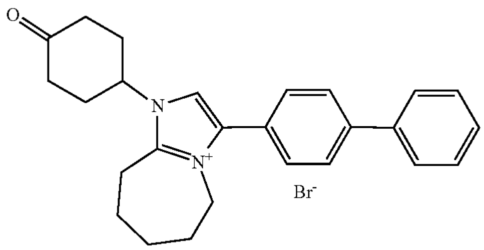

56

Imidazolium 56. The general procedure A was applied for the synthesis of intermediate g. To a solution of g (150 mg, 0.35 mmol) in MeOH (4 mL) was added $K_2CO_3$ (121 mg, 0.87 mmol), and the mixture was stirred at the room temperature for 12 h. The reaction mixture was filtered, concentrated under reduced pressure and EtOAc (50 mL) was added. The organic phase was washed with water and saturated brine and then dried over anhydrous $Na_2SO_4$. After evaporation of the solvent, the residue was purified by silica gel column chromatography (hexane:EtOAc=3:1) to afford intermediate h.

To a solution of h (80 mg, 0.21 mmol) in $CH_2Cl_2$ (4 mL) was added Dess Martin periodinane (118 mg, 0.28 mmol), and the mixture was stirred at the room temperature for 6 h. The reaction mixture was then concentrated under reduced pressure, and the resulting residue was purified by silica gel column chromatography (MeOH:$CH_2Cl_2$=1:20) to afford 56. $^1$H NMR (300 MHz, $CDCl_3$) δ 7.75 (d, J=8.1 Hz, 2H), 7.40-7.67 (m, 2H), 7.44-7.55 (m, 5H), 7.31 (s, 1H), 5.11-5.16 (m, 1H), 4.56 (d, J=8.1 Hz, 2H), 3.67-3.70 (m, 2H), 3.28 (s, 2H), 3.05 (s, 3H), 2.61-2.66 (m, 2H), 2.43-2.70 (m, 4H), 2.22-2.31 (m, 2H), 1.98-2.07 (m, 3H), 1.59-1.74 (m, 3H). HRMS (m/z): calc. for $C_{26}H_{29}N_2O$ (M+) 385.2274, obs. 385.2272.

(57)

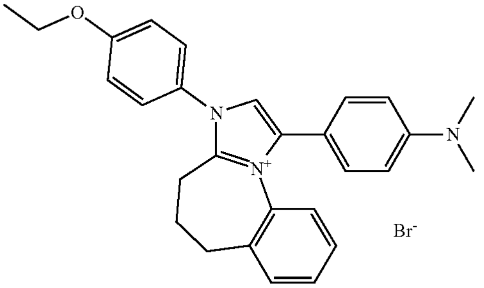

Imidazolium 57. General procedure A. $^1$H NMR (300 MHz, $CDCl_3$) δ 7.86 (d, J=8.7 Hz, 2H), 7.41-7.55 (m, 4H), 7.24-7.27 (m, 1H), 7.07-7.18 (m, 5H), 6.64 (d, J=8.7 Hz, 2H), 4.08-4.17 (m, 2H), 2.96-2.99 (m, 2H), 2.96 (s, 6H), 2.04-2.88 (m, 6H), 1.44-1.50 (m, 3H). HRMS (m/z): calc. for $C_{28}H_{30}N_3O$ (M+) 424.2383, obs. 424.2382.

(58)

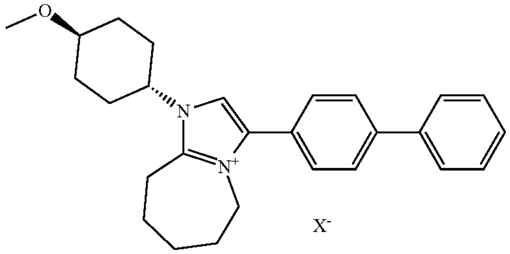

Imidazolium 58. General procedure A. $^1$H NMR (500 MHz, $CDCl_3$) δ 7.71 (d, J=8.0 Hz, 2H), 7.62 (d, J=7.5 Hz, 2H), 7.58 (s, 1H), 7.40-7.50 (m, 2H), 4.69 (t, J=5.0 Hz, 2H), 4.21 (m, 1H), 3.60 (q, J=3.5 Hz, 2H), 3.31 (s, 3H), 3.17 (m, 1H), 2.21 (s, 1H), 2.18 (d, J=4.5 Hz, 2H), 2.14 (s, 2H), 2.07-2.10 (m, 2H), 1.95-2.04 (m, 2H), 1.88 (s, 2H), 1.17-1.25 (m, 3H). HRMS (m/z): calc. for $C_{27}H_{33}N_2O$ (M+) 401.2587, obs. 401.2580.

(59)

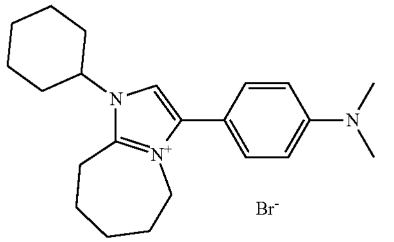

Imidazolium 59. General procedure A. $^1$H NMR (400 MHz, $CDCl_3$) δ 7.34 (s, 1H), 7.17 (d, J=6.3 Hz, 2H), 6.75 (d, J=6.3 Hz, 2H), 4.63-4.66 (m, 2H), 4.10-4.20 (m, 1H), 3.54-3.57 (m, 2H), 3.03 (s, 6H), 3.03-3.08 (m, 1H), 1.67-2.11 (m, 12H), 1.20-1.28 (m, 4H). HRMS (m/z): calc. for $C_{22}H_{32}N_3$ (M+) 338.2591, obs. 338.2590.

(60)

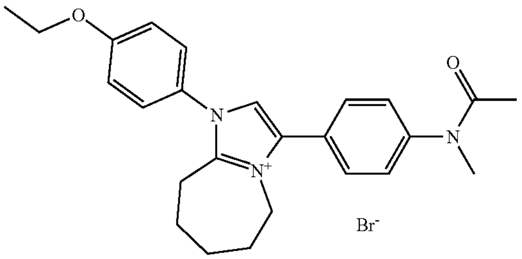

Imidazolium 60. General procedure A. $^1$H NMR (400 MHz, $CDCl_3$) δ 7.68 (d, J=6.8 Hz, 2H), 7.61 (d, J=8.8 Hz, 2H), 7.37 (d, J=8.0 Hz, 2H), 7.17 (s, 1H), 7.04 (d, J=8.8 Hz, 2H), 4.48-4.49 (m, 2H), 4.11 (q, J=6.8 Hz, 2H), 3.32-3.35 (m, 5H), 1.93-2.07 (m, 9H), 1.47 (t, J=6.8 Hz, 3H). HRMS (m/z): calc. for $C_{25}H_{30}N_3O_2$ (M+) 404.2333, obs. 404.2322.

(61)

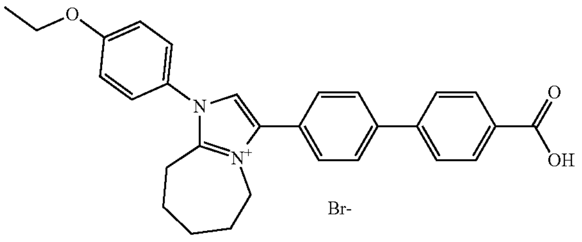

Imidazolium 61. General procedure A. $^1$H NMR (500 MHz, $CDCl_3$) δ 7.93 (s, 2H), 7.61-7.63 (m, 4H), 7.37-7.56 (m, 4H), 7.22 (s, 1H), 6.97 (d, J=7.5 Hz, 2H), 4.40 (s, 2H), 4.01 (q, J=6.0 Hz, 2H), 3.26 (s, 2H), 2.06 (s, 1H), 1.90-1.97 (m, 4H), 1.78 (s, 2H), 1.40 (t, J=7.0 Hz, 3H). HRMS (m/z): calc. for $C_{29}H_{29}N_2O_3$ (M+) 453.2173, obs. 453.2081.

(62)

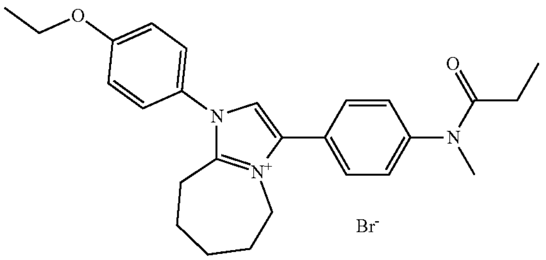

Imidazolium 62. General procedure A. $^1$H NMR (300 MHz, $CDCl_3$) δ 7.62-7.69 (m, 4H), 7.37 (d, J=9.3 Hz, 2H), 7.15 (s, 1H), 7.06 (d, J=9.0 Hz, 2H), 4.49 (br, 2H), 4.07-4.13 (m, 2H), 3.68-3.75 (m, 2H), 3.37 (br, 2H), 3.32 (s, 3H), 2.20 (d, J=7.5 Hz, 2H), 2.05-2.10 (m, 2H), 1.95 (br, 2H), 1.86 (q, J=3.6 Hz, 3H), 1.49 (q, J=6.9 Hz, 3H). HRMS (m/z): calc. for $C_{26}H_{32}N_3O_2$ (M+) 418.2489, obs. 418.2489.

(63)

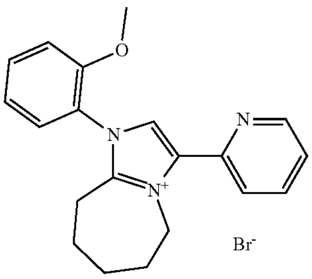

Imidazolium 63. General procedure A. $^1$H NMR (300 MHz, $CDCl_3$) δ 8.72 (d, J=4.5 Hz, 1H), 8.00 (d, J=7.8 Hz, 1H), 7.88-7.95 (m, 2H), 7.54-7.59 (m, 2H), 7.41 (dd, J=1.8, 6.9 Hz, 1H), 7.18 (t, J=7.5 Hz, 1H), 7.10 (d, J=8.4 Hz, 1H), 4.76-5.01 (m, 2H), 3.88 (s, 3H), 2.97-3.44 (m, 2H), 1.66-2.11 (m, 6H). HRMS (m/z): calc. for $C_{20}H_{22}N_3O$ (M+) 320.1757, obs. 320.1757.

(64)

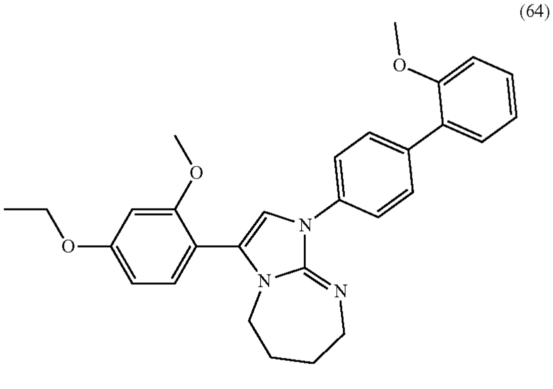 [SMILES: CCOc1ccc(C2=CN(c3ccc(-c4ccccc4OC)cc3)C3=NCCCCN23)c(OC)c1]

Guanidine 64. General procedure B. $^1$H NMR (400 MHz, $CD_3CN$) δ 7.80 (s, J=8.8 Hz, 2H), 7.55 (s, J=7.2 Hz, 2H), 7.44-7.38 (m, 2H), 7.27 (d, J=8 Hz, 1H), 7.16-7.08 (m, 2H), 7.03 (s, 1H), 6.69-6.64 (m, 2H), 4.14 (q, 2H), 3.90 (s, 3H), 3.85 (s, 3H), 3.76-3.73 (m, 2H), 3.37-3.34 (m, 2H), 2.25-2.15 (m, 4H), 1.41 (t, 3H). LRMS (m/z) calc. for $C_{29}H_{32}N_3O_3$ (M+H) 470.2, obs. 470.3.

(65)

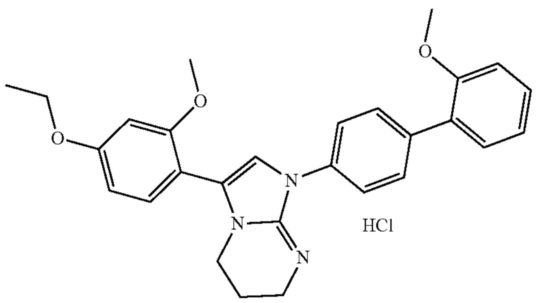

Guanidine 65. General procedure B. $^1$H NMR (400 MHz, DMSO-d6) δ 8.52 (brs, 1H), 7.73-7.71 (d, J=8.0 Hz, 2H), 7.65-7.63 (d, J=8.4 Hz, 2H), 7.43-7.39 (m, 2H), 7.35-7.28 (m, 2H), 7.19-7.17 (d, J=7.6 Hz, 1H), 7.10-7.06 (t, J=7.6 Hz, 1H), 6.75 (s, 1H), 6.69-6.67 (d, J=8 Hz, 1H), 4.14-4.09 (q, 2H), 3.86 (s, 3H), 3.80 (s, 3H), 3.74 (bs, 2H), 3.40 (bs, 2H), 2.01 (bs, 2H), 1.36 (t, J=7.0 Hz, 3H).

(66)

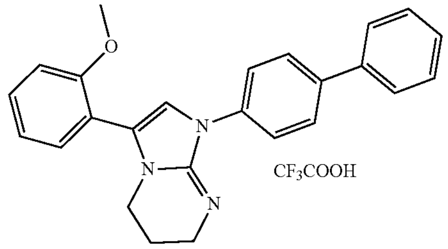

Guanidine 66. General procedure B. $^1$H NMR (400 MHz, $CDCl_3$) δ 9.91 (s, 1H), 7.65-7.60 (m, 3H), 7.58-7.30 (m, 5H), 7.18-7.06 (m, 2H), 6.72 (s, 1H), 3.95 (s, 3H), 3.85-3.82 (m, 2H), 3.75-3.60 (m, 2H), 2.20-2.10 (m, 2H). LRMS (m/z) calc. for $C_{25}H_{24}N_3O$ (M+H) 382.2, obs. 382.3.

(67)

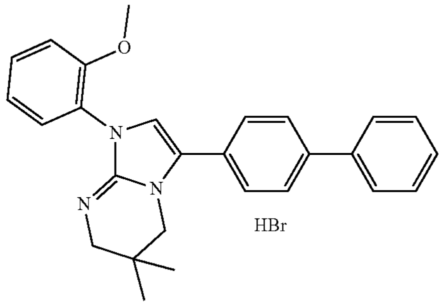

Guanidine 67. General procedure B. $^1$H NMR (400 MHz, $CDCl_3$) δ 7.73 (d, J=7.6 Hz, 2H), 7.62 (d, J=7.0 Hz, 2H), 7.56-7.44 (m, 6H), 7.41 (s, 2H), 7.34 (s, 1H), 7.17-7.09 (m, 2H), 6.69 (s, 1H), 3.97 (s, 3H), 3.67 (s, 2H), 3.38 (s, 2H), 1.12 (s, 6H). HRMS (m/z): calc. for $C_{27}H_{28}N_3O$ (M+) 410.2232, obs. 410.2230.

(68)

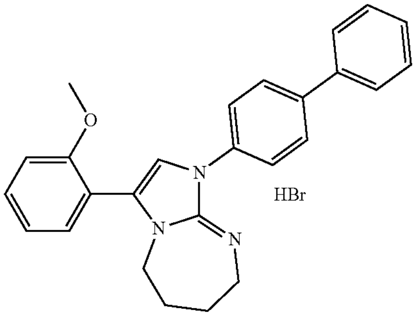

Guanidine 68. General procedure B. $^1$H NMR (500 MHz, $CDCl_3$) δ 7.83 (d, J=8.5 Hz, 2H), 7.73 (d, J=8.5 Hz, 2H), 7.62 (d, J=1.0 Hz, 2H), 7.55 (t, 1H), 7.44-7.48 (m, 2H), 7.39 (d, J=7.0 Hz, 1H), 7.32 (dd, J=1.5, 7.5 Hz, 1H), 7.11 (t, 1H), 7.06 (d, J=8.5 Hz, 1H), 6.80 (s, 1H), 3.93 (s, 3H), 3.80 (t, 2H), 3.67 (d, J=5.0 Hz, 2H), 1.97-2.01 (m, 4H). HRMS (m/z): calc. for $C_{26}H_{26}N_3O$ (M+) 396.2076, obs. 396.2068.

(69)

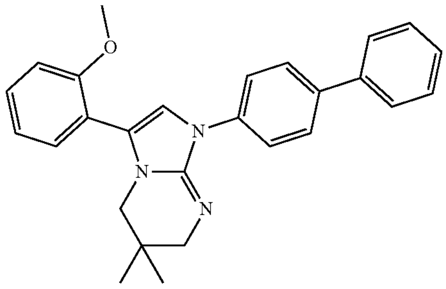

Guanidine 69. General procedure B. $^1$H NMR (400 MHz, DMSO-d6) δ 8.66 (s, 1H), 7.94 (d, J=8.4 Hz, 2H), 7.77-7.73 (m, 3H), 7.60-7.52 (m, 4H), 7.47-7.39 (m, 2H), 7.24 (d, J=8.4 Hz, 1H), 7.12 (t, J=7.6 Hz, 1H), 3.88 (s, 3H), 3.53 (s, 2H), 3.13 (s, 2H), 1.05 (s, 6H). LRMS (m/z): calc. for $C_{27}H_{28}N_3O$ (M+H) 410.2, obs. 410.3.

(70)

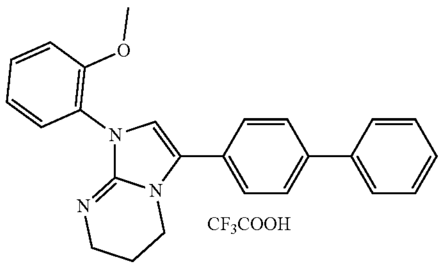

Guanidine 70. General procedure B. $^1$H NMR (400 MHz, $CDCl_3$) δ 10.52 (s, 1H), 7.77 (s, J=8.4 Hz, 2H), 7.66 (s, J=7.2 Hz, 2H), 7.55-7.51 (m, 5H), 7.48-7.44 (m, 2H), 7.16-7.12 (m, 2H), 6.70 (s, 1H), 4.08-4.06 (m, 2H), 3.96 (s, 3H), 3.75-3.65 (m, 2H), 2.22-2.15 (m, 2H). LRMS (m/z): calc. for $C_{25}H_{24}N_3O$ (M+H) 382.2, obs. 382.3.

(71)

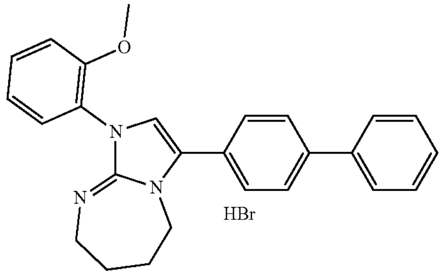

Guanidine 71. General procedure B. $^1$H NMR (300 MHz, $CDCl_3$) δ 7.74 (d, J=8.2 Hz, 2H), 7.62 (d, J=7.2 Hz, 2H), 7.53-7.42 (m, 7H), 7.15 (dt, J=11.2, 6.1 Hz, 2H), 6.71 (s, 1H), 3.99 (s, 6H), 3.65 (s, 2H), 2.03 (d, J=8.2 Hz, 5H). HRMS (m/z): calc. for $C_{26}H_{26}N_3O$ (M+H) 396.2076, obs. 396.2073.

(72)

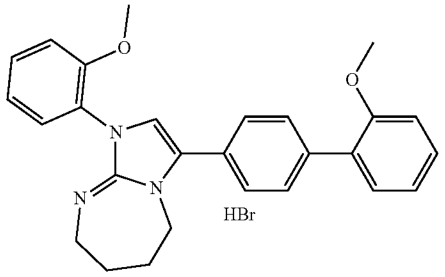

Guanidine 72. General procedure B. $^1$H NMR (400 MHz, $CDCl_3$) δ 7.69 (d, J=7.2 Hz, 2H), 7.57-7.48 (m, 1H), 7.48-7.35 (m, 3H), 7.34 (d, J=7.5 Hz, 1H), 7.20-7.10 (m, 1H), 7.04 (dt, J=19.5, 9.1 Hz, 2H), 6.69 (s, 1H), 3.99 (s, 4H), 3.85 (s, 3H), 3.65 (s, 2H), 3.31 (s, 1H), 2.11-1.93 (m, 5H). HRMS (m/z): calc. for $C_{27}H_{28}N_3O_2$ (M+H) 426.2182, obs. 426.2180.

(73)

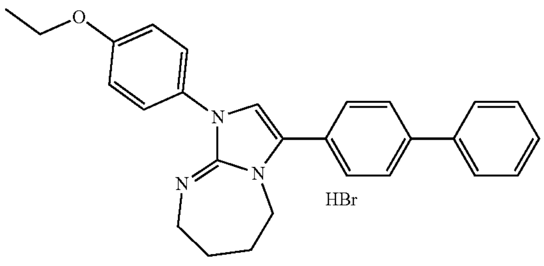

Guanidine 73. General procedure B. $^1$H NMR (500 MHz, $CDCl_3$) δ 7.73 (d, J=8.0 Hz, 2H), 7.61 (d, J=7.5 Hz, 3H), 7.41-7.50 (m, 6H), 7.04 (d, J=8.5 Hz, 2H), 6.77 (s, 1H), 4.07 (t, J=7.0 Hz, 2H), 3.99 (d, J=5.0 Hz, 1H), 3.64 (s, 1H), 2.20 (t, J=7.5 Hz, 2H), 2.09 (s, 2H), 1.62-2.02 (m, 2H), 1.40 (q, J=7.0 Hz, 3H). HRMS (m/z): calc. for $C_{27}H_{28}N_3O$ (M+H) 410.2232, obs.

(74)

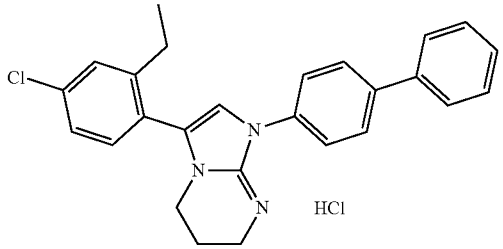

Guanidine 74 General procedure B. $^1$H NMR (400 MHz, DMSO-$d_6$) δ 7.87 (d, J=8.0 Hz, 2H), 7.71 (d, J=8.0 Hz, 2H), 7.62 (d, J=8.0 Hz, 2H), 7.53-7.31 (m, 7H), 3.62-3.59 (m, 2H), 3.44-3.41 (m, 2H), 2.67 (q, J=8 Hz, 2H), 2.08-2.02 (m, 2H), 1.17 (t, J=8 Hz, 3H). HRMS (m/z) calc. for $C_{26}H_{24}ClN_3$ (M+H) 414.1737, obs. 414.1725

(75)

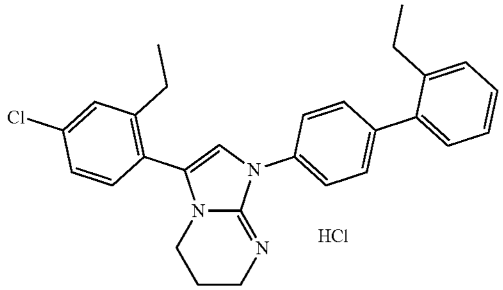

Guanidine 75 General procedure B. $^1$H NMR (DMSO-$d_6$) δ 7.68-7.66 (m, 2H), 7.59-7.56 (m, 4H), 7.47-7.28 (m, 5H), 7.19 (d, J=8.0 Hz, 1H), 3.67-3.64 (m, 2H), 3.44-3.39 (m, 2H), 2.71-2.57 (m, 4H), 2.08-2.01 (m, 2H), 1.16 (t, J=8.0 Hz, 3H), 1.09 (t, J=8.0 Hz 3H). HRMS (m/z) calc. for $C_{28}H_{28}ClN_3$ (M+H) 442.2050, obs. 442.2033.

(76)

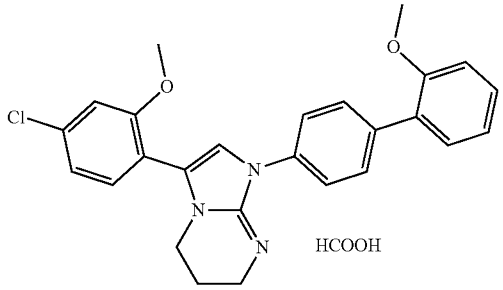

Guanidine 76 General procedure B. $^1$H NMR (400 MHz, $CD_3CN$) δ 7.71 (d, J=4 Hz, 2H), 7.49 (d, J=8.0 Hz, 2H), 7.40-7.30 (m, 3H), 7.18-7.01 (m, 5H), 3.87-3.86 (m, 3H), 3.79-3.75 (m, 3H), 3.58-3.57 (m, 2H), 3.41-3.38 (m, 2H), 2.03-1.99 (m, 2H). HRMS (m/z) calc. for $C_{26}H_{24}ClN_3O_2$ (M+H) 446.1635, obs. 446.1624.

(77)

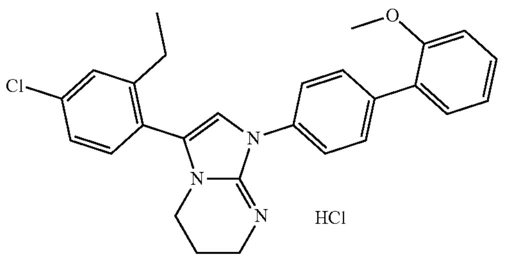

Guanidine 77 General procedure B. $^1$H NMR ($CD_3CN$) δ 7.73-7.71 (m, 2H), 7.52-7.46 (m, 3H), 7.40-7.29 (m, 4H), 7.10-7.03 (m, 2H), 7.97 (s, 1H), 3.78 (s, 3H), 3.60-3.57 (m, 2H), 3.40-3.37 (m, 2H), 2.63 (q, J=8.0 Hz, 2H), 2.05-2.0 (m, 2H), 1.13 (t, J=8.0 Hz, 3H). HRMS (m/z) calc. for $C_{27}H_{26}ClN_3O$ (M+H) 444.1842, obs. 444.1824.

(78)

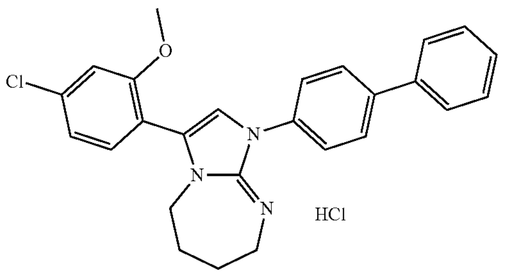

Guanidine 78 General procedure B. $^1$H NMR (400 MHz, $CD_3CN$) δ 7.91-7.89 (d, J=8 Hz, 2H), 7.74-7.72 (d, J=8.0 Hz, 2H), 7.61-7.43 (m, 5H), 7.35-7.33 (d, J=8 Hz, 1H), 7.22 (s, 1H), 7.15-7.13 (d, J=8 Hz, 1H), 7.08 (s, 1H), 6.34-6.33 (m, 1H), 3.91 (s, 3H), 3.74-3.72 (m, 2H), 3.37-3.34 (m, 2H), 2.95-1.93 (m, 2H), 1.38-1.27 (m, 1H). HRMS (m/z) calc. for $C_{26}H_{24}ClN_3O$ (M+H) 430.1686, obs. 430.1665.

(79)

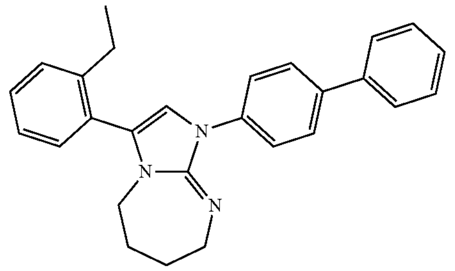

Guanidine 79 General procedure B. $^1$H NMR (400 MHz, $CD_3CN$) δ 7.85-7.83 (d, J=8.0 Hz, 2H), 7.74-7.72 (m, 4H), 7.54-7.44 (m, 5H), 7.40-7.30 (m, 2H), 6.94 (s, 1H), 3.51-3.49 (m, 2H), 3.41-3.41 (m, 2H), 2.77-2.71 (q, J=8.0 Hz, 2H), 2.00-1.80 (m, 4H), 1.21 (t, J=8.0 Hz, 3H). HRMS (m/z) calc. for $C_{27}H_{27}N_3$ (M+H) 394.2283, obs. 394.2265.

(80)

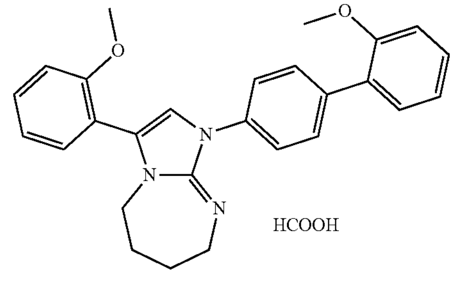

Guanidine 80 General procedure B. $^1$H NMR (400 MHz, $CD_3CN$) δ 7.70 (d, J=8 Hz, 2H), 7.59-7.53 (m, 3H), 7.41-7.36 (m, 3H), 7.17 (d, J=8.4 Hz, 1H), 7.13-7.05 (m, 3H), 6.98 (s, 1H), 3.91 (s, 3H), 3.82 (s, 3H), 3.79 (t, J=5.8 Hz, 2H), 3.45 (t, J=5.4 Hz, 2H), 2.07-1.95 (m, 2H). HRMS (m/z) calc. for $C_{26}H_{25}N_3O_2$ (M+H) 412.2025, obs. 412.2009.

(81)

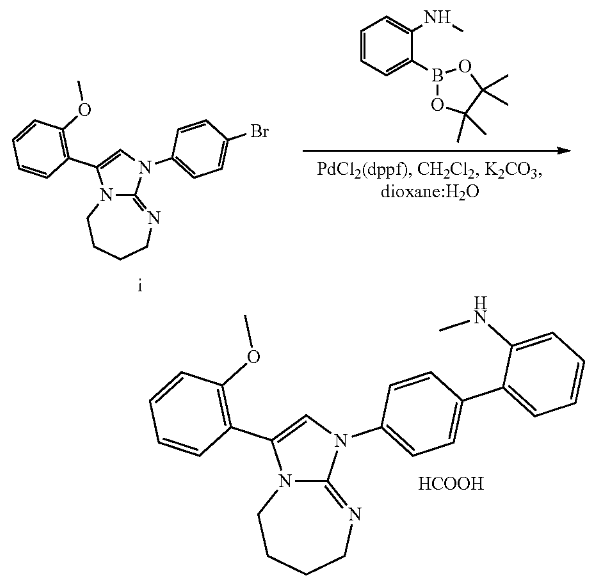

Guanidine 81 The general procedure B was applied for synthesis of i. To a solution of intermediate i in dioxane: water (2:0.2 ml) was added N-methyl-2-(4,4,5,5-tetramethyl-1,3,2-dioxaborolan-2-yl)aniline (0.351 g, 1.5 mmol) and $K_2CO_3$ (0.207 g, 1.5 mmol) at room temperature, and then the mixture was stirred under a $N_2$ atmosphere. $PdCl_2$(dppf)·$CH_2Cl_2$ (0.04 g, 0.05 mmol) was added, and the mixture was refluxed at 110° C. for 1 h. After completion of reaction as monitored by TLC, the reaction mixture was diluted with water (50 ml) and extracted with $CH_2Cl_2$ (3×30 ml). The combined organic layer was washed with brine, dried over anhydrous $Na_2SO_4$ and concentrated under reduced pressure. The obtained crude was further purified by prep HPLC (0.1% formic acid in water and acetonitrile). Appropriate pure fractions were combined and concentrated by lyophilization to afford 75. $^1$H NMR (400 MHz, DMSO-$d_6$) δ 7.71-7.69 (d, J=8 Hz, 2H), 7.61-7.47 (m, 3H), 7.48 (s, 1H), 7.40-7.39 (d, J=6.8 Hz, 1H), 7.26-7.24 (d, J=8 Hz, 2H), 7.14-7.11 (t, J=7.2 Hz, 1H), 7.04-7.02 (d, J=7.2 Hz, 1H), 6.73-6.66 (m, 2H), 4.78 (s, 1H), 3.89 (s, 3H), 3.70 (s, 2H), 3.50-3.40 (m, 2H), 2.71-2.70 (d, 3H), 1.93 (s, 2H), 1.83 (s, 2H). HRMS (m/z) calc. for $C_{27}H_{28}N_4O$ (M+H) 425.2341, obs. 425.2323.

(82)

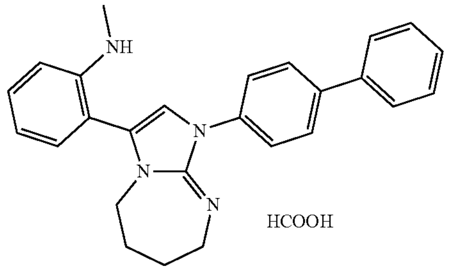

Guanidine 82 General procedure B. $^1H$ NMR (400 MHz, $CD_3CN$) δ 7.89-7.87 (d, J=8.4 Hz, 2H), 7.75-7.73 (d, J=7.2 Hz, 2H), 7.69-7.67 (d, J=8.4 Hz, 2H), 7.56-7.52 (m, 2H), 7.47-7.39 (m, 2H), 7.17-7.15 (d, J=7.2 Hz, 1H), 6.99 (s, 1H), 6.78-6.74 (m, 2H), 4.88 (s, 1H), 3.63 (s, 2H), 3.43-3.42 (m, 2H), 2.83 (s, 3H), 1.90 (s, 4H). HRMS (m/z) calc. for $C_{26}H_{26}N_4$ (M+H) 395.2235, obs. 395.2217.

(83)

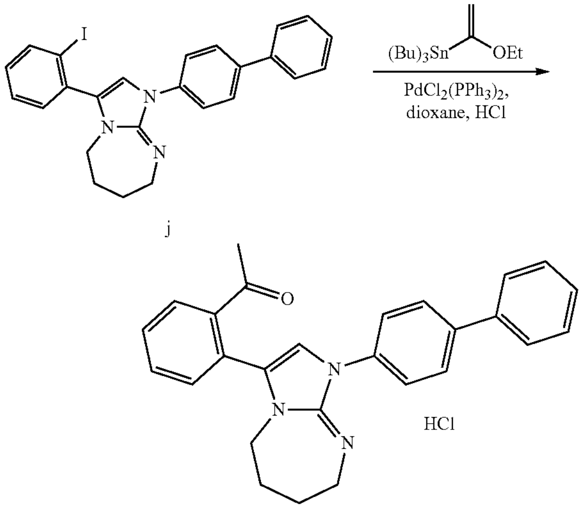

Guanidine 83 The general procedure B was applied for synthesis of j. To a solution of intermediate j (0.13 g, 0.264 mmol) in dioxane (3 ml), 1,1'-Bis(triphenylphosphine)palladium(II) dichloride (0.018 g, 0.026 mmol) and tributyl(1-ethoxyvinyl)tin (0.19 g, 0.529 mmol) were added. The reaction mixture was stirred at 80° C. for 12h. After completion of reaction as monitored by TLC, reaction mixture was poured into water (50 ml) and extracted with EtOAc (3×20 ml). The combined organic layer was dried over anhydrous $Na_2SO_4$ and concentrated under reduced pressure. The obtained crude product was further purified by prep HPLC (0.05% formic acid in water and acetonitrile). Appropriate pure fractions were combined and concentrated under lyophilization to afford 77. $^1H$ NMR (400 MHz, DMSO-$d_6$) δ 8.13 (d, J=7.2 Hz, 1H), 7.95 (d, J=8.4 Hz, 2H), 7.81-7.75 (m, 4H), 7.69 (d, J=8.8 Hz, 2H), 7.57-7.52 (m, 3H), 7.48-7.45 (m, 2H), 3.64 (s, 2H), 3.50 (s, 2H), 2.62 (s, 3H), 1.83 (s, 4H). HRMS (m/z) calc. for $C_{27}H_{25}N_3O$ (M+H) 408.2076, obs. 408.2056.

(84)

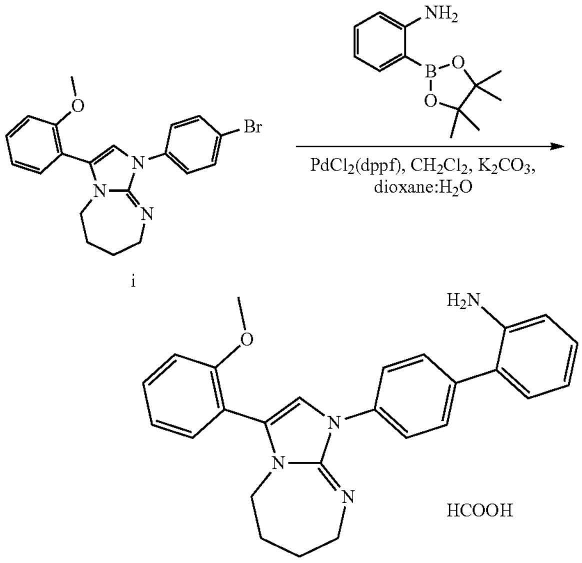

Guanidine 84 The general procedure B was applied for synthesis of compound i. To a solution of i (0.1 g, 0.2 mmol) in dioxane:water (2:0.2 ml), 2-(4,4,5,5-tetramethyl-1,3,2-dioxaborolan-2-yl)aniline (0.168 g, 0.7 mmol) and $K_2CO_3$ (0.207 g, 1.5 mmol) were added, and the mixture was put under a $N_2$ atmosphere. $PdCl_2(dppf)\cdot CH_2Cl_2$ (0.04 g, 0.05 mmol) was added, and the reaction mixture was refluxed at 110° C. for 1 h. After completion of reaction as monitored by TLC, reaction mixture was diluted with water (50 ml) and extracted with $CH_2Cl_2$ (3×20 ml). The combined organic layer was dried over anhydrous $Na_2SO_4$ and concentrated under reduced pressure. The crude product was purified by prep HPLC (0.1% formic acid in water and acetonitrile). Appropriate pure fractions were combined and concentrated under lyophilization to afford 78. $^1H$ NMR (400 MHz, $CD_3CN$) δ 7.66-7.54 (m, 5H), 7.40 (d, 1H, J=7.2 Hz), 7.19-7.10 (m, 4H), 7.04 (s, 1H), 6.81-6.75 (m, 2H), 4.40 (s, 2H), 3.93 (s, 3H), 3.72-3.71 (m, 2H), 3.45-3.42 (m, 2H), 2.00-1.90 (m, 4H). HRMS (m/z) calc. for $C_{26}H_{26}N_4O$ (M+H) 411.2185, obs. 411.2178.

(85)

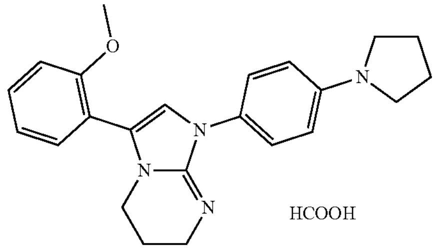

Guanidine 85 The general procedure B was applied for synthesis of j. To a solution of intermediate j (0.13 g, 0.264 mmol) in dioxane (3 ml), 1,1'-Bis(triphenylphosphine)palladium(II) dichloride (0.018 g, 0.026 mmol) and tributyl(1-ethoxyvinyl)tin (0.19 g, 0.529 mmol) were added. The reaction mixture was stirred at 80° C. for 12h. After completion of reaction as monitored by TLC, reaction mixture was poured into water (50 ml) and extracted with EtOAc (3×20 ml). The combined organic layer was dried over anhydrous $Na_2SO_4$ and concentrated under reduced pressure. The obtained crude product was further purified by prep HPLC (0.05% formic acid in water and acetonitrile). Appropriate pure fractions were combined and concentrated under lyophilization to afford 77. $^1$H NMR (400 MHz, DMSO-$d_6$) δ 8.13 (d, J=7.2 Hz, 1H), 7.95 (d, J=8.4 Hz, 2H), 7.81-7.75 (m, 4H), 7.69 (d, J=8.8 Hz, 2H), 7.57-7.52 (m, 3H), 7.48-7.45 (m, 2H), 3.64 (s, 2H), 3.50 (s, 2H), 2.62 (s, 3H), 1.83 (s, 4H). HRMS (m/z) calc. for $C_{21}H_2sN3Q$ (M+H) 408.2076, obs. 408.2056.

(86)

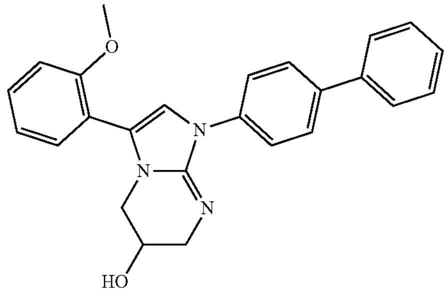

Guanidine 86 General procedure B. $^1$H NMR (400 MHz, $CD_3CN$) δ 7.91 (d, J=8.4 Hz, 3H), 7.76-7.74 (d, J=7.6 Hz, 2H), 7.69-7.67 (d, J=8.4 Hz, 2H), 7.60-7.41 (m, 3H), 7.21-7.10 (m, 3H), 4.36-4.34 (m, 1H), 3.99-3.96 (m, 2H), 3.92 (s, 3H), 3.76-3.73 (m, 2H), 3.57-3.54 (m, 2H), 3.48-3.45 (m, 2H). HRMS (m/z) calc. for $C_{25}H_{23}N_3O_2$ (M+H) 398.1868, obs. 398.1847.

(87)

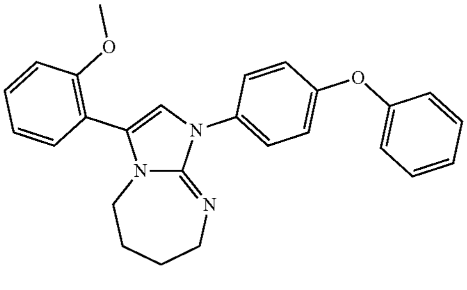

Guanidine 87 General procedure B. $^1$H NMR (400 MHz, $CD_3CN$) δ 7.57 (d, J=8.4 Hz, 2H), 7.51-7.44 (m, 3H), 7.36 (d, J=7.2 Hz, 1H), 7.27-7.21 (m, 1H), 7.17-7.14 (m, 3H), 7.12-7.10 (m, 3H), 6.95 (s, 1H), 3.91 (s, 3H), 3.62-3.60 (t, J=5 Hz, 2H), 3.39-3.36 (t, J=5 Hz, 2H), 2.00-1.86 (m, 4H). HRMS (88)

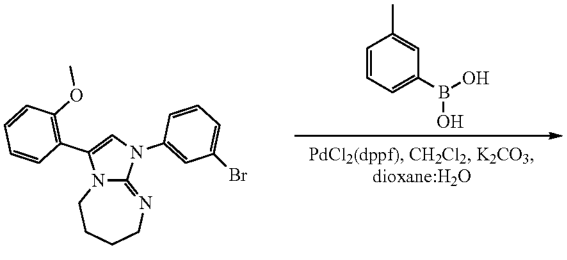

k

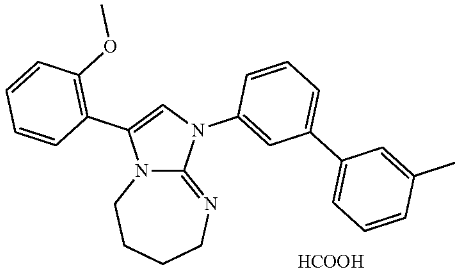

HCOOH

Guanidine 88 The general procedure B was applied for synthesis of compound k. To a solution of k (0.13 g, 0.32 mmol) in dioxane:water (5:0.5 ml) was added $K_2CO_3$ (0.132 g, 0.96 mmol) and m-tolylboronic acid (0.133 g, 0.97 mmol) at room temperature under $N_2$ atmosphere. $PdCl_2$(dppf) ·$CH_2Cl_2$ (0.026 g, 0.032 mmol) was added and the reaction mixture was heated to 100° C. for 1 h. After completion of reaction as indicated by TLC, the reaction mixture was poured into water (50 ml) and extracted with $CH_2Cl_2$ (3×30 ml). The combined organic layer was dried over $Na_2SO_4$ and concentrated under reduce pressure to get crude product. The crude was purified by column chromatography using silica gel (60-120 mesh silica gel, 6% MeOH in $CH_2Cl_2$). The isolated material was further purified by prep HPLC (0.1% formic acid in water and acetonitrile). The appropriate fractions were combined and concentrated by lyophilization to afford 85. $^1$H NMR (400 MHz, $CD_3CN$) δ 7.83 (m, 2H), 7.69 (t, J=7.8 Hz, 1H), 7.58-7.53 (m, 4H), 7.43-7.38 (m, 2H), 7.29 (d, J=7.2 Hz, 1H), 7.19 (d, J=8.4 Hz, 1H), 7.14-7.09 (m, 2H), 3.92 (s, 3H), 3.75-3.72 (m, 2H), 3.42-3.40 (m, 2H), 2.44 (s, 3H), 2.00-1.89 (m, 4H). HRMS (m/z) calc. for $C_{27}H_{27}N_3O$ (M+H) 41 0.2232, obs. 41 0.2220.

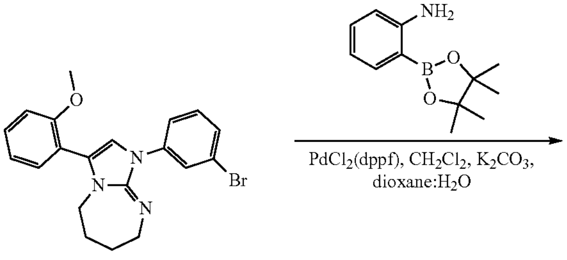

k

-continued

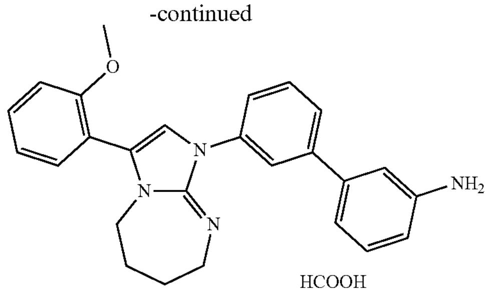

HCOOH

Guanidine 89 The general procedure B was applied for synthesis of compound k. To a solution of k (0.25 g, 0.62 mmol) in dioxane:water (2:0.2 ml) was added 3-(4,4,5,5-tetramethyl-1,3,2-dioxaborolan-2-yl)aniline (0.40 g, 1.8 mmol) and $K_2CO_3$ (0.259 g, 1.8 mmol) at room temperature under a $N_2$ atmosphere. $PdCl_2(dppf)\cdot CH_2Cl_2$ (0.051 g, 0.0062 mmol) was added and the reaction mixture was heated at 100° C. for 1 h. After completion of reaction as monitored by TLC, the reaction mixture was diluted with water (50 ml) and extracted with $CH_2Cl_2$ (3x20 ml). The combined organic layer was washed with brine, dried over anhydrous $Na_2SO_4$ and concentrated under reduce pressure. The crude product was purified by prep HPLC (0.1% formic acid in water and acetonitrile). The appropriate pure fractions were combined and concentrated by lyophilization to afford 88. $^1$H NMR (400 MHz, DMSO) δ 7.80 (s, 1H), 7.75 (d, J=7.6 Hz, 1H), 7.68 (t, J=7.8 Hz, 1H), 7.60-7.53 (m, 3H), 7.39 (d, J=7.6 Hz, 1H), 7.24 (d, J=8.4, 1H), 7.13 (dd, J=8.0 Hz, 2H), 6.97-6.87 (m, 2H), 6.63-6.54 (m, 2H), 5.23 (s, 2H), 3.89 (s, 3H), 3.70-3.68 (m, 2H), 3.39-3.37 (m, 2H), 1.92 (s, 2H), 1.83-1.81 (m, 2H). HRMS (m/z) calc. for $C_{26}H_{26}N_4O$ (M+H) 411.2185, obs. 411.2174.

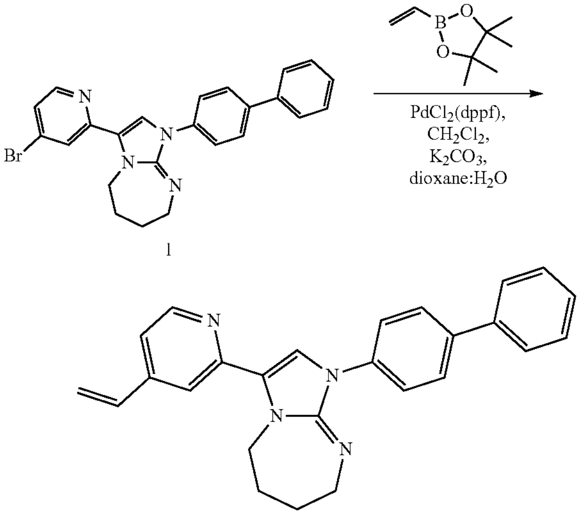

1

Guanidine 90 The general procedure B was applied for synthesis of compound I. To a stirred solution of 1 (0.15 g, 0.336 mmol) in dioxane (2.0 ml) was added 4,4,5,5-tetramethyl-2-vinyl-1,3,2-dioxaborolane (0.08 g, 0.51 mmol) and $K_2CO_3$ (0.16 g, 1.17 mmol, dissolved in 0.5 ml water) at room temperature under $N_2$ atmosphere. $PdCl_2$ (dppf) $\cdot CH_2Cl_2$ (0.03 g, 0.034 mmol) was added, and the reaction mixture was refluxed at 110° C. for 1 h under microwave irradiation. After completion of reaction monitored by TLC, the reaction mixture was filtered through pad of celite bed. The filtrate was diluted with water and extracted with $CH_2Cl_2$ (3x30 ml). The organic layer was washed with brine solution, dried over anhydrous $Na_2SO_4$ and concentrated under reduced pressure to get crude product. The crude product was purified by prep HPLC purification in 0.1% formic acid, acetonitrile and water to afford 89. $^1$H NMR (400 MHz, $CD_3CN$) δ 8.67 (d, J=4.8 Hz, 1H), 8.30 (s, 1H) 7.95 (d, J=8 Hz, 2H), 7.77-7.73 (m, 3H), 7.64 (d, J=8.4 Hz, 2H), 7.58-7.54 (m, 2H), 7.50-7.46 (m, 2H), 6.86-6.78 (m, 1H), 6.19 (d, J=17.6 Hz, 1H), 5.63 (d, J=10.8, 1H), 4.46-4.43 (m, 2H), 3.43 (s, 2H), 2.10 (s, 2H), 1.96 (s, 2H). HRMS (m/z) calc. for $C_{26}H_{24}N_4$ (M+H) 393.2079, obs. 393.2071.

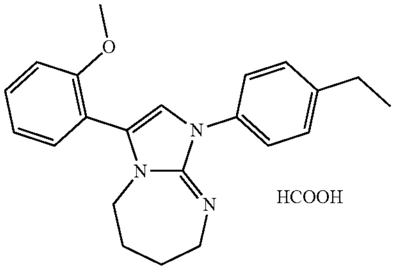 [SMILES: CCc1ccc(N2C=C(c3ccccc3OC)N3CCCCN=C32)cc1 ; "HCOOH"]

HCOOH

Guanidine 91 General procedure B. $^1$H NMR (400 MHz, $CD_3CN$) δ 7.56 (t, J=8.0 Hz, 1H), 7.49-7.44 (m, 4H), 7.37 (d, J=7.2 Hz, 1H), 7.18 (d, J=8.4 Hz, 1H), 7.12 (t, J=7.4 Hz, 1H), 7.01 (s, 1H), 3.91 (s, 3H), 3.73-3.71 (m, 2H), 3.37-3.34 (m, 2H), 2.75 (q, J=7.6 Hz, 2H), 2.05-1.88 (m, 4H), 1.28 (t, J=7.6 Hz, 3H). HRMS (m/z) calc. for $C_{22}H_{25}N_3O$ (M+H) 348.2076, obs.

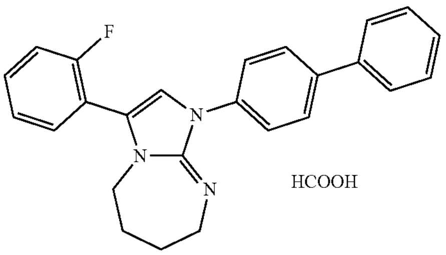 [SMILES: Fc1ccccc1C1=CN(c2ccc(-c3ccccc3)cc2)C2=NCCCCN12 ; "HCOOH"]

HCOOH

Guanidine 92 General procedure B. $^1$H NMR (400 MHz, DMSO) δ 7.93 (d, J=8.0 Hz, 2H), 7.77-7.75 (m, 4H), 7.69 (s, 1H), 7.60-7.42 (m, 7H), 3.78 (s, 2H), 3.41 (s, 2H), 1.96 (s, 2H), 1.83 (s, 2H). HRMS (m/z) calc. for $C_{25}H_{22}FN_3$ (M+H) 384.1876, obs. 384.1862.

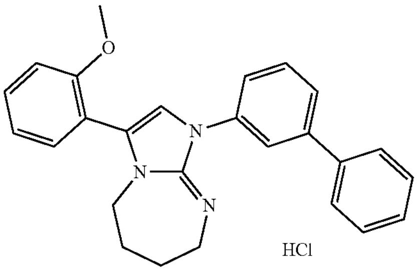 [SMILES: COc1ccccc1C1=CN(c2cccc(-c3ccccc3)c2)C2=NCCCCN12 ; Cl]

HCl

Guanidine 93 General procedure B. $^1$H NMR (400 MHz, DMSO-$d_6$) δ 7.92 (d, J=7.6 Hz, 1H), 7.80 (d, J=7.2 Hz, 2H), 7.76-7.72 (m, 2H), 7.68-7.50 (m, 5H), 7.46-7.39 (m, 2H), 7.26 (d, J=8.4 Hz, 1H), 7.14 (t, J=7.6 Hz, 1H), 3.89 (s, 3H), 3.73-3.71 (m, 2H), 3.35 (s, 2H), 1.96-1.91 (m, 2H), 1.83 (s, 2H). HRMS (m/z) calc. for $C_{25}H_{25}N_3O$ (M+H) 396.2076, obs. 396.2062.

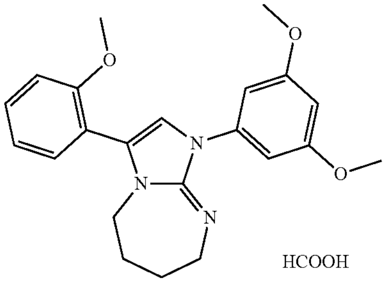 [SMILES: COc1cc(OC)cc(N2C=C(c3ccccc3OC)N3CCCCN=C32)c1 ; "HCOOH"]

Guanidine 94 General procedure B. $^1H$ NMR (400 MHz, $CD_3CN$) δ 8.53 (s, 1H), 7.56 (t, J=7.2 Hz, 1H), 7.37 (d, J=7.6 Hz, 1H), 7.18 (d, J=8.4 Hz, 1H), 7.12 (t, J=7.4 Hz, 1H), 7.02 (s, 1H), 6.70 (s, 2H), 6.67 (s, 1H), 3.91 (s, 3H), 3.86 (s, 6H), 3.72 (t, J=4.8 Hz, 2H), 3.39 (t, J=5.4 Hz, 2H), 2.05-1.89 (m, 2H). HRMS (m/z) calc. for $C_{22}H_{25}N_3O_3$ (M+H) 380.1974, obs. 380.1964.

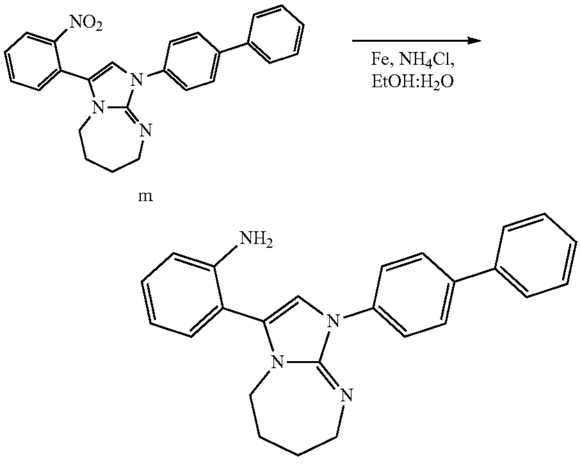

Guanidine 95 The general procedure B was applied for synthesis of compound m. To a solution of m (0.34 g, 0.83 mmol) in EtOH:water (9: 1), Fe (0.370 g, 6.63 mmol) and NH4Cl (1.62 g, 6.63 mmol) were added. The reaction mixture was stirred at 80° C. temperature for 5h. After completion of reaction as indicated by TLC, the reaction mixture was poured into water (100 ml) and filtered through a celite bed and washed with EtOAc. The organic layer was separated and washed with water (3x30 ml). The combined organic layer was dried over anhydrous $Na_2SO_4$ and concentrated under reduced pressure. The crude product was further purified by prep HPLC (0.1% formic acid in water and acetonitrile) to afford 95. $^1H$ NMR (400 MHz, $CD_3CN$): δ 7.96 (d, J=8.3 Hz, 2H), 7.76 (d, J=7.6 Hz, 2H), 7.67 (d, J=8.3 Hz, 2H), 7.53 (t, J=7.6 Hz, 2H), 7.45 (d, J=8.8 Hz, 2H), 7.27-7.14 (m, 1H), 7.08 (d, J=7.4 Hz, 1H), 6.78 (d, J=8.2 Hz, 1H), 6.64 (t, J=7.3 Hz, 1H), 5.47 (s, 2H), 3.64 (s, 2H), 3.36-3.32 (m, 2H), 1.91-1.81 (m, 4H). HRMS (m/z) calc. for $C_{25}H_{24}N_4$ (M+H) 381.2079, obs. 381.2073.

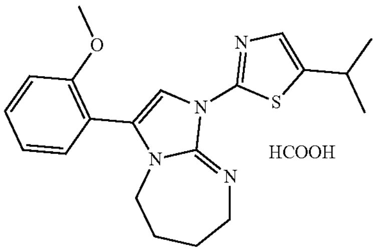 [SMILES: COc1ccccc1C1=CN(c2ncc(C(C)C)s2)C2=NCCCCN12 ; "HCOOH"]

Guanidine 96 General procedure B. $^1H$ NMR (400 MHz, $CD_3CN$) δ 7.52 (t, 7.6 Hz, 1H), 7.37 (d, J=7.2 Hz, 1H), 7.32 (s, 1H), 7.26 (s, 1H), 7.15 (d, J=8.4 Hz, 1H), 7.10 (t, J=7.4 Hz, 1H), 3.90 (s, 3H), 3.62-3.59 (m, 2H), 3.55 (t, J=4.8 Hz, 2H), 3.26-3.23 (m, 1H), 2.0-1.80 (m, 4H), 1.37 (s, 3H), 1.36 (s, 3H). HRMS (m/z) calc. for $C_{20}H_{26}N_4OS$ (M+H) 369.1749, obs. 369.1736.

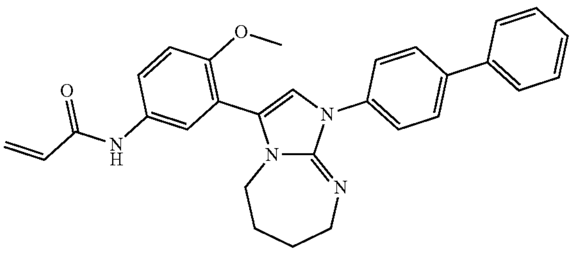 [SMILES: C=CC(=O)Nc1ccc(OC)c(C2=CN(c3ccc(-c4ccccc4)cc3)C3=NCCCCN23)c1]

Guanidine 97 General procedure B. $^1H$ NMR (400 MHz, $CD_3CN$): δ 8.57 (s, 1H), 7.99 (d, J=2.4 Hz, 1H), 7.92 (d, J=8.8 Hz, 2H), 7.84-7.81 (m, 1H), 7.75 (d, J=7.2 Hz, 2H), 7.63 (d, J=8.4, 2H), 7.57-7.53 (t, J=7.4 Hz, 2H), 7.49-7.45 (m, 1H), 7.15-7.13 (m, 2H), 6.61-6.54 (m, 1H), 6.34-6.29 (m, 1H), 5.74-5.71 (m, 1H), 3.90 (s, 3H), 3.80-3.78 (m, 2H), 3.37-3.35 (m, 2H), 2.20-1.91 (m, 4H). HRMS (m/z) calc. for $C_{29}H_{28}N_4O_2$ (M+H) 465.2290, obs. 465.2275.

Figure 1:
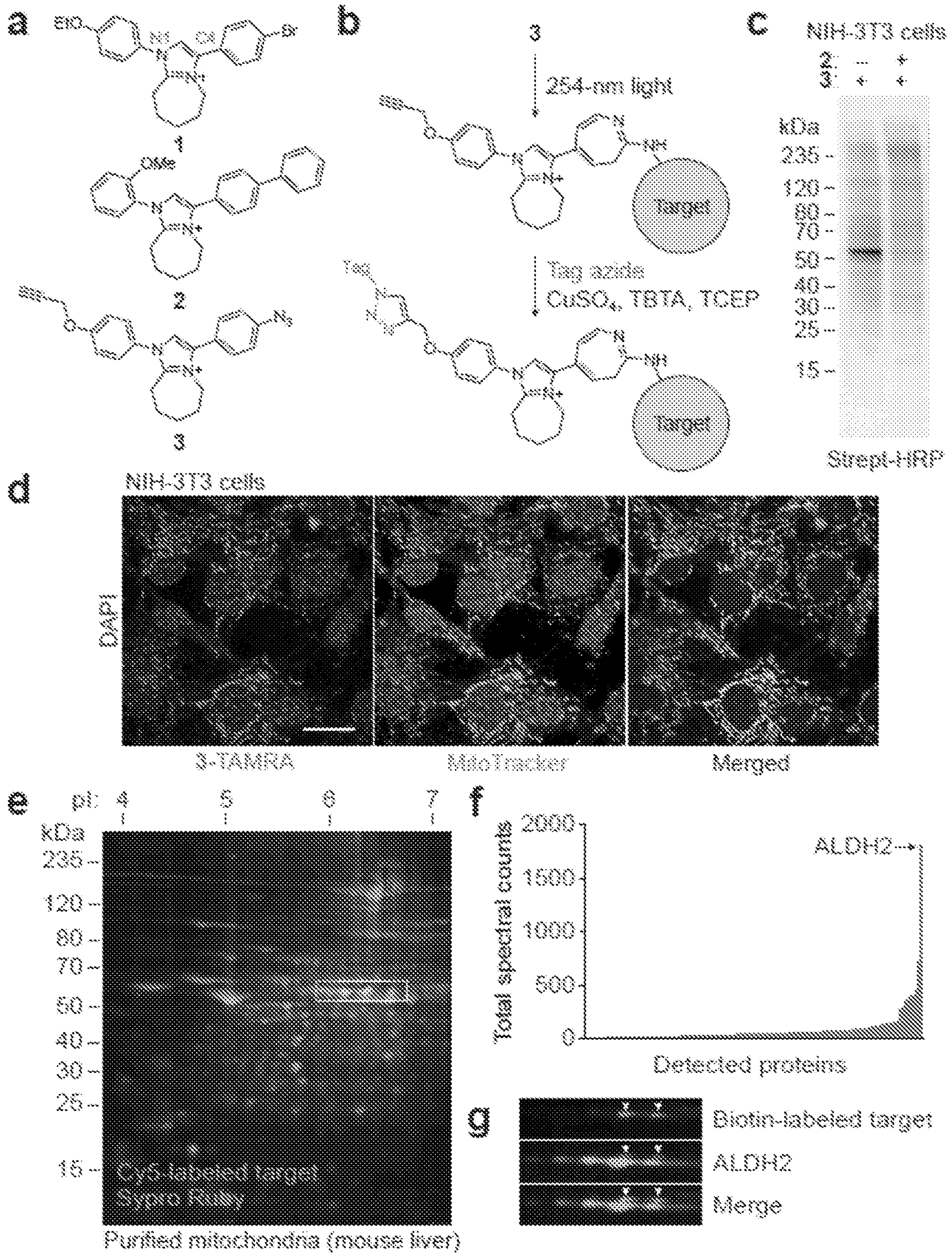
FIG. 1, Identification of ALDH2 as a target of bicyclic imidazolium derivatives. (A) Chemical structures of imidazoliums, including the Hh pathway screen hit 1, more potent Hh pathway inhibitor 2, and photoaffinity analog 3. N1 and C4 positions on the imidazolium ring are labeled. (B) Reaction scheme for target photo-crosslinking and click chemistry tagging. (C) Photoaffinity labeling of a 55-kDa imidazolium-binding protein in live NIH-3T3 cells. Biotin-azide was used to tag the photo-crosslinked protein, which was then detected by far-western blot analysis. (D) Photoaffinity labeling and TAMRA-azide tagging of live NIH-3T3 cells, demonstrating the mitochondrial localization of the imidazolium target. Scale bar: 10 μm. (E) Photoaffinity labeling and Cy5-azide tagging of the 55-kDa protein (dashed box) in intact, purified mitochondria from mouse liver. The mitochondrial lysate was resolved by two-dimensional gel electrophoresis, and Sypro Ruby was used to fluorescently stain the mitochondrial proteome. (F) Mass spectrometry sequencing of gel spots corresponding to the photoaffinity-labeled proteins, revealing ALDH2 as the most abundant candidate target. (G) Confirmation of imidazolium 3-ALDH2 photocrosslinking by biotin tagging and western blot analysis. Arrowheads label proteins that are both biotinylated and stained by anti-ALDH2 antibody.

Example 2: Identification of ALDH2 as a Target of Bicyclic Imidazolium Derivatives As disclosed herein it was discovered that exemplary imidazolium derivatives that can potently inhibit ALDH1B1 and other ALDH isoforms. The initial lead compound emerged in a high-throughput screen for Hedgehog (Hh) signaling inhibitors (FIG. 1, panel A; 1, $IC_{50}$~4 μM in Hh pathway assays). Subsequently a more potent analog was identified (3, $IC_{50}$~0.6 μM), and a photoaffinity reagent was prepared with a "click chemistry" handle to facilitate target identification (2, $IC_{50}$~0.7 μM). Using the latter probe and biotin tagging, a 55-kDa protein was specifically labeled (FIG. 1, panels B and C), and further studies with a tetramethylrhodamine (TAMRA) tag demonstrated that this binding protein is mitochondrial (FIG. 1, panel D). The target was then fluorescently labeled in intact, purified mitochondria, the reaction mixture was resolved by two-dimensional gel electrophoresis, and the fluorescent protein spots were analyzed by mass spectrometry (FIG. 1, panel E). These studies revealed ALDH2 as the photocrosslinked target. Mass spectrometry sequencing of gel spots corresponding to the photoaffinity-labeled proteins, indicated that ALDH2 was the most abundant candidate target. Confirmation of imidazolium 2A-ALDH2 photocrosslinking by biotin tagging and western blot analysis is shown in FIG. 1, panel G. Arrowheads label proteins that are both biotinylated and stained by anti-ALDH2 antibodies.

FIG. 1, panels A-G illustrates the identification of ALDH2 as a target of bicyclic imidazolium derivatives. Panel A: Chemical structures of imidazoliums, including the Hh pathway screening hit 1, photoaffinity analog 3, and more potent Hh pathway inhibitor 2. N1 and C4 positions on the imidazolium ring are labeled. Panel B: Reaction scheme for target photocrosslinking and click chemistry tagging. Panel C: Photoaffinity labeling of a 55-kDa imidazolium-binding protein in live NIH-3T3 cells. Biotin azide was used to tag the photocrosslinked protein, which was then detected by far-western blot analysis. Panel D: Photoaffinity labeling and TAMRA azide tagging of mitochondrial targets in NIH-3T3 cells. Scale bar: 10 μm. Panel E: Photoaffinity labeling and Cy5 azide tagging of the 55-kDa protein (dashed box) in intact, purified mitochondria from mouse liver. The mitochondrial lysate was resolved by 2D gel electrophoresis, and Sypro Ruby was used to fluorescently stain the mitochondrial proteome. Panel F: Mass spectrometry sequencing of gel spots corresponding to the photoaffinity-labeled proteins, revealing ALDH2 as the most abundant candidate target. Panel G: Confirmation of imidazolium 3-ALDH2 photocrosslinking by biotin tagging and western blot analysis. Arrowheads label proteins that are both biotinylated and stained by anti-ALDH2 antibodies.

Example 3: Identification of an ALDH1B1-Selective Imidazolium

Figure 2:
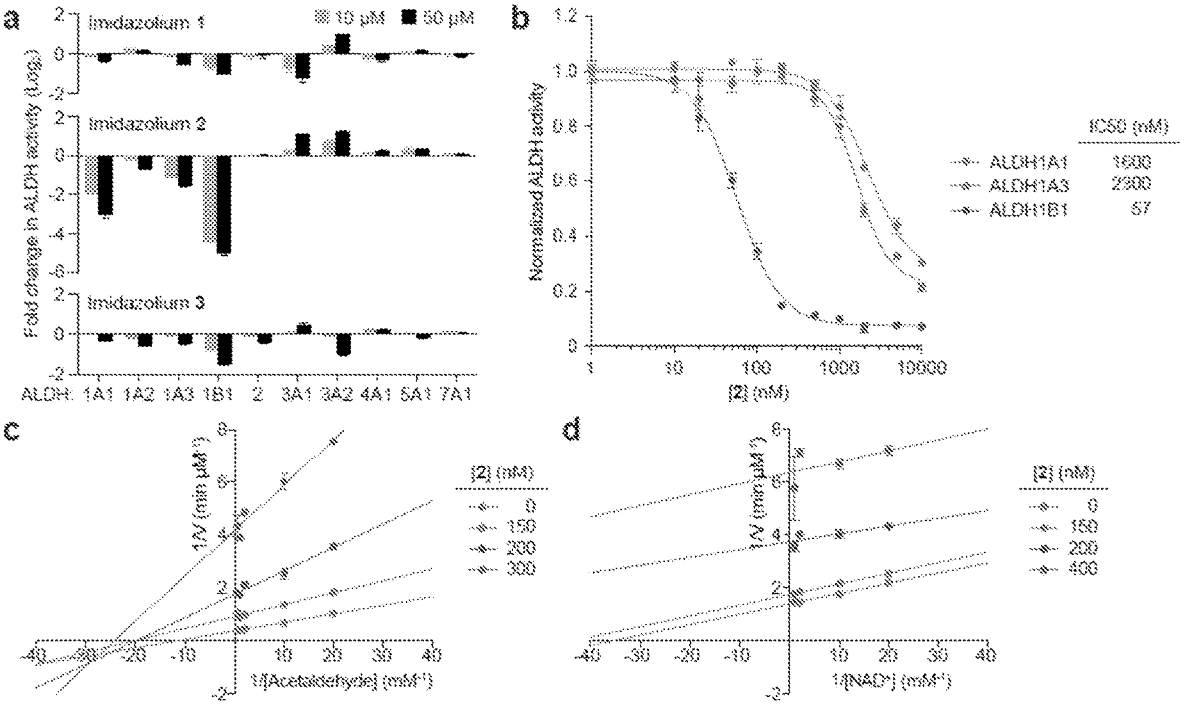
FIG. 2, Identification of an ALDH1B1-selective imidazolium. (A) Activities of imidazoliums 1-3 against selected ALDH isoforms in enzyme kinetics assays. Data are the average of at least two biological replicates±s.d. (B) Dose-response curves of 2 against ALDH1A1, ALDH1A3, and ALDH1B1. Data are the average of three biological replicates±s.e.m. (C-D) Lineweaver-Burk plots demonstrating that 2 exhibits non-competitive inhibition with respect to acetaldehyde (C) and uncompetitive inhibition with respect to NAD (D). Data are the average of at least two biological replicates±s.e.m.

All three of compounds 1-3 were observed to inhibit ALDH1B1, with compound 2 being the most potent (FIG. 2, panel A). FIG. 2, panel B shows the dose-response curves of compound 2 against ALDH1A1, ALDH1A3 and ALDH1B1. To better understand the mechanism of aldazole action, enzyme kinetics assays were conducted with purified recombinant ALDH1B1. Aldazole 2 activity was assessed in the presence of varying acetaldehyde concentrations, observing kinetic behaviors consistent with non-competitive inhibition (FIG. 2, panel C).

FIG. 2, panels A-D illustrates the identification of an ALDH1B1-selective imidazolium. Panel A: Profiling of imidazoliums 1-3 against selected ALDH isoforms in enzyme kinetics assays. Data are the average of at least two biological replicates±s.d. Panel B: Dose-response curves of 3 against ALDH1A1, ALDH1A3, and ALDH1B1. Data are the average of three biological replicates±s.e.m. Panels C-D: Lineweaver-Burk plots demonstrating that 2 exhibits non-competitive inhibition with respect to acetaldehyde, and uncompetitive inhibition with respect to NAD+(panel C). Panel D data are the average of at least two biological replicates±s.e.m.

Figure 3:
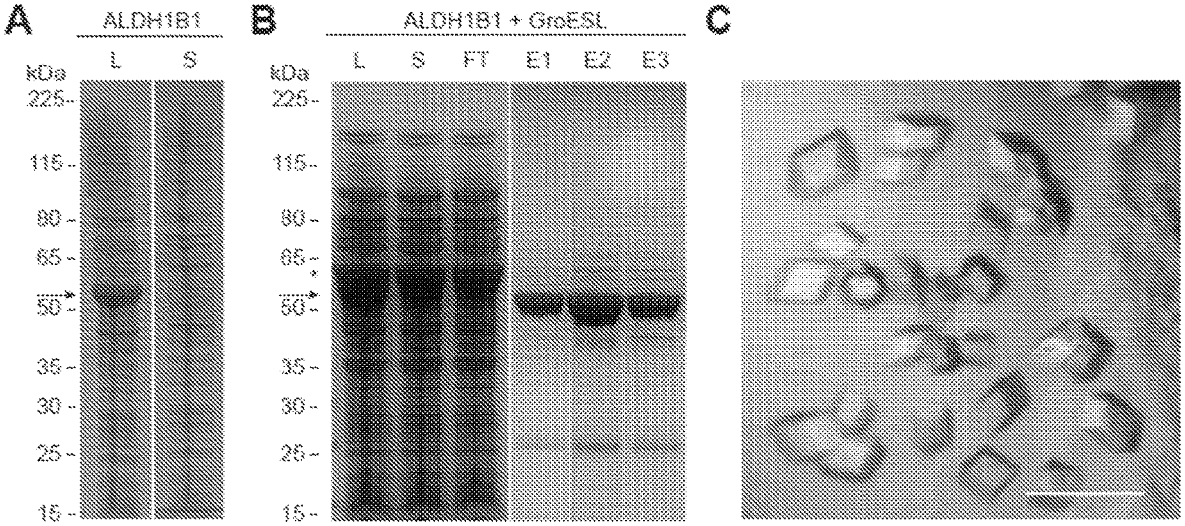
FIG. 3, Bacterial expression of ALDH1B1 protein with GroEL/ES chaperones. (A) SDS-PAGE analysis of bacterial cultures expressing His6-tagged ALDH1B1 (arrow). Coomassie-stained lanes containing total bacterial lysate (L) and the soluble fraction (S) are shown. (B) SDS-PAGE analysis of bacterial cultures co-expressing His6-tagged ALDH1B1 (arrow), GroEL (asterisk), and GroES. Coomassie-stained lanes containing total bacterial lysate (L), the soluble fraction (S), the Ni-NTA chromatography flow-through (FT), and elution fractions (E1, E2, and E3) are shown. (C) Micrograph of ALDH 1 B 1 crystals formed in the presence of NAD+ and imidazolium 3. Scale bar: 100 μm.

FIG. 3, panels A-C illustrate the bacterial expression of ALDH1B1 protein with the molecular chaperone GroESL. Panel A: SDS-PAGE analysis of bacterial cultures expressing His6-tagged ALDH1B1 (arrow). Coomassie-stained lanes containing total bacterial lysate (L) and the soluble fraction (S) are shown. Panel B: SDS-PAGE analysis of bacterial cultures co-expressing His6-tagged ALDH1B1 (arrow) and GroESL (asterisk). Coomassie-stained lanes containing total bacterial lysate (L), the soluble fraction (S), and Ni-NTA chromatography flow-through (FT) and elution fractions (E1, E2, and E3) are shown. Panel C: Micrograph of ALDH1B1 crystals formed in the presence of NAD+ and imidazolium 2. Scale bar: 100 μm.

Figure 4:
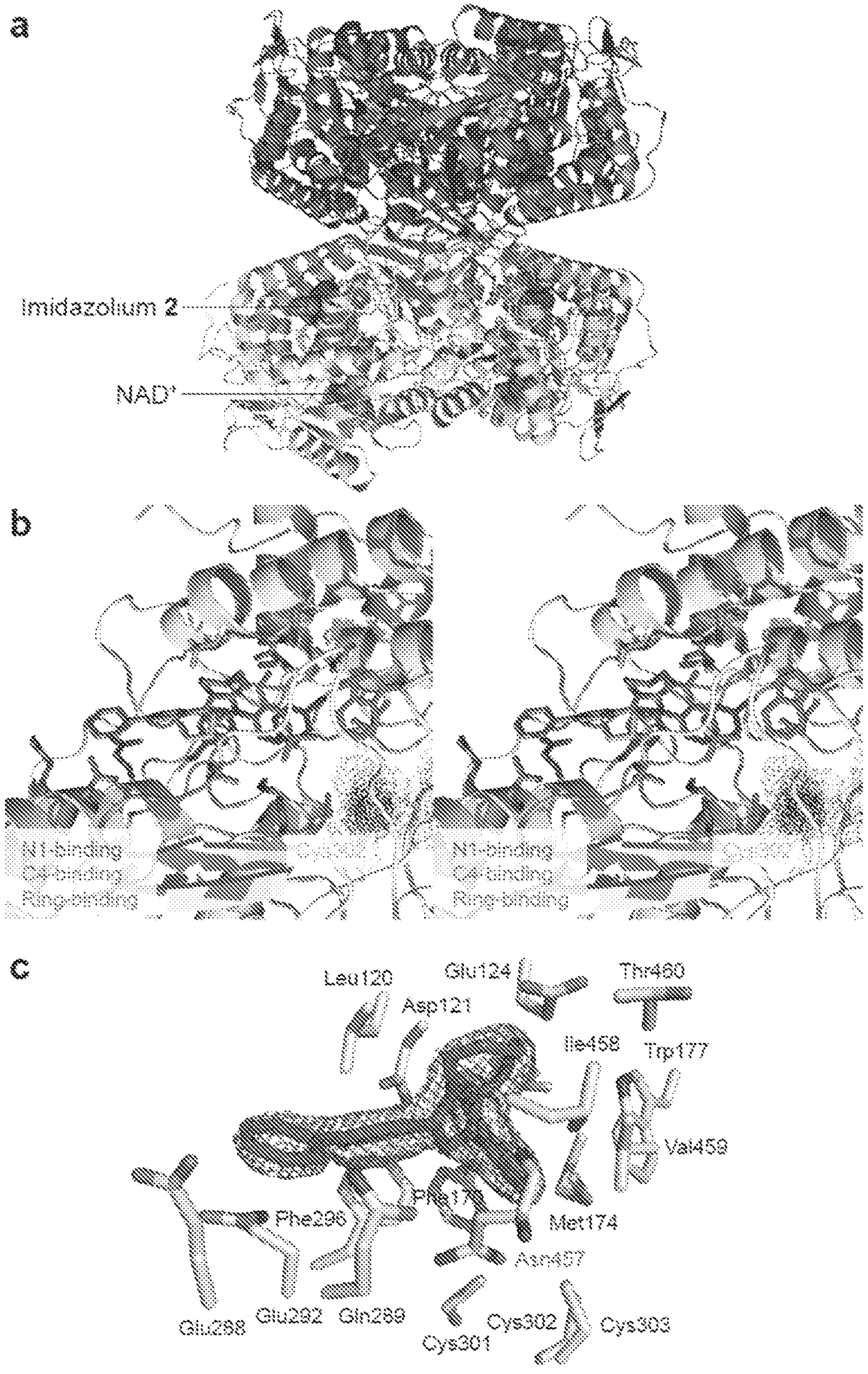
FIG. 4, Molecular basis of ALDH1B1-imidazolium binding. (A) Tetrameric structure of the ALDH1B1/imidazolium 2 complex. (B) Stereoview of the molecular interactions in the inhibitor-binding site. Imidazolium 2 is shown as a blue stick model, and $NAD^+$ is represented as dots. ALDH1B1 residues that interact with N1, C4, or ring substituents of the inhibitor are colored red, orange, and green, respectively. The catalytic residue Cys302 is also shown. (C) Electron density map (blue mesh) of imidazolium 2 with binding site residues shown as stick models. The red dashed line indicates an n-to-π* interaction between the Asn457 backbone carbonyl and the imidazolium ring. The map was calculated with coefficients 2Fo-Fc, contoured at 1 s, and superimposed with the refined model.

FIG. 4, panels A-C illustrate the crystal structure of an ALDH1B1-imidazolium complex. Panel A: Tetrameric structure of the ALDH1B1/imidazolium 2 complex. Panel B: Stereoview of the molecular interactions in the inhibitor-binding site. Imidazolium 2 is shown as a dark gray space-filling model, and NAD+ are represented as dots. Panel C: Electron density map (mesh) of imidazolium 3 with binding site residues shown as stick models. The white dashed line indicates an n-to-π* interaction between the Asn457 backbone carbonyl and imidazolium ring.

Structural studies of ALDH1B1 and the ALDH1B1/compound 2 complex were pursued by X-ray crystallography. The three-dimensional structure of ALDH1B1 had not been previously reported. Without being bound to any particular theory, it is possible that this is due to the challenges associated with expressing ALDH1B1 in bacteria. Indeed, the first studies of ALDH1B1 function relied on recombinant human protein expressed in Sf9 insect cells (Stagos, D. et al. (2010) *Drug Metab. Dispos.* 38, 1679-1687). The present inventors overcame this challenge by co-expressing bacterial GroEL/GroES chaperones to enhance ALDH1B1 folding and solubility, to obtain multi-milligram quantities of active protein. Crystals of ALDH1B1/NAD+ in the absence or presence of compound 2, employing the vapor-diffusion method. Diffraction-quality crystals were obtained using buffer composed of 10% PEG 4000, 20% glycerol, 0.1 M bicine/Trizma base, pH 8.5 and a mixture of alcohols. Both crystals were in the same trigonal space group with two polypeptide chains per asymmetric unit, and one NAD+ and one inhibitor (when included, e.g., compound 2) per polypeptide chain. Refinement of the crystallographic data provided the structures of ALDH1B1 and the ALDH1B1/compound 3 complex with resolutions of 2.8 Å and 2.2 Å, respectively (FIG. 4, panel A).

The crystal structures demonstrate that exemplary imidazolium compounds (e.g., as described herein) contact ALDH1B1 through all three imidazolium substituents, interacting with various residues that contribute to the substrate-binding site (FIG. 4, panel B). With reference to compound 2, the N1 2-methoxyphenyl group engages a channel that approaches the catalytic cysteine (Asp121, Glu124, Phe170, Val173, Met174, Trp177, Phe296, Cys301, Cys303, and Val459; due to the close homology of ALDH1B1 and ALDH2, structurally equivalent residues in the mature proteins have identical numbers). The C4 biphenyl substituent interacts with an extended cleft (Glu288, Gln289, Glu292, Phe296, and Asn457), and the tetrahydroazepine ring occupies a pocket that bridges the two sites (Leu120, Glu124, Ile458, and Thr460). Neither the 2-methoxyphenyl-imidazolium nor biphenyl-imidazolium systems are planar, and the tetrahydroazepine ring adopts a boat-like conformation. Of particular note is a close contact between the Asn457 backbone carbonyl and the imidazolium ring (3.3 Å) that likely reflects an n->π* interaction (FIG. 4, panel C). Previous studies have shown that such lone pair-aromatic interactions are particularly stabilizing when the aromatic ring is electron-deficient (Egli, M. & Sarkhel, S. (2007) *Acc. Chem. Res.* 40, 197-205; Singh, S. K. & Das, A. (2015) *Phys. Chem. Chem. Phys.* 17, 9596-9612). This can be achieved through protonation of a ring heteroatom, or in this case through the intrinsic cationic character of the imidazolium system.

Engagement of the ALDH1B1 substrate-binding site by compound 2 might seem counterintuitive given the noncompetitive behavior of this antagonist in enzyme assays. In addition, the ALDH1B1 backbone structure is not significantly altered by inhibitor binding (RMSD=0.24 A). However, other ALDH ligands with non-competitive inhibition have been observed to target the substrate-binding site (Morgan, C. A. & Hurley, T. D. J. (2015) *Med. Chem.* 58, 1964-1975), and ALDH agonists interact with this region as well (Perez-Miller, S. J. & Hurley, T. D. (2003) *Biochemistry* 42, 7100-7109). Without being bound to any particular theory, it was speculated that the non-competitive behavior of imidazoliums could reflect the ordered, multi-step mechanism of ALDH action, as has been observed in other bisubstrate enzymes (Blat, Y. (2010) *Chem. Biol. Drug Des.* 75, 535-540; Sahni-Arya, B. et al. (2007) *Biochim. Biophys. Acta* 1774, 1184-1191). For example, if the small-molecule ligand prevents thioester hydrolysis or NADH dissociation, it can block the formation of new ALDH/NAD+ complexes that are capable of aldehyde binding. Like ALDH1B1, most ALDH enzymes are tetramers composed of dimer pairs, and it has been shown that only one subunit with each dimer is active per catalytic cycle and that the two subunits exhibit cooperativity. Imidazoliums therefore might alter ALDH function through mechanisms that are difficult to observe through crystallographic methods.

Figure 5:
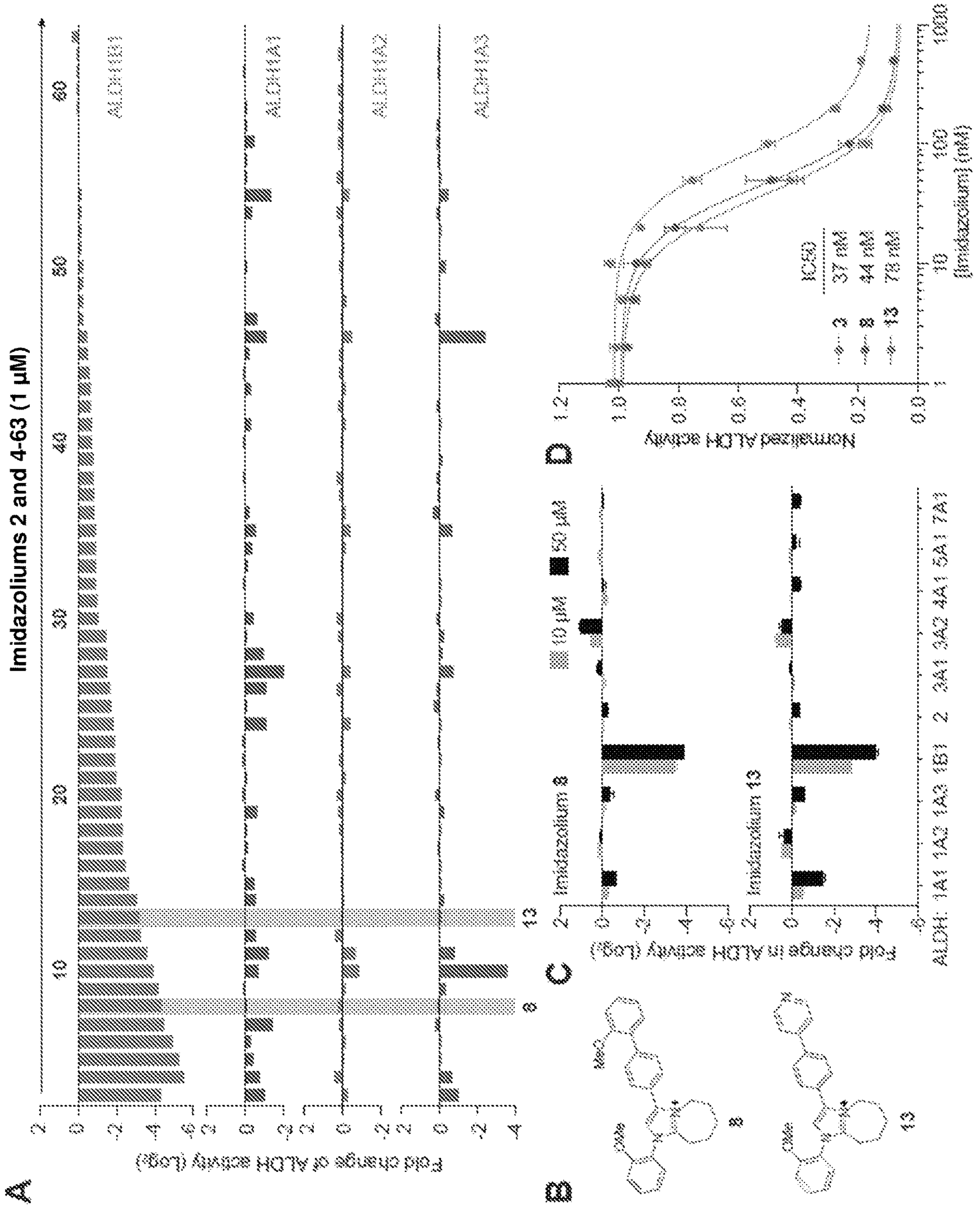
FIG. 5, Structure-activity relationship analysis of the imidazolium pharmacophore. (A-B) Compound activities against ALDH1 isoforms in enzyme kinetics assays. The compounds were tested at a 1-μM dose, and data are the average of at least two biological replicates. Chemical structures are shown for representative imidazoliums, which are also highlighted in the compound activity profiles with gray bars. (C) Profiling of imidazoliums 8 and 13 against a broader panel of ALDH isoforms. Data are the average of two biological replicates±s.d. (D) Dose-response curves for 2, 8, and 13 in ALDH1B1 enzyme kinetics assays. Data are the average of three biological replicates±s.e.m.

Example 4: Structure-Activity Relationship Analysis of the Imidazolium Pharmacophore To explore the structure-activity landscape of imidazolium, a library of additional analogs was synthesized (e.g., as described herein), and their activities against ALDH1 isoforms were determined (FIG. 5, panel A). Through this pilot screen, ALDH1B1 inhibitors with varying degrees of selectivity were determined. In particular compounds 8 and 13 were identified as ALDH1B1-specific inhibitors. In addition, ALDH1A3 inhibitors with varying degrees of selectivity were determined. In particular, compound 10 was identified as an inhibitor of both ALDH1B1 and ALDH1A3, and compound 46 was identified as an ALDH1A3-specific inhibitor.

In the case of ALDH1B1, it was observed that the N1 2-methoxyphenyl and C4 biphenyl groups appear to participate in key interactions, and the enzyme can accommodate both tetrahydroazepine and dihydroquinoline structures at the N3 and C2 positions of the imidazolium ring.

FIG. 5, Panels A-D illustrate the structure-activity relationship analysis of the imidazolium pharmacophore. Panel A: Compound activities against ALDH1 isoforms in enzyme kinetics assays, revealing imidazoliums 8 and 13 as ALDH1B1-specific inhibitors. The compounds were tested at a 1-μM dose, and data are the average of at least two biological replicates. Panel B: Chemical structures of 8 and 13. Panel C: Profiling of 8 and 13 against selected ALDH isoforms Data are the average of two biological replicates±s.d. Panel D: Dose-response curves for 2, 8, and 13 in ALDH1B1 enzyme kinetics assays. Data are the average of three biological replicates±s.e.m. (note that imidazolium 2 is labeled as "3" in panel D).

Example 5: Biological Studies

Figure 6:
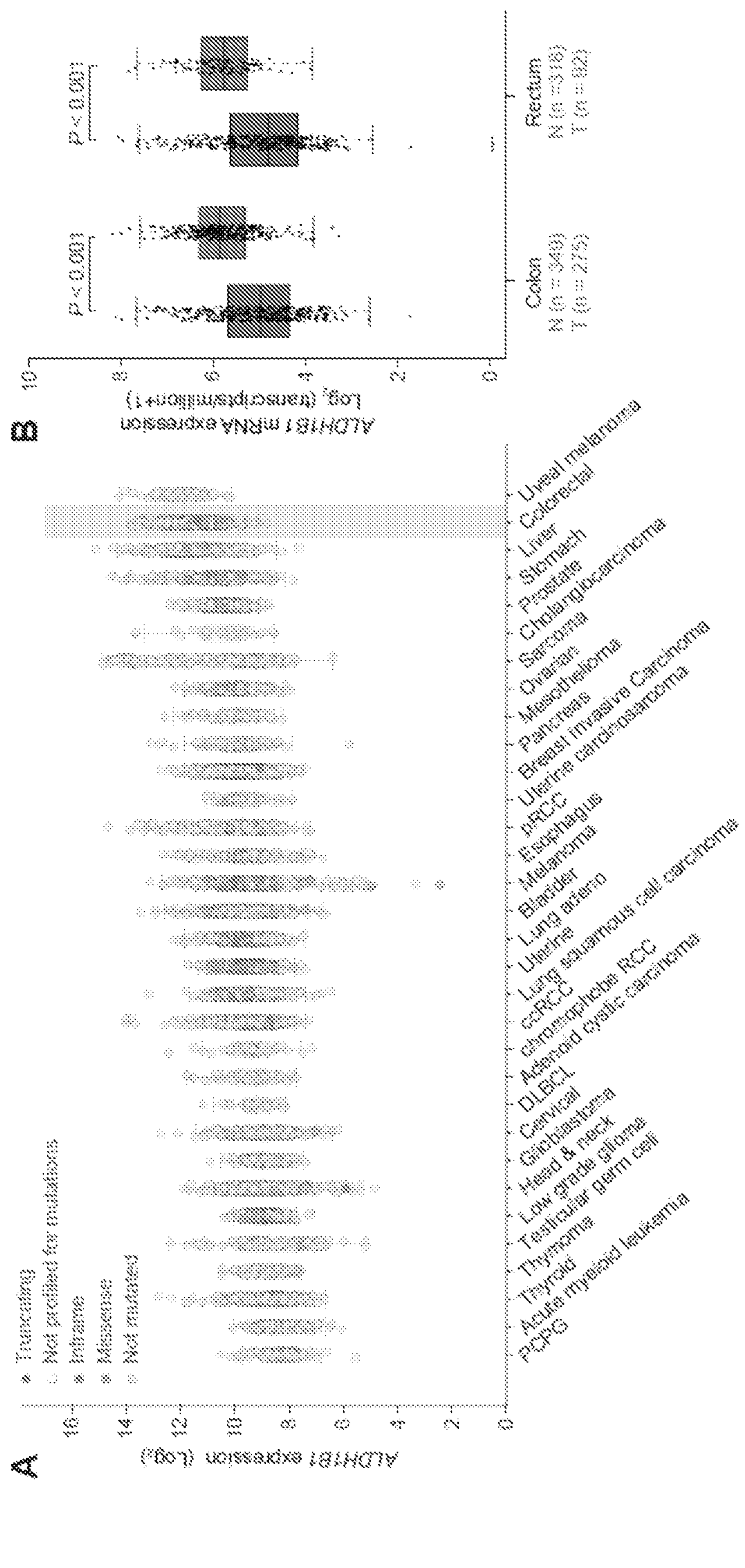
FIG. 6, Upregulation of ALDH1B1 expression in colorectal cancer. (A) ALDH1B1 expression across various cancer types with colorectal cancer highlighted in gray PCPG, pheochromocytoma/paraganglioma; DLBCL, diffuse large B cell lymphoma; RCC, renal carcinoma; ccRCC, clear cell renal carcinoma; pRCC, papillary renal cell carcinoma. (B) Comparison of ALDH1B1 expression in normal (N) versus tumor (T) samples derived from colon or rectum tissues.

FIG. 6, Panels A-B illustrates upregulation of ALDH1B1 expression in colorectal cancer. Panel A: ALDH1B1 expression across various cancer types with colorectal cancer highlighted in gray. PCPG, pheochromocytoma/paraganglioma; DLBCL, diffuse large B cell lymphoma; RCC, renal carcinoma; ccRCC, clear cell renal carcinoma; pRCC, papillary renal cell carcinoma. Panel B: Comparison of ALDH1B1 expression in normal (N) versus tumor (T) samples derived from colon or rectum tissues.

Figure 7:
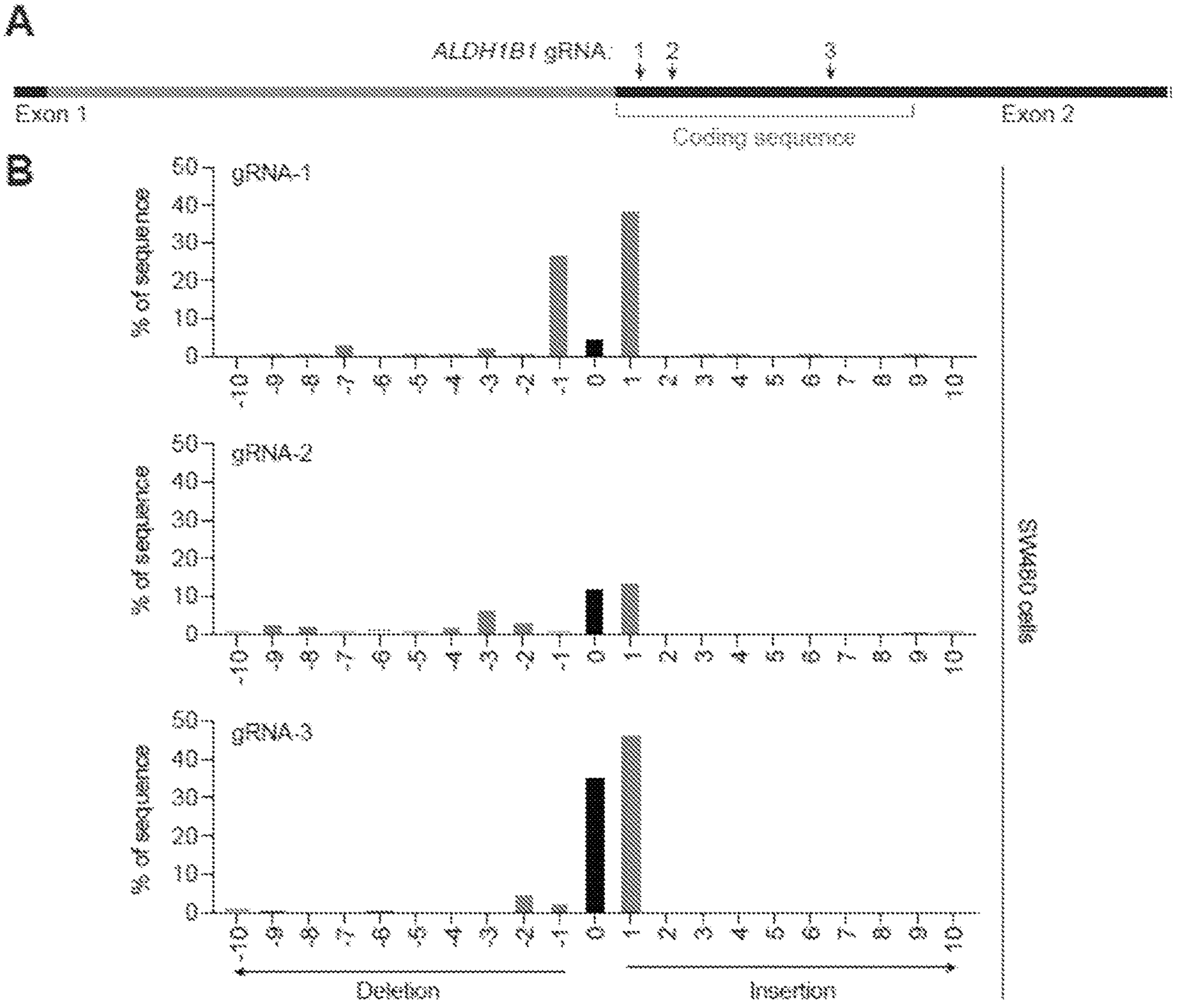
FIG. 7, CRISPR/Cas9-mediated disruption of ALDH1B1 in SW480 cells. (A) Schematic representation of the human ALDH1B1 gene and the target sites of three gRNAs. (B) TIDE analyses of indels produced in SW480 cells by Cas9 and individual ALDH1B1 gRNAs. Wild-type and mutant alleles are depicted as black and red bars, respectively.

FIG. 7, panels A-B illustrates CRISPR/Cas9-mediated ALDH1B1 knockout in SW480 cells. Panel A: Schematic representation of the human ALDH1B1 gene and the target sites of three gRNAs. Panel B: TIDE analyses of indels produced in SW480 cells by Cas9 and individual ALDH1B1 gRNAs.

Figure 8:
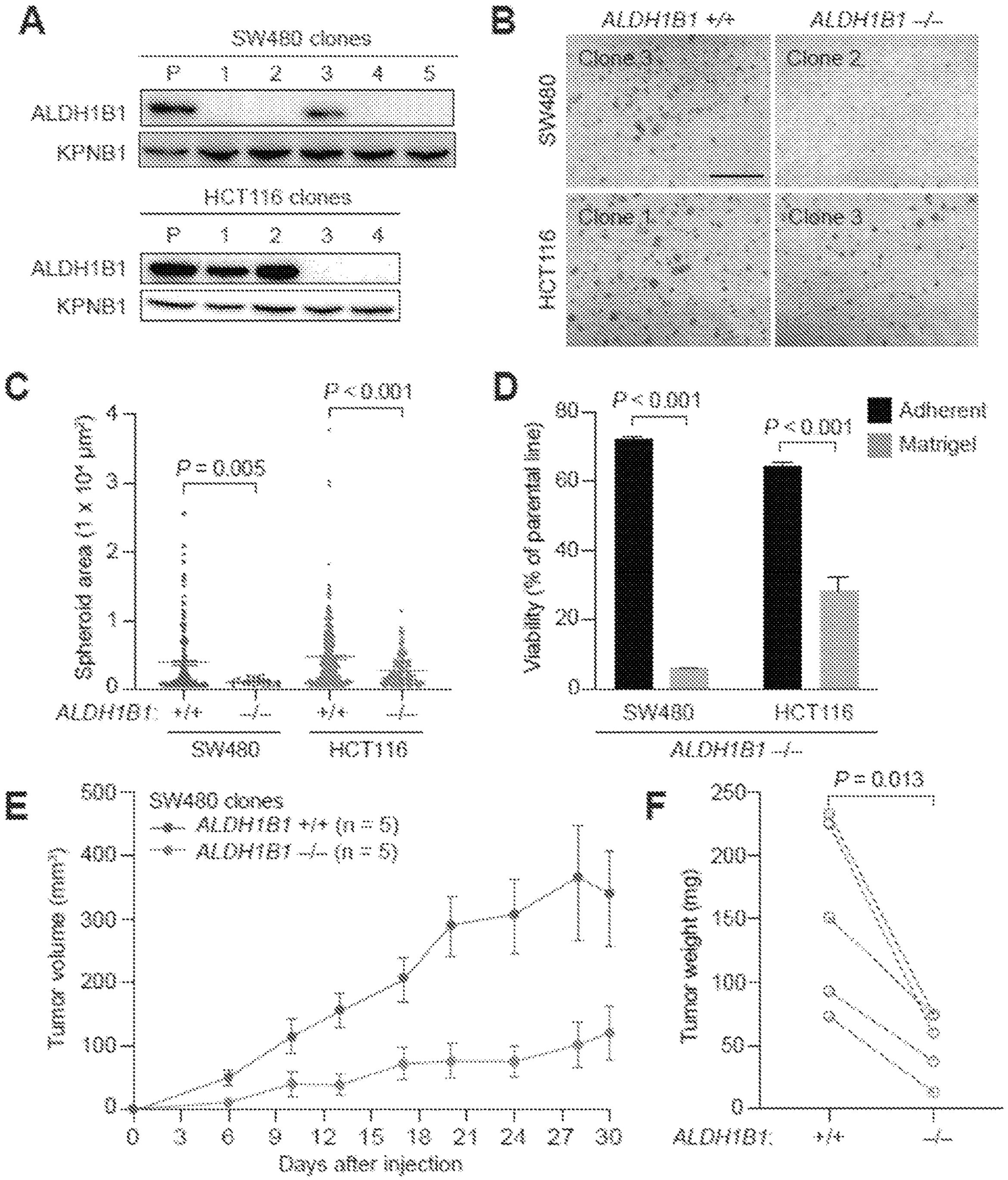
FIG. 8, ALDH1B1 promotes colorectal cancer cell growth in spheroid cultures and tumor xenografts. (A) Western blot detection of ALDH1B1 protein in individual SW480 and HCT116 cell clones that were transiently transfected with Cas9 and ALDH1B1 gRNA-1 and gRNA-2. Lysates from the parental lines (P) are also shown, and KPNB1 was used as a loading control. (B) Phase-contrast micrographs of spheroid cultures derived from SW480 and HCT116 cells with differing ALDH1B1 genotypes. Scale bar: 1 mm. (C) Quantification of spheroid sizes in B. Each dot represents an individual spheroid that has >500 μm2 area in the micrograph. (D) Viability of ALDH1B1−/− clones normalized to that of their ALDH1B1+/+ counterparts cultured in either adherent or spheroid conditions. Data are the average of at least four biological replicate±s.e.m. (E) Growth curves of SW480 clones with differing ALDH1B1 genotypes in nude mice. The ALDH1B1+/+ and ALDH1B1−/− colorectal cancer cells were injected subcutaneously into the left and right flanks of each mouse, respectively. (F) Tumor weights at 30 days after SW480 cell injection. Each pair indicates the two tumors from the same mouse.

FIG. 8, Panels A-F illustrate that ALDH1B1 promotes colorectal cancer cell growth in spheroid cultures and tumor xenografts. Panel A: Western blot detection of ALDH1B1 protein in individual SW480 and HCT116 cell clones that were transiently transfected with Cas9 and ALDH1B1 gRNA-1 and gRNA-2. Lysates from the parental lines (P) are also shown, and KPNB1 was used as a loading control. Panel B: Phase-contrast micrographs of spheroid cultures derived from SW480 and HCT116 cells with differing ALDH1B1 genotypes. Scale bar: 1 mm. Panel C: Quantification of spheroid sizes in B. Each dot represents an individual spheroid that has >500 μm2 area in the micrograph. Panel D: Viability of ALDH1B1−/− clones normalized to that of their ALDH1B1+/+ counterparts cultured in either adherent or spheroid conditions. Data are the average of at least four biological replicate±s.e.m. Panel E: Growth curves of SW480 clones with differing ALDH1B1 genotypes in nude mice. The ALDH1B1+/+ and ALDH1B1−/− colorectal cancer cells were injected subcutaneously into the left and right flanks of each mouse, respectively. Panel F: Tumor weights at 30 days after SW480 cell injection. Each pair indicates the two tumors from the same mouse.

Figure 9:
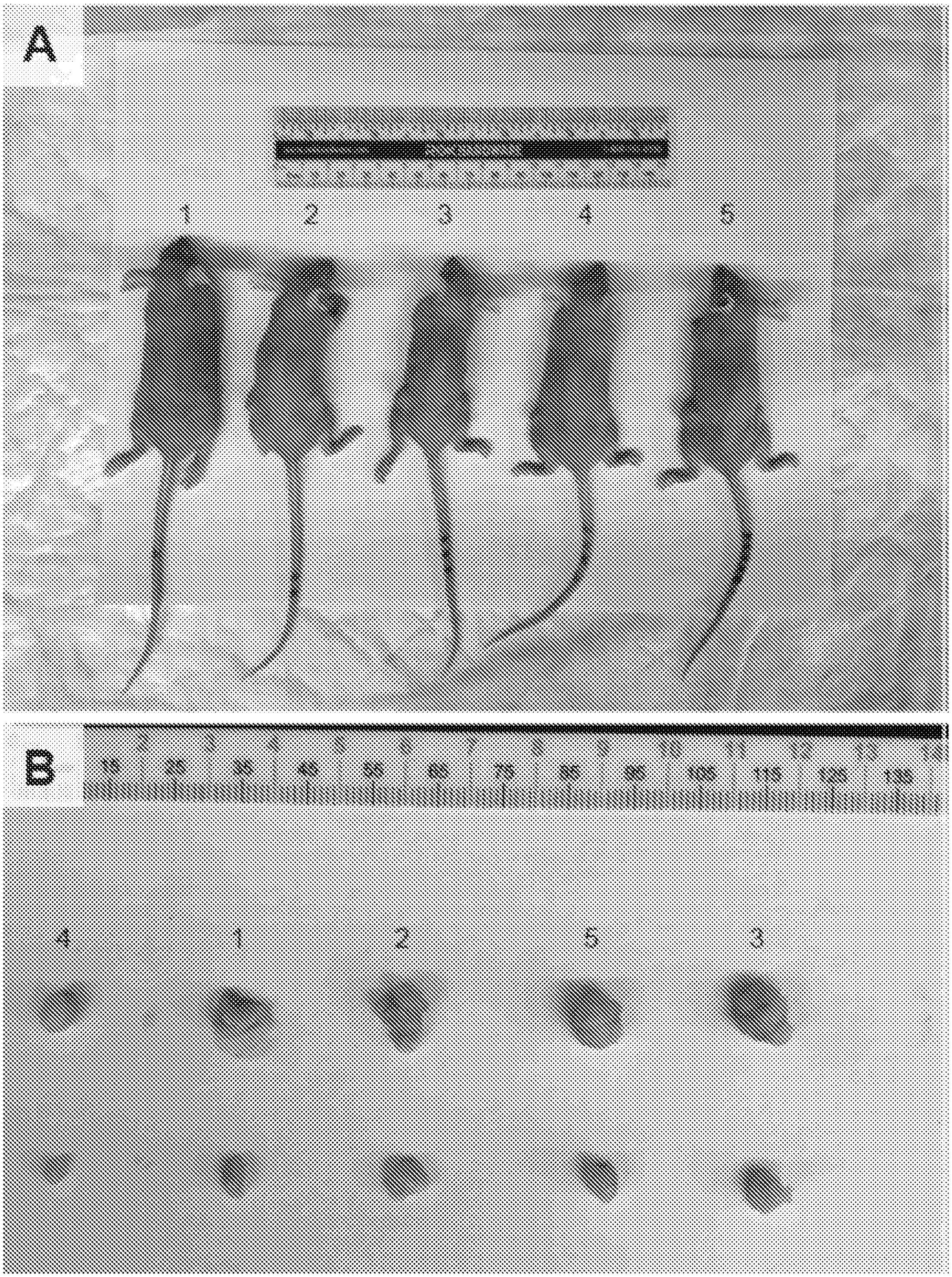
FIG. 9, SW480 xenograft studies (related to FIG. 5E-F). (A) Nude mice after 30 days of colorectal cancer xenograft growth. ALDH1B1+/+ and ALDH1B1−/− SW480 cells were injected subcutaneously into the left and right flanks of each mouse, respectively. (B) Tumors isolated from the mice shown in (A), with ALDH1B1+/+ and ALDH1B1−/− xenografts aligned on the top and bottom rows, respectively.

FIG. 9, Panels A-B depict SW480 xenograft studies (related to FIG. 8, Panels A-F). Panel A: Nude mice after 30 days of colorectal cancer xenograft growth. ALDH1B1+/+ and ALDH1B1−/− SW480 cells were injected subcutaneously into the left and right flanks of each mouse, respectively. Panel B: Tumors isolated from the mice shown in panel A, with ALDH1B1+/+ and ALDH1B1−/− xenografts aligned on the top and bottom rows, respectively.

Figure 10:
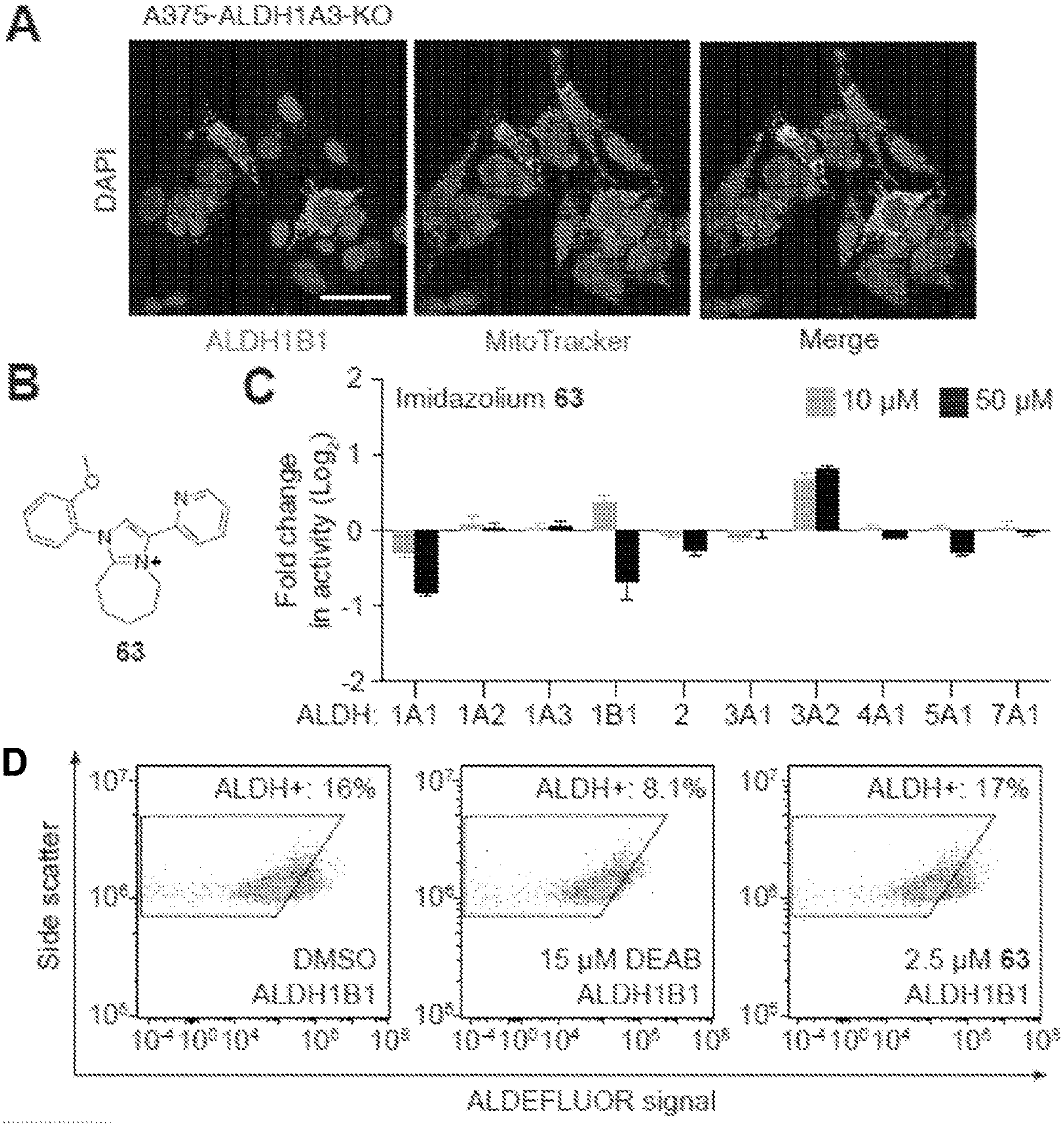
FIG. 10, FACS-based assay for cellular ALDH1B1 activity. (A) Immunofluorescence staining of A375-ALDH1A3-KO cells transiently transfected with ALDH1B1, demonstrating the mitochondrial localization of the exogenous protein. Scale bar: 40 μm. (B) Chemical structure of the imidazolium 63. (C) Profiling of 63 against selected ALDH isoforms. Data are the average of three biological replicates±s.d. (C) FACS plots of ALDH1B1-overexpressing A375-ALDH1A3-KO cells that were incubated with the pan-ALDH inhibitor DEAB or the inactive imidazolium 63 and then treated with ALDEFLUOR reagent.

FIG. 10, Panels A-D shows a FACS-based assay for cellular ALDH1B1 activity. Panel A: Immunofluorescence staining of A375-ALDH1A3-KO cells transiently transfected with ALDH1B1, demonstrating the mitochondrial localization of the exogenous protein. Scale bar: 40 μm. Panel B: Chemical structure of the imidazolium 63. Panel C: Profiling of 63 against selected ALDH isoforms. Data are the average of three biological replicates±s.d. Panel D: FACS plots of ALDH1B1-overexpressing A375-ALDH1A3-KO cells that were incubated with the pan-ALDH inhibitor DEAB or the inactive imidazolium 63 and then treated with ALDEFLUOR reagent.

Figure 11:
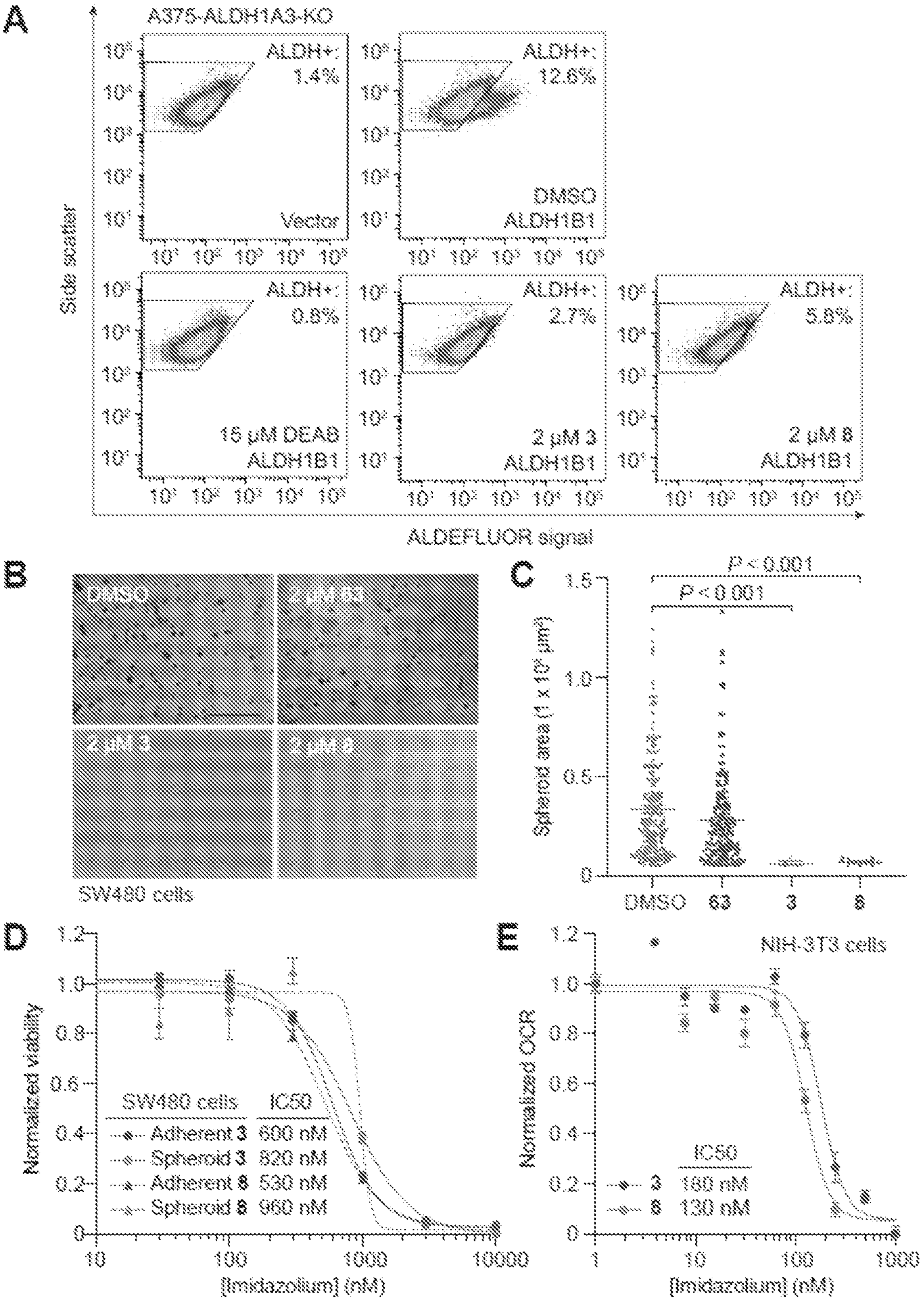
FIG. 11, Imidazoliums can inhibit ALDH1B1 activity in cells. (A) FACS-based assays of ALDH1B1 activity using A375-ALDH1A3-KO cells. The cells were transiently transfected with ALDH1B1 cDNA or a vector control, incubated with the designated compounds, and then treated with ALDEFLUOR reagent. (B) Brightfield micrographs of SW480 spheroid cultures treated with the designated compounds and then stained with crystal violet. Scale bar: 1 mm. (C) Quantification of spheroid sizes in B. Each dot represents an individual spheroid that has >500 μm2 area in the micrograph. (D) Dose-response curves for imidazolium 3 and 8 on SW480 cells cultured in either adherent or spheroid conditions. Data are the average of three biological replicates±s.e.m. (E) Dose-response curves for imidazoliums 2 and 8 in oxygen-consumption-rate (Seahorse) assays of NIH-3T3 cells. Data are the average of three biological replicates (each with three technical replicates)±s.e.m. (note that imidazolium 2 is labeled as "3" in panels C, D & E).

FIG. 11, Panels A-E illustrate that exemplary imidazoliums can inhibit ALDH1B1 activity in cells. Panel A: FACS-based assays of ALDH1B1 activity using A375 ALDH1A3-KO cells. The cells were transiently transfected with ALDH1B1 cDNA or a vector control, incubated with the designated compounds, and then treated with ALDEFLUOR reagent. Panel B: Brightfield micrographs of SW480 spheroid cultures treated with the designated compounds and then stained with crystal violet. Scale bar: 1 mm. Panel C: Quantification of spheroid sizes in panel B. Each dot represents an individual spheroid that has >500 μm2 area in the micrograph. Panel D: Dose-response curves for imidazolium 2 and 8 on SW480 cells cultured in either adherent or spheroid conditions. Data are the average of three biological replicates±s.e.m. Panel E: Dose-response curves for imidazoliums 2 and 8 in oxygen-consumption-rate (Seahorse) assays of NIH-3T3 cells. Data are the average of three biological replicates (each with three technical replicates) ±s.e.m. (note that imidazolium 2 is labeled as "3" in panels C, D & E).

ALDH1B1 has been implicated in colorectal cancer progression. It has been shown that ALDH1B1 shRNAs suppress colon cancer spheroid growth and xenograph growth (Singh, S. et al. (2015) *PLoS One* 10, e0121648). Results disclosed herein support an important role for this metabolic enzyme in colorectal cancer stem cells (CSCs). Across cancer types, ALDH1B1 is expressed in colon cancer at particularly high levels (FIG. 6, panel A), and it is upregulated in colon and rectal tumors in comparison to normal colorectal tissues (FIG. 6, panel A).

An important role for ALDH1B1 in colorectal cancer growth can be demonstrated by its targeted loss by CRISPR-mediated mutagenesis, using guide RNAs that target 5' coding sequences (FIG. 7, panels A-B). Loss of ALDH1B1 function suppresses the ability of colorectal cancer cells to grow in spheroid cultures (FIG. 8, panels B-C), while having minimal effects on adherent cultures of these cells (FIG. 8, panel D). Three-dimensional spheroid cultures are more representative of tumor growth in vivo than two-dimensional adherent cultures, and tumors spheroids are also more dependent on CSCs for their growth. The selective effect of ALDH1B1 loss on colorectal cancer spheroids therefore provides further evidence that ALDH1B1 plays an important role in CSC maintenance. Accordingly, it is shown that loss of ALDH1B1 suppresses colon cancer xenograft growth in mouse models (FIG. 8, panels E-F; FIG. 9, panels A-B).

As shown in FIG. 10, panels A-D, cellular ALDH1B1 activity can be assayed using a cell line with low levels of endogenous ALDH1 expression (A375-ALDH1A3-KO cells). Transiently transfecting these cells with an ALDH1B1 construct leads to the expression of exogenous ALDH1B1 that is properly localized to mitochondria in these cells (FIG. 10, panel A). The transfected cells also exhibit increased fluorescence when treated with ALDEFLUOR reagent, and this signal is inhibited by the pan-ALDH inhibitor DEAB and imidazolium-based ALDH1B1-selective inhibitors (FIG. 11, panel A) but not an imidazolium derivative that is inactive against this ALDH isoform (FIG. 10, panels B-D). Consistent with the ability of the subject imidazoliums to inhibit ALDH1B1 in cells, they can suppress the growth of colorectal cancer spheroids (FIG. 11, panels B-D). However, these compounds also inhibit adherent cultures of colorectal cancer cells (FIG. 11, panel D), suggesting that they can target other proliferative pathways. For example, the compounds can inhibit mitochondrial respiration at comparable doses (FIG. 11, panel E).

Example 6: Development of Guanidine-Based ALDH1B1 Antagonists

Figure 12:
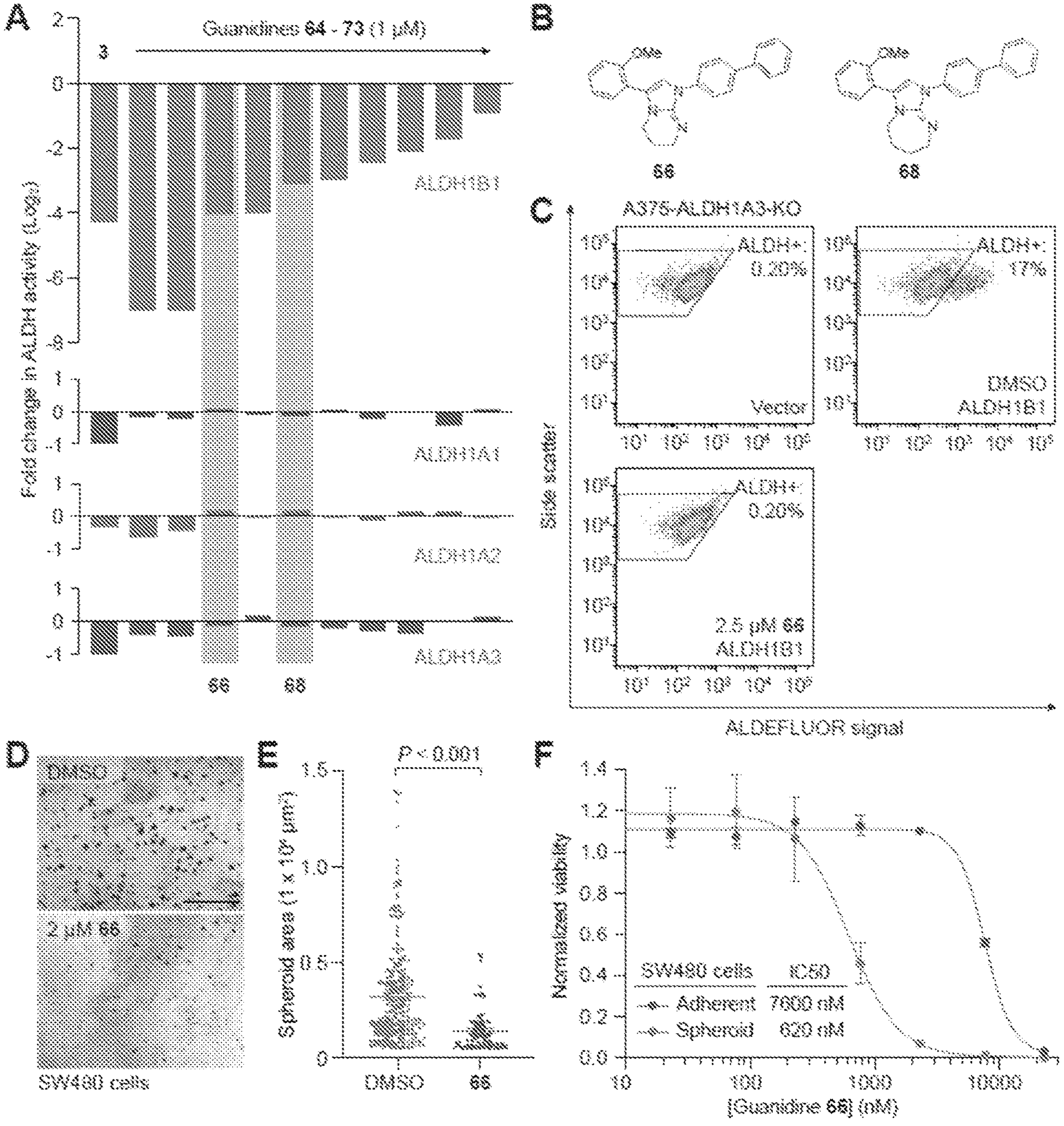
FIG. 12, Development of guanidine-based ALDH1B1 antagonists. (A) Compound activities against ALDH1 isoforms in enzyme kinetics assays, revealing several ALDH1B1-selective guanidines such as derivatives 66 and 68. The compounds were tested at a 1-μM dose, and data are the average of at least two biological replicates. (B) Chemical structures of guanidines 66 and 68. (C) FACS-based ALDEFLUOR assays demonstrating the ability of 66 to inhibit cellular ALDH1B1 activity. (D) Brightfield micrographs of SW480 spheroid cultures treated with 66 and then stained with crystal violet. Scale bar: 1 mm. (E) Quantification of spheroid sizes in D. Each dot represents an individual spheroid that has >500 μm2 area in the micrograph. (F) Dose-response curves for 66 on SW480 cells cultured in either adherent or spheroid conditions. Data are the average of three biological replicates±s.e.m.

FIG. 12, Panels A-F illustrates the development of guanidine-based ALDH1B1 antagonists. Panel A: Compound activities against ALDH1 isoforms in enzyme kinetics assays, revealing several ALDH1B1-selective guanidines such as derivatives 66 and 68. The compounds were tested at a 1-μM dose, and data are the average of at least two biological replicates. Panel B: Chemical structures of guanidines 66 and 68. Panel C: FACS-based ALDEFLUOR assays demonstrating the ability of 66 to inhibit cellular ALDH1B1 activity. Panel D: Brightfield micrographs of SW480 spheroid cultures treated with 66 and then stained with crystal violet. Scale bar: 1 mm. Panel E: Quantification of spheroid sizes in panel D. Each dot represents an individual spheroid that has >500 μm2 area in the micrograph. Panel F: Dose-response curves for 66 on SW480 cells cultured in either adherent or spheroid conditions. Data are the average of three biological replicates±s.e.m.

Figure 13:
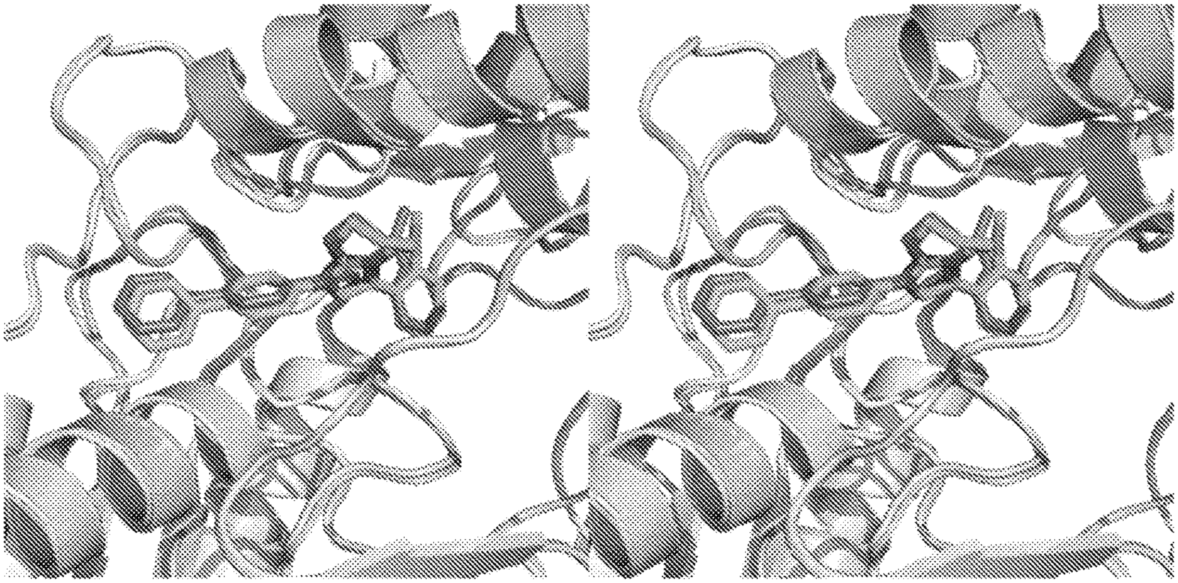
FIG. 13, Comparison of imidazolium and guanidine binding to ALDH1B1. Stereoview overlay of the ALDH1B1/imidazolium 2 (light blue cartoon and blue stick model) and ALDH1B1/guanidine 68 (light green cartoon and green stick model) structures.

FIG. 13, illustrates a comparison of imidazolium and guanidine binding to ALDH1B1. Stereoview overlay of the ALDH1B1/imidazolium 2 (dark gray) and ALDH1B1/guanidine 68 (light gray) structures.

Figure 14:
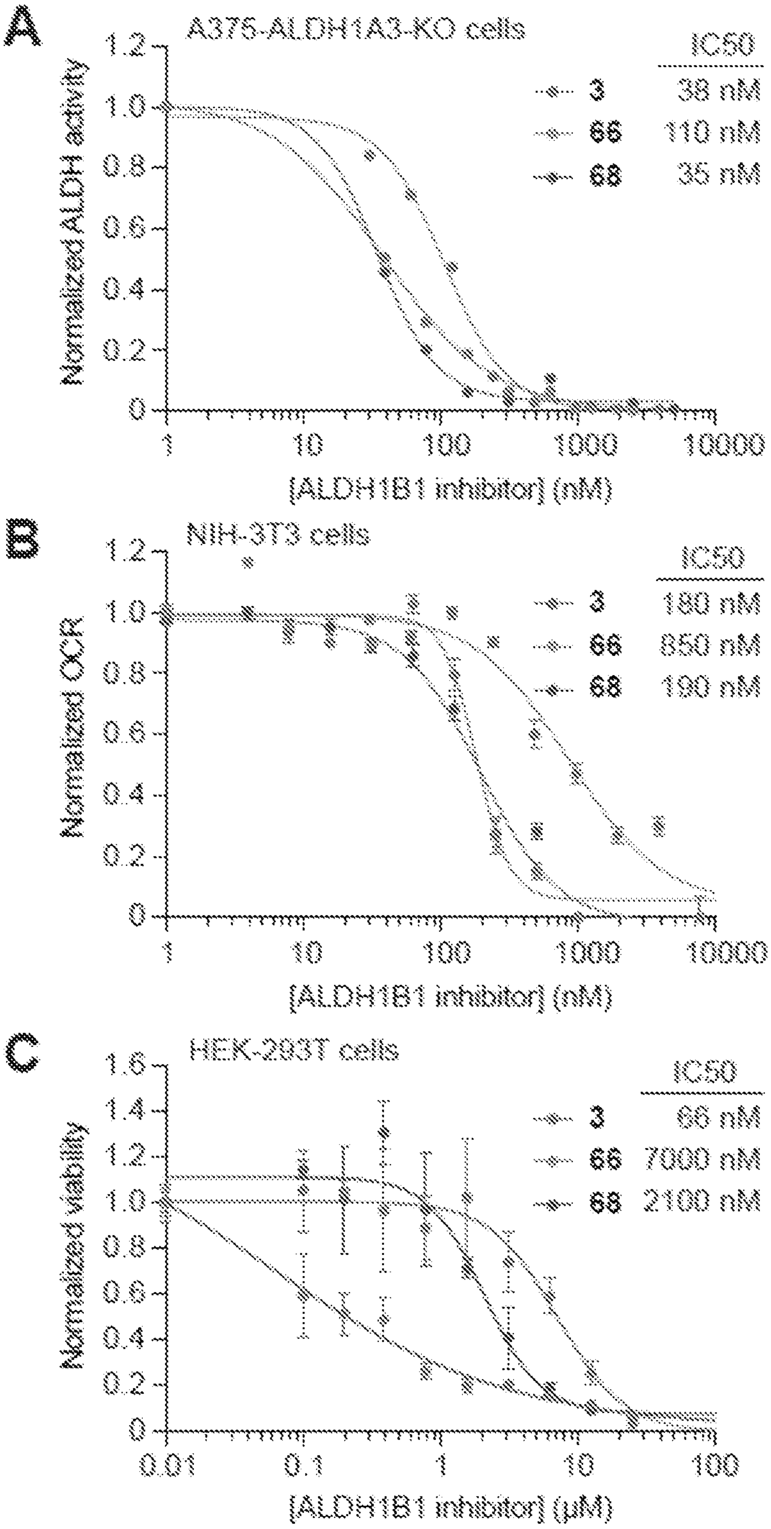
FIG. 14, Activity profiles of selected ALDH1B1 inhibitors with imidazolium or guanidine scaffolds. (A) Dose-response curves in the ALDEFLUOR assay using ALDH1B1-overexpressing A375-ALDH1A3-KO cells. Data represent the results of one FACS assay for each compound dose. (B) Dose-response curves in the oxygen-consumption-rate (Seahorse) assay using NIH-3T3 cells. Data are the average of three biological replicates (each with three technical replicates)±s.e.m. (C) Dose-response curves in a cell-viability assay using adherent HEK-293T cultures. Data are the average of three biological replicates±s.e.m. (note that imidazolium 2 is labeled as "3" in panels A, B & C).

FIG. 14, Panels A-C illustrate the activity profiles of selected ALDH1B1 inhibitors with imidazolium or guanidine scaffolds. Panel A: Dose-response curves in the ALDEFLUOR assay using ALDH1B1-overexpressing A375-ALDH1A3-KO cells. Data represent the results of one FACS assay for each compound dose. Panel B: Dose-response curves in the oxygen-consumption-rate (Seahorse) assay using NIH-3T3 cells. Data are the average of three biological replicates (each with three technical replicates) ±s.e.m. Panel C: Dose-response curves in a cell-viability assay using adherent HEK-293T cultures. Data are the average of three biological replicates±s.e.m. (note that imidazolium 2 is labeled as "3" in panels A, B & C).

As disclosed herein a number of compounds based on a cyclic guanidine scaffold have been prepared (e.g., see compounds depicted herein in Table 1). The activity of exemplary guanidine compounds against ALDH1 isoforms were investigated in kinetics assays (see, e.g., FIG. 12, panels A-B). The kinetics assay indicated that a number of exemplary cyclic guanidine compounds are ALDH1B1-selective inhibitors (e.g., compounds 66 and 68). FIG. 12, panel C demonstrates that an exemplary cyclic guanidine compound (e.g., compound 66) inhibits cellular ALDH1B1 activity. Consistent with their ability to inhibit ALDH1B1 in cells, cyclic guanidine analogs can suppress the growth of colorectal cancer spheroids, while having limited activity against adherent cultures of these tumor-derived cells (FIG. 12, panel F). The compounds' preferential inhibition of three-dimensional spheroid cultures mirrors the ALDH1B1−/− phenotype for colorectal cancer cells.

TABLE 3

Crystallographic data collection and refinement statistics

| | ALDH1B1-NAD$^+$ | ALDH1B1-NAD$^{+-}$ Imidazolium 2 | ALDH1B1-NAD$^{+-}$ guanidine 80 |
|---|---|---|---|
| Data collection | | | |
| Beamline | SSRL BL12-2 | SSRL BL12-2 | SSRL BL9-2 |
| Wavelength (Å) | 0.97946 | 0.97946 | 0.97946 |
| Space group | P3$_2$ 2 1 | P3$_2$ 2 1 | P3$_2$ 2 1 |
| Cell dimensions | | | |
| a = b, c (Å) | 101.35, 186.69 | 102.04, 187.04 | 101.69, 188.86 |
| Unit cell volume (Å$^3$) | 1,660,748 | 1,677,532 | 1,691,194 |

TABLE 3-continued

| Crystallographic data collection and refinement statistics | | | |
|---|---|---|---|
| | ALDH1B1-NAD$^+$ | ALDH1B1-NAD$^{+-}$ Imidazolium 2 | ALDH1B1-NAD$^{+-}$ guanidine 80 |
| Mosaicity (°)[a] | 0.79 | 0.29 | 0.09 |
| Wilson B factor[b] | 53.7 | 42.5 | 74.6 |
| Matthews coefficient (Å$^3$/Da)[c] | 2.46 | 2.49 | 2.56 |
| Solvent content (%) | 50 | 51 | 52 |
| Resolution (Å)[d] | 93.35 (2.67) | 39.40 (2.12) | 39.55 (2.45) |
| No. of reflections/unique | 95,888/30,654 | 431,121/64,238 | 141,295/41,041 |
| $R_{merge}$[e] | 0.124(0.853) | 0.081(0.793) | 0.035(0.824) |
| I/σ/ratio[f] | 6.0(1.3) | 11.4(2.3) | 14.9(1.6) |
| CC1/2 ratio | 0.992(0.545) | 0.998(0.805) | 0.999(0.691) |
| Completeness (%)[g] | 96.5(98.4) | 99.9(100) | 97.2(98.5) |
| Redundancy[h] | 3.1(3.2) | 6.7(6.9) | 3.4(3.5) |
| Refinement | | | |
| Resolution (Å) | 30.0-2.67 | 30.3-2.12 | 30.0-2.45 |
| No. reflections/test set | 28,975/1,552 | 60,846/3,300 | 38,916/2,069 |
| $R_{work}/R_{free}$[i] | 19.8/25.3 | 18.0/21.9 | 24.0/29.0 |
| $F_{obs}$ − $F_{calc}$correlation[j] | 0.95 | 0.96 | 0.95 |
| No. atoms | | | |
| Protein | 7,704 | 7,704 | 7,520 |
| Inhibitor | — | 60 | 30 |
| Other ligand/ion | 90 (88 NAD$^+$, 2 Na$^+$) | 180 (88 NAD$^+$, 2 Na$^+$, 12 glycerol, 78 ethyleneglycol) | 94 (54 NAD$^+$, 2 Na$^+$, 4 ethyleneglycol) |
| Water | 58 | 181 | 55 |
| B-factors | | | |
| Protein | 62 | 46 | 84 |
| Inhibitor | — | 62 (A: 60; B: 64) | 87 |
| Ligand/Ion | 56 (NAD$^+$)/55 (Na$^+$) | 44 (NAD$^+$)/44 (Na$^+$) | 85 (NAD$^+$)/79 (Na$^+$) |
| R.m.s. deviations | | | |
| Bond lengths (Å) | 0.009 | 0.011 | 0.008 |
| Bond angles (°) | 1.35 | 1.53 | 1.27 |
| Ramachandran statistics[k] | | | |
| Most favored regions (%) | 100 | 100 | 99.8 |
| Disallowed regions (%) | 0 | 0 | 0.2 |

[a]Degree of crystal imperfection, a higher mosaicity contributes to broader (less sharply defined) diffraction intensity profiles

[b]Overall B-factor value, an approximation to the fall-off of atomic scattering with resolution

[c]Ratio of the volume of the asymmetric unit to the molecular weight of all protein molecules in the asymmetric unit

[d]Value in parentheses is for the highest-resolution shell: 2.67-2.82 Å in ALDH1B1-NAD$^+$; 2.12-2.23 Å in the ALDH1B1-NAD$^+$ imidazolium 2; 2.45-2.58 Å and in the ALDH1B1-NAD$^{+-}$guanidine 80 complex.

[e]Reliability factor for symmetry-related reflections calculated as: $R_{merge} = \Sigma_{hkl} \Sigma_j = 1$ to N | $I_{hld} - I_{hld}$ (j) |/$\Sigma_{hkl}$ Σj = 1 to N $I_{hdl}$ (j), where N is the redundancy of the data. In parentheses, the cumulative value at the highest-resolution shell

[f]Ratio of mean intensity to the mean standard deviation of the intensity over the entire resolution range

[g]Fraction of measured reflections to possible observations at the resolution range

[h]Number of measurements of individual, symmetry unique reflections

[I]Average deviation between the observed and calculated structure factors calculated as: $R_{work} = \Sigma_{hkl}$ ||$F_{obs}$| − |$F_{calc}$||/$\Sigma_{hkl}$ |$F_{obs}$|, where the $F_{obs}$ and $F_{calc}$ are the observed and calculated structure factor amplitudes of reflection hkl. $R_{free}$ is equal to $R_{tactor}$ but for a randomly selected 5.0% subset of reflections that were held aside throughout refinement for cross-validation

[J]Correlation coefficient between observed and calculated structure factor amplitudes

[k]According to Procheck for non-proline and non-glycine residues

The binding of an exemplary imidazolium compound (compound 3) was compared to the binding of an exemplary cyclic guanidine compound (compound 68), as depicted in FIG. 13. With reference to FIG. 13, it was observed that the bicyclic imidazolium and guanidine compounds place their substituents essentially in the same orientations and positions within the ALDH1B1 active site. Although exemplary cyclic imidazolium and guanidine compounds can both inhibit ALDH1B1 in a similar manner and with comparable potency, it was observed that the guanidine-based antagonists exhibit less general cytotoxicity (FIG. 14)

Example 7: Targeting Colorectal Cancer with Small-Molecule Inhibitors of Aldehyde Dehydrogenase 1B1

A. Abstract

Aldehyde dehydrogenase (ALDH) isoforms are highly upregulated in cancer stem cells and required for their self-renewal, making these metabolic enzymes promising drug targets. Individual ALDH family members have been associated with specific malignancies, and we have discovered the first selective small-molecule antagonists of ALDH1B1, a mitochondrial isoform that promotes colorectal and pancreatic adenocarcinomas. We describe bicyclic imidazoliums and guanidines that can inhibit ALDH1B1, structure-activity profiles for these compounds, crystal structures of ALDH1B1 and ALDH1B1-inhibitor complexes, and the development of analogs with enhanced potency and selectivity. The two inhibitor classes target the ALDH1B1 active site through equivalent molecular interactions, and they can effectively block ALDH1B1 activity in cells. The guanidine-based ALDH1B1 antagonists exhibit markedly less off-target cytotoxicity than the imidazolium derivatives, and they can suppress colon cancer spheroid growth with minimal effects on adherent cultures, recapitulating the genetic loss-of-function phenotype. We have also used both genetic and pharmacological perturbations to elucidate the ALDH1B1-dependent transcriptome in colorectal cancer cells, revealing potential roles for this enzyme in stemness maintenance, mitochondrial metabolism, and ribosomal function. Our findings support an essential role for ALDH1B1 in colorectal cancer, provide selective chemical probes for studying ALDH1B1 functions, and yield molecular leads for the development of ALDH1B1-targeting therapies.

B. Introduction

Cellular heterogeneity is an important hallmark of tumor biology and a significant barrier to the treatment of human cancers. Cell populations with distinct but potentially mutable phenotypic traits contribute to tumor progression, and most cancer drugs target the mitotic machinery and signaling pathways required for rapid cell division. While such therapies can induce tumor regressions, slow-cycling malignant cells with stem-like properties often persist and lead to tumor relapse. Drugs that can selectively disrupt other oncogenic pathways, particularly those associated with these stem-like populations, therefore could lead to durable clinical responses.

One unique feature of stem and progenitor cells is their high levels of aldehyde dehydrogenase (ALDH) activity relative to other cell types. ALDHs are $NAD(P)^+$-dependent enzymes that oxidize aldehyde substrates through a stepwise, irreversible reaction cycle, and the human ALDH family consists of 19 isozymes with varying substrate specificities and subcellular localizations. ALDH-expressing stem cells have been identified in a wide range of organs, including the bone marrow (Storms, R. W. et al. (2005) *Blood* 106, 95-102; Hess, D. A. et al. (2006) *Blood* 107, 2162-2169), brain (Corti, S. et al. (2006) *Stem Cells* 24, 975-985; Obermair, F. J. et al. (2010) *Stem Cell Res.* 5, 131-143), breast (Tanei, T. et al. (2009) *Clin. Cancer Res.* 15, 4234-4241; Balicki, D. (2007) *Cell Stem Cell* 1, 485-487), prostate (Burger, P. E. et al. (2009) *Stem Cells* 27, 2220-2228), liver (Dolle, L. et al. (2012) *Hepatology* 55, 540-552), and pancreas (Rovira, M. et al. (2010) *Proc. Natl. Acad. Sci. U.S.A.* 107, 75-80; Oakie, A. et al. (2018) *Stem Cells Dev.* 27, 275-286; Giannios, I. et al. (2019) *Stem Cells* 37, 640-651). Cells with high ALDH activities have also been observed in several cancers, and these stem-like populations exhibit greater tumorigenicity, chemo-radioresistance, and metastatic behaviors (Clark, D. W. & Palle, K. (2016) *Ann. Transl. Med.* 4, 518; Xu, X. et al. (2015) *Cancer Lett.* 369, 50-57). Specific ALDH isoforms have been linked to distinct types of cancer. For example, high levels of ALDH1A1 and ALDH1A3 have been reported in breast (Ginestier, C. et al. (2007) *Cell Stem Cell* 1, 555-567; Croker, A. K. & Allan, A. L. (2012) *Breast Cancer Res. Treat.* 133, 75-87; Marcato, P. et al. (2011) *Stem Cells* 29, 32-45), melanoma (Sarvi, S. et al. (2018) *Cell Chem. Biol.* 25, 1456-1469 e1456; Luo, Y. et al. (2012) *Stem Cells* 30, 2100-2113), ovarian (Saw, Y. T. et al. (2012) *BMC Cancer* 12, 329; Silva, I. A. et al. (2011) *Cancer Res.* 71, 3991-4001; Chefetz, I. et al. (2019) *Cell Rep.* 26, 3061-3075 e3066), and non-small cell lung (Jiang, F. et al. (2009) *Mol. Cancer Res.* 7, 330-338; Shao, C. et al. (2014) *Clin. Cancer Res.* 20, 4154-4166; Li, X. et al. (2012) *Thorac. OncoL* 7, 1235-1245) cancer stem cells. ALDH1B1 has been implicated in the tumor-initiating cells of colorectal and pancreatic adenocarcinomas (Singh, S. et al. (2015) *PLoS One* 10, e0121648; Mameishvili, E. et al. (2019) *Proc. Natl. Acad. Sci. U.S.A.* 116, 20679-20688).

Genetic studies have shown that these ALDHs are not only biomarkers for cancer stem cells; the enzymes can also promote stem-like activities. Lentiviral shRNAs against ALDH1A1 suppresses the ability of melanoma cells to form tumors in mice (Yue, L. et al. (2015) *Melanoma Res.* 25, 138-148), and knocking down ALDH1A3 similarly impairs the tumorigenicity of lung cancer cells (Shao, C. et al. (2014) *Clin. Cancer Res.* 20, 4154-4166). The mounting evidence for a pivotal oncogenic role of ALDH isozymes has spurred the pursuit of small molecules that can inhibit these targets. Isoform-specific antagonists are a major challenge, as several ALDH family members are closely related in structure. To date, only a few selective inhibitors have been reported, including compounds that preferentially target ALDH1A1 (Morgan, C. A. & Hurley, T. D. *J.* (2015) *Med. Chem.* 58, 1964-1975; Yang, S. M. et al. (2018) *J. Med. Chem.* 61, 4883-4903; Huddle, B. C. et al. (2018) *J. Med. Chem.* 61, 8754-8773), ALDH1A3 (Gelardi, E. L. M. et al. (2021) *Cancers* (Basel) 13), ALDH2 (Overstreet, D. H. et al. (2009) *Pharmacol. Biochem. Behav.* 94, 255-261; Wang, B. et al. (2014) *J. Chem. Inf. Model* 54, 2105-2116), ALDH3A1 (Parajuli, B. et al. (2014) *Chembiochem* 15, 701-712; Parajuli, B. et al. (2014) *J. Med. Chem.* 57, 449-461), or ALDH4A1 (Kreuzer, J. et al. (2014) *Chem. Sci.* 6, 237-245). Antagonists for other ALDH enzymes that drive tumor progression are needed to explore the potential of this therapeutic approach.

Here we report the first specific small-molecule antagonists of ALDH1B1, a mitochondria ALDH isoform that can oxidize a broad range of substrates, including short- and medium-chain aliphatic aldehydes, retinaldehyde, and lipid peroxidation products (Stagos, D. et al. (2010) *Drug Metab. Dispos.* 38, 1679-1687). ALDH1B1 is normally expressed at the base of colonic crypts where intestinal stem cells reside and in adult pancreas progenitors (Mameishvili, E. et al. (2019) *Proc. Natl. Acad. Sci. U.S.A.* 116, 20679-20688; Chen, Y. et al. (2011) *Biochem. Biophys. Res. Commun.* 405, 173-179). Although Aldh1b1 knockout mice are viable and only exhibit increased alcohol sensitivity and age-related glucose intolerance (Singh, S. et al. (2015) *Biochem. Biophys. Res. Commun.* 463, 768-773; Anastasiou, V. et al. (2016) *Diabetologia* 59, 139-150; Muller, M. F. et al. (2017) *J. Pathol.* 241, 649-660), this isoenzyme plays important roles in cancer. ALDH1B1 is highly expressed in colorectal adenocarcinoma (Chen, Y. et al. (2011) *Biochem. Biophys. Res. Commun.* 405, 173-179), and ALDH1B1 silencing suppresses colon cancer spheroid and xenograft growth (Singh, S. et al. (2015) *PLoS One* 10, e0121648). ALDH1B1 is also markedly upregulated in pancreatic cancer cells and required for KRAS-driven pancreatic adenocarcinoma in murine models (Mameishvili, E. et al. (2019) *Proc. Natl. Acad. Sci. U.S.A.* 116, 20679-20688).

We demonstrate that bicyclic imidazoliums and guanidines can inhibit ALDH1B1, and we have developed derivatives with nanomolar potencies and isoform selectivity. We have also solved the crystal structures of ALDH1B1 and the enzyme bound to imidazolium- and guanidine-based antagonists, revealing that the two pharmacophores engage the active site through analogous interactions. Both inhibitor classes can effectively suppress mitochondrial ALDH1B1 activity in cells; however, the guanidine derivatives avoid off-target effects on oxidative phosphorylation that are observed with their imidazolium counterparts. Accordingly, guanidine-based ALDH1B1 antagonists can block the growth of colon cancer spheroids with minimal effects on adherent cultures or non-cancerous cells, and the compounds are effective against spheroids that have acquired resistance to 5-fluorouracil (5-FU), the standard therapy for advanced colorectal adenocarcinoma (Vodenkova, S. et al. (2020) *Pharmacol. Ther.* 206, 107447). Finally, using an ALDH1B1 inhibitor, CRISPR mutagenesis, and comparative transcriptomics, we have uncovered the ALDH1B1-dependent expression of genes that regulate stemness maintenance, mitochondrial metabolism, and ribosomal function. Taken together, our studies further establish ALDH1B1 as a promising cancer target, provide valuable small-molecule probes of ALDH1B1 function, and take important first steps toward ALDH1B1-directed therapies.

C. Results

1. Bicyclic Imidazoliums can Modulate ALDH Enzymes

Our discovery of new ALDH-targeting pharmacophores was a fortuitous result of a high-throughput chemical screen for Hedgehog (Hh) pathway antagonists. We previously identified bicyclic imidazolium 1 as a suppressor of Gli transcription factor activity and developed more potent analogs such as compound 2 (FIG. 1, panel A) (Hom, M. E. et al. (2020) *Chem Med Chem* 15, 1044-1049). To determine potential protein targets for the bicyclic imidazoliums, we developed photoaffinity probe 3, which contains an aryl azide for light-dependent crosslinking and a propargyl group for click-chemistry tagging (FIG. 1, panel A). Since the imidazoliums can suppress Hh signaling in NIH-3T3 cells (Hom, M. E. et al. (2020) *Chem Med Chem* 15, 1044-1049), we treated live cultures of these fibroblasts with probe 3, using imidazolium 2 as a competitive inhibitor. We then exposed the cultures to 254-nm light, lysed the cells, and labeled the photocrosslinked proteins with biotin-azide (FIG. 1, panel B). SDS-PAGE and far-western blotting of the lysates revealed a specifically labeled protein with an apparent molecular weight of 55 kDa (FIG. 1, panel C). As a complementary approach, we determined the subcellular localization of imidazolium 3 by fixing the compound-treated NIH-313 cells after photocrosslinking and tagging the probe with tetramethylrhodamine (TAMRA)-azide. Fluorescence imaging revealed that the bicyclic imidazolium strongly localized to mitochondria (FIG. 1, panel D).

Figure 18:
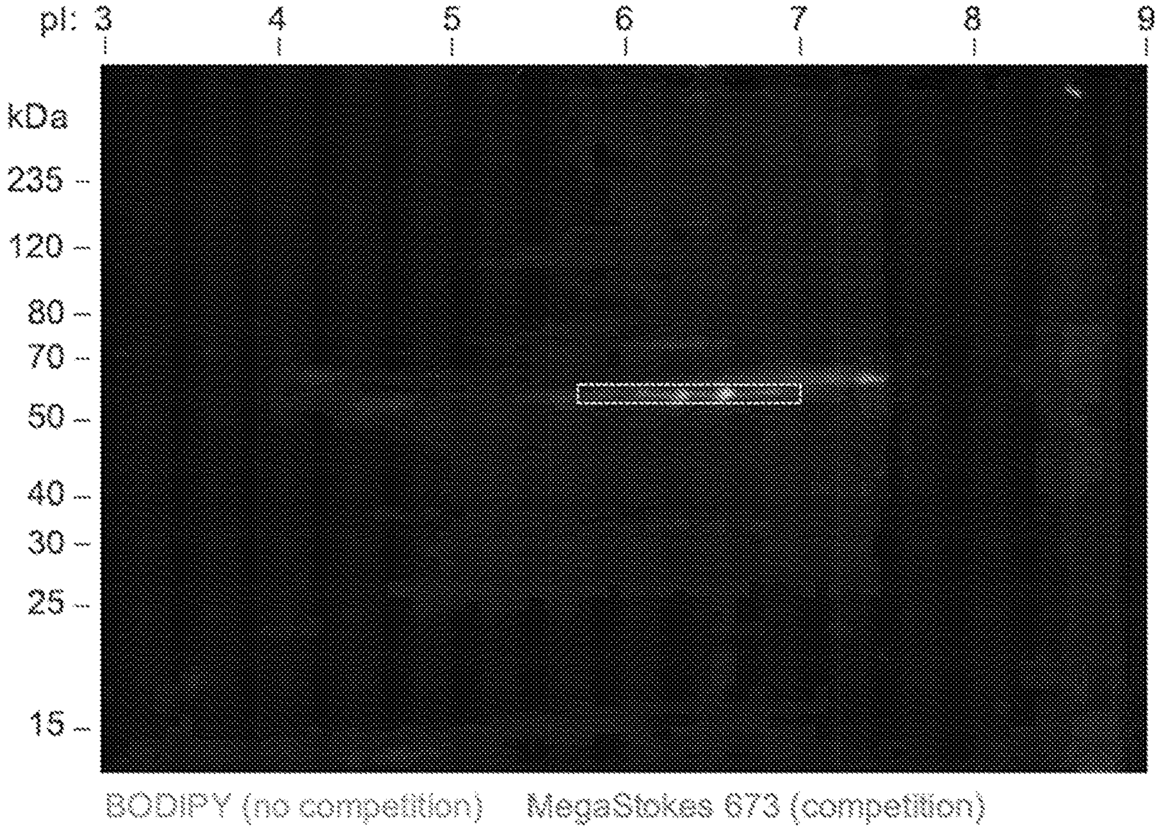
FIG. 18, Photoaffinity labeling of imidazolium-binding proteins. Mouse liver mitochondria were photocrosslinked with probe 3 in the absence or presence of competitor (imidazolium 2). The mitochondria were then homogenized, reacted with BODIPY azide (no competitor) or MegaStrokes 673 azide (competitor), and resolved by two-dimensional gel electrophoresis. Protein spots that were specifically labeled by probe 3 (dashed box) were then isolated for mass spectrometry-based sequencing.

Guided by these results, we exploited the limited size of the mitochondrial proteome to determine the identity of the 55-kDa imidazolium-binding protein. We treated isolated murine mitochondria with probe 3, irradiated the mixture with 254-nm light, lysed the mitochondria, and tagged the photocrosslinked proteins with an azide-functionalized fluorophore. The reaction mixture was then resolved by two-dimensional electrophoresis, revealing fluorescent protein spots in the 55-kDa range (FIG. 1, panel E and FIG. 18). Mass spectrometry-based sequencing of these samples identified ALDH2 as the most abundant candidate target (FIG. 1, panel F). We further confirmed the presence of ALDH2 in the photoaffinity-labeled species by western blotting (FIG. 1, panel G).

Figure 19:
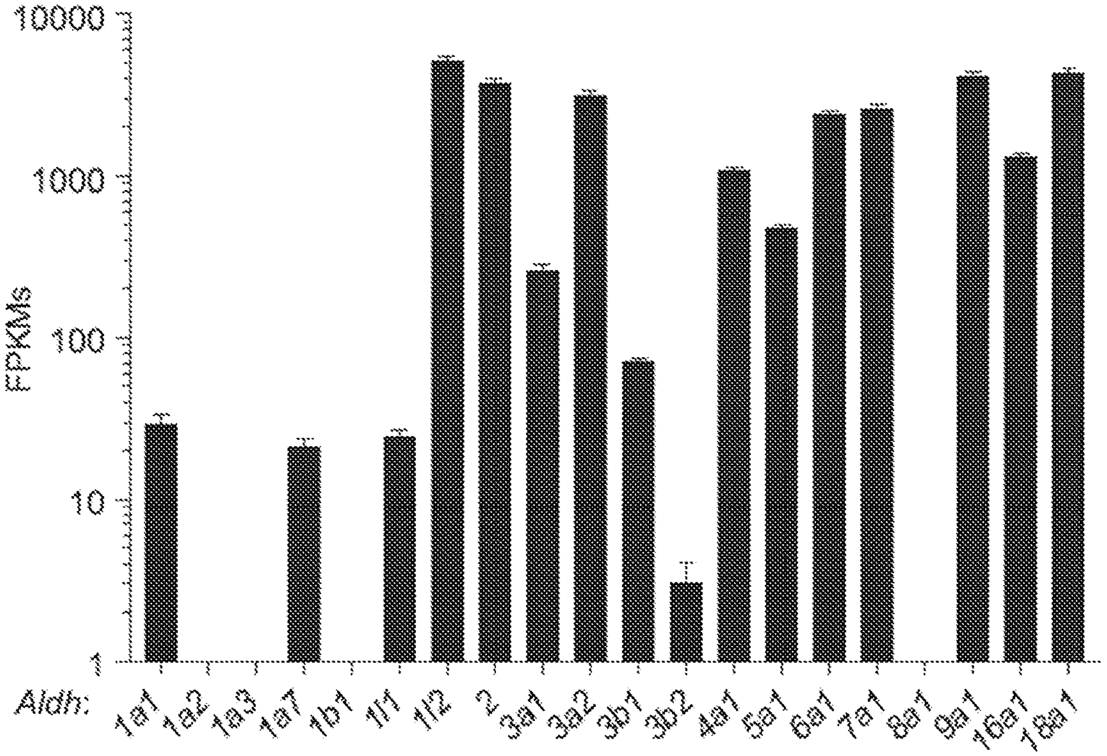
FIG. 19, Aldehyde dehydrogenase expression in NIH-3T3 cells. Transcript levels for the 20 murine Aldh isoforms in NIH-3T3 fibroblasts as determined by RNA-seq. Expression values are presented as the Fragments Per Kilobase of transcript per Million mapped reads (FPKMs), and data are the average of three biological replicates±s.e.m. With the exception of Aldh1a7, each of these murine enzymes has a human homolog.

Since ALDH2 is not known to functionally interact with the Hh pathway, we reasoned that its targeting by the bicyclic imidazoliums represents a distinct mechanism of action and pharmacological opportunity. To examine whether imidazolium derivatives can affect the function of ALDH2 or other ALDH family members, we tested the compounds against a panel of ten bacterially expressed and purified human isozymes, using NAD as the cofactor and acetaldehyde as substrate. Surprisingly, neither imidazolium 1 or 2 could inhibit ALDH2 activity at a 50-μM compound concentration, and 3 only partially suppressed this enzyme at that dose (FIG. 2, panel A). Yet each derivative was able to suppress or enhance the activity of other ALDH isoforms, with imidazolium 2 preferentially inhibiting members of the ALDH1 subfamily. Dose-response experiments established 2 as a potent ALDH1B1 antagonist (1050=57 nM) with over an order of magnitude weaker activity against other ALDH1 enzymes (FIG. 2, panel B). ALDH1B1 is not expressed at detectable levels in NIH-3T3 cells (FIG. 19), and therefore the enzyme is unlikely to be the relevant target for imidazolium-mediated Hh pathway inhibition. However, imidazolium 2 provided us with a valuable lead molecule for the development for ALDH1B1-specific antagonists, and we focused our subsequent efforts toward this goal.

2. Structural Basis of ALDH1B1 Inhibition by Bicyclic Imidazoliums

To understand the mechanism of ALDH1B1 inhibition, we conducted enzyme kinetic assays with imidazolium 2 and varying concentrations of either acetaldehyde or $NAD^+$. The inhibitor acted in a non-competitive manner with respect to the aldehyde substrate (FIG. 2, panel C) and exhibited an uncompetitive relationship with NAD (FIG. 2, panel D). These findings are consistent with a sequential ordered mechanism of inhibition, in which cofactor binding is a prerequisite for ALDH1B1-imidazolium complexation. The inability of acetaldehyde to competitively suppress imidazolium action also suggested that the inhibitor either targets an allosteric site or prevents the enzyme from cycling through its aldehyde-binding state.

Figure 21:
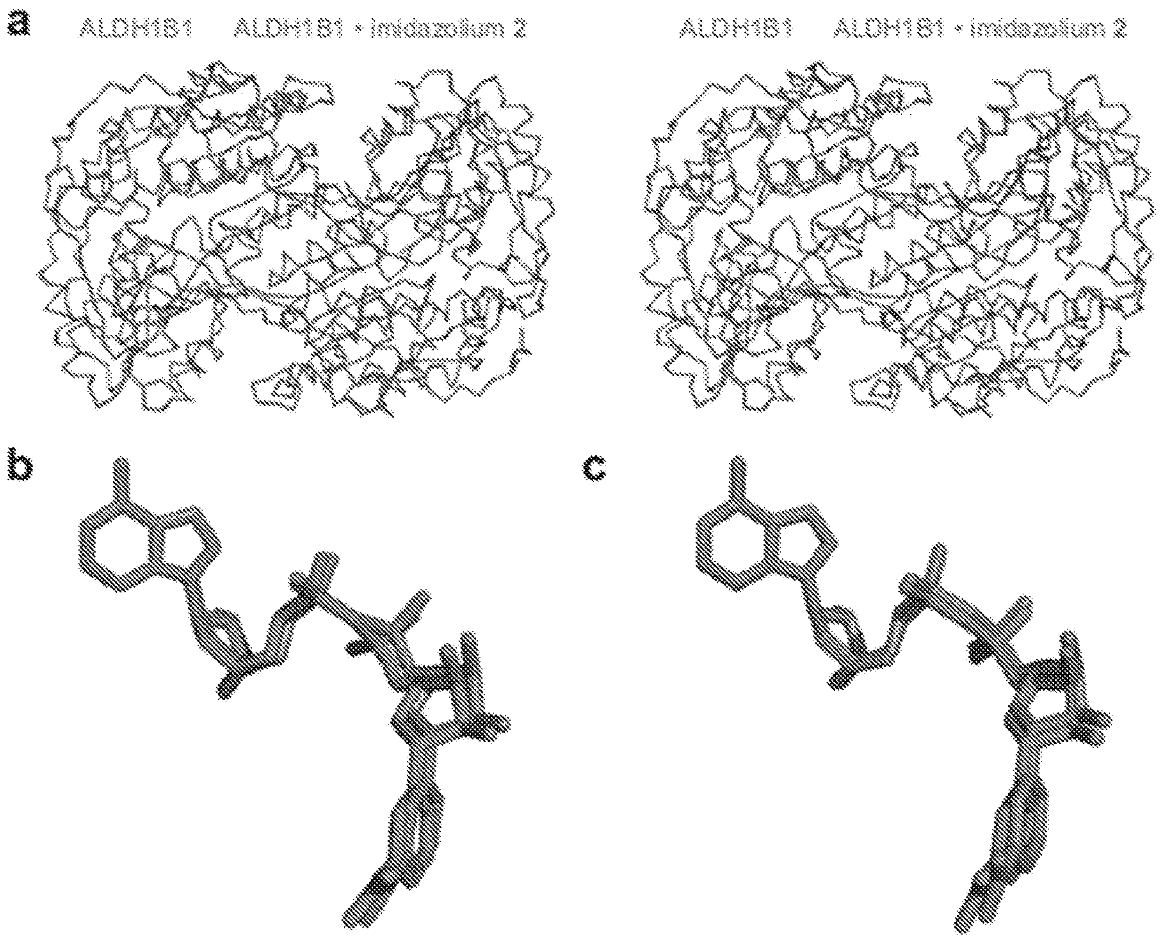
FIG. 21, Comparison of the inhibitor-free and imidazolium-bound ALDH1B1 structures. (a) Stereoview of inhibitor-free (red) and imidazolium 2-bound (blue) ALDH1B1 dimers shown as superimposed Cα traces. (b) Binding modes of the NAD+ cofactors in the inhibitor-free ALDH1B1 dimer. The individual conformers for each ALDH1B1 monomer are differentially colored and superimposed according to their adenine bases. (c) Binding modes of the NAD+ cofactors in the imidazolium 2-bound ALDH1B1 dimer.

We next pursued structural studies of ALDH1B1 and the enzyme bound to imidazolium 2. To obtain the milligram quantities of ALDH1B1 required for X-ray crystallography, we co-expressed the enzyme with GroEL/GroES chaperones, which enhanced ALDH1B1 folding and solubility (FIG. 3, panels A-B). We then employed the vapor-diffusion method to grow crystals of ALDH1B1/$NAD^+$ in the absence or presence of inhibitor 2 (FIG. 3, panel C). Both enzyme complexes formed crystals in the same trigonal space group, with two polypeptide chains per asymmetric unit and one NAD and one inhibitor (when included) per polypeptide chain. Like other ALDH1 family members and ALDH2 (Moore, S. A. et al. (1998) *Structure* 6, 1541-1551; Lamb, A. L. et al. (1999) *Biochemistry* 38, 6003-6011; Moretti, A. et al. (2016) *Sci. Rep.* 6, 35710; Steinmetz, C. G. et al. (1997) *Structure* 5, 701-711), the ALDH1B1 enzyme forms a tetramer composed of two dimers. Refinement of the crystallographic data provided us with structures of ALDH1B1 and the ALDH1B1/imidazolium 2 complex with resolutions of 2.68 Å and 2.12 Å, respectively (Table 3 and FIG. 21 panel a-b). The root-mean-square deviation (RMSD) of the two superimposed structures was 0.28 Å (FIG. 21 panel a), indicating that inhibitor binding does not coincide with major changes in ALDH1B1 conformation. The NAD+ cofactors in the free and inhibitor-bound enzymes also adopted comparable conformations (FIG. 21 panel b-c).

The crystal structures reveal that 2 interacts with ALDH1B1 through all three imidazolium ring substituents, interacting with various residues that contribute to the substrate-binding site (FIG. 4, panels A-B). The N1 2-methoxyphenyl group engages the aldehyde-binding pocket that is lined by hydrophobic and charged residues (Asp121, Glu124, Phe170, Val173, Met174, Trp177, Phe296, Cys301, Cys303, and Val459; residue numbering is based on the mature mitochondrial protein) and the catalytic cysteine (Cys302). The C4 1,1'-biphenyl substituent interacts with an extended cleft (Glu288, Gln289, Glu292, Phe296, and Asn457), and the tetrahydroazepine ring occupies a pocket that bridges the two sites (Leu120, Glu124, Ile458, and Thr460). Neither the 2-methoxyphenyl-imidazolium nor 1,1'-biphenyl-imidazolium systems are planar, and the tetrahydroazepine ring adopts a boat-like conformation. The electron density map also reveals a close contact between the Asn457 backbone carbonyl and the imidazolium ring (3.3 Å) that likely reflects an n-to-π* interaction (FIG. 4, panel C). Previous studies have shown that such lone pair-aromatic interactions are particularly stabilizing when the aromatic ring is electron-deficient (Egli, M. & Sarkhel, S. (2007) *Acc. Chem. Res.* 40, 197-205; Singh, S. K. & Das, A. (2015) *Phys. Chem. Chem. Phys.* 17, 9596-9612). This can be achieved through protonation of a ring heteroatom, or in this case through the intrinsic cationic character of the imidazolium system.

Figure 22:
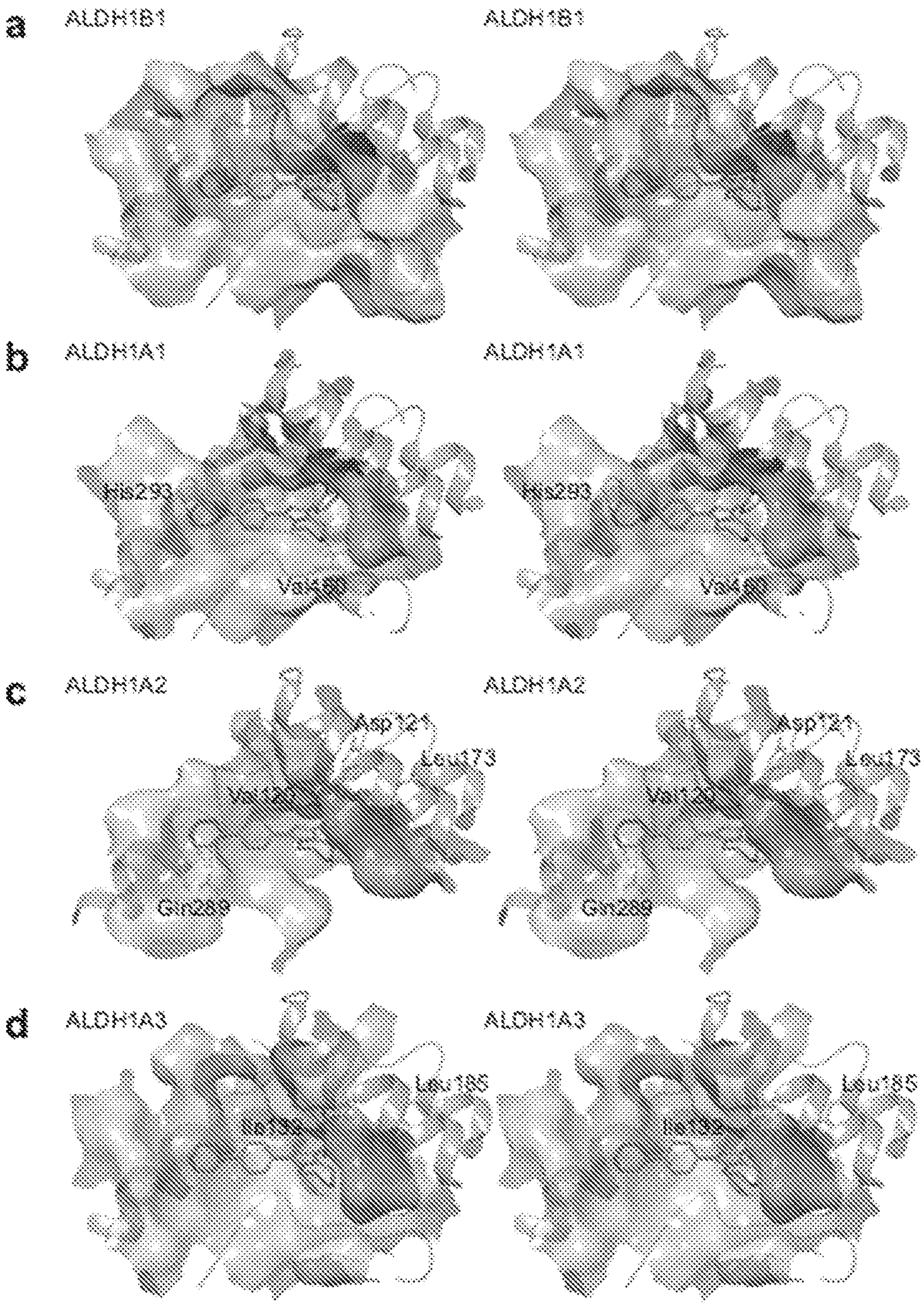
FIG. 22, Structural basis for selective ALDH1B1 inhibition. (a) Stereoview of the ALOH1 81/imidazolium 2 crystal structure, focusing on the inhibitor-binding site. (b-d) Structural models of other ALOH1 family members complexed with 2, which were generated by aligning the ALOH1 81/imidazolium 2 structure with that of ALOH1A 1 (b; P08 10: 4WPN), ALOH1A2 (c; P08: 10: 4×2Q), or ALOH1A3 (d; P08 10: 5FHZ) using Schi'Odinger Maestro software. Stereoviews for each model are shown with 2 depicted as a blue stick model. ALOH1 surface features within 7 A and secondary structures within 10 A of the inhibitor are shown in gray and orange, respectively. Protein residues predicted to sterically clash with 2 are labeled, and specific repulsive interactions are depicted as red dashed lines.

To gain insights into the molecular basis of inhibitor specificity, we aligned the ALDH1B1/imidazolium 2 structure with those of ALDH1A1, ALDH1A2, and ALDH1A3 (FIG. 22). These overlays reveal potential steric clashes between the imidazolium substituents and several active site residues in the ALDH1A paralogs. For example, His293 and Val460 in ALDH1A1 are predicted to diminish protein interactions with the C4 1,1'-biphenyl group and the tetrahydroazepine ring, respectively. The biphenyl system could be occluded by Gln289 in ALDH1A2, and multiple residues in this isoform (Val120, Asp121, and Leu173) likely abrogate binding of the N1 2-methoxyphenyl group. Our models also indicate that a subset of the analogous residues in ALDH1A3 (Ile132 and Leu185) could sterically clash with the 2-methoxyphenyl group. These observations are consistent with our enzyme kinetic studies, and they suggest that the ALDH1B1 selectivity of imidazolium 2 stems from multiple repulsive interactions with the other ALDH1 isoforms.

3. Imidazolium-Based Inhibitors with Enhanced Isoform Specificity

Figure 15:
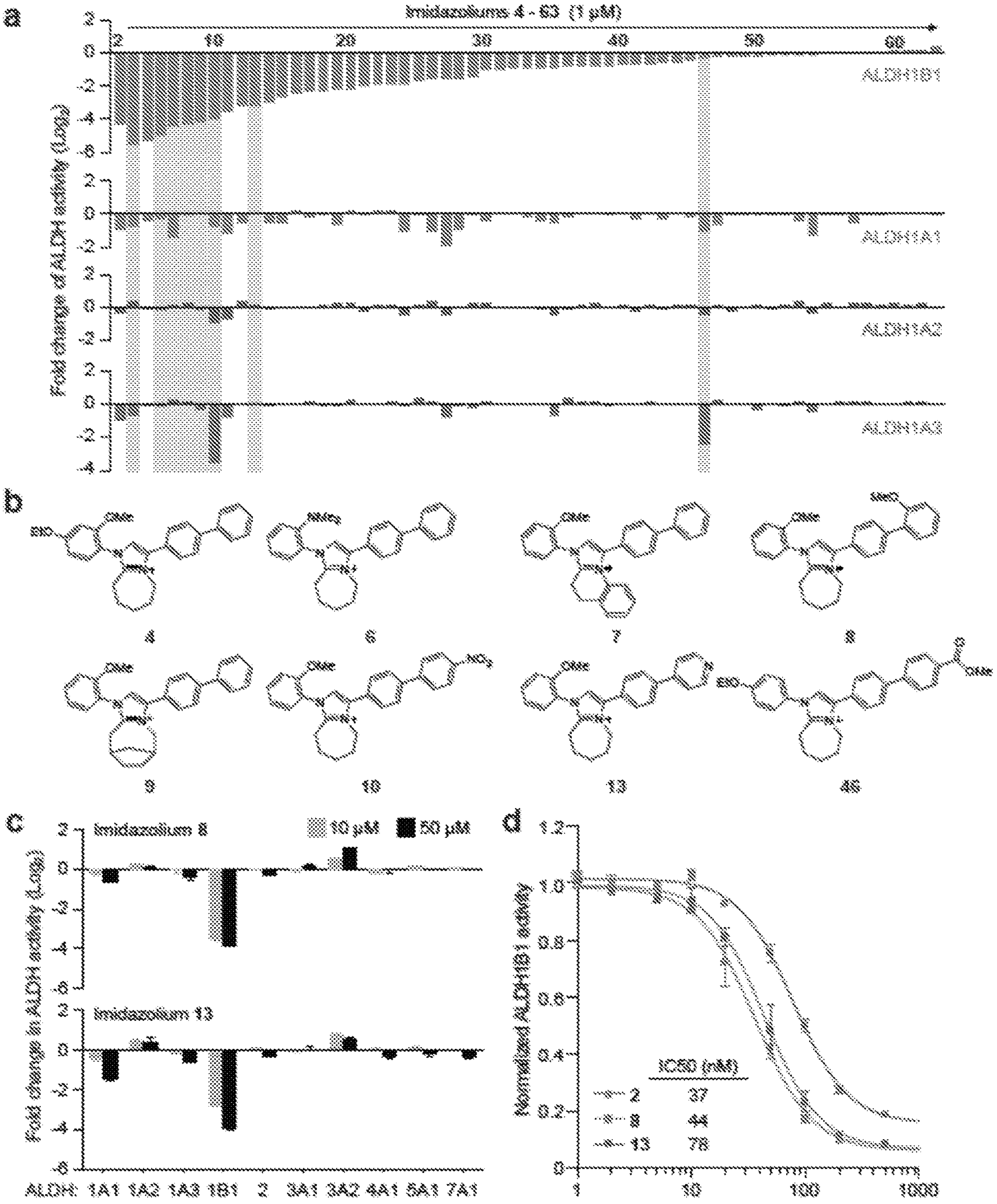
FIG. 15, Structure-activity relationship analysis of the imidazolium pharmacophore. (a-b) Compound activities against ALDH1 isoforms in enzyme kinetics assays. The compounds were tested at a 1-μM dose, and data are the average of at least two biological replicates. Chemical structures are shown for representative imidazoliums, which are also highlighted in the compound activity profiles with gray bars. (c) Profiling of imidazoliums 8 and 13 against a broader panel of ALDH isoforms. Data are the average of two biological replicates±s.d. (d) Dose-response curves for 2, 8, and 13 in ALDH1B1 enzyme kinetics assays. Data are the average of three biological replicates±s.e.m.

Since the ALDH1B1/imidazolium 2 structure revealed protein contacts with each of the imidazolium ring substituents, we examined how chemical modifications at these sites would influence inhibitor potency and isoform selectivity. We synthesized 60 additional imidazolium derivatives and assessed their activities against all four ALDH1 isozymes. Acetaldehyde was again used as the substrate in these in vitro assays, and each analog was tested at a 1-μM dose. The focused library of imidazoliums exhibited a broad range of potencies against ALDH1B1, with the most active analogs suppressing enzyme activity by at least 16-fold (FIG. 15, panel a). In contrast, the compounds had modest effects on ALDH1A1 and ALDH1A2, and only two analogs inhibited ALDH1A3 by more than 4-fold.

The structure-activity relationship (SAR) profiles of the imidazoliums revealed certain trends. The ALDH1B1 active site could accommodate both 2- and 4-substituted phenyl groups at the N1 site (e.g., imidazoliums 4 and 6) and various cyclic systems fused to the imidazolium ring (e.g., imidazoliums 7 and 9). Substituents on the C4 1,1'-biphenyl system also altered isoform specificity. For example, adding a 2'-methoxy group or replacing the distal ring with pyridin-4-yl group increased inhibitor selectivity for ALDH1B1 (8 and 13, respectively), and functional groups at the 4' position could promote ALDH1A3 binding (10 and 46). To further examine the isoform selectivity of imidazoliums 8 and 13, we profiled their activities against the broader panel of ten ALDH family members. Both derivatives had enhanced specificity for ALDH1B1 in comparison to imidazolium 2 (FIG. 15, panel c). Imidazoliums 2 and 8 also had comparable potencies against this ALDH isozyme, while that of 13 was approximately 2-fold lower (FIG. 15, panel d).

4. Cellular Activities of Imidazolium-Based ALDH1B1 Inhibitors

Figure 23:
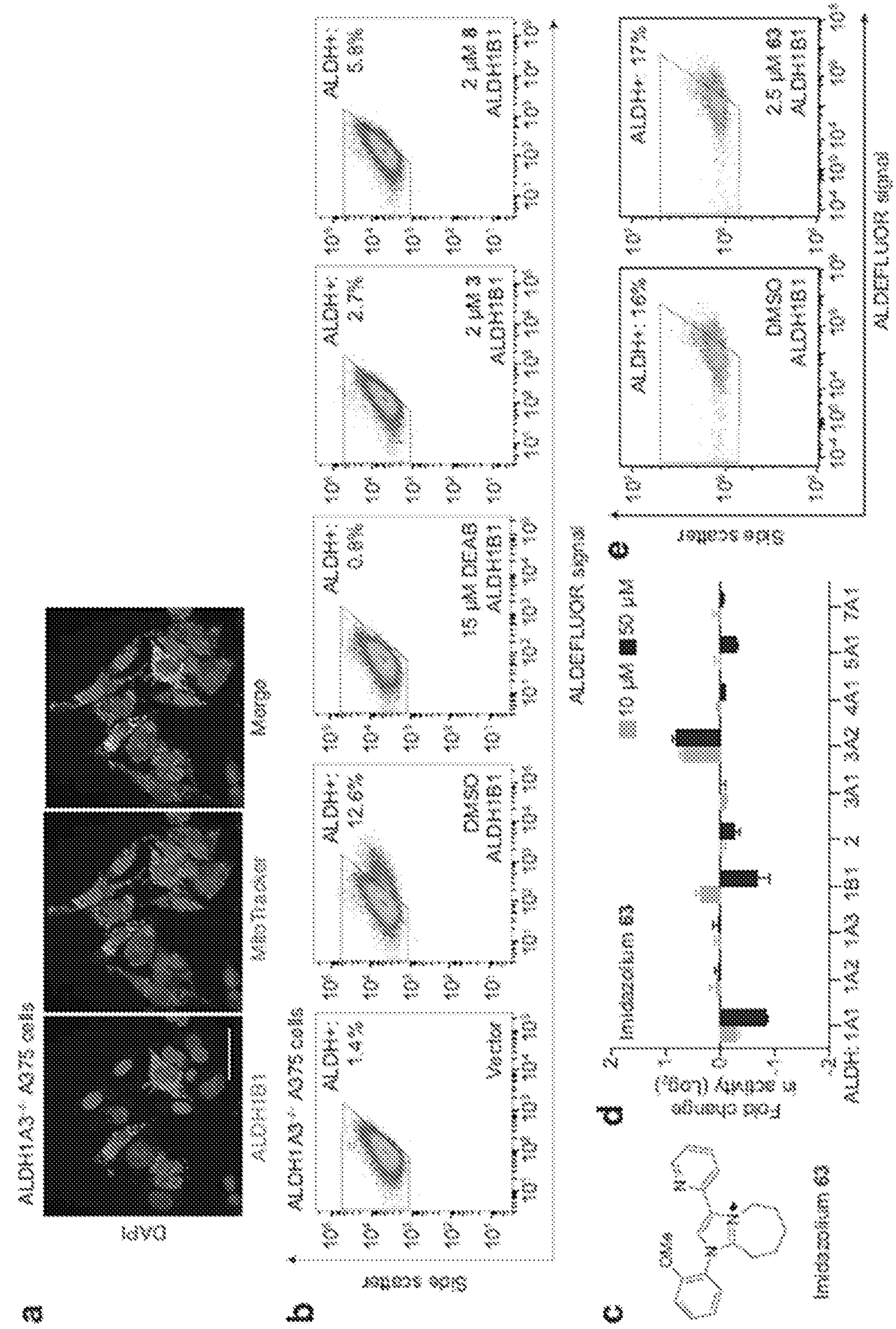
FIG. 23, Inhibition of cellular ALDH1B1 activity by imidazolium derivatives. (a) Immunofluorescence staining of $ALDH1A3^{-/-}$ A375 cells transiently transfected with ALDH1B1, demonstrating the mitochondrial localization of the exogenous protein. Scale bar: 40 μm. (b) Flow cytometry-based assays of ALDH1B1 activity and its pharmacological inhibition using $ALDH1A3^{-/-}$ A375 cells. The cells were transiently transfected with ALDH1B1 cDNA or a vector control. incubated with the designated compounds, and then treated with ALDEFLUOR reagent. The percentage of cells outside of the negative control gate is shown for each condition, and DMSO and the pan-ALDH inhibitor DEAB were used as negative and positive controls, respectively. (c) Chemical structure of imidazolium 63, which is inactive against ALDH1B1. (d) Activity of imidazolium 63 against selected ALDH isoforms. Data are the average of three biological replicates±s.d. (e) Fluorescence-activated cell sorting (FACS) plots of ALDH1B1-overexpressing $ALDH1A3^{-/-}$ A375 cells that were incubated with DMSO or imidazoliumt3 and then treated with ALDEFLUOR reagent.

Having developed ALDH1B1-selective imidazolium derivatives with nanomolar activities in vitro, we next evaluated their ability to suppress ALDH1B1 activity in cells. We first tested selected analogs in an ALDEFLUOR assay, which uses a fluorescent aldehyde probe to quantify cellular ALDH activity. For these experiments, we transiently transfected an ALDH1B1 overexpression vector into ALDH1A3$^{-/-}$ A375 cells, a melanoma line with minimal endogenous ALDH expression (Sarvi, S. et al. (2018) *Cell Chem. Biol.* 25, 1456-1469 e1456). The exogenous ALDH1B1 protein localized to the mitochondria in these cells, as demonstrated by immunofluorescence microscopy (FIG. 23 panel a), and it promoted the oxidation and intracellular trapping of the ALDEFLUOR reagent, which could be quantified by flow cytometry. This ALDH1B1-dependent ALDEFLUOR signal was abrogated by the pan-ALDH1 antagonist N-diethylaminobenzaldehyde (DEAB) and ALDH1B1-selective imidazoliums (FIG. 23 panel b). In contrast, an inactive imidazolium derivative 63 had no effect on the fluorescence intensities of the ALDEFLUOR-treated cells (FIG. 23 panel c-e).

We next assessed the effects of the ALDH1B1 antagonists on colon cancer cells. Publicly available databases indicate that ALDH1B1 is highly upregulated in colorectal adenocarcinoma relative to other cancer types and normal colorectal tissues (FIG. 6). In addition, previous studies have shown that ALDH1B1 shRNAs can inhibit the growth of SW480 colon cancer spheroids in vitro and xenografts in murine models. Since RNA interference can have off-target effects (Jackson, A. L. et al. (2003) *Nat. Biotechnol.* 21, 635-637; Svoboda, P. (2007) *Curr. Opin. Mol. Ther.* 9, 248-257; Putzbach, W. et al. (2017) Elife 6), we re-examined ALDH1B1 function in colon cancer cells using CRISPR gene editing. We first used lentiviral vectors to constitutively express Cas9 and three individual ALDH1B1-targeting guide RNAs (gRNAs) in SW480 cells and another colon cancer-derived line, HCT116 cells. As determined by TIDE (Tracking of Indels by Decomposition) analysis (Brinkman, E. K. et al. (2014) *Nucleic Acids Res.* 42, e168), two of the gRNAs (gRNA-1 and gRNA-2) could efficiently induce loss of wild-type ALDH1B1 alleles (FIG. 7).

Figure 16:
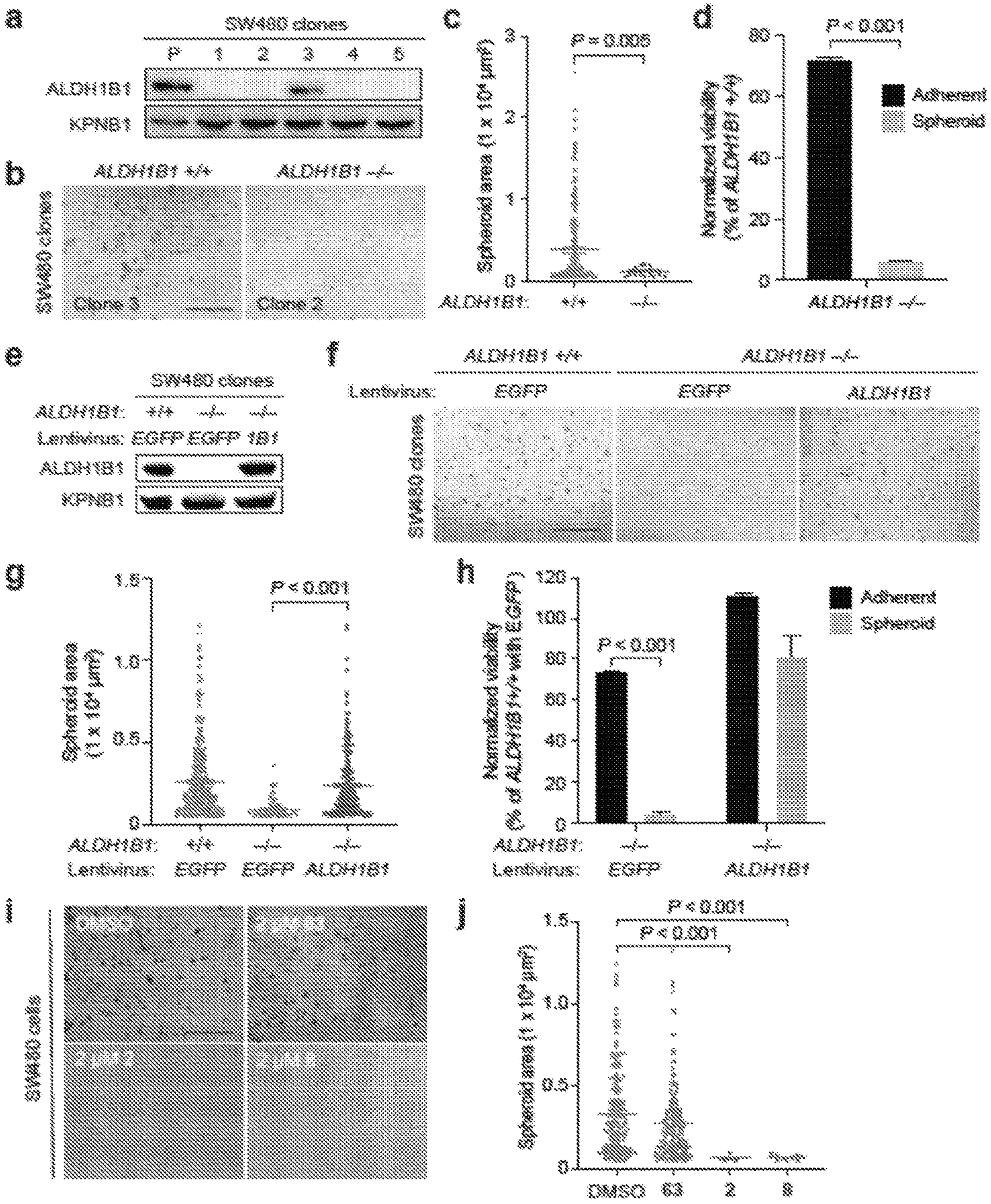
FIG. 16, ALDH1B1 promotes colorectal cancer cell spheroid growth. (a) Western blot detection of ALDH1B1 protein in individual SW480 cell clones that were transiently transfected with Cas9 and ALDH1B1 gRNA-1 and gRNA-2. Lysates from the parental lines (P) are also shown, and KPNB1 was used as a loading control. (b) Phase-contrast micrographs of spheroid cultures derived from SW480 cells with differing ALDH1B1 genotypes. SW480 clone 3 and clone 2 were used as $ALDH1B1^{+/+}$ and $ALDH1B1^{-/-}$ clones for subsequent studies. (c) Quantification of spheroid sizes for the micrographs shown in (b). Each dot represents an individual spheroid with an area that is >500 $\mu m^2$ in the image. (d) Viability of the $ALDH1B1^{-/-}$ clone cultured in either adherent or spheroid conditions, as determined by cellular ATP levels and normalized to that of the $ALDH1B1^{+/+}$ clone. Data are the average of at least four biological replicates±s.e.m. (e) Western blot analysis of SW480 clones with the indicated ALDH1B1 genotypes and lentivirally transduced with either EGFP or exogenous ALDH1B1. (f) Spheroid cultures of the SW480 clones described in (e). (g) Quantification of spheroid sizes for the micrographs shown in (f) as described above. (h) Viability of the $ALDH1B1^{-/-}$ SW480 clone transduced with EGFP or ALDH1B1 and cultured in either adherent or spheroid conditions, as determined by cellular ATP levels and normalized to that of the $ALDH1B1^{+/+}$ clone transduced with EGFP. Data are the average of four biological replicates±s.e.m. (i) Brightfield micrographs of SW480 spheroid cultures treated with the designated imidazolium derivatives and then stained with crystal violet. (j) Quantification of spheroid sizes in (i) as described above. Scale bars: 1 mm.
Figure 24:
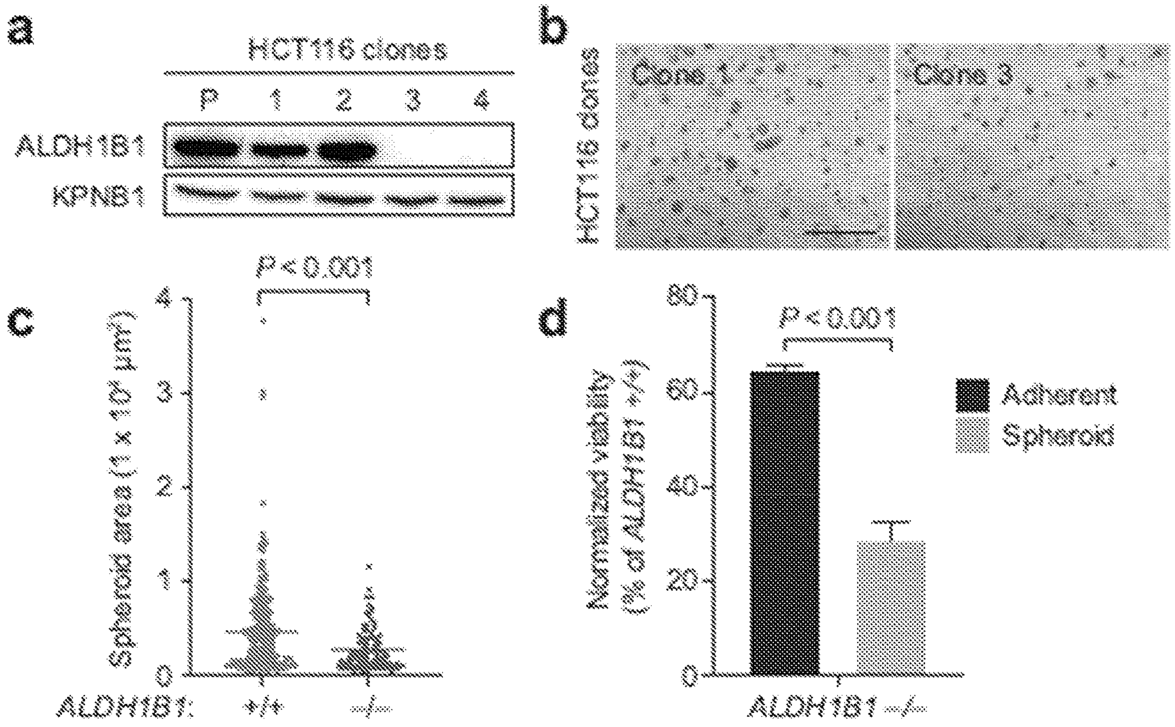
FIG. 24, ALDH1B1 promotes HCT116 cell growth in spheroid culture. (a) Western blot detection of ALDH1B1 protein in individual HCT116 cell clones that were transiently transfected with Cas9 and ALDH1B1 gRNA-1 and gRNA-2. Lysates from the parental lines (P) are also shown, and KPNB1 was used as a loading control. (b) Phase-contrast micrographs of spheroid cultures derived from HCT116 cells with differing ALDH1B1 genotypes. (c) Quantification of spheroid sizes for the micrographs shown in (b). Each dot represents an individual spheroid with an area that is >500 $\mu m^2$ in the image. (d) Viability of the $ALDH1B1^{-/-}$ clone in either adherent or spheroid conditions, as determined by cellular ATP levels and normalized to that of the $ALDH1B1^{-/-}$ clone. Data are the average of at least four biological replicates±s.e.m. Scale bar: 1 mm.

To minimize possible off-target effects caused by constitutive CRISPR activity, we then transiently transfected plasmids encoding Cas9, an EGFP reporter, gRNA-1, and gRNA-2 into SW480 and HCT116 cells. Transfected cells were sorted by their green fluorescence and clonally expanded, and multiple clones were characterized by DNA sequencing and western blot analysis (FIG. 16, panel a and FIG. 24 panel a). Homozygously edited clones with complete loss of ALDH1B1 function (SW480 clone 2 and HCT116 clone 3, FIG. 30) and unedited clones (SW480 clone 3 and HCT116 clone 1) were then selected for further study. Consistent with the previous shRNA results (Singh, S. et al. (2015) *PLoS One* 10, e0121648), the ALDH1B1 knockout lines were markedly less viable than the unedited cells when grown in Matrigel-based three-dimensional cultures under serum-free conditions (FIG. 16, panels b-c and FIG. 24 panel b-c). This inhibitory effect was specific to spheroid growth, as adherent cultures of the two colon cancer lines did not exhibit the same ALDH1B1 dependency (FIG. 16, panel d and FIG. 24 panel d). SW480 spheroids also appeared to have a greater need for ALDH1B1 activity than their HCT116 counterparts, possibly reflecting phenotypic differences between colorectal cancer subtypes.

To ensure that these cellular phenotypes are due to loss of ALDH1B1 and not clonal variation, we examined the effects of exogenous ALDH1B1 on SW480 spheroid cultures. ALDH1B1 was re-introduced into the knockout clone by lentiviral transduction, and western blot analysis confirmed the restoration of ALDH1B1 expression to endogenous-like levels (FIG. 16, panel e). EGFP was similarly transduced into the knockout and unedited clones to provide comparison controls. Lentiviral expression of ALDH1B1 but not EGFP rescued the viability of ALDH1B1 knockout SW480 cells under spheroid conditions, whereas both genetic perturbations had minimal effects on adherent growth (FIG. 16, panels f-h). These results firmly establish ALDH1B1 as an essential driver of colon cancer spheroid growth.

The spheroid-specific effects of genetic ALDH1B1 perturbations is indicative of a unique role for this enzyme in colon cancer cells with stem-like features. We consequently used this phenotype to evaluate the efficacy and specificity of our ALDH1B1-targeting inhibitors. Imidazoliums 2 and 8 strongly suppressed SW480 spheroid formation at a 2-μM dose, and the inactive analog 63 did not impede the growth of these Matrigel-based cultures (FIG. 16, panels i-j). However, the imidazolium-based ALDH1B1 inhibitors had comparable anti-proliferative activities against adherent SW480 cells (FIG. 25 panel a). We hypothesized that this lack of pharmacological selectivity was due to an off-target cytotoxicity activity, which we surmised was related to the mitochondrial localization of imidazolium derivatives. Other hydrophobic cations have been found to accumulate in mitochondria and disrupt oxidative phosphorylation (Rogers, K. S. & Higgins, E. S. (1973) *J. Biol. Chem.* 248, 7142-7148; Rogers, K. S. & Higgins, E. S. (1976) *Chem. Biol. Interact.* 12, 71-79; Rottenberg, H. J. (1984) *Membr. Biol.* 81, 127-138; Trnka, J. et al. (2015) *PLoS One* 10, e0121837). Consistent with this idea, Seahorse assays revealed that our imidazolium-based ALDH1B1 antagonists suppress the oxygen consumption rate (OCR) of SW480 cells in an ALDH1B1-independent manner (FIG. 25 panel b).

5. Isosteric Guanidine-Based ALDH1B1 Inhibitors

Figure 20:
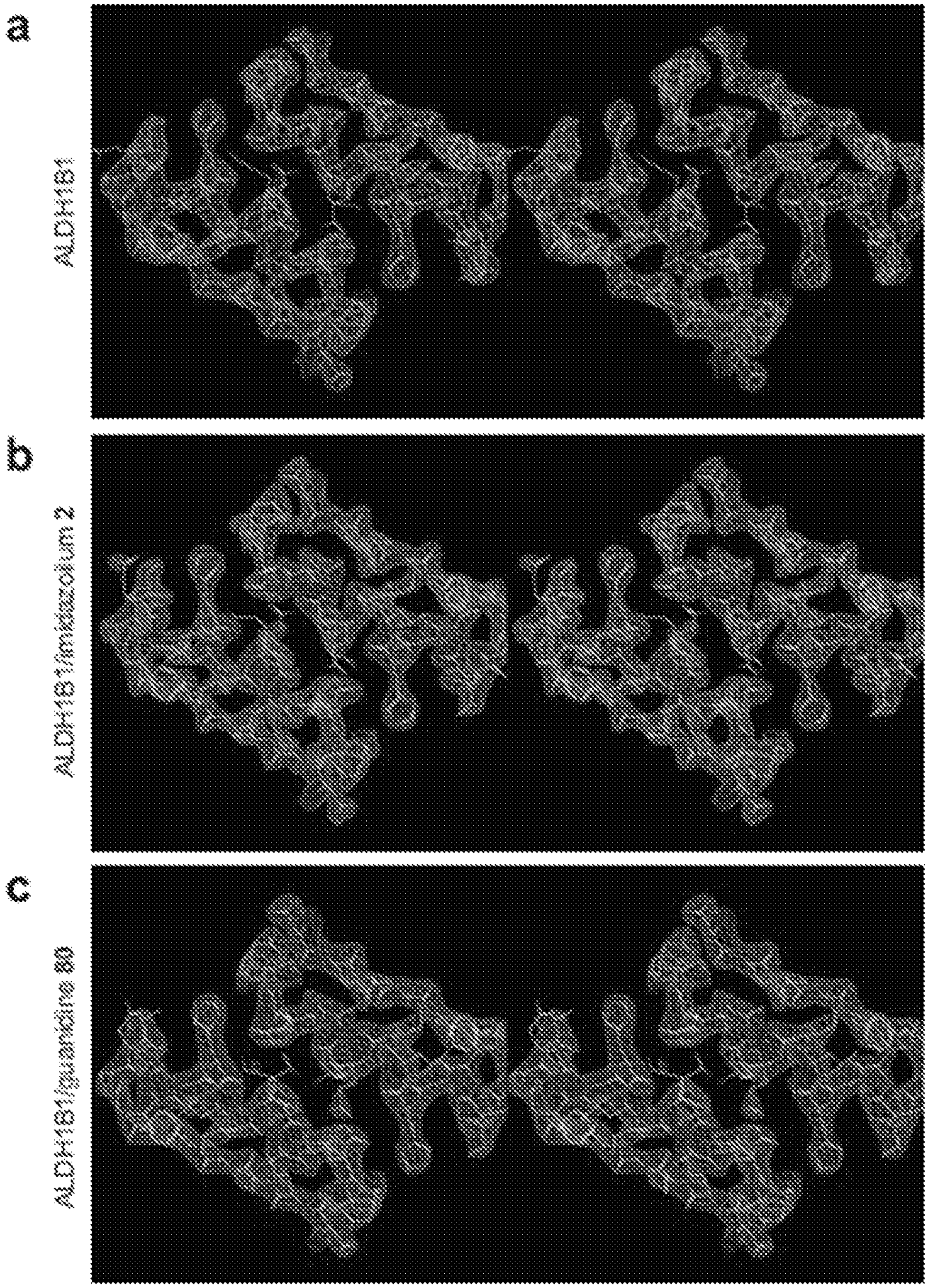
FIG. 20, Electron density maps. (a-e) Stereoviews of electron-density maps for the ALDH1B1 (a), ALDH1B1/imidazolium 2 (b), and ALDH1B1/guanidine 80 (c) crystal structures, focusing on residues 239-261 at the dimer interface. The maps were calculated with coefficients 2Fo-Fc and contoured at 26, and the refined models are superimposed.

Due to the off-target mitochondrial toxicity of imidazolium-based ALDH1B1 inhibitors, we explored whether the constitutively cationic imidazolium system could be replaced with an isosteric guanidine scaffold, which would become positively charged upon protonation. Several bicyclic guanidine analogs could inhibit ALDH1B1 with potencies and isoform selectivities that were similar to those of their imidazolium counterparts (FIG. 17, panel a), and the compounds exhibited identical kinetic behaviors with respect to the aldehyde and NAD substrates (FIG. 26 panel a). The guanidine-based scaffold also accommodated the same ALDH1B1-interacting substituents identified in our SAR studies of imidazolium derivatives. To further investigate how guanidine and imidazolium derivatives inhibit ALDH1B1, we solved the crystal structure of ALDH1B1 bound to guanidine 80 at 2.45 Å resolution (Table 3 and FIG. 20 panel c). Overlays of the structure of ALDH1B1/guanidine 80 and that of the ALDH1B1/imidazolium 2 complex confirmed that the two inhibitor classes adopt nearly identical binding modes (FIG. 26 panel b).

Figure 17:
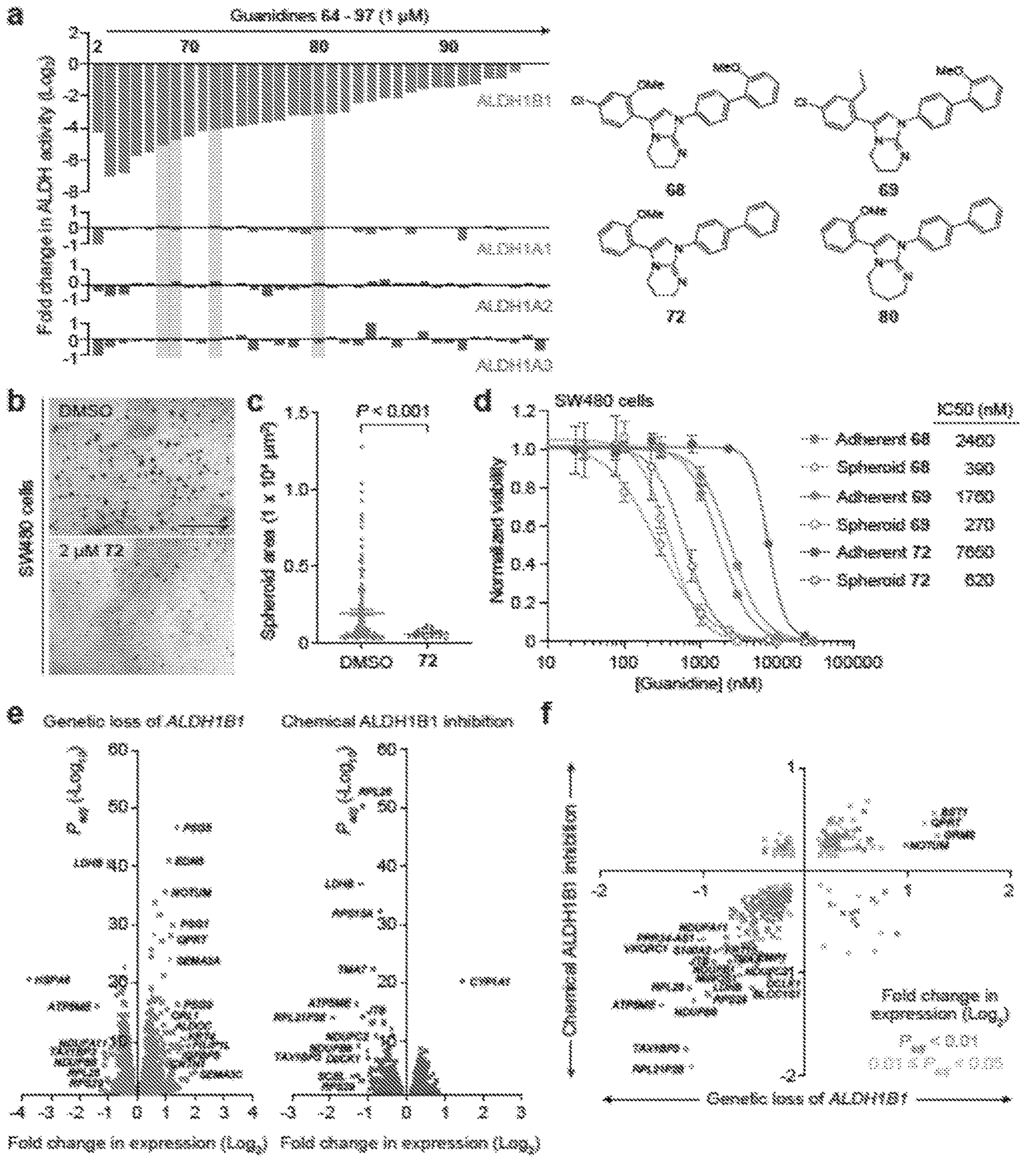
FIG. 17, Development of guanidine-based ALDH1B1 antagonists. (a) Compound activities against ALDH1 isoforms in enzyme kinetics assays, revealing several ALDH1B1-selective guanidines. The compounds were tested at a 1-μM dose, and data are the average of at least two biological replicates. Chemical structures are shown for representative imidazoliums, which are also highlighted in the compound activity profiles with gray bars. (b) Brightfield micrographs of SW480 spheroid cultures treated with guanidine 72 and then stained with crystal violet. Scale bar: 1 mm (c) Quantification of spheroid sizes for the micrographs shown in (b) as described in FIG. 5. (d) Dose-response curves for guanidine 66, 69 and 72 on SW480 cells cultured in either adherent or spheroid conditions. Data are the average of three biological replicates±s.e.m. (e) Volcano plots of the transcriptional perturbations caused by genetically or chemically induced loss of ALDH1B1 function. Gene expression changes with adjusted P values (Padj)<0.05 are graphed, and selected transcripts are annotated. ALDH1B1 is excluded in the volcano plot for the genetic loss of ALDH1B1 function since its Padj value exceeds the range of the y-axis. (f) Comparison of transcriptional changes caused by the genetic and chemical perturbations. Transcripts with statistically significant changes in expression for both datasets are graphed, and those that are most dependent on ALDH1B1 activity are annotated. The distribution of transcripts across quadrants is also shown.

Like the imidazolium-based inhibitors, the guanidine analogs effectively targeted ALDH1B1 in cells, as assessed by the ALDEFLUOR assay (FIG. 27 panel a). However, this new class of ALDH1B1 antagonists did not inhibit the OCR of SW480 cells (FIG. 27 panel b), and they could preferentially suppress the spheroid growth of these colon cancer cells (FIG. 17, panels b-d). The guanidine derivatives were also much less cytotoxic than the imidazoliums to HEK293T cells, a non-cancerous line (FIG. 27 panel c), and they had markedly reduced potency against Hh signaling in NIH-3T3 cells (FIG. 27 panel d).

We next compared how SW480 cells respond to guanidine-based ALDH1B1 inhibitors and 5-FU, the current mainstay of treatment for advanced colorectal cancer (Vodenkova, S. et al. (2020) *Pharmacol. Ther.* 206, 107447). When used in combination, guanidine 72 and 5-FU block SW480 spheroid growth with an efficacy that closely matched the product of their individual activities ($F_{guanidine+5\text{-}FU}=f_{guandine}\times f_{5\text{-}FU}$) (FIG. 28 panel a), corroborating their independent mechanisms of action. We also generated a 5-FU-resistant SW480 line by culturing the colon cancer cells in the presence of this chemotherapy drug for multiple passages. These cells were 50-fold less sensitive to 5-FU than the parental line, but guanidine 69 could suppress the spheroid growth of both lines with comparable potency (FIG. 28 panel b). These results suggest that ALDH1B1 antagonists could be effective treatments for advanced colorectal cancer, either alone or in combination with other therapies.

6. Identification of ALDH1B1-Dependent Genes

Our findings establish bicyclic guanidines as ALDH1B1 inhibitors with the potency and specificity required for functional studies of this ALDH isoform. Toward that goal, we employed one of these guanidine derivatives to characterize the ALDH1B1-transcriptome in colon cancer cells. We used RNA sequencing (RNA-seq) to compare the effects of genetic and pharmacological perturbations of ALDH1B1 function on SW480 cells, exploiting specificity of CRISPR mutagenesis and the temporal control afforded by small molecules (FIG. 17, panel e). One RNA-seq dataset examined the transcriptomes of clonal ALDH1B1-knockout SW480 cells that were lentivirally transduced with either EGFP or exogenous ALDH1B1. A second dataset analyzed the transcriptomes of the parental SW480 cells after 24 hours of treatment with DMSO or 2 μM of guanidine 68.

To facilitate the identification of ALDH1B1-dependent genes, we focused on genes with statistically significant transcriptional changes ($P_{adj}$<0.05) in both datasets (FIG. 17, panel f). In particular, several genes were downregulated by both genetic and chemical loss of ALDH1B1 function. Gene Ontology (GO) enrichment analyses of these differentially transcribed genes revealed significant enrichment for genes associated with mitochondrial metabolism (ATP5ME, ATP5PO, LDHB, NDUFB1, NDUFB8, NDUFC2, NDUF1A, NDFUA9, NDUFA11, and UQCR11), and ribosomal biogenesis and function (RPL15A, RPL21, RPL26, RPL29, RPL38, and TMA7) (FIG. 29). Both perturbations also reduced the expression of KRT15 and DCLK1, which are genetic markers of colorectal cancer stem cells (Giroux, V. et al. (2018) *Stem Cell Reports* 10, 1947-1958; Nakanishi, Y. et al. (2013) *Nat Genet* 45, 98-103).

In addition to these conserved transcriptional changes, genetic disruption of ALDH1B1 coincided with the upregulation of genes that were not induced by the ALDH1B1 inhibitor (FIG. 17, panel e), potentially reflecting cellular phenotypes caused by prolonged ALDH1B1 deficiency. In principle, these transcripts could encode oncogenes that are activated through compensatory mechanisms or tumor suppressors that are negatively regulated by ALDH1B1. Consistent with this idea, this latter set of ALDH1B1-dependent genes includes multiple members of the pregnancy-specific glycoprotein (PSG1, PSG2, PSG5, PSG6, and PSG9) and semaphorin (SEM3A and SEM3C) families, some of which are known drivers of gastrointestinal malignancies (Yang, L. et al. (2016) *Oncotarget* 7, 61562-61574; Casazza, A. et al. (2013) *Cancer Cell* 24, 695-709; De Vlaeminck, Y. et al. (2020) *Cancers* (Basel) 12). Sustained loss of ALDH1B1 function also induced other colorectal cancer-associated factors that are either overexpressed and correlate with poor clinical prognoses (e.g., AGPAT4, BST2, CACNA1F, CNTN1, IGF1, HSD17B2, ITIH3, ORL1, and PLOD2) (Zhang, D. et al. (2020) *Signal Transduct. Target. Ther.* 5, 24; Mukai, S. et al. (2017) *Ann. Surg. Oncol.* 24, 594-602; Li, G. et al. (2020) Cancer Biomark; Yang, W. J. et al. (2020) *Cancer Med.* 9, 179-193; Vigneri, P. G. et al. (2015) *Front. Oncol.* 5, 230; Lee, Y. E. et al. (2015) *Tumour Biol.* 36, 7675-7683; Kopylov, A. T. et al. (2020) *Molecules* 25; Du, W. et al. (2020) *Biochem. Cell Biol.* 98, 386-395) or function as tumor suppressors (e.g., CEACAM1, EDN3, FILIP1L, and TREM2)(Neumaier, M. et al. (1993) *Proc. Natl. Acad. Sci. U.S.A.* 90, 10744-10748; Wang, R. et al. (2013) *Int. J. Cancer* 132, 1004-1012; Park, Y. L. et al. (2016) *Oncotarget* 7, 72229-72241; Kim, S. M. et al. (2019) *Cancers* (Basel) 11). Together, these transcriptomic datasets support a model in which ALDH1B1 mobilizes metabolic and translational pathways in colon cancer cells that maintain stemness and promote tumor progression.

TABLE 4

| Compound name | Compound no. in manuscript | Structure |
| --- | --- | --- |
| STL8-T-0001 | 69 | 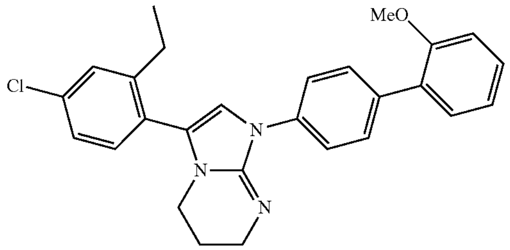 [SMILES: CCc1cc(Cl)ccc1C1=CN(c2ccc(-c3ccccc3OC)cc2)C2=NCCCN12] |
| STL5-T-0057 | 68 | 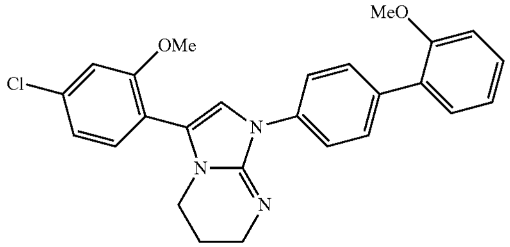 [SMILES: COc1cc(Cl)ccc1C1=CN(c2ccc(-c3ccccc3OC)cc2)C2=NCCCN12] |
| STL5-T-0002 | 66 | 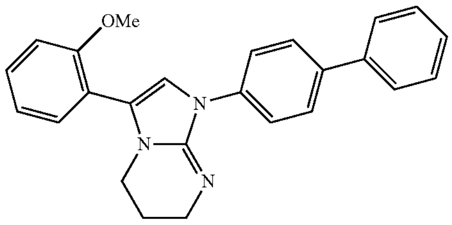 [SMILES: COc1ccccc1C1=CN(c2ccc(-c3ccccc3)cc2)C2=NCCCN12] |
| STL5-T-030A | 78 | 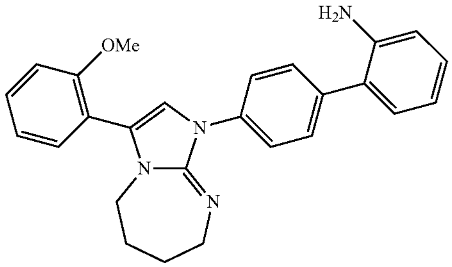 [SMILES: COc1ccccc1C1=CN(c2ccc(-c3ccccc3N)cc2)C2=NCCCCN12] |

TABLE 4-continued
| Compound name | Compound no. in manuscript | Structure |
| --- | --- | --- |
| AO-I-008 | 2 | 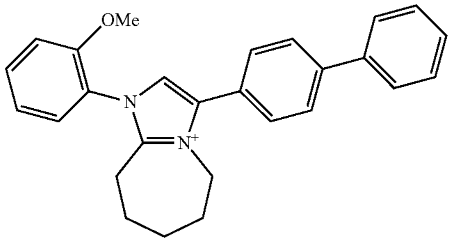 [SMILES: COc1ccccc1-n1cc(-c2ccc(-c3ccccc3)cc2)[n+]2c1CCCCC2] |
| STL5-T-0048 | 74 | 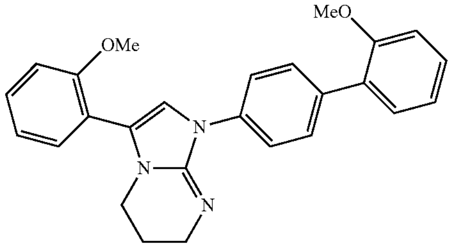 [SMILES: COc1ccccc1C1=CN(c2ccc(-c3ccccc3OC)cc2)C2=NCCCN12] |
| HPI-225 | 8 | 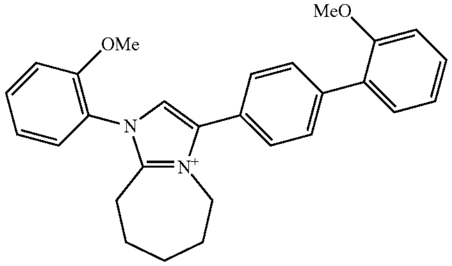 [SMILES: COc1ccccc1-c1ccc(-c2cn(-c3ccccc3OC)c3[n+]2CCCCC3)cc1] |
| STL5-T-0004 | 64 | 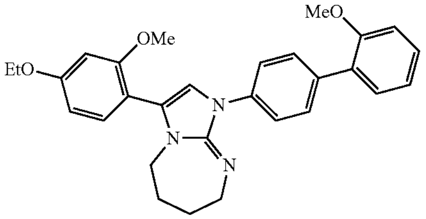 [SMILES: CCOc1ccc(C2=CN(c3ccc(-c4ccccc4OC)cc3)C3=NCCCCN23)c(OC)c1] |
| STL5-T-0001 | 70 | 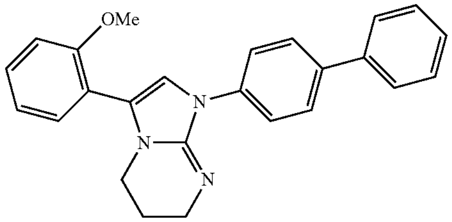 [SMILES: COc1ccccc1C1=CN(c2ccc(-c3ccccc3)cc2)C2=NCCCN12] |
| HPI-273 | 68 | 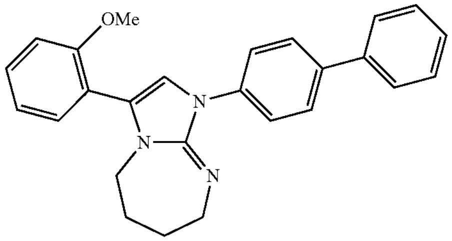 [SMILES: COc1ccccc1C1=CN(c2ccc(-c3ccccc3)cc2)C2=NCCCCN12] |

TABLE 4-continued
| Compound name | Compound no. in manuscript | Structure |
|---|---|---|
| STL5-T-0022 | 65 | 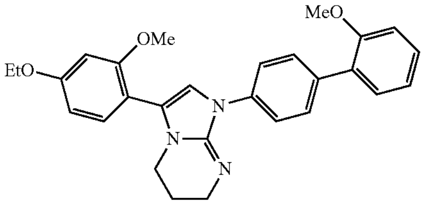 [SMILES: CCOc1ccc(C2=CN(c3ccc(-c4ccccc4OC)cc3)C3=NCCCN23)c(OC)c1] |
| STL5-T-0029 | 76 | 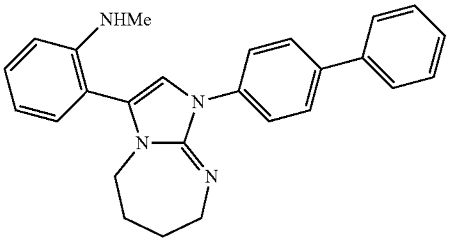 [SMILES: CNc1ccccc1C1=CN(c2ccc(-c3ccccc3)cc2)C2=NCCCCN12] |
| STL5-T-0025 | 70 | 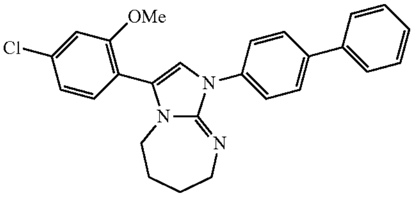 [SMILES: COc1cc(Cl)ccc1C1=CN(c2ccc(-c3ccccc3)cc2)C2=NCCCCN12] |
| STL5-T-0027 | 71 | 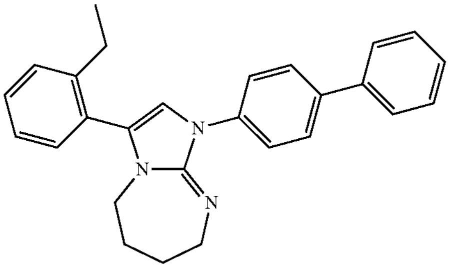 [SMILES: CCc1ccccc1C1=CN(c2ccc(-c3ccccc3)cc2)C2=NCCCCN12] |
| STL8-T-0002 | 66 | 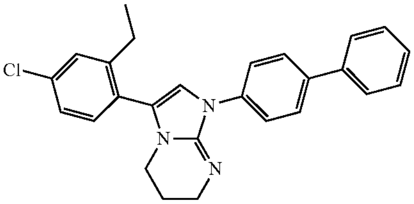 [SMILES: CCc1cc(Cl)ccc1C1=CN(c2ccc(-c3ccccc3)cc2)C2=NCCCN12] |
| STL5-T-0028 | 77 | 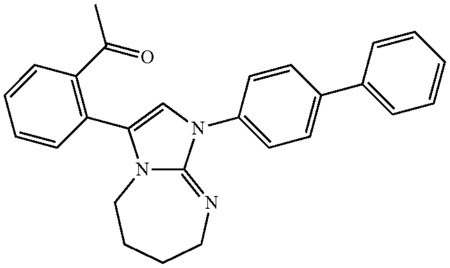 [SMILES: CC(=O)c1ccccc1C1=CN(c2ccc(-c3ccccc3)cc2)C2=NCCCCN12] |

TABLE 4-continued
| Compound name | Compound no. in manuscript | Structure |
| --- | --- | --- |
| STL5-T-0030 | 75 | 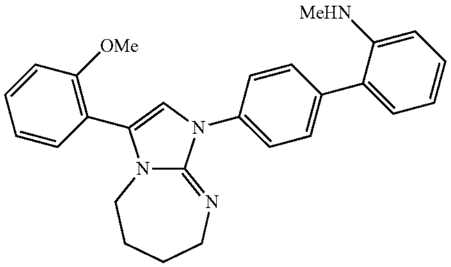 [SMILES: CNc1ccccc1-c1ccc(N2C=C(c3ccccc3OC)N3CCCCN=C32)cc1] |
| STL8-T-0003 | 67 | 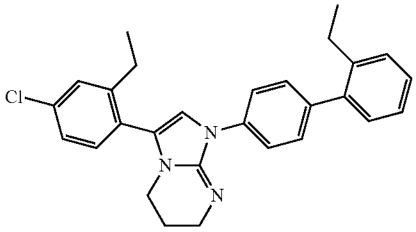 [SMILES: CCc1cc(Cl)ccc1C1=CN(c2ccc(-c3ccccc3CC)cc2)C2=NCCCN12] |
| HPI-269 | 71 | 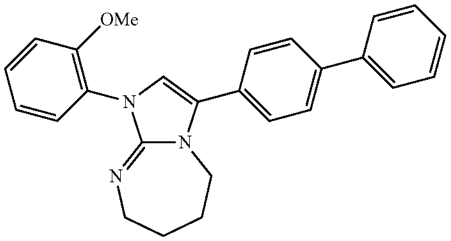 [SMILES: COc1ccccc1N1C=C(c2ccc(-c3ccccc3)cc2)N2CCCCN=C21] |
| HPI-279 | 67 | 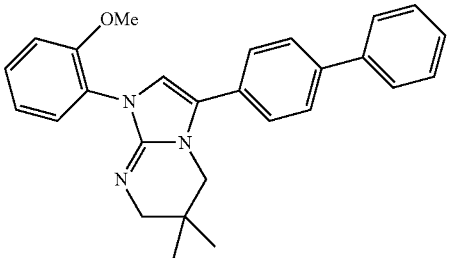 [SMILES: COc1ccccc1N1C=C(c2ccc(-c3ccccc3)cc2)N2CC(C)(C)CN=C21] |
| HPI-208 | 73 | 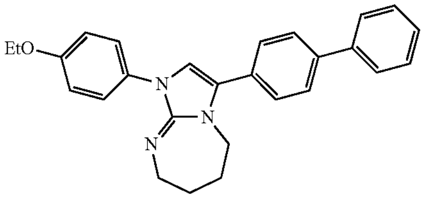 [SMILES: CCOc1ccc(N2C=C(c3ccc(-c4ccccc4)cc3)N3CCCCN=C32)cc1] |
| HPI-214 | 53 | 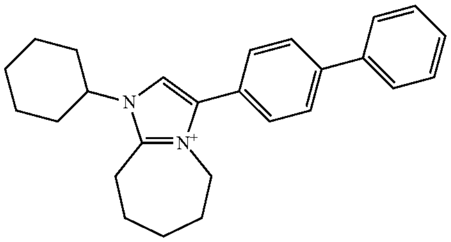 [SMILES: c1ccc(-c2ccc(-c3cn(C4CCCCC4)c4[n+]3CCCCC4)cc2)cc1] |

TABLE 5

| Compound name | ALDH1B1(in vitro) IC50 (nM) | ALDH1B1(in cellulo) IC50 (nM) | HEK293T GI50 (nM) | Seahorse assay (NIH3T3) IC50 (nM) | Seahorse assay (SW480) IC50 (nM) | Adherent SW480 GI50 (nM) | Spheroid SW480 GI50 (nM) |
|---|---|---|---|---|---|---|---|
| STL8-T-0001 | 59 | | 1700 | | | 1900 | 230 |
| STL5-T-0057 | 30 | | 1700 | | | 2700 | 440 |
| STL5-T-0002 | 120 | 110 | 8900 | 850 | NA | 8200 | 750 |
| STL5-T-030A | 44 | | 9100 | | | 8400 | 750 |
| AO-I-008 | 42 | 38 | 230 | 180 | 540 | 570 | 820 |
| STL5-T-0048 | | | 1700 | | | 3110 | 850 |
| HPI-225 | 47 | 22 | 160 | 130 | 340 | 850 | 960 |
| STL5-T-0004 | 100 | | | | | 1300 | 1100 |
| STL5-T-0001 | 98 | | | | | 1900 | 1500 |
| HPI-273 | 47 | 35 | 2800 | 190 | NA | 5800 | 1600 |
| STL5-T-0022 | 130 | | | | | 2900 | 1600 |
| STL5-T-0029 | 22 | | 5300 | | | | |
| STL5-T-0025 | 42 | | 5200 | | | | |
| STL5-T-0027 | 44 | | 4300 | | | | |
| STL8-T-0002 | 52 | | 1500 | | | | |
| STL5-T-0028 | 68 | | 6100 | | | | |
| STL5-T-0030 | 70 | | | | | | |
| STL8-T-0003 | 74 | | 1300 | | | | |
| HPI-269 | 81 | 110 | 3400 | 580 | | | |
| HPI-279 | 82 | 110 | | | | | |
| HPI-208 | 1900 | 6700 | | 2400 | | | |
| HPI-214 | NA | | | 170 | | 820 | |

D. Discussion

ALDH1 upregulation in human malignancies was first recognized as a direct mechanism of chemoresistance, exemplified by the ability of these enzymes to metabolize the active form of cyclophosphamide (Cox, P. J. et al. (1975) *Cancer Res.* 35, 3755-3761; Cox, P. J. et al. (1976) *Cancer Treat. Rep.* 60, 321-326; Radin, A. I. et al. (1991) *Biochem. Pharmacol.* 42, 1933-1939; Magni, M. et al. (1996) *Blood* 87, 1097-1103). Subsequent studies have shown that ALDH1 isoforms are predominantly expressed in the stem-like populations that drive tumor initiation and progression, with high ALDH1 activity in tumors frequently correlating with poor clinical outcomes (Ginestier, C. et al. (2007) *Cell Stem Cell* 1, 555-567; Pearce, D. J. et al. (2005) *Stem Cells* 23, 752-760; Seigel, G. M. et al. (2005) *Mol. Vis.* 11, 729-737). ALDH1 function in cancer stem cells is not limited to drug detoxification, as the genetic suppression of individual isoforms has been shown to reduce tumorigenicity and metastasis (Shao, C. et al. (2014) *Clin. Cancer Res.* 20, 4154-4166; Singh, S. et al. (2015) *PLoS One* 10, e0121648; Yue, L. et al. (2015) *Melanoma Res.* 25, 138-148). Although the precise roles of ALDH1 isoforms in these self-renewing populations remain unclear, their requirement for stemness maintenance has spurred the development of small-molecule ALDH1 antagonists. Several ALDH1A1-selective inhibitors have been reported, including quinoline-, theophylline-, and thiopyrimidinone-based compounds (Morgan, C. A. & Hurley, T. D. J. (2015) *Med. Chem.* 58, 1964-1975; Yang, S. M. et al. (2018) *J. Med. Chem.* 61, 4883-4903; Huddle, B. C. et al. (2018) *J. Med. Chem.* 61, 8754-8773; Yang, S. M. et al. (2015) *J. Med. Chem.* 58, 5967-5978), and some have been used to selectively inhibit tumor spheroid growth (Yang, S. M. et al. (2018) *J. Med. Chem.* 61, 4883-4903). The thiopyrimidone scaffold has also yielded compounds with modest selectivity for ALDH1A2 or ALDH1A3 (Huddle, B. C. et al. (2018) *J. Med. Chem.* 61, 8754-8773).

To the best of our knowledge, the bicyclic imidazoliums and guanidines reported here are the first selective inhibitors of ALDH1B1. This mitochondrial ALDH isoform is most closely related in structure to the ALDH1A and ALDH2 enzymes, with sequence identities ranging from 70 to 80%. Our most specific antagonists exhibit nanomolar potencies against ALDH1B1 in vitro and in cells, and at micromolar concentrations they have minimal effects on ALDH1A isoforms, ALDH2, and at least 6 other ALDH family members. While these compounds inhibit ALDH1B1 in a manner that is non-competitive with respect to aldehyde substrate, our crystallographic studies reveal that they engage the substrate-binding pocket rather than an allosteric site. We speculate that this kinetic behavior reflects an ordered, multi-step mechanism of ALDH1B1 action, as has been observed in other bisubstrate enzymes (Blat, Y. (2010) *Chem. Biol. Drug Des.* 75, 535-540; Sahni-Arya, B. et al. (2007) *Biochim. Biophys. Acta* 1774, 1184-1191). In addition, other ALDH enzymes composed of dimer pairs, including ALDH1A1, have been found to have one active subunit in each dimer per catalytic cycle, which may result from negative cooperativity among the tetramer subunits (Weiner, H. et al. (1976) *J. Biol. Chem.* 251, 3853-3855; Zhou, J. & Weiner, H. (2000) *Biochemistry* 39, 12019-12024; Perez-Miller, S. J. & Hurley, T. D. (2003) *Biochemistry* 42, 7100-7109; Yoval-Sanchez, B. et al. (2013) *Proteins* 81, 1330-1339). According to these models, compounds that block completion of the ALDH1B1 reaction cycle will also impede formation of new ALDH/$NAD^+$ complexes that are capable of aldehyde binding. We note that a theophylline-based antagonist of ALDH1A1 was found to be an active-site ligand that is kinetically non-competitive with aldehyde substrate (Morgan, C. A. & Hurley, T. D. J. (2015) *Med. Chem.* 58, 1964-1975), and analogous mechanisms may be at play.

Consistent with the isosteric nature of the bicyclic imidazoliums and guanidines, our structural studies also demonstrate that both pharmacophores bind to ALDH1B1 through equivalent molecular interactions. The ALDH1B1 antagonists adopt a pin-wheel-like conformation, with the imidazolium- or guanidine-based scaffold participating a core n-to-$\pi^*$ interaction with the Asn457 backbone carbonyl. Inhibitor potency and selectivity are enhanced by substituents that extend from and are non-planar with the central imidazolium or guanidine ring, engaging contiguous but distinct pockets in the active site. In comparison, structural studies of non-covalent ALDH1A1 and ALDH1A3 antagonists reveal that these planar, multi-ringed structures derive their core binding energy through hydrophobic $\pi$ interactions (Morgan, C. A. & Hurley, T. D. *J.* (2015) *Med. Chem.* 58, 1964-1975; Yang, S. M. et al. (2018) *J. Med. Chem.* 61, 4883-4903; Huddle, B. C. et al. (2018) *J. Med. Chem.* 61, 8754-8773; Gelardi, E. L. M. et al. (2021) *Cancers* (Basel) 13; Yang, S. M. et al. (2015) *J. Med. Chem.* 58, 5967-5978). Our imidazolium and guanidine derivatives therefore represent an alternative mode for targeting the ALDH1 active site. These findings likely extend beyond ALDH1B1, as certain imidazolium analogs can inhibit ALDH1A3. We anticipate that bicyclic cationic compounds could be developed to specifically target this isoform, which is essential for the maintenance of breast and non-small lung cancer stem cells (Marcato, P. et al. (2011) *Stem Cells* 29, 32-45; Shao, C. et al. (2014) *Clin. Cancer Res.* 20, 4154-4166).

Although imidazolium- and guanidine-based ALDH1B1 inhibitors have comparable activities in enzyme kinetics assays, our studies uncover key differences between the cellular functions of these compounds. Both pharmacophores can target ALDH1B1 in cells with potencies comparable to those required for ALDH1B1 inhibition in vitro, likely due to the uptake of lipophilic cations by mitochondria (Rottenberg, H. J. (1984) *Membr. Biol.* 81, 127-138). On the other hand, the accumulation of organic cations in this organelle can also disrupt its membrane potential, the electron transport chain, and likely other mitochondrial functions (Rogers, K. S. & Higgins, E. S. (1973) *J. Biol. Chem.* 248, 7142-7148; Rogers, K. S. & Higgins, E. S. (1976) *Chem. Biol. Interact.* 12, 71-79; Trnka, J. et al. (2015) *PLoS One* 10, e0121837). We observed such mitochondrial off-target effects with the imidazolium derivatives but not their guanidine counterparts, possibly due to the latter's reversible cationic character, greater total polar surface area, and/or hydrogen-bonding capabilities. Only the guanidine-based ALDH1B1 inhibitors could selectively suppress colon cancer spheroid growth, recapitulating the ALDH1B1 knockout phenotype. The ability of guanidine derivatives to circumvent the ALDH1B1-independent effects of imidazoliums on cell growth and Hh signaling provides further evidence of their greater on-target specificity.

The cellular potency and specificity of the guanidine-based antagonists make them valuable tools for interrogating ALDH1B1 functions. As with other members of ALDH1 subfamily, how ALDH1B1 drives tumor initiation and progression is an unresolved question. Genetic silencing of ALDH1B1 in SW480 cells has been reported to downregulate Wnt, Notch, and phosphoinositide 3-kinase/Akt signaling (Singh, S. et al. (2015) *PLoS One* 10, e0121648), pathways that are known to contribute to colon cancer tumorigenesis (Kinzler, K. W. et al. (1991) *Science* 253, 661-665; Korinek, V. et al. (1997) *Science* 275, 1784-1787; Morin, P. J. et al. (1997) *Science* 275, 1787-1790; Fre, S. et al. (2009) *Proc. Natl. Acad. Sci. U.S.A.* 106, 6309-6314; Philp, A. J. et al. (2001) *Cancer Res.* 61, 7426-7429). However, the mechanisms by which ALDH1B1 promotes these pathways are not yet known. By applying both CRISPR mutagenesis and our small-molecule probes to these colorectal cancer cells, we have gained new insights into how ALDH1B1 drives tumor progression. In particular, our findings demonstrate an intimate link between ALDH1B1 activity, mitochondrial metabolism, ribosomal function, and stemness. While the epistatic relationships between the latter processes are yet to be determined, there is growing evidence that cancer stem cells prefer mitochondrial oxidative metabolism for energy production and rely upon specialized ribosomes (Snyder, V. et al. (2018) *Front. Oncol.* 8, 203; Bastide, A. & David, A. (2018) *Oncogenesis* 7, 34). Moreover, our combined approach allows these immediate transcriptional changes to be discerned from others that occur over a longer timeframe. Unlike pharmacological ALDH1B1 blockade, CRISPR-mediated disruption of ALDH1B1 resulted in the upregulation of numerous oncogenes and tumor suppressors associated with colorectal cancer. The expression levels of these factors can correlate with patient survival, and additional ALDH1B1-dependent genes from our study could have similar prognostic value. We further anticipate that our small-molecule probes will be valuable tools for elucidating the ALDH1B1-dependent metabolome in cancer cells and uncovering the connections between these metabolites, oncogenic signaling, and stemness.

In addition to enabling these mechanistic investigations, our guanidine-based ALDH1B1 inhibitors provide a starting point for the design of ALDH1B1-targeting drugs. Our findings and those by other laboratories establish an essential role for ALDH1B1 in colorectal and pancreatic adenocarcinoma. Anti-mitotic drugs remain the standard first-line treatment for these malignancies (Aparicio, J. et al. (2020) *J. Clin. Med.* 9; Nevala-Plagemann, C. et al. (2020) *Nat. Rev. Clin. Oncol.* 17, 108-123), and most patients with advanced cases succumb to the disease within five years (Siegel, R. L. et al. (2020) *CA Cancer J. Clin.* 70, 7-30). Consistent with these clinical observations, 5-FU has been reported to promote the stemness of patient-derived colorectal cancer cells (Cho, Y. H. et al. (2020) *Nat. Commun.* 11, 5321), and FOLFIRINOX (folinic acid, 5-FU, irinotecan, and oxaliplatin) has the same effect on some pancreatic cancer lines (Cong, J. et al. (2017) *Cancer Lett.* 409, 9-19). Small-molecule ALDH1B1 antagonists could provide a means for targeting the stem-like populations that sustain colorectal and pancreatic cancer growth, leading to single-agent or combination therapies with more durable clinical responses. The efficacy of ALDH1B1 inhibitors against 5-FU-resistant SW480 spheroids lends support for this therapeutic paradigm. Moreover, the viability of Aldh1b1 knockout mice predicts that ALDH1B1 blockade will have tolerable effects on normal physiology. Developing ALDH1B1 antagonists with drug-like properties will be an important next step toward this goal.

F. Methods

1. Chemical Synthesis

Synthetic routes and structural characterization data for the bicyclic imidazoliums and guanidines are described above in Example 1.

2. Cell Lines

SW480 and HCT116 colorectal cancer cells were purchased from ATCC and maintained in RPMI-1640 containing 10% fetal bovine serum (FBS; MilliporeSigma), 100 U/mL penicillin, and 100 μg/mL streptomycin. ALDH1A3$^{-/-}$ A375 melanoma cells (Sarvi, S. et al. (2018) *Cell Chem. Biol.* 25, 1456-1469 e1456) were provided by E. Patton (University of Edinburgh) and maintained in DMEM containing 10% FBS, 5 μg/mL L-glutamine, 100 U/mL penicillin, 100 μg/mL streptomycin, and 0.8 μg/mL puromycin. NIH-3T3 cells were purchased from ATCC and maintained in DMEM containing 10% calf serum (CS), 1% sodium pyruvate, 100 U/mL penicillin, and 100 μg/mL streptomycin. HEK293T cells were purchased from ATCC and maintained in DMEM containing 10% FBS, 2 mM L-glutamine, 100 U/mL penicillin, and 100 μg/mL streptomycin. Shh-LIGHT cells (Taipale, J. et al. (2000) *Nature* 406, 1005-1009) were maintained in DMEM containing 10% CS, 1% sodium pyruvate, 100 U/mL penicillin, 100 μg/mL streptomycin, 150 μg/mL zeocin, and 400 μg/mL G418. All cells were cultured at 37° C. with 5% $CO_2$.

3. Photoaffinity Crosslinking of Imidazolium-Binding Proteins

To detect imidazolium-binding proteins, NIH-3T3 cells were seeded into a 15-cm plate (800,000 cells/plate) for 48-60 h to reach 85-90% confluence. The growth media was aspirated, and the cells were incubated with low-serum (0.5% CS), phenol red-free media containing photoaffinity probe 3 (7 μM) and either competitor 2 (10 μM) or an equivalent amount of DMSO vehicle (0.01%, v/v) at 37° C. for 30 min. The cells were washed once with cold phosphate-buffered saline (PBS) and maintained in PBS on ice. The lid was removed from each plate, and the cells were exposed to 254-nm UV light using a photocrosslinker (UV Stratalinker 2400; Stratagene) for 20 s at a power of 250,000 μJ/cm$^2$. Cells were then dislodged by scraping in PBS, pelleted by centrifugation at 750×g for 5 min at 4° C., and washed with 2×10 mL fresh, ice-cold PBS. The cell pellet was dissolved in 0.1% SDS in PBS and sonicated at room temperature using a probe-tip sonicator. Total protein concentration was measured using the Pierce 660 Protein Assay Kit (Thermo Fisher Scientific). Biotin-azide (1.92 μL of a 5 mM solution in DMSO, Sigma) was added to 20 μg cell lysate in 75 μL 0.1% SDS in PBS in 1.5-mL microcentrifuge tubes. In a glass vial, 200 μL $CuSO_4$ (50 mM in $H_2O$) was added to a solution of 600 μL TBTA (1.7 mM in t-BuOH-DMSO (4:1)) and 200 μL TCEP (50 mM in $H_2O$, adjusted to pH 7-8 immediately before use). The resulting catalyst mixture was vortexed, a 9.6-4 aliquot was added to each tube, and tubes were incubated with shaking at 30° C. for 30 min. To quench the reaction and remove excess reagents, protein was precipitated with 1 mL acetone at −20° C., tubes were incubated at −20° C. for 30 min, and protein was collected by centrifugation at 20,000×g for 10 min at 4° C. The resulting supernatant was aspirated, and the pellet was washed two times with cold acetone in the same manner. After the last wash, residual acetone was removed by air-drying the pellet at room temperature for 5 min. The samples were then solubilized in SDS-PAGE loading buffer and resolved on 4-12% Criterion Bis-Tris protein gel (Bio-Rad) at 150 V for 1.5 h at room temperature.

The gel proteins were next transferred to an Immun-Blot Low Fluorescence PVDF membrane (Bio-Rad) using a Trans-Blot Turbo transfer system (Bio-Rad) at a current of 2.5 Å for 7 min at room temperature. For far-western analysis of biotinylated target proteins, the membrane was incubated with blocking buffer (I-Block, Invitrogen) in 0.1% Tween-20 in PBS (PBST) for 1 h at room temperature and then treated with Pierce High Sensitivity Streptavidin-HRP (1:10,000 dilution; Thermo Fisher Scientific) in blocking buffer for 1.5 hat room temperature. The membrane was washed with 3×5 min PBST and chemiluminescent signal was generated using Supersignal West Dura ECL reagent (Thermo Fisher Scientific) and detected using a ChemiDoc imaging system (Bio-Rad).

To determine the subcellular localization of the imidazolium-binding protein, NIH-3T3 cells were seeded in a 24-well plate (60,000 cells/well) containing poly-D-lysine-coated coverslips and cultured for 48-60 h to reach 85-90% confluence. The growth media was aspirated, and the cells were incubated with low-serum (0.5% CS), phenol red-free media containing photoaffinity probe 3 (7 μM) and either competitor 2 (10 μM) or an equivalent amount of DMSO vehicle (0.01%, v/v) at 37° C. for 30 min. To assess mitochondrial morphology, cells were co-treated with 500 nM MitoTracker Deep Red FM (Invitrogen). The plate then cooled on ice, the lid was removed, and cells were exposed to 254-nm UV light as described above. Compound media was aspirated, and the cells were washed 3×5 min with PBS. After washing, cells were fixed with MeOH for 20 min at −20° C. Fixed cells were washed 3×2 min with PBS, and TAMRA-azide (1.28 μL of a 5 mM solution in DMSO) in 200 μL PBS was added. Each well was then treated with 25.6 μL of the $CuSO_4$/TBTA/TCEP catalyst mixture described above, and the plate was covered in foil and rocked gently for 45 min at room temperature. The reaction mixture was aspirated, and the cells were washed 3×5 min with PBS, once with dd$H_2O$, and mounted on glass slides in ProLong Gold mounting media (Invitrogen). The coverslips were then imaged on a Zeiss LSM 700 confocal microscope.

To determine the identity of the imidazolium-binding protein, intact mitochondria were isolated from murine liver as previously described (Hoppel, C. et al. (1979) *J. Biol. Chem.* 254, 4164-4170). 100 μg of purified mitochondria were diluted in 75 Å PBS, and photoaffinity probe 3 (7 μM) and either competitor 2 (10 μM) or an equivalent amount of DMSO vehicle (0.02%, v/v) were added. The mixture was rocked gently at 37° C. for 30 min and then transferred to one well of a 24-well plate. The lid of the plate was removed, and the mitochondria were exposed to 254-nm UV light as described above. The photocrosslinked mitochondria were transferred to a 1.5-mL microcentrifuge tube, homogenized in PBS containing 0.1% SDS, and the appropriate fluorophore-azide (1.92 μL of a 5 mM solution in DMSO) was added to 75 μL of this mixture. For in-gel fluorescence analysis, the competitor- and DMSO-treated samples were clicked to Cy3-azide and Cy5-azide (Click Chemistry Tools), respectively. For mass spectrometry analysis, the competitor- and DMSO-treated samples were clicked to MegaStokes 673-azide (Sigma) and BODIPY-azide (BDT (Wolfram, S. et al. (2014) *J. Org. Chem.* 10, 2470-2479), provided by G. Ponhert, Friedrich Schiller University), respectively. Each tube was treated with a 9.6-μL aliquot of the $CuSO_4$/TBTA/TCEP catalyst mixture and incubated with shaking at 30° C. for 30 min.

For in-gel fluorescence analysis, competitor- and DMSO-treated samples were mixed in 1:1 ratio at the end of the reaction. For mass spectrometry analysis, the competitor- and DMSO-treated samples were mixed in a ratio of 10:1 at the end of the reaction. After mixing, protein was immediately was precipitated with 1 mL acetone at −20° C. to quench the reaction and remove excess reagents. The acetone suspensions were incubated at −20° C. for 30 min, and protein was collected by centrifugation at 20,000×g for 10 min at 4° C. The resulting supernatant was aspirated, and the pellet was washed two times with cold acetone in the same manner. After the last wash, residual acetone was removed by air-drying the pellet at room temperature for 5 min. Protein samples were re-dissolved in 125 μL rehydration buffer (7 M urea, 2 M thiourea, 4% CHAPS), supplemented with 20 μL DTT (2 M), 5 μL Pharmalyte 3-10 IPG buffer (GE Healthcare), and trace bromothymol blue, and resolved on a pH 3-10 Immobiline Drystrip (GE Healthcare) using an Ettan IPGphor IEF System (GE Healthcare) for 50,000 Vh (8,000 V and 45 μA) for 14 h. The IPG strip was incubated with gentle agitation in equilibration buffer (6 M urea, 30% (w/v) glycerol, 2% (w/v) SDS, 0.05 M Tris-HCl, pH 8.8) supplemented with 10 mg/mL DTT, then in equilibration buffer supplemented with 40 mg/mL iodoacetamide for 15 min each. The IPG strip was rinsed with MES running buffer then mounted on a 4-12% Criterion Bis-Tris protein gel (Bio-Rad) and immobilized in agarose, and proteins were resolved at 150 V for 1.5 h at room temperature.

For in-gel fluorescence analysis, fluorescently labeled protein spots were detected using the ChemiDoc imaging system, and total protein was visualized with Sypro Ruby (Thermo Fisher Scientific). For mass spectrometry analysis, fluorescently labeled spots were visualized on a UV transilluminator, excised with a cut 25-μL pipette tip, and subjected to in-gel digestion for mass spectrometry-based sequencing. All mass spectrometry experiments were performed using an Orbitrap Fusion Tribrid mass spectrometer (Thermo Fisher Scientific) with an Acquity M-Class UPLC system (Waters) for reverse phase separations. Separations were performed on an in-house pulled-and-packed fused silica chromatography column. The fused silica has an inner diameter of 100 microns, and was packed with a C18 ReproSil-Pur 1.8-μm stationary phase to a length of 25 cm. The UPLC system was set to a flow rate of 300 nL/min, where mobile phase A was 0.2% formic acid in water and mobile phase B was 0.2% formic acid in acetonitrile. Peptides were directly injected onto the chromatography column, with a gradient of 2-45% mobile phase B, followed by a high-B wash over a total 80 minutes. The mass spectrometer was operated in a data-dependent mode using CID fragmentation for MS/MS spectral generation.

The resulting mass spectra were analyzed using Byonic v 2.0-25 (Protein Metrics) against the Uniprot database for murine proteins concatenated with a database of commonly observed protein contaminants. Precursor mass tolerances were set to 10 ppm with fragment tolerances set to 0.25 Da for CID fragmentation. Data were validated using the standard reverse-decoy technique at a 1% false discovery rate as described previously[103]. To confirm ALDH2 as the photocrosslinked and fluorescently tagged target, intact mitochondria were photocrosslinked with probe 3, homogenized, clicked with biotin-azide, and resolved on a two-dimensional gel as described above. The gel proteins were transferred to a PVDF membrane, which was then probed with a goat polyclonal anti-ALDH2 antibody (1:1,000 dilution; Santa Cruz Biotechnology, sc-48837), an Alexa Fluor 488-conjugated donkey polyclonal anti-goat IgG antibody (1:1,000 dilution; Thermo Fisher Scientific, A11055), and Alexa Fluor 546-conjugated streptavidin (1:5,000 dilution; Thermo Fisher Scientific, S11223). Fluorescently stained proteins were then detected using the ChemiDoc imaging system.

5. Protein Expression and Purification

Cloning, expression, and purification of human recombinant ALDH1A1, ALDH1A3, ALDH2, ALDH3A1, ALDH3A2, ALDH4A1, ALDH5A1 and ALDH7A1 isozymes were conducted as described previously (Chen, C. H. et al. (2015) *Proc. Natl. Acad. Sci. U.S.A.* 112, 3074-3079). Human ALDH1A2 (Origene, SC109995) and ALDH1B1 (T. Hurley, Indiana University) plasmids were cloned into the pET-15b expression vector (Novagen, 69661-3) containing an N-terminal hexahistidine tag. The mitochondria-targeting sequence of ALDH1B1 was also removed. For protein expression without chaperones, the pET-15b based plasmids were transformed into competent BL21 *E. coli* cells, which were subsequently grown in 1 L of Luria-Bertani medium containing 100 μg/mL ampicillin at 37° C. Once the $OD_{600}$ value reached 0.6, the culture was transferred to 16° C. and 0.5 mM isopropyl β-d-1-thiogalactopyranoside was introduced to induce protein expression overnight. The bacteria were then pelleted by centrifugation (3000×g, 4° C. for 30 rain) and harvested. 40 mL BugBuster Master Mix buffer (MilliporeSigrna) containing a protease inhibitor cocktail (cOmplete; Roche) was added, and the cells were lysed by mechanically rolling the suspension at room temperature for 25 min. The lysate was centrifuged (16000×g, 4° C. for 30 min), and the soluble fraction was collected and mixed with 2 mL of Ni-NTA Superflow resin (Qiagen). After the mixture was avowed to rock at 4° C. for 1 h, it was used to create a 10-mL gravity column, which was sequentially treated with 40 mL of wash buffer 1 (20 mM sodium phosphate, 500 mM NaCl, 1 mM DTT, 20 mM imidazole, 5% glycerol, pH 7.4) and 25 mL of wash buffer 2 (20 mM sodium phosphate, 500 mM NaCl, 1 mM DTT, 40 mM imidazole, 5% glycerol, pH 7.4). The hexahistidine-tagged protein was then recovered by treated the column with 5 mL elution buffer (20 mM sodium phosphate, 500 mM NaCl, 1 mM DTT, 400 mM imidazole, 5% glycerol, pH 7.4) and collecting 500-μL fractions. The protein concentration for each fraction was measured (500 μL elution volume was collected as one fraction and was immediately mixed with 500 μL glycerol. The protein concentration for each fraction was measured (600 nm Protein Assay Reagent; Thermo Fisher Scientific), and protein-containing fractions were diluted with an equal volume of glycerol and stored at −80° C. Samples from each step were also collected for SDS-PAGE gel analysis. For ALDH1B1 protein co-expression with chaperones, pET-15b-ALDH1B1 and GroEL/GroES (Addgene, plasmid pBB541) plasmids were co-transformed into competent BL21 *E. coli* cells, which were subsequently grown in 1 L of Luria-Bertani medium containing 100 μg/mL ampicillin and 50 μg/mL spectinomycin at 37° C. The hexahistidine-tagged ALDH1B1 protein was then expressed and purified as described above.

6. Enzyme Kinetics Assays

To evaluate compound activities against ALDH isoforms, reaction mixtures consisting of enzyme assay buffer (100 mM sodium phosphate, 1 mM $MgCl_2$, pH 8.0) and 0.1% DMSO, 1 mM β-mercaptoethanol, 1 mM $NAD^+$, and the bacterially expressed protein were prepared in white opaque 96-well assay plates (100 μL/well, flat-bottom and non-treated; Corning Costar). 5 μg/mL ALDH enzyme was used for single-dose (1, 10, 50 μM) compound test, and 1 μg/mL ALDH enzyme was used for IC50s determination. Acetaldehyde was then added to each well to achieve an initial substrate concentration of 1 mM, and the resulting enzymatic activity was measured based on NADH fluorescence. The fluorescence signal was read over the course of 10 min on a SpectraMax M2e microplate reader (340-nm excitation and 460-nm emission; Molecular Devices) operated by SoftMax Pro software. Compound activities were normalized to a DMSO control, and dose-response inhibition curves were fitted with four-parameter non-linear regression using Prism software. Steady-state kinetic measurements of ALDH1B1 inhibitors were also conducted with the general protocol described above, using 5 μg/mL ALDH1B1 and varying concentrations of acetaldehyde, NAD+, and the small-molecule antagonist.

7. X-Ray Crystallography

Stock solutions of the ALDH1B1 protein were buffer-exchanged with the crystallization buffer (100 mM ACES, 10 mM $NAD^+$, 10 μM DTT, pH 7.0) and concentrated to 20 mg/mL using a 30-kDa MWCO Amicon centrifugal filter (MilliporeSigma) at 4° C. ALDH1B1 inhibitor was subsequently added to a final concentration of 1 mM, and the protein solution (usually 0.15-0.3 μL) was then mixed with an equal volume of various crystallization buffers from commercial sources. Crystals were grown using sitting drop vapor diffusion in a 12° C. incubator, and crystallization experiments were set-up using an Oryx8 Nanodrop dispensing robot (Douglas Instruments). Within one to two weeks, crystals were harvested and cryocooled under liquid $N_2$ stream. In general, crystals harvested even from a single crystallization condition showed a wide variation in X-ray diffracting power, and therefore a large number were screened for initial data quality assessment. The best candidates were selected and stored for further data collection, and in some cases, X-ray diffracting raster sampling was used to locate the best diffracting region on the crystal. Then, a full dataset collection was performed. Data collections to a minimum Bragg spacing of 2.12 Å (ALDH1B1/$NAD^+$/imidazolium 2), 2.45 Å (ALDH1B1/$NAD^+$/guanidine 80), and of 2.68 Å (ALDH1B1-$NAD^+$) were performed at 100K using Stanford Synchrotron Radiation Lightsource (SSRL) beamlines BL9-2, BL12-1 and BL12-2 (SLAC National Accelerator Laboratory).

All ALDH1B1 diffraction-quality crystals were obtained from crystallization or co-crystallization (in case of ligand added to the protein solution) from a precipitant solution composed of 10% polyethyleneglycol 4000 and 20% glycerol with different combinations of buffers/additives: 0.1 M Tris-Bicine, pH 8.5, and a mixture of alcohols (0.02 M of each 1,6-hexanediol, 1-butanol, 1,2-propanediol, 2-propanol, 1,4-butanediol, and 1,3-propanediol) for ALDH1B1/$NAD^+$; 0.1 M Tris-Bicine, pH 8.5, and a mixture of ethylene-glycols (0.03 M of each di-, tri-, tetra-, and pentaethylene glycol) for ALDH1B1/$NAD^+$/imidazolium 2; and 0.1 M imidazole/MES, pH 6.5, and the above mixture of ethylene-glycols for ALDH1B1/$NAD^+$/guanidine 80. Structures were solved by the molecular replacement method with Phaser (McCoy, A. J. et al. (2007) *J. Appl. Crystallogr.* 40, 658-674) using the polypeptide chain of apo ALDH2 (PDB ID: 3N80) as the search model and the search was carried over the enantiomorphic pair to fix handedness. Each of the crystals belonged to the trigonal space group P $3_2$ 2 1 and contained two polypeptide chains per asymmetry unit. Residues 8-500 were unambiguously traced in the electron density maps, and extra electron density was evident after structure solution and accounted for one NAD cofactor molecule and one inhibitor molecule per polypeptide chain (further extra density accounting for the organic ligands in the crystallization buffer was detected). Throughout refinement with REFMAC (Murshudov, G. N. et al. (1997) *Acta Crystallogr. D Biol. Crystallogr.* 53, 240-255) manual adjustments on the polypeptide chain were made in COOT (Emsley, P. et al. (2010) *Acta Crystallogr. D Biol. Crystallogr.* 66, 486-501). Solvent water molecules were first assigned based on their hydrogen bonding properties; in later stages of refinement, further water molecules were automatically added. Refinement progressed to convergence and reached an excellent agreement between the model and the experimental data. Table 1 presents data collection, refinement, and structure quality check parameters. Datasets were collected at SSRL/SLAC synchrotron beam lines (Russi, S. et al. (2016) *J. Appl. Crystallogr.* 49, 622-626). Data was reduced with XDS (Kabsch, W. Xds. (2010) *Acta Crystallogr. D Biol. Crystallogr.* 66, 125-132), scaled with SCALA (Evans, P. R. (2011) *Acta Crystallogr. D Biol. Crystallogr.* 67, 282-292) and analyzed with different computing modules within the CCP4 suite (Winn, M. D. et al. (2011) *Acta Crystallogr. D Biol. Crystallogr.* 67, 235-242). Graphic renderings were prepared with PyMOL software.

8. Generation of ALDH1B1 Knockout Cell Lines

To target the ALDH1B1 locus by CRISPR/Cas9 mutagenesis, the following gRNAs were evaluated (PAM sequences in bold): gRNA-1 CGGTGGTAGGGTTGACCGTCGGG (SEQ ID NO:01); gRNA-2 GGAGCGGGATCGAGTCTACTTGG (SEQ ID NO:02); gRNA-3 CGAAACGCTCTCCGCCACAGAGG (SEQ ID NO:03). Each gRNA was cloned into the lentiCRISPRv2 vector (Addgene, plasmid 98290) by BsmBI digestion and DNA ligation, and lentivirus was generated using procedures as previously described (Campeau, E. et al. (2009) *PLoS One* 4, e6529). Briefly, the lentiCRISPRv2-derived gRNA plasmids and a $3^{rd}$ generation lentiviral system (Addgene, plasmids 12251, 12253, and 12259) were co-transfected into HEK-293T cells. The resulting lentivirus was collected from the media and used to infect SW480 cells. Stable populations were selected by puromycin treatment (2.0 μg/mL), and genomic DNA PCR and DNA TIDE sequencing analysis (Brinkman, E. K. et al. (2018) *Nucleic Acids Res.* 46, e58) was performed to assess the frequency of targeted mutations. The PCR primers used for these studies were: gRNA-1 forward, 5'-CTTAGCCTCCAGGGCAGGAC-3'(SEQ ID NO:04; gRNA-1 reverse, 5'-GGAAAGCCTGCCTCCTTGAT-3' (SEQ ID NO:05); gRNA-2 forward, 5'-CCCAGACATCCCCTACAACC-3' (SEQ ID NO:06); gRNA-2 reverse, 5'-GCCATACCCCGTGATGATGT-3' (SEQ ID NO:07); gRNA-3 forward, 5'-GGCGATTCCAACCTCAAGAGA-3' (SEQ ID NO:08); gRNA-3 reverse: 5'-TTAAGCCCATCCTCACCCCAG-3' (SEQ ID NO:09). The reverse primers were also used for sequencing. To generate ALDH1B1$^{-/-}$ colon cancer lines, gRNA-1 and gRNA-2 were separately cloned into the pX458 vector (Addgene, plasmid 48138) by BbsI digestion and DNA ligation. The resulting constructs were co-transfected into SW480 and HCT116 cells using FuGENE HD transfection reagent (Promega) according to the manufacturer's guidelines. The cells were then cultured for 48 h, and single cells from the top 5% EGFP positive population were sorted into 96-well plates using an FACSAria II cell sorter (BD Biosciences). The single clones were cultured and characterized by genomic DNA PCR and sequencing, using the following primers: forward, 5'-CTTAGCCTCCAGGGCAGGAC-3 (SEQ ID NO:10); reverse, 5'-GCCATACCCCGTGATGATGT-3' (SEQ ID NO:11).

To conduct rescue experiments with ALDH1B1 cells, EGFP and human ALDH1B1 cDNAs were separately cloned into the pCDH-CMV-MCS-EF1-Puro vector (System Biosciences) to make pCDH-CMV-GFP-EF1-Puro and pCDH-CMV-ALDH1B1-EF1-Puro plasmids. Each plasmid was separately packaged in HEK-2931 cells using the $3^{rd}$ generation lentiviral system described above, and the resulting lentiviruses were used to infect ALDH1B1$^{+/+}$ (clone 3) and/or ALDH1B1$^{-/-}$ (clone 2) SW480 cells. Stable clones were then selected by puromycin treatment (2.0 μg/mL).

9. Generation of 5-FU-Resistant SW480 Cells

The parental SW480 cells were cultured in RPMI-1640 medium containing 10% FBS, 100 U/mL penicillin, 100 μg/mL streptomycin, and 1 μM 5-FU for two weeks. The 5-FU concentration in the culture medium was then increased to 5 μM and after another two weeks raised further to 10 μM. The resulting 5-FU-resistant SW480 cells were maintained in culture medium with 10 μM 5-FU.

10. Immunoblot Analyses

To analyze lysates derived from SW480 and HCT116 cells, adherent cultures were grown to 70-80% confluence, detached from the plates with trypsin, and pelleted by centrifugation at 480×g for 5 min at 4° C. The cell pellets were washed once with PBS and lysed in cold RIPA buffer (Thermo Fisher Scientific) containing with protease (cOmplete; Roche) and phosphatase (PhosSTOP; Roche) inhibitor. Lysates were kept on ice for 15 min with intermittent vortexing, and then clarified by centrifugation at 16,000×g for 15 min at 4° C. The resulting supernatant was analyzed to determine total protein levels (600 nm Protein Assay Reagent; Thermo Fisher Scientific), and the final protein concentration in each sample was adjusted to 1.0 μg/μL, mixed with 6×SDS-SAGE loading buffer (240 mM Tris-HCl, 6% SDS, 0.3 M DTT, 30% glycerol, 0.018% bromophenol blue, pH 6.8). The samples were then resolved on 4-12% Criterion Bis-Tris protein gels (Bio-Rad) at 130 V for 1.5 h at room temperature.

The gel proteins were next transferred to PVDF membranes using the Trans-Blot Turbo Transfer System (Bio-Rad), and the membranes were blocked with 5% non-fat dry milk in 1× Tris-buffered saline containing 0.1% Tween 20 (TBST) for 1 h at room temperature. The blots were then probed with the primary antibody in the same blocking buffer overnight at 4° C. The membranes were washed 4×5 min with TBST and then incubated with horseradish peroxidase (HRP)-conjugated secondary antibody in blocking buffer for 2 h at room temperature. After the membranes were washed 4×5 min TBST, the secondary antibodies were detected by chemiluminescence using SuperSignal West Dura Extended Duration Substrate (Thermo Fisher Scientific) and a Gel Doc XR imaging system (Bio-Rad). Stripping buffer (Thermo Fisher Scientific, 21059) was used to remove antibodies when the membranes needed to be re-probed with another primary antibody. Antibodies used for these experiments include: mouse monoclonal anti-ALDH1B1 (1:500 dilution; Santa Cruz Biotechnology, sc-393583); rabbit polyclonal anti-KPNB1 antibody (1:1,000 dilution; Santa Cruz Biotechnology, sc-11367); HRP-conjugated sheep polyclonal anti-mouse IgG (1:1,000; GE Healthcare, NA931-1ML); HRP-conjugated donkey polyclonal anti-rabbit IgG (1:1000 dilution; GE Healthcare, NA934-1ML).

11. Matrigel Spheroid Cultures

To prepare Matrigel-coated culture plates, 96-well and 24-well plates were placed on ice and coated with 25 μL or 300 μL, respectively, of Matrigel matrix (Corning, LDEV-free) that had been thawed overnight at 4° C. The plates were then placed in a 37° C. incubator for 30 min to allow the Matrigel to solidify. SW480 or HCT116 cells were suspended in spheroid culture medium (RPMI-1640 containing 20 ng/mL recombinant human epidermal growth factor (Abcam, ab9697), 20 ng/mL recombinant human fibroblast growth factor (BioVision, 4037), 5 μg/mL heparin (Sigma), 1× N-2 supplement (Thermo Fisher Scientific), 100 U/mL penicillin, and 100 μg/mL streptomycin) and then seeded into the 96-well and 24-well Matrigel-coated plates at densities of 1,000 or 5,000 cells/well and total well volumes of 2004 or 1 mL, respectively. Compounds were diluted in spheroid culture medium and added to the wells, and the spheroid were grown at 37° C. with 5% $CO_2$ for 7 days.

To quantify spheroid growth at the 7-day endpoint, unstained spheroids were imaged with phase-contrast illumination using a Keyence BZ-X710 microscope. Some cultures were also stained with crystal violet to enable brightfield imaging. Briefly, the Matrigel spheroids cultures were treated with PBS containing 0.5% crystal violet and 5% methanol for 15 min at 37° C. and then gently washed 4×5 min with PBS. Spheroid sizes were quantified with ImageJ (Fiji) software using masks created with the default "Threshold" function and foreground/background adjustments to optimize masking fidelity. The full field of view was then selected for "Analyze Particles" analysis, providing numbered list of each spheroid and its area in the micrograph. In the few cases that two adjacent spheroids were treated as one object by the image processing software, their measurements were manually corrected using the "Freehand Selections" tool. To exclude background and debris from dead cells, spheroids with areas less than 500 $\mu m^2$ were excluded from the image analyses.

12. Cell Viability Assays

SW480 or HCT116 cells were seeded into regular or Matrigel-coated 96-well plates at a density of 1000 cells/well. The cells were cultured in the corresponding adherent or spheroid culture medium (200 μL/well) containing the designated compounds or an equivalent amount of DMSO vehicle. Each culture was maintained for 7 days, and then cell viabilities were measured using a CellTiter-Glo 3D Cell Viability Assay kit (Promega). Briefly, 100 μL of the culture medium was removed from each well and replaced with 100 μL 3D Cell Assay reagent. The cells in each well were next homogenized by vigorous pipetting, and the plate was incubated for 10 min at room temperature to stabilize the chemiluminescent signal. A 150-μL aliquot from each well was then transferred into a white opaque 96-well assay plate (flat-bottom and non-treated; Corning Costar) and luminescence intensities were measured with a Veritas microplate luminometer (Turner BioSystems).

13. Immunofluorescence Microscopy

ALDH1A3$^{-/-}$ A375 cells were seeded into a 6-well plate at a density of $6\times10^5$ cells/well and cultured for 24 h. The cells were then transfected with either pCMV6-entry vector (Origene, PS100001) or pCMV6-ALDH1B1 (created by obtaining the ALDH1B1 sequence with the mitochondria targeting signal from SW480 cDNA and subcloning it into the PCMV6-entry vector by Gibson assembly) using Fugene HD (Promega) at a 3:1 DNA:Fugene HD ratio according to the manufacturer's protocols. The cells were cultured for another 24 h, removed from the plate by trypsinization, and re-seeded at a density of $1.2\times10^5$ cells/well into a 24-well plate containing poly-D-lysine coated glass coverslips. After another 24 h of cell growth, the culture media was removed, and the cells were incubated with fresh media containing 500 nM MitoTracker Deep Red (Invitrogen, M22426) for 30 min at 37° C. and subsequently fixed with PBS containing 4% PFA for 10 min at room temperature. After permeabilization with PBS containing 0.3% Triton X-100, the cells were incubated with anti-ALDH1B1 antibody (1:100 dilution, Santa Cruz Biotechnology, sc-393583) overnight at 4° C. Cells were then incubated with Alexa Fluor 488-conjugated goat polyclonal anti-mouse IgG (Invitrogen, A32723) and DAPI (Thermoe Fisher P36931) for 1 h at room temperature in the dark. Coverslips were imaged on a Zeiss LSM 800 confocal Microscope using ZenBlue software.

14. ALDEFLUOR Assays

ALDH1A3$^{-/-}$ A375 cells were seeded into a 6-well plate at a density of $5\times10^5$ cells/well and cultured for 24 h. The cells were then transfected with either pCMV6-entry, pCMV6-GFP (Addgene, plasmid 11153), or pCMV-ALDH1B1. After 24 h, the media was replaced and transfection efficiencies were estimated by the EGFP-positive cells in the pCMV-GFP-transfected well. The cells were cultured for another 24 h and their ALDH activities were quantified using the ALDEFLUOR assay. Briefly, the cells were isolated from the plate with trypsin and resuspended in ALDEFLUOR assay buffer (STEMCELL Technologies) at a concentration of $4\times10^5$ cells/mL. Each ALDEFLUOR assay used 0.5 mL of this cell suspension, and the cells were treated with individual compounds for 15 min at 37° C. and 5% $CO_2$. The cell suspensions were then treated with 2.5 μL ALDEFLUOR reagent and incubated for an additional 30 min at 37° C. and 5% $CO_2$. The cells were then collected by centrifugation (450×g) for 5 min at room temperature, resuspended in 200 μL assay buffer, and analyzed with an LSR II flow cytometer (BD Biosciences) at the Stanford FACS facility.

15. Seahorse XF Mito Stress Assays

SW480 cells were seeded into a XF96 microplate (Agilent) at a density of $2\times10^4$ cells/well and cultured for 24 h. The cells were then incubated for 1 h at 37° C. in a non-$CO_2$ incubator, and the plate was then loaded into a 96-well Seahorse XF analyzer (Agilent) and sequentially injected with the indicated compounds, 1 μM oligomycin A, 1 μM FCCP, or 0.5 μM rotenone/antimycin according to the Agilent Mito Stress protocol. The oxygen consumption rates (OCRs, pmol/min) for each well were measured every 5 min for a 15-min period. Basal OCR values was normalized as 100% for data analyses.

16. HEK-293T Cytotoxicity Assays

HEK-293T cells were seeded into a 96-well plate at a density of $5\times10^3$ cells/well and treated with varying concentrations of selected compounds or an equivalent amount of DMSO vehicle. The cells were cultured for 4-5 days without a media change, and after the DMSO-treated cells approached 100% confluence, the cell viabilities were measured using a CellTiter-Glo 3D Cell Viability Assay kit (Promega) and a Veritas microplate luminometer (Turner BioSystems) as described above.

17. Shh-LIGHT2 Assays

NIH-3T3 cells stably transfected with Gli-dependent firefly luciferase reporter (Shh-LIGHT2 cells (Taipale, J. et al. (2000) *Nature* 406, 1005-1009) were seeded into 96-well plates at a density of $2\times10^4$ cells/well and cultured for 24 h. The cells were then cultured in low-serum (0.5% CS) media containing 100 U/mL penicillin, 100 μg/mL streptomycin, and 200 nM Smoothened agonist (SAG) (Chen, J. K. et al. (2002) *Proc. Natl. Acad. Sci. U.S.A.* 99, 14071-14076; Frank-Kamenetsky, M. et al. (2002) *J. Biol.* 1, 10) for 30 h. CellTiter AQueous One (20 μL/well; Promega) was added to the cells and incubated for 30 min at 37° C., and cell viabilities were measured as the 490-nm absorbance of the culture media using a Spectramax M2e microplate reader (Molecular Devices). The cells were then washed with PBS and incubated with Bright-Glo reagent (100 μL/well; Promega) for 5 min at room temperature. The resulting chemiluminescence was measured on a Veritas microplate luminometer (Turner BioSystems) and normalized to the CellTiter signal. The normalized luciferase activities for each compound treatment regimen were normalized further to the DMSO control, and dose-responsive curves were generated using Prism software (GraphPad).

18. Transcriptome Profiling

RNA-seq analysis of NIH-3T3 cells was conducted as described previously (Tran, U. et al. (2020) *ACS Chem. Biol.* 15, 1321-1327). RNA-seq analyses of parental SW480 cells and an ALDH1B1$^{-/-}$ clone were conducted as three biological replicates as follows. To identify gene expression changes associated with chemical loss of ALDH1B1 function, parental SW480 cells were seeded into 6-well plates at density of $0.8\times10^6$ cells/well and cultured for 24 h. The cells were then treated with either 2 μM guanidine 68 or an equivalent amount of DMSO vehicle for 24 h. To identify gene expression changes associated with genetic loss of ALDH1B1 function, ALDH1B1$^{-/-}$ SW480 cells (clone 2) that were lentivirally transduced with either EGFP or exogenous ALDH1B1 were seeded into 6-well plates as described above and cultured for 48 h. Total mRNA was extracted from each sample using an RNeasy Mini kit (Qiagen) according to the manufacturer's protocols, and RNA libraries were constructed using NEBNext Ultra II RNA Library Prep Kit for Illumina (New England Biolabs). For each sample, approximately 40 million paired-end reads were obtained, and raw data of FASTQ were processed through fastp. Paired-end clean reads were aligned to the reference genome using the Spliced Transcripts Alignment to a Reference (STAR) software, and FeatureCounts was used to count the read numbers mapped of each gene. Differential expression analysis was performed using DESeq2R package. The resulting Pvalues were adjusted using the Benjamini and Hochberg's approach for controlling the False Discovery Rate (Benjamini, Y. & Hochberg, Y. J. R. (1995) *Stat. Soc Series B. Stat. Methodol.* 57, 289-300). Raw and processed RNA-seq data for the SW480 cells are publicly available in the Gene Expression Omnibus database (GEO accession: GSE165621).

19. Statistical Analyses

Descriptions of the error bars and number of replicates are included in the corresponding figure legends. Student's t-test (two-tailed) or one-way ANOVA analysis in the Prism software were used to compare results and calculate P values. Exact P values are shown unless they are less than 0.001 which are otherwise indicated as <0.001.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A compound of the formula (II):

(II)

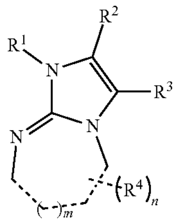

wherein:

each ------ represents a C—C bond, wherein one or more of the C—C bonds is optionally unsaturated;

$R^1$ and $R^3$ are each independently selected from aryl, substituted aryl;

$R^2$ is selected from H, alkyl, substituted alkyl, alkenyl, substituted alkenyl, alkynyl, substituted alkynyl, alkoxy, substituted alkoxy, halogen, hydroxyl, acyl, substituted acyl, carboxy, substituted carboxy, amino, substituted amino, aryl, substituted aryl, heterocycle, substituted heterocycle, heteroaryl, substituted heteroaryl, cycloalkyl, and substituted cycloalkyl;

$R^4$ is an optional substituent selected from alkyl, substituted alkyl, hydroxy, carbonyl, amino, substituted amino, halogen, nitrile, nitro, acyl, substituted acyl, carboxy, and substituted carboxy;

n is an integer from 0 to 10; and m is an integer from 0 to 2, wherein if m is 0, then n is an integer from 0 to 6, and if m is 1, then n is an integer from 0 to 8; or or a pharmaceutically acceptable salt, solvate, or prodrug thereof.

2. The compound of claim 1, wherein the compound of formula (II) is of one formulae (IIA)-(IIG):

(IIA)

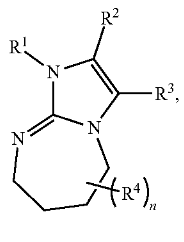

-continued (IIB)

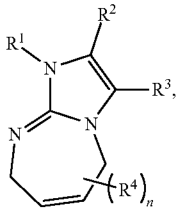

(IIC)

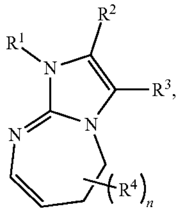

(IID)

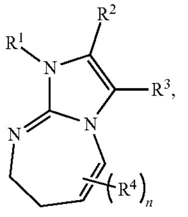

(IIE)

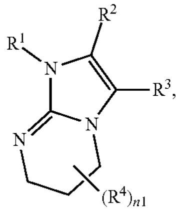

(IIF)

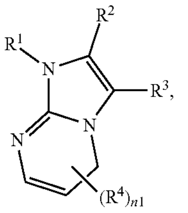

and (IIG)

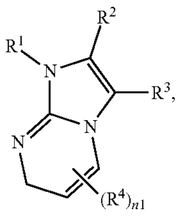

wherein n and n1 are each an integer from 0 to 6.

3. The compound of claim 1, of the formula (III):

(III)

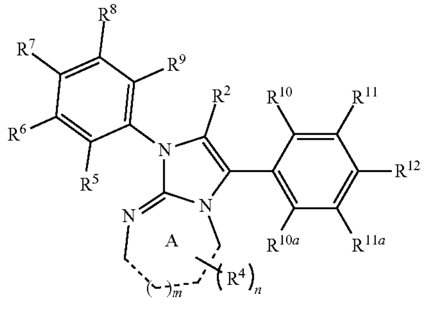

wherein:

each ------ represents a C—C bond, wherein one or more of the C—C bonds is optionally unsaturated; $R^2$ is selected from H, alkyl, substituted alkyl, alkenyl, substituted alkenyl, alkynyl, substituted alkynyl, alkoxy, substituted alkoxy, halogen, hydroxyl, acyl, substituted acyl, carboxy, substituted carboxy, amino, substituted amino, aryl, substituted aryl, heterocycle, substituted heterocycle, heteroaryl, substituted heteroaryl, cycloalkyl, and substituted cycloalkyl;

$R^5$-$R^{12}$ are each independently selected from H, alkyl, substituted alkyl, alkenyl, substituted alkenyl, alkynyl, substituted alkynyl, alkoxy, substituted alkoxy, halogen, hydroxy, nitro, nitrile, amino, substituted amino, acyl, substituted acyl, carboxy, substituted carboxy, aryl, substituted aryl, heterocycle, substituted heterocycle, heteroaryl, substituted heteroaryl, cycloalkyl, and substituted cycloalkyl; or any two adjacent $R^5$-$R^{12}$ groups together with the atoms to which they are attached form an optionally substituted cyclic group;

$R^4$ is an optional substituent selected from alkyl, substituted alkyl, hydroxy, carbonyl, amino, substituted amino, halogen, nitrile, nitro, acyl, substituted acyl, carboxy, and substituted carboxy;

n is an integer from 0 to 10; and m is an integer from 0 to 2, wherein if m is 0, then n is an integer from 0 to 6, and if m is 1, then n is an integer from 0 to 8.

4. The compound of claim 3, wherein $R^5$-$R^{12}$ are each independently selected from H, alkyl, substituted alkyl, alkoxy, substituted alkoxy, halogen, hydroxy, nitro, amino, substituted amino, acyl, substituted acyl, carboxy, and substituted carboxy.

5. The compound of claim 3, of the formula (IV):

(IV)

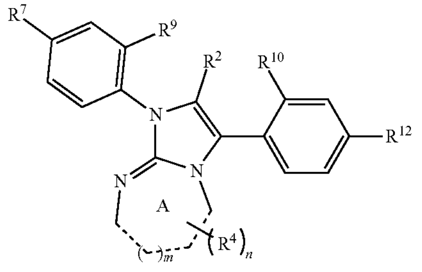

wherein:

each ------ represents a C—C bond, wherein one or more of the C—C bonds is optionally unsaturated;

$R^2$ is selected from H, alkyl, substituted alkyl, alkenyl, substituted alkenyl, alkynyl, substituted alkynyl, alkoxy, substituted alkoxy, halogen, hydroxyl, acyl, substituted acyl, carboxy, substituted carboxy, amino, substituted amino, aryl, substituted aryl, heterocycle, substituted heterocycle, heteroaryl, substituted heteroaryl, cycloalkyl, and substituted cycloalkyl;

$R^9$ and $R^{10}$ are independently selected from H, alkyl, substituted alkyl, alkoxy, substituted alkoxy, halogen, hydroxy, acyl, substituted acyl, carboxy, substituted carboxy, amino, and substituted amino;

$R^7$ and $R^{12}$ are each independently selected from H, aryl, substituted aryl, heteroaryl, substituted heteroaryl, heterocycle, substituted heterocycle, cycloalkyl, substituted cycloalkyl, alkyl, substituted alkyl, alkoxy, substituted alkoxy, halogen, hydroxy, acyl, substituted acyl, carboxy, substituted carboxy, amino, and substituted amino;

$R^4$ is an optional substituent selected from alkyl, substituted alkyl, hydroxy, amino, substituted amino, halogen, nitrile, nitro, acyl, substituted acyl, carboxy, and substituted carboxy;

n is an integer from 0 to 10; and m is an integer from 0 to 2, wherein if m is 0, then n is an integer from 0 to 6, and if m is 1, then n is an integer from 0 to 8.

6. The compound of claim 5, wherein:

$R^9$ and $R^{10}$ are independently selected from H, alkoxy, substituted alkoxy, halogen, hydroxy, amino, and substituted amino; and $R^7$ and $R^{12}$ are each independently selected from H, aryl, substituted aryl, heteroaryl, substituted heteroaryl, alkoxy, substituted alkoxy, halogen, hydroxy, amino, and substituted amino.

7. The compound of claim 5, of the formula (VA) or (VB):

(VA)

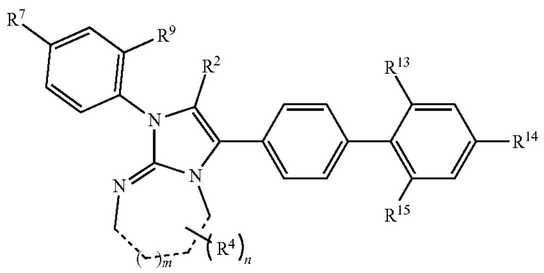

(VB)

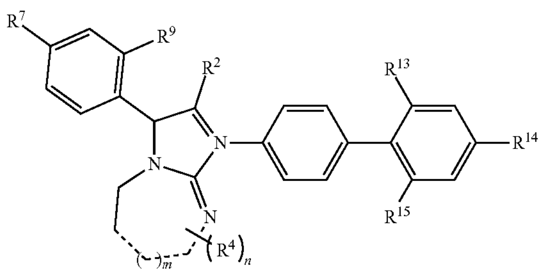

wherein:

each ------ represents a C—C bond, wherein one or more of the C—C bonds is optionally unsaturated;

$R^2$ is selected from H, alkyl, substituted alkyl, alkenyl, substituted alkenyl, alkynyl, substituted alkynyl, alkoxy, substituted alkoxy, halogen, hydroxyl, acyl, substituted acyl, carboxy, substituted carboxy, amino, substituted amino, aryl, substituted aryl, heterocycle, substituted heterocycle, heteroaryl, substituted heteroaryl, cycloalkyl, and substituted cycloalkyl;

$R^9$ is selected from H, alkyl, substituted alkyl, alkoxy, substituted alkoxy, halogen, hydroxy, acyl, substituted acyl, carboxy, substituted carboxy, amino, and substituted amino;

$R^7$, and $R^{13}$-$R^{15}$ are each independently selected from H, aryl, substituted aryl, alkyl, substituted alkyl, alkoxy, substituted alkoxy, halogen, hydroxy, acyl, substituted acyl, carboxy, substituted carboxy, amino, and substituted amino;

$R^4$ is an optional substituent selected from alkyl, substituted alkyl, hydroxy, amino, substituted amino, halogen, nitrile, nitro, acyl, substituted acyl, carboxy, and substituted carboxy;

n is an integer from 0 to 10; and m is an integer from 0 to 2, wherein if m is 0, then n is an integer from 0 to 6, and if m is 1, then n is an integer from 0 to 8.

8. The compound of claim 7, wherein each ------ C—C bond is a single bond.

9. The compound of claim 7, wherein one ------ C—C bonds bond is a double bond, and the remaining ------ C—C bonds are single bonds.

10. The compound of claim 7, wherein:

$R^9$, $R^{13}$, and $R^{15}$ are independently selected from H, alkoxy, substituted alkoxy, halogen, hydroxy, amino, and substituted amino; and $R^7$ and $R^{14}$ are each independently selected from H, alkoxy, substituted alkoxy, halogen, hydroxy, acyl, substituted acyl, carboxy, substituted carboxy, amino, and substituted amino.

11. A pharmaceutical composition, comprising:

a compound of claim 1; and a pharmaceutically acceptable excipient.

12. A method of inhibiting an aldehyde dehydrogenase (ALDH), the method comprising:

contacting a sample comprising an ALDH with a compound of claim 1 to inhibit the ALDH.

13. The method of claim 12, wherein the compound selectively inhibits an isoform of ALDH.

14. The method of claim 13, wherein the ALDH isoform is ALDH1B1.

15. The method of claim 13, wherein the ALDH isoform is ALDH1A3.

16. A method of treating a subject having cancer, the method comprising administering to the subject a therapeutically effective amount of a compound of claim 1.

17. The method of claim 16, wherein the cancer is a solid tumor cancer, and the administering inhibits the tumor growth.

18. The method of claim 16, wherein the cancer is colorectal cancer.

19. The method of claim 16, wherein the cancer is breast cancer, melanoma, or glioblastoma.

* * * * *

SEQUENCE LISTING

```
<160> NUMBER OF SEQ ID NOS: 14

<210> SEQ ID NO 1
<211> LENGTH: 23
<212> TYPE: DNA
<213> ORGANISM: Artificial Sequence
<220> FEATURE:
<223> OTHER INFORMATION: gRNA for ALDH1B1 knockout

<400> SEQUENCE: 1

cggtggtagg gttgaccgtc ggg                                              23


<210> SEQ ID NO 2
<211> LENGTH: 23
<212> TYPE: DNA
<213> ORGANISM: Artificial Sequence
<220> FEATURE:
<223> OTHER INFORMATION: gRNA for ALDH1B1 knockout

<400> SEQUENCE: 2

ggagcgggat cgagtctact tgg                                              23


<210> SEQ ID NO 3
<211> LENGTH: 23
<212> TYPE: DNA
<213> ORGANISM: Artificial Sequence
<220> FEATURE:
<223> OTHER INFORMATION: gRNA for ALDH1B1 knockout

<400> SEQUENCE: 3

cgaaacgctc tccgccacag agg                                              23


<210> SEQ ID NO 4
<211> LENGTH: 20
<212> TYPE: DNA
<213> ORGANISM: Artificial Sequence
<220> FEATURE:
<223> OTHER INFORMATION: synthetic sequence

<400> SEQUENCE: 4

cttagcctcc agggcaggac                                                  20


<210> SEQ ID NO 5
<211> LENGTH: 20
<212> TYPE: DNA
<213> ORGANISM: Artificial Sequence
<220> FEATURE:
<223> OTHER INFORMATION: synthetic sequence

<400> SEQUENCE: 5

ggaaagcctg cctccttgat                                                  20


<210> SEQ ID NO 6
<211> LENGTH: 20
<212> TYPE: DNA
<213> ORGANISM: Artificial Sequence
<220> FEATURE:
<223> OTHER INFORMATION: synthetic sequence

<400> SEQUENCE: 6

cccagacatc ccctacaacc                                                  20


<210> SEQ ID NO 7
<211> LENGTH: 20
<212> TYPE: DNA
<213> ORGANISM: Artificial Sequence
```

<220> FEATURE:
<223> OTHER INFORMATION: synthetic sequence

<400> SEQUENCE: 7
gccatacccc gtgatgatgt 20

<210> SEQ ID NO 8
<211> LENGTH: 21
<212> TYPE: DNA
<213> ORGANISM: Artificial Sequence
<220> FEATURE:
<223> OTHER INFORMATION: synthetic sequence

<400> SEQUENCE: 8
ggcgattcca acctcaagag a 21

<210> SEQ ID NO 9
<211> LENGTH: 20
<212> TYPE: DNA
<213> ORGANISM: Artificial Sequence
<220> FEATURE:
<223> OTHER INFORMATION: synthetic sequence

<400> SEQUENCE: 9
ttaagcccat cctcacccag 20

<210> SEQ ID NO 10
<211> LENGTH: 20
<212> TYPE: DNA
<213> ORGANISM: Artificial Sequence
<220> FEATURE:
<223> OTHER INFORMATION: synthetic sequence

<400> SEQUENCE: 10
cttagcctcc agggcaggac 20

<210> SEQ ID NO 11
<211> LENGTH: 20
<212> TYPE: DNA
<213> ORGANISM: Artificial Sequence
<220> FEATURE:
<223> OTHER INFORMATION: synthetic sequence

<400> SEQUENCE: 11
gccatacccc gtgatgatgt 20

<210> SEQ ID NO 12
<211> LENGTH: 450
<212> TYPE: DNA
<213> ORGANISM: Homo sapiens

<400> SEQUENCE: 12
atgctgcgct tcctggcacc ccggctgctt agcctccagg gcaggaccgc ccgctactcc 60
tcggcagcag ccctcccaag ccccattctg aacccagaca tcccctacaa ccagctgttc 120
atcaacaatg aatggcaaga tgcagtcagc aagaagacct tcccgacggt caaccctacc 180
accggggagg tcattgggca cgtggctgaa ggtgaccggg ctgatgtgga tcgggccgtg 240
aaagcagccc gggaagcctt ccgcctgggg tccccatggc gccggatgga tgcctctgag 300
cggggccggc tgctgaaccg cctggcagac ctagtggagc gggatcgagt ctacttggcc 360
tcactcgaga ccttggacaa tgggaagcct ttccaagagt cttacgcctt ggacttggat 420
gaggtcatca aggtgtatcg gtactttgct 450

-continued

<210> SEQ ID NO 13
<211> LENGTH: 266
<212> TYPE: DNA
<213> ORGANISM: Artificial Sequence
<220> FEATURE:
<223> OTHER INFORMATION: ALDH1B1 with deletion for knockout

<400> SEQUENCE: 13

```
atgctgcgct tcctggcacc ccggctgctt agcctccagg gcaggaccgc ccgctactcc     60

tcggcagcag ccctcccaag ccccattctg aacccagaca tcccctacaa ccagctgttc    120

atcaacaatg aatggcaaga tgcagtcagc aagaagacct tcccgacgac ttggcctcac    180

tcgagacctt ggacaatggg aagcctttcc aagagtctta cgccttggac ttggatgagg    240

tcatcaaggt gtatcggtac tttgct                                         266
```

<210> SEQ ID NO 14
<211> LENGTH: 433
<212> TYPE: DNA
<213> ORGANISM: Artificial Sequence
<220> FEATURE:
<223> OTHER INFORMATION: ALDH1B1 with deletion for knockout

<400> SEQUENCE: 14

```
atgctgcgct tcctggcacc ccggctgctt agcctccagg gcaggaccgc ccgctactcc     60

tcggcagcag ccctcccaag ccccattctg aacccagaca tcccctacaa ccagctgttc    120

atcaacaatg aatggcaaga tgcagtcagc aagaagacct accaccgggg aggtcatcgg    180

gcacgtggct gaaggtgacc gggctgatgt ggatcgggcc gtgaaagcag cccgggaagc    240

cttccgcctg gggtccccat ggcgccggat ggatgcctct gagcggggcc ggctgctgaa    300

ccgcctggca gacctagtgg agcgggatcg agtctacttg gcctcactcg agaccttgga    360

caatgggaag cctttccaag agtcttacgc cttggacttg gatgaggtca tcaaggtgta    420

tcggtacttt gct                                                       433
```